(12) United States Patent
Ulm, III

(10) Patent No.: US 9,962,177 B2
(45) Date of Patent: *May 8, 2018

(54) CLOT RETRIEVAL SYSTEM

(71) Applicant: Legacy Ventures LLC, Nashville, TN (US)

(72) Inventor: Arthur John Ulm, III, Nashville, TN (US)

(73) Assignee: Legacy Ventures LLC, Nashville, TN (US)

( * ) Notice: Subject to any disclaimer, the term of this patent is extended or adjusted under 35 U.S.C. 154(b) by 123 days.

This patent is subject to a terminal disclaimer.

(21) Appl. No.: 14/794,783

(22) Filed: Jul. 8, 2015

(65) Prior Publication Data

US 2015/0320431 A1    Nov. 12, 2015

Related U.S. Application Data

(63) Continuation-in-part of application No. 14/558,712, filed on Dec. 2, 2014, now Pat. No. 9,155,552, which is a continuation of application No. 14/558,705, filed on Dec. 2, 2014, now Pat. No. 9,173,668, which is a continuation-in-part of application No. 14/147,491, filed on Jan. 3, 2014, now Pat. No. 8,900,265, application No. 14/794,783, filed on Jul. 8, 2015, which is a continuation-in-part of application No. PCT/US2015/010178, filed on Jan. 5, 2015, which is a continuation-in-part of application No. 14/558,712, filed on Dec. 2, 2014, now Pat. No. 9,155,552, which is a continuation of application No. 14/558,705, filed on Dec. 2, 2014, now Pat. No. 9,173,668, which is a continuation-in-part of application No. 14/147,491, filed on Jan. 3, 2014, now Pat. No. 8,900,265, said application No. 14/794,783 is a continuation-in-part of application No. PCT/US2015/031447, filed on May 18, 2015.

(60) Provisional application No. 61/994,934, filed on May 18, 2014.

(51) Int. Cl.
*A61B 17/221*   (2006.01)
*A61B 17/00*    (2006.01)

(52) U.S. Cl.
CPC ...... *A61B 17/221* (2013.01); *A61B 17/00234* (2013.01); *A61B 2017/00323* (2013.01); *A61B 2017/00477* (2013.01); *A61B 2017/00778* (2013.01); *A61B 2017/00867* (2013.01); *A61B 2017/2212* (2013.01)

(58) Field of Classification Search
CPC .... A61F 2/00; A61F 2/01; A61F 2/013; A61F 2/02; A61B 17/221; A61B 2017/2212
See application file for complete search history.

(56) References Cited

U.S. PATENT DOCUMENTS 6,702,834 B1 *   3/2004   Boylan ............... A61F 2/013
                                                    604/106

* cited by examiner

*Primary Examiner* — Thomas McEvoy
(74) *Attorney, Agent, or Firm* — Shane Cortesi

(57) ABSTRACT

A platform of devices for removing obstructions and other objects within a blood vessel or other interior lumen of an animal is provided. The system may be deployed in the lumen from a catheter(s) and the system includes a proximal hub, and a distal basket comprised of a plurality of cells. A number of different baskets designs are disclosed. Methods of manufacturing such baskets out of a single tube of a memory metal without the need for any welding or soldering, and methods of use are also disclosed.

21 Claims, 79 Drawing Sheets

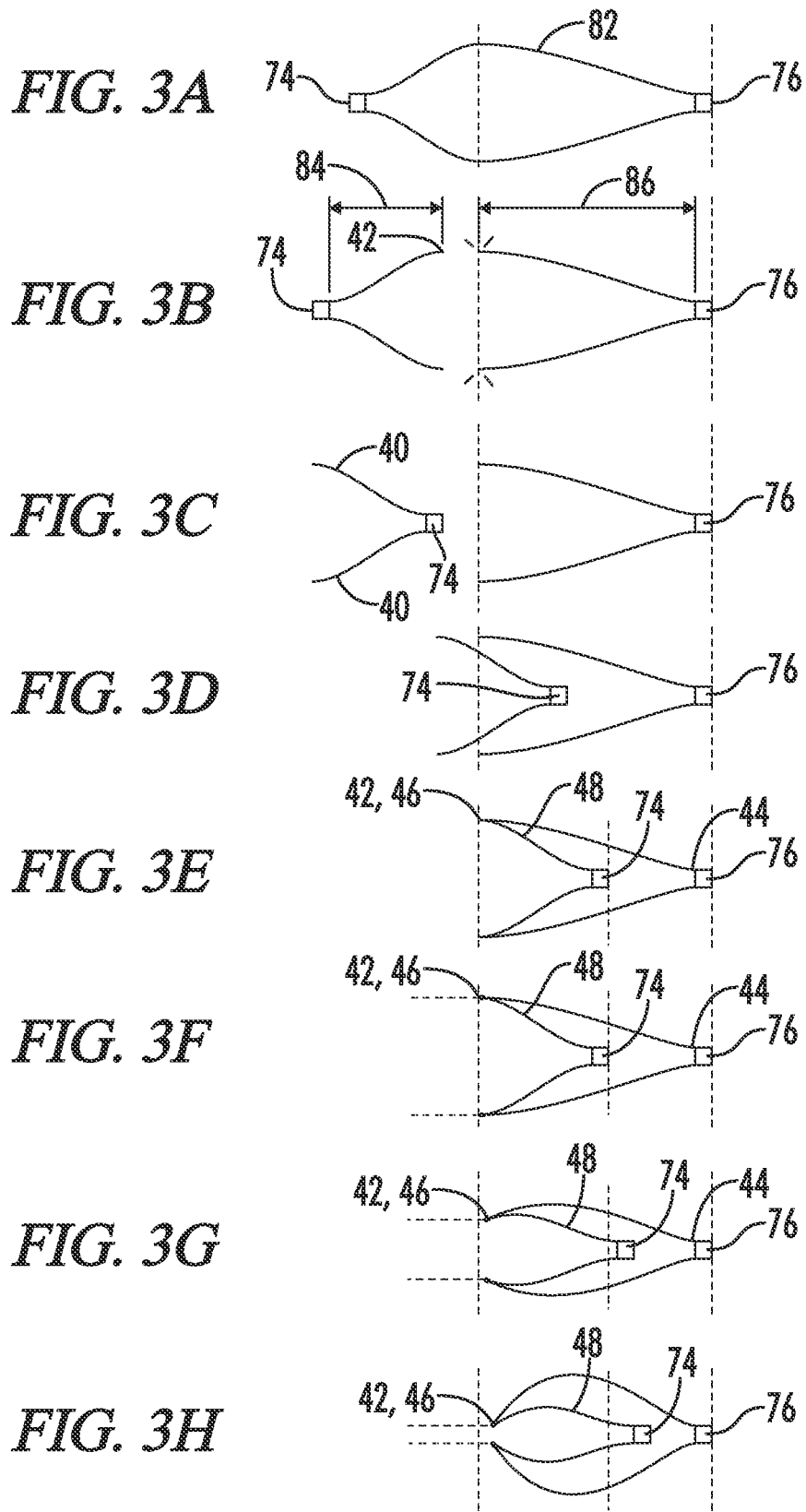

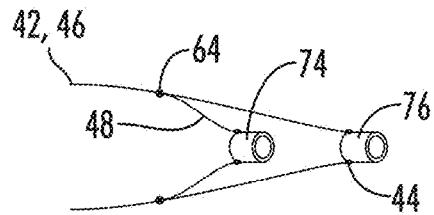
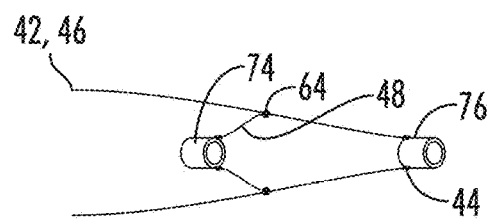
FIG. 5
FIG. 6
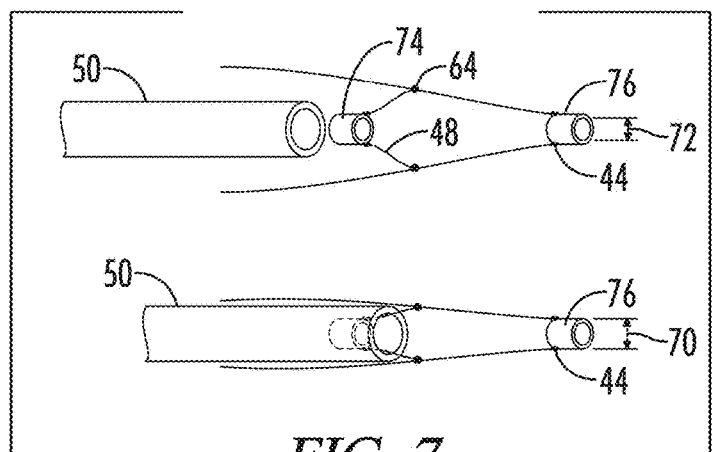
FIG. 7
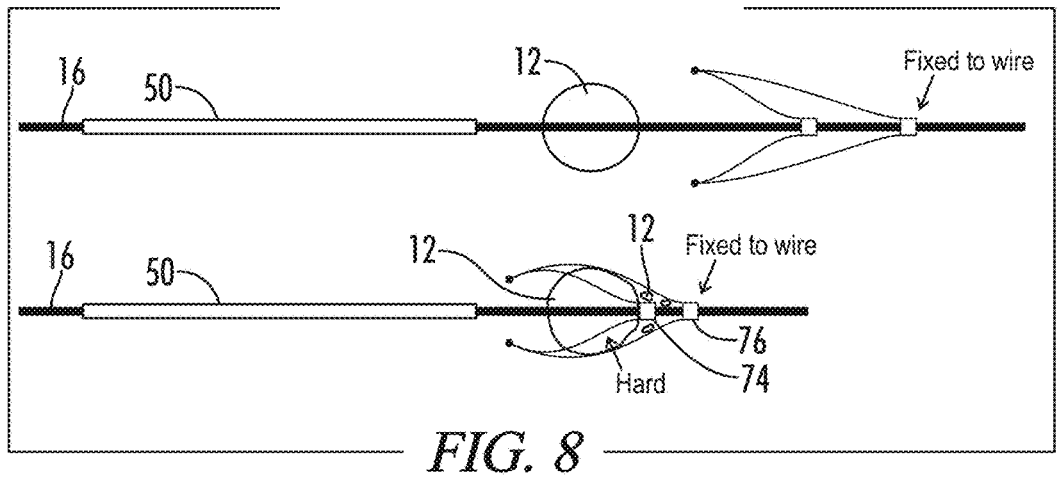
FIG. 8

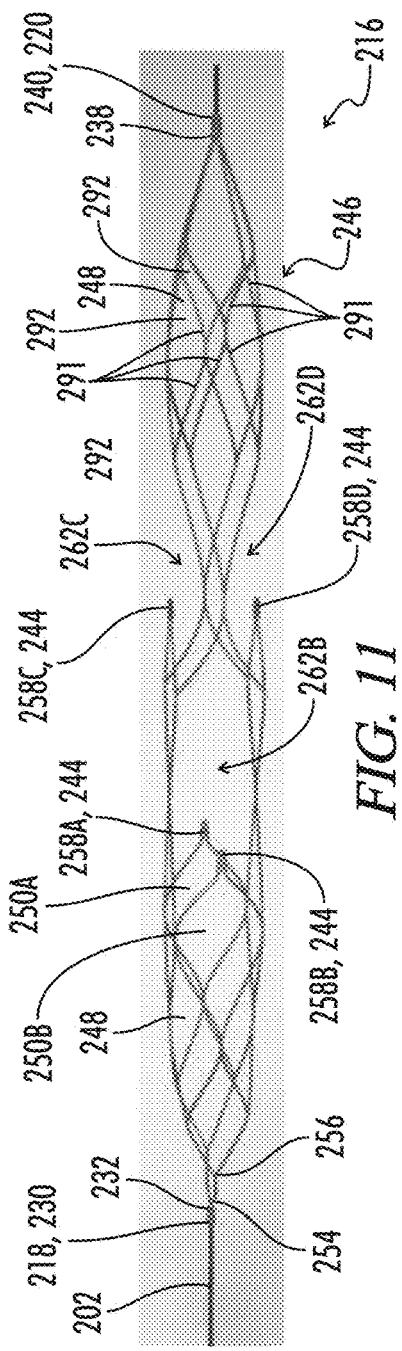
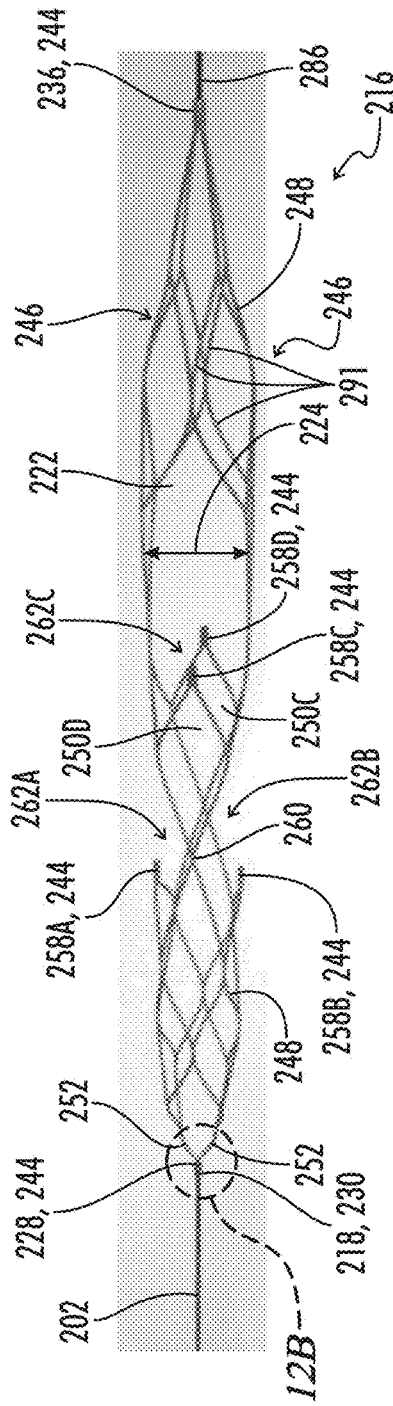
FIG. 11
FIG. 12A
FIG. 12B

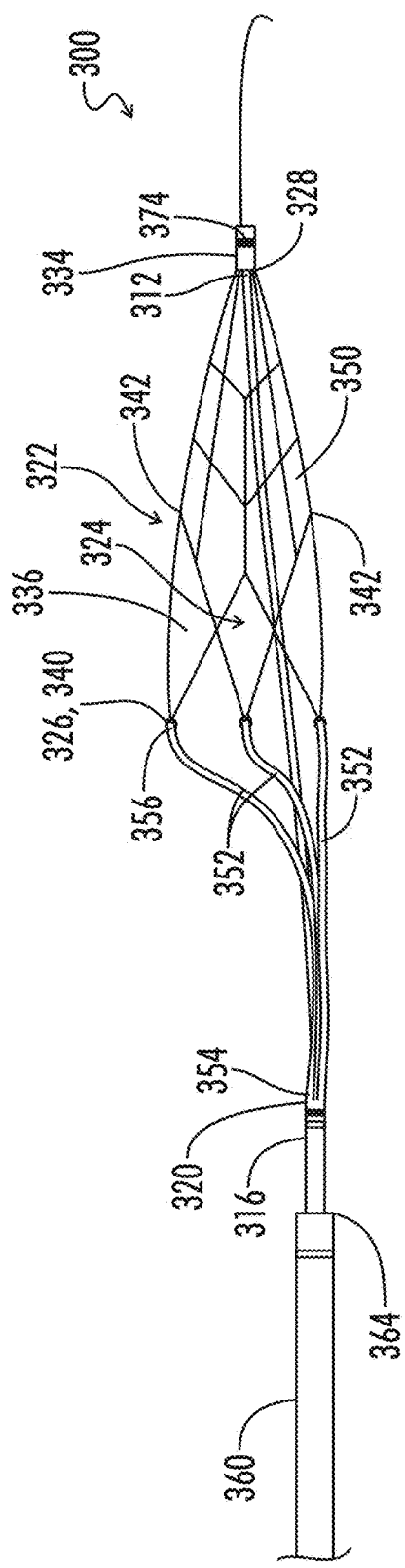
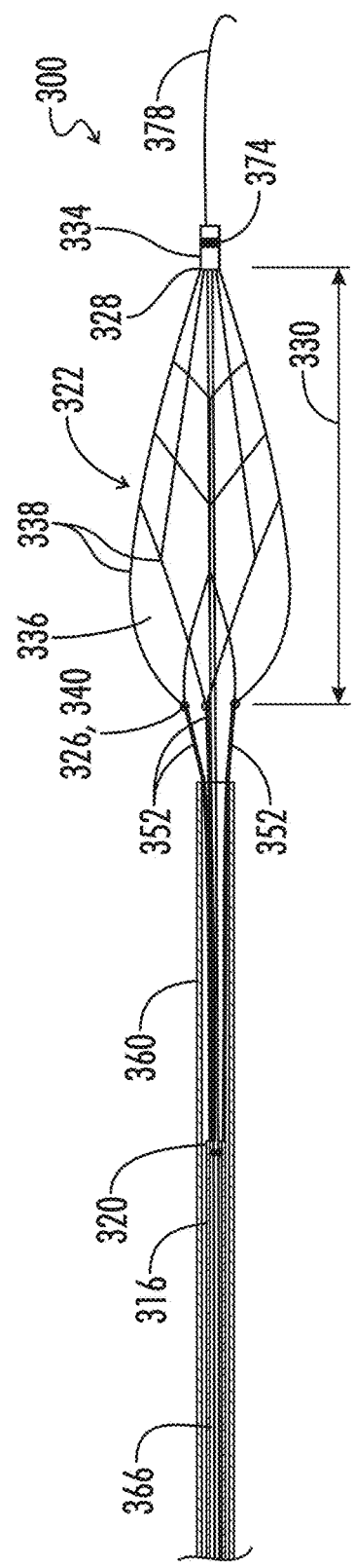
FIG. 30A
FIG. 30B

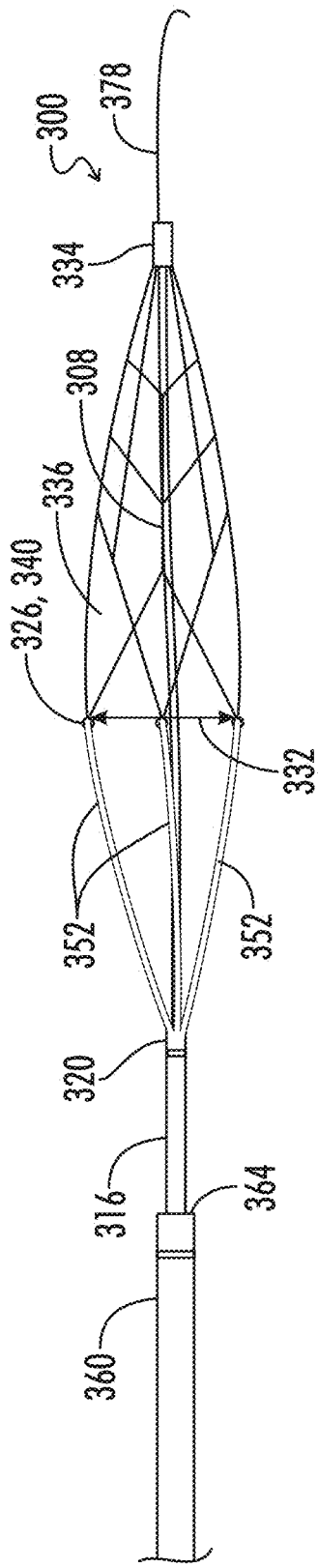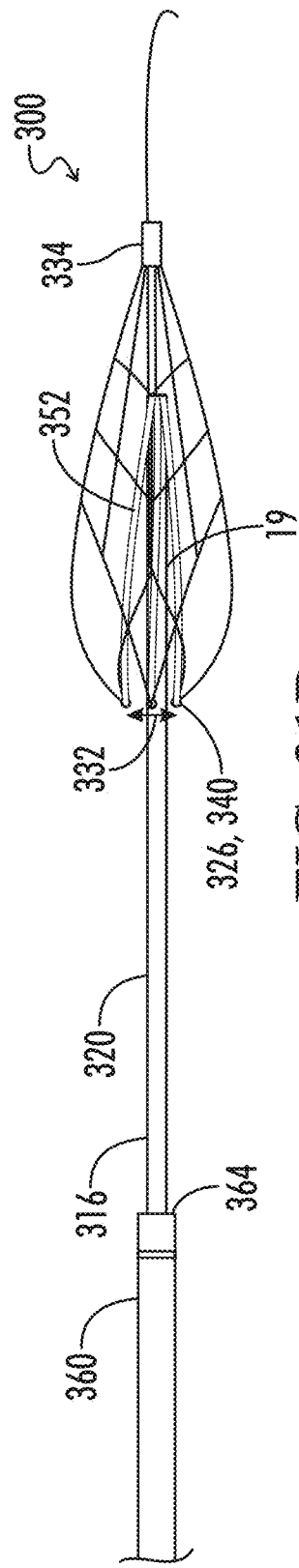

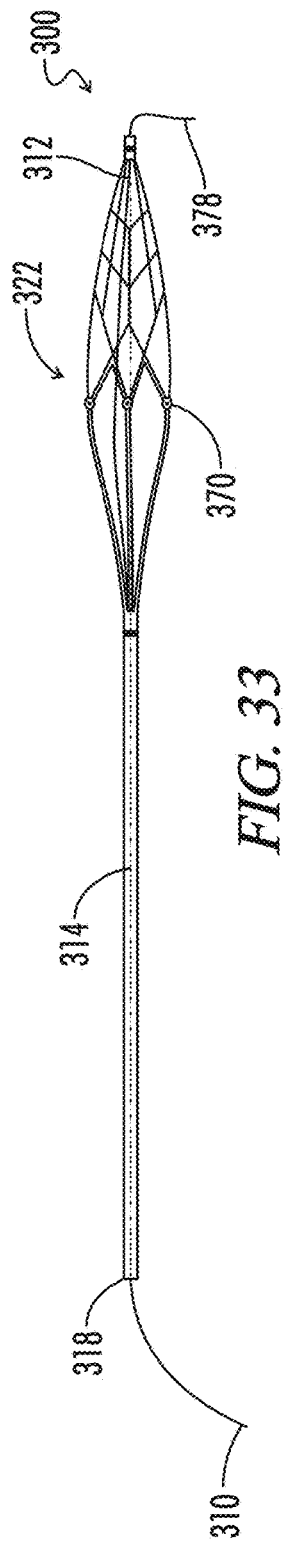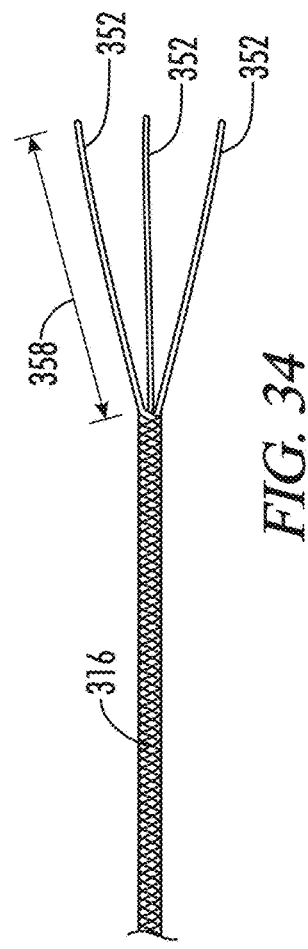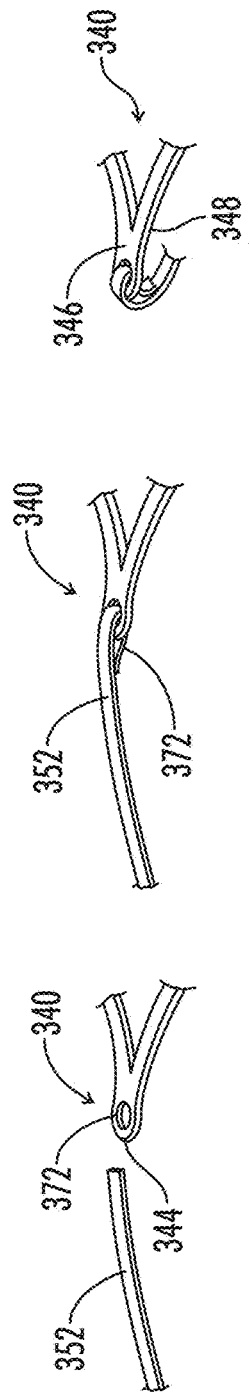
FIG. 33
FIG. 34
FIG. 35A
FIG. 35B
FIG. 35C

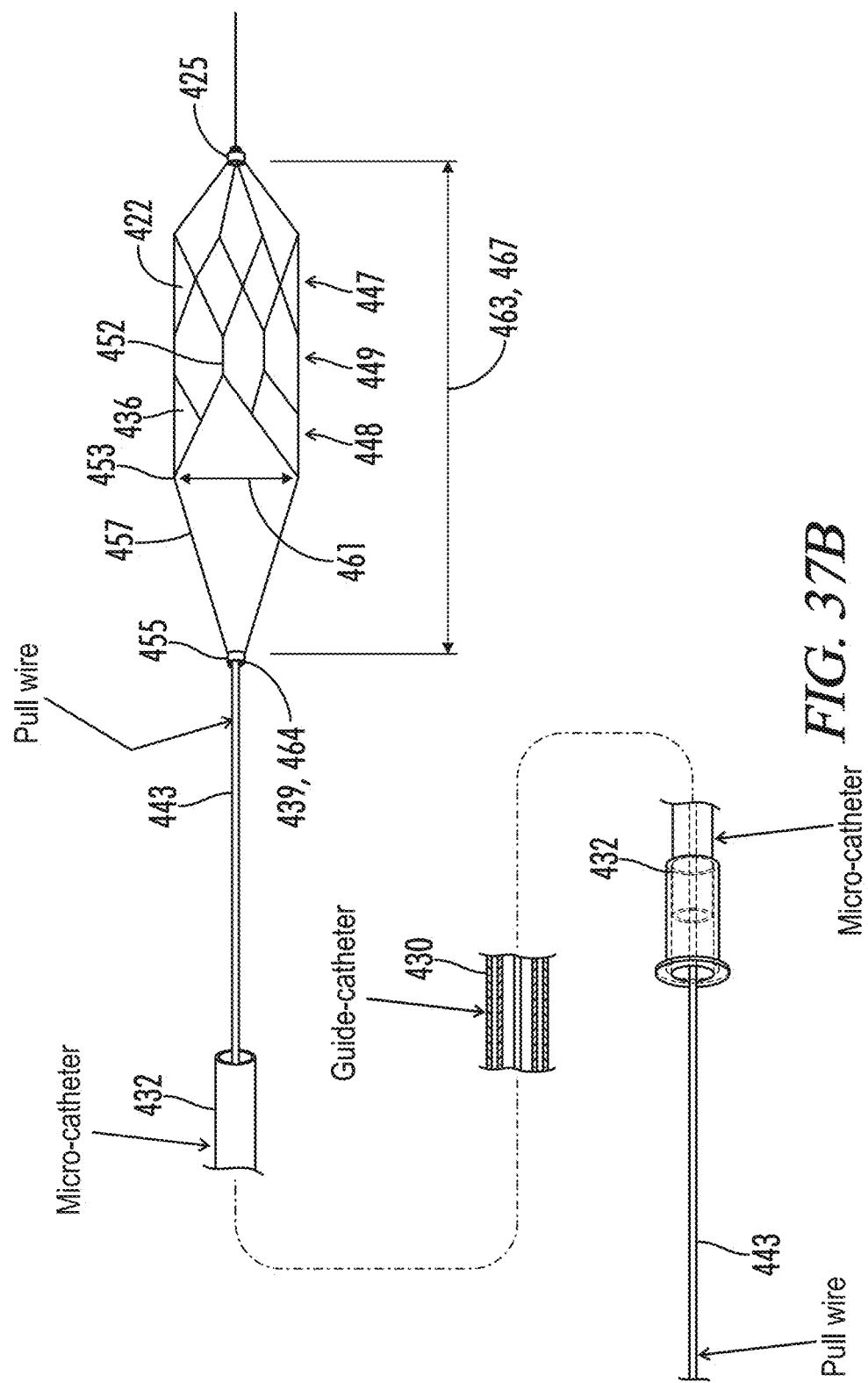

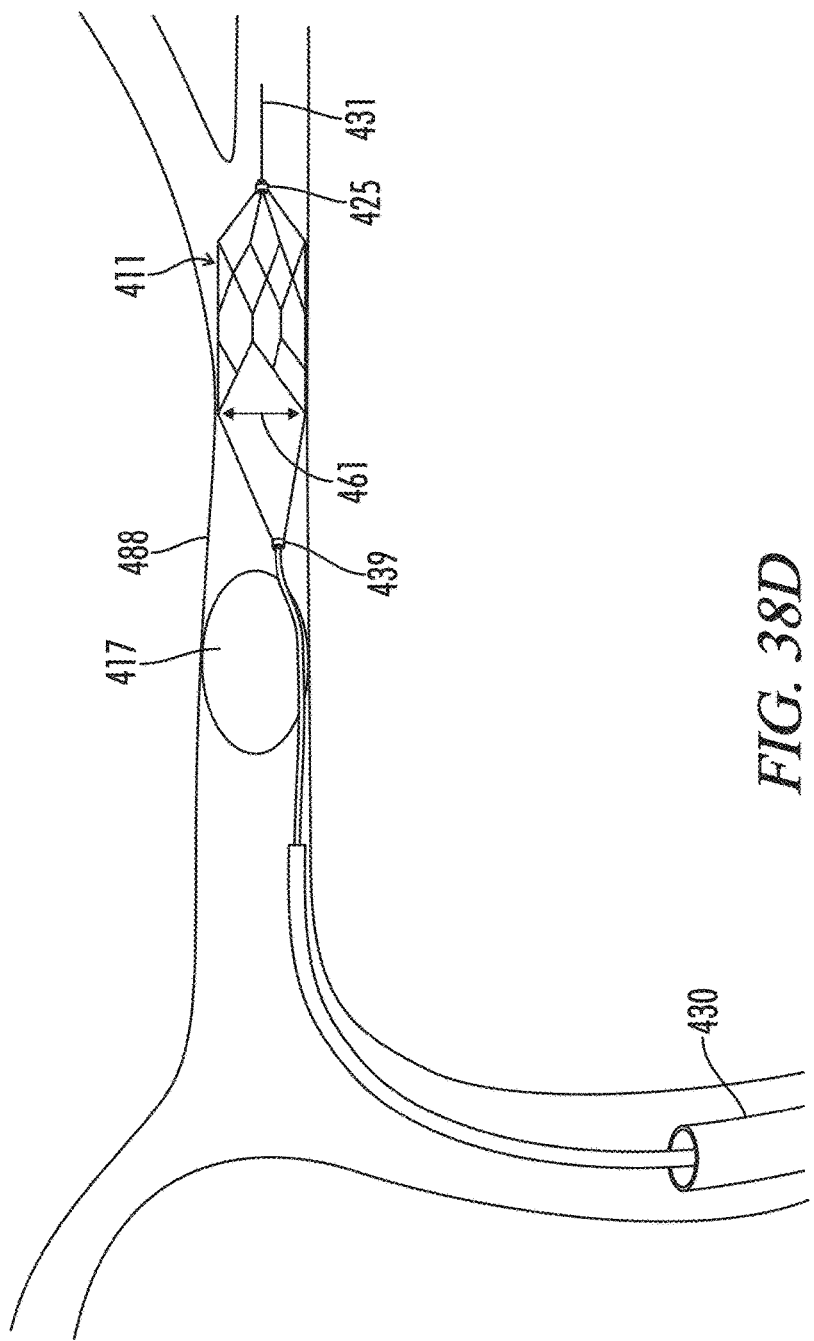

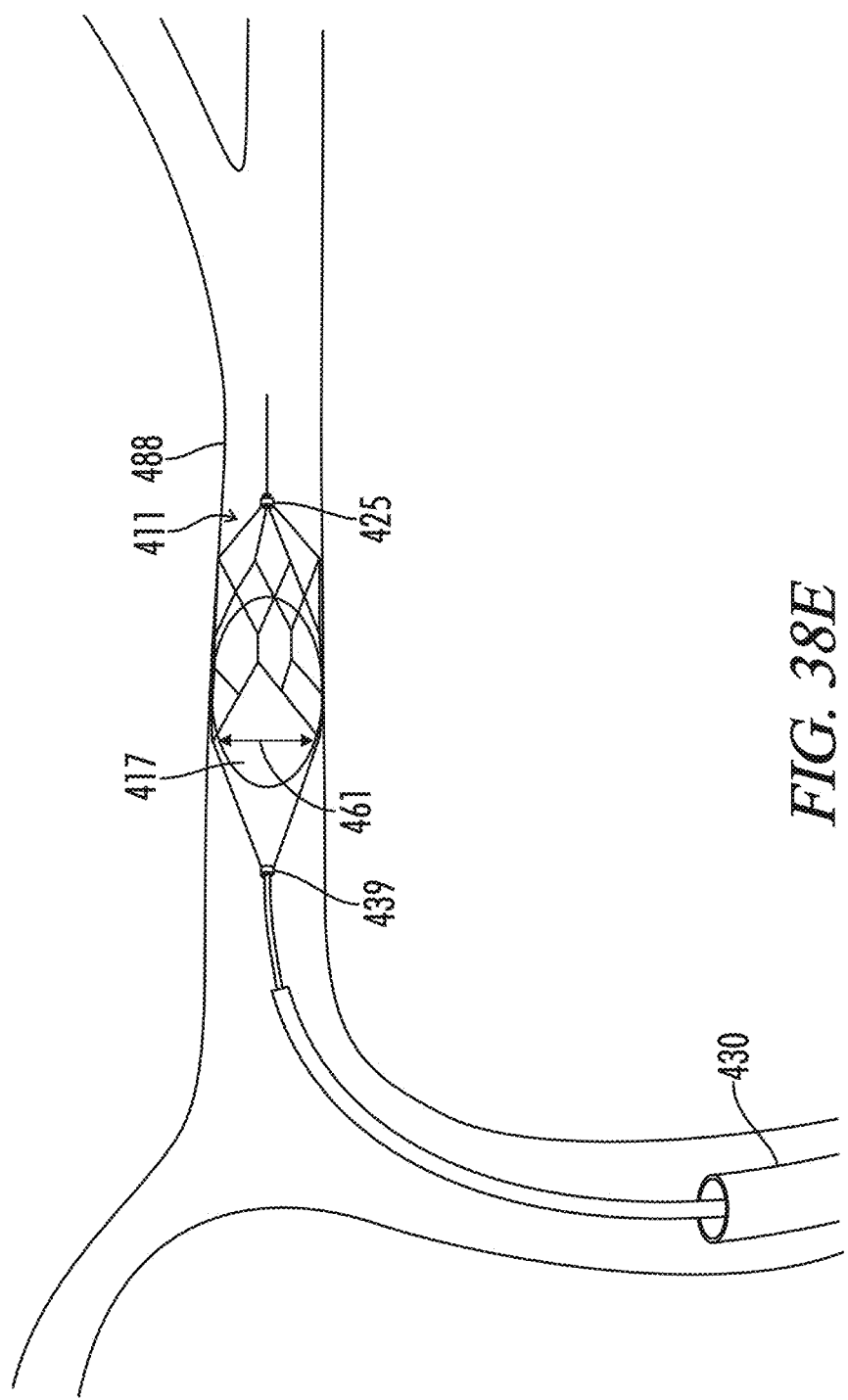

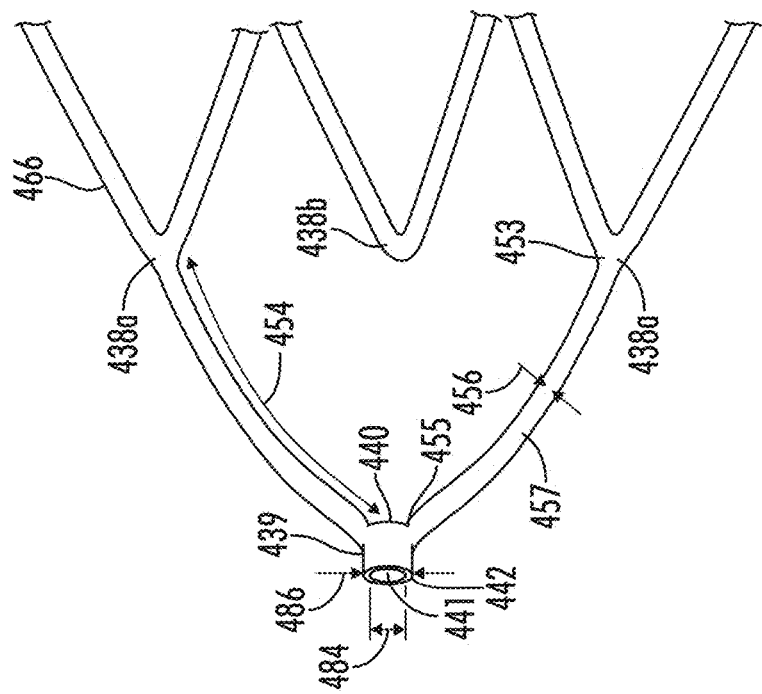
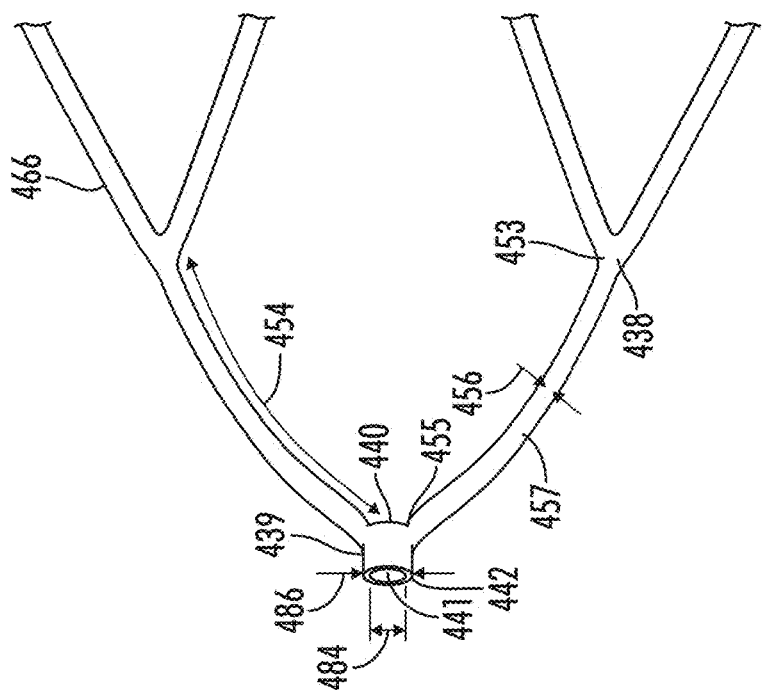

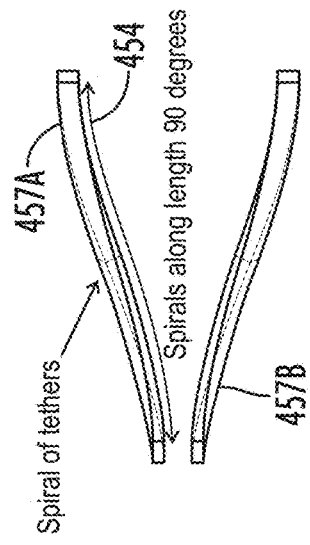
FIG. 43B
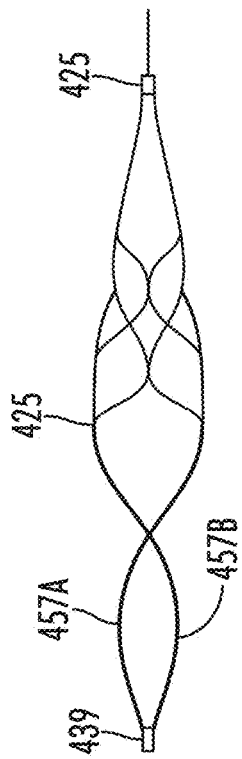
FIG. 43E
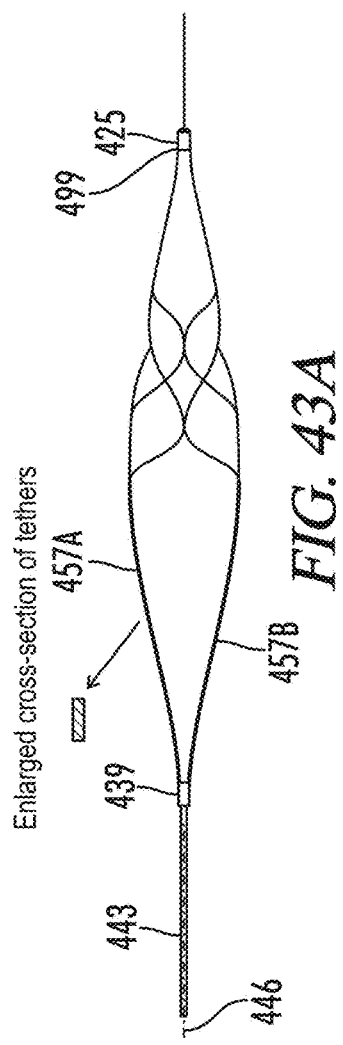
FIG. 43A
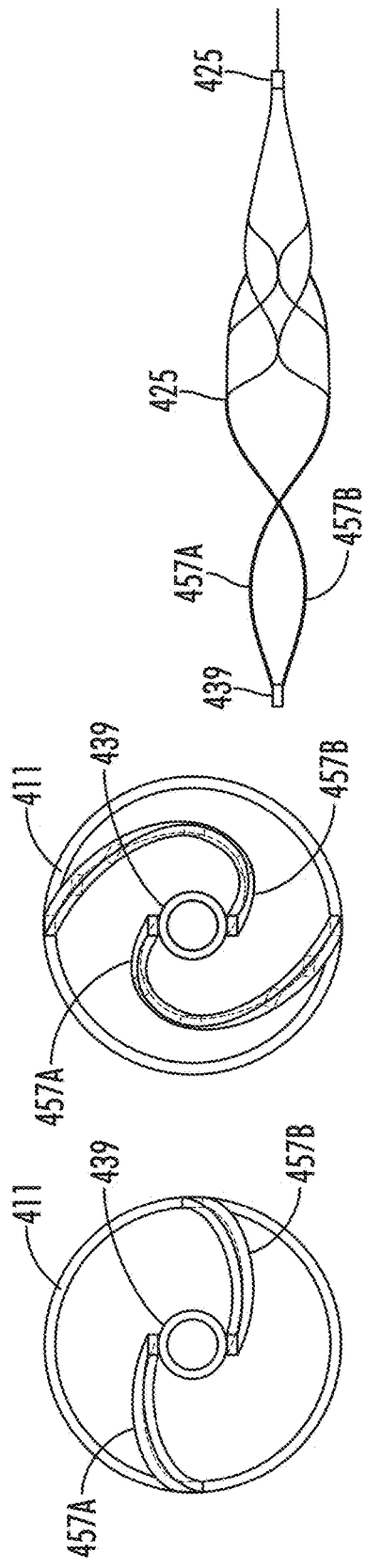
FIG. 43D
FIG. 43C

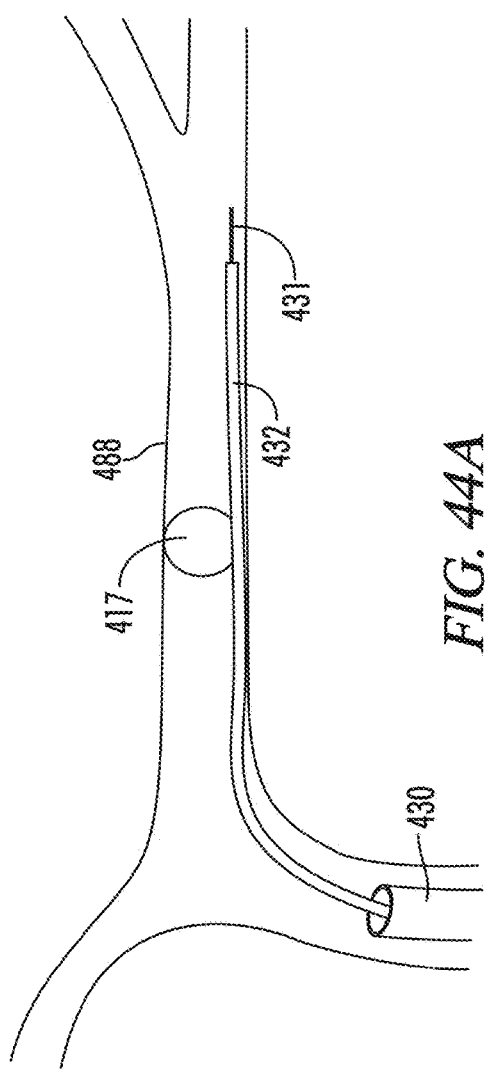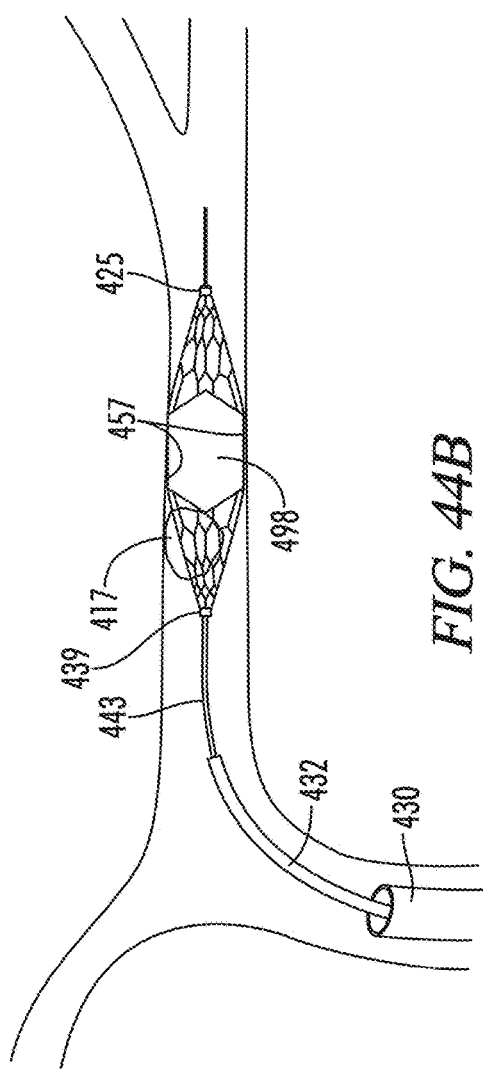

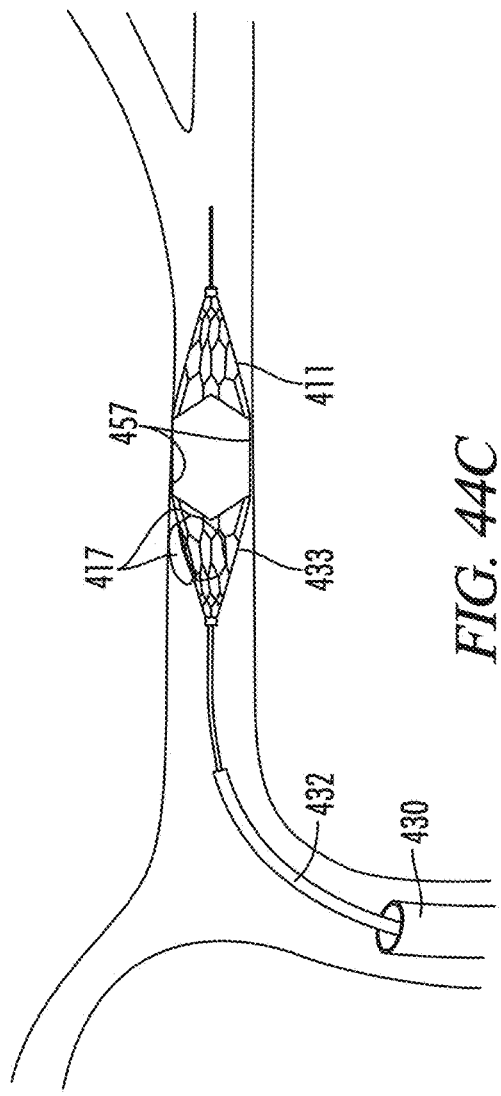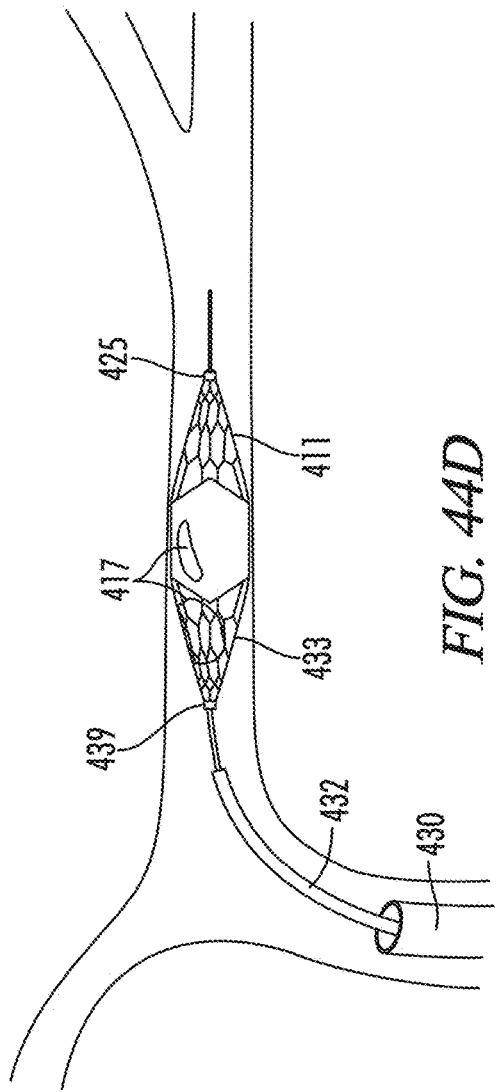

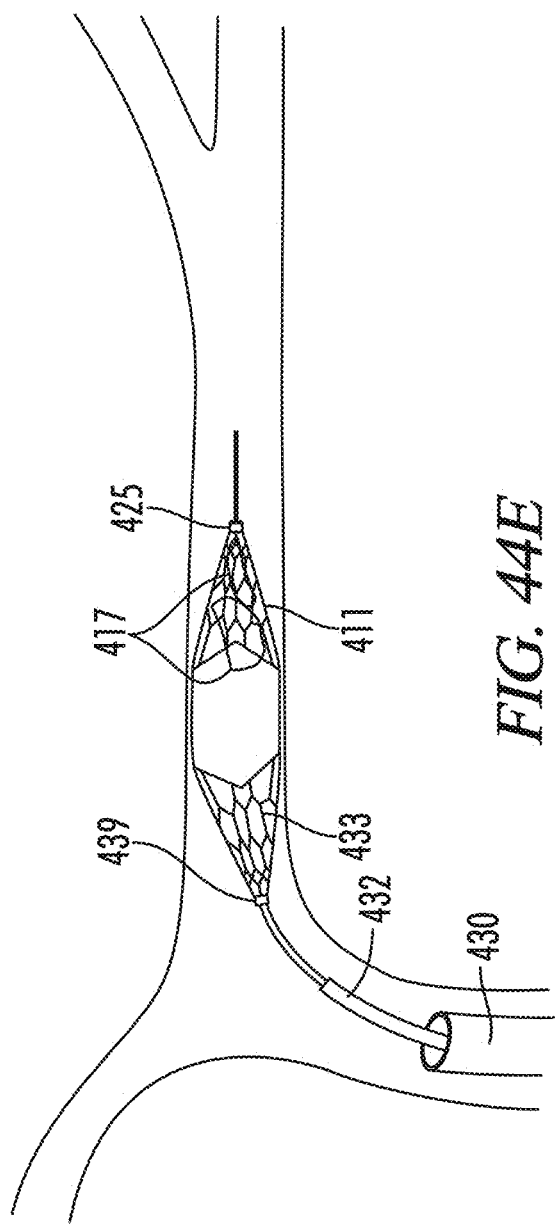

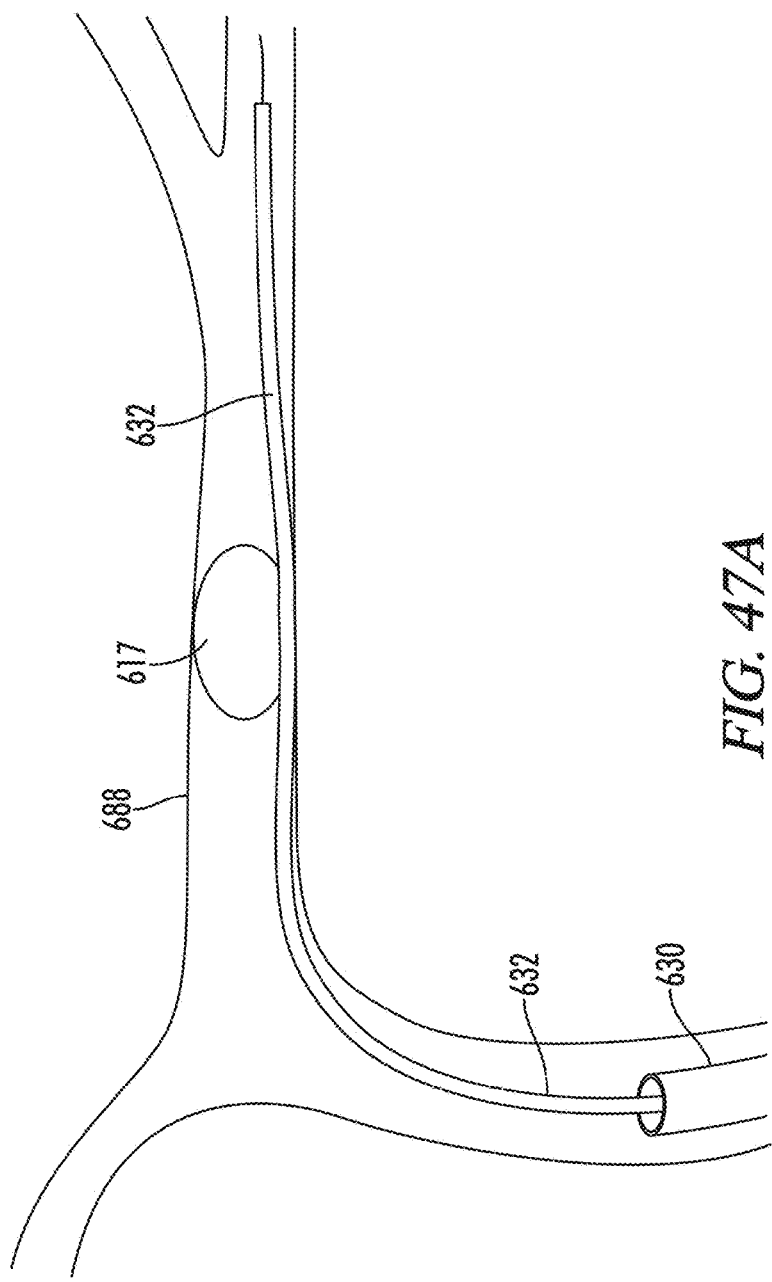

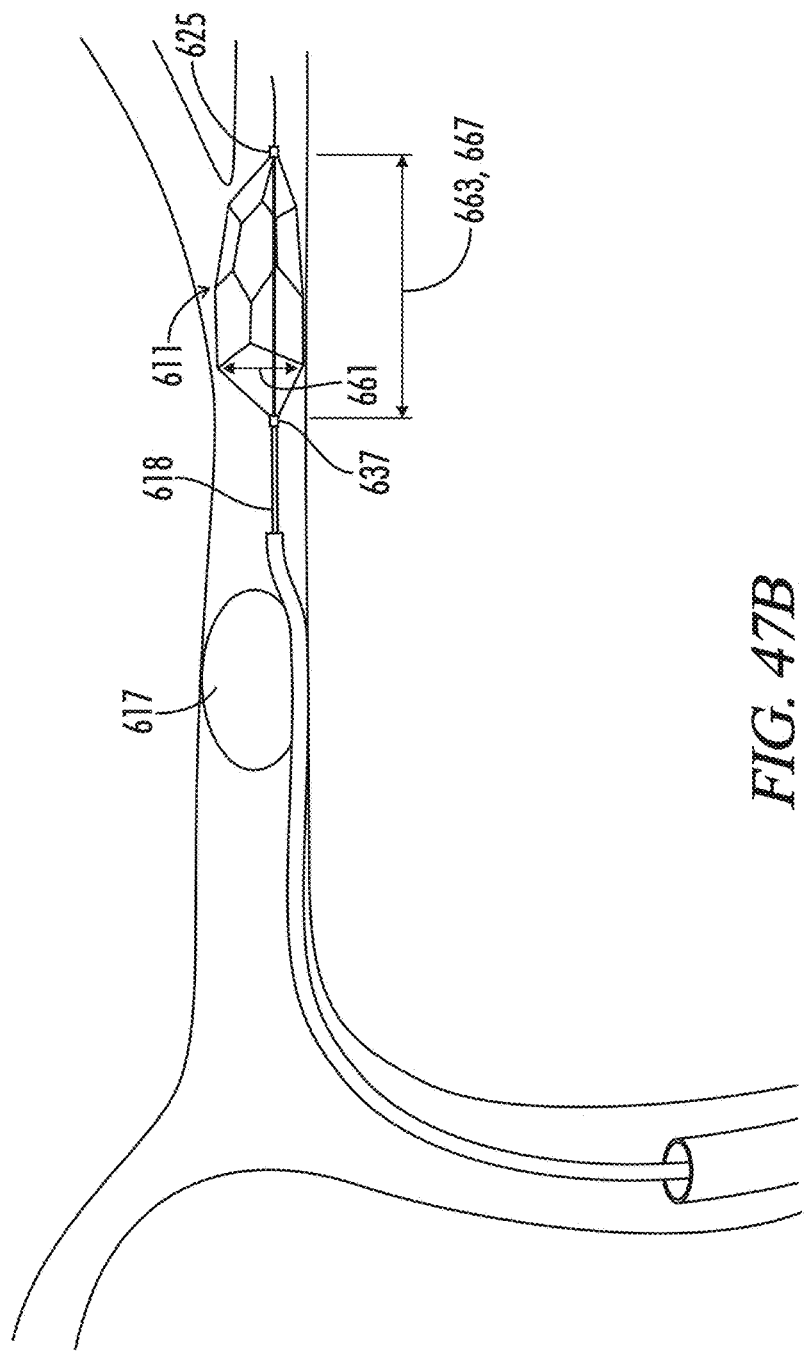

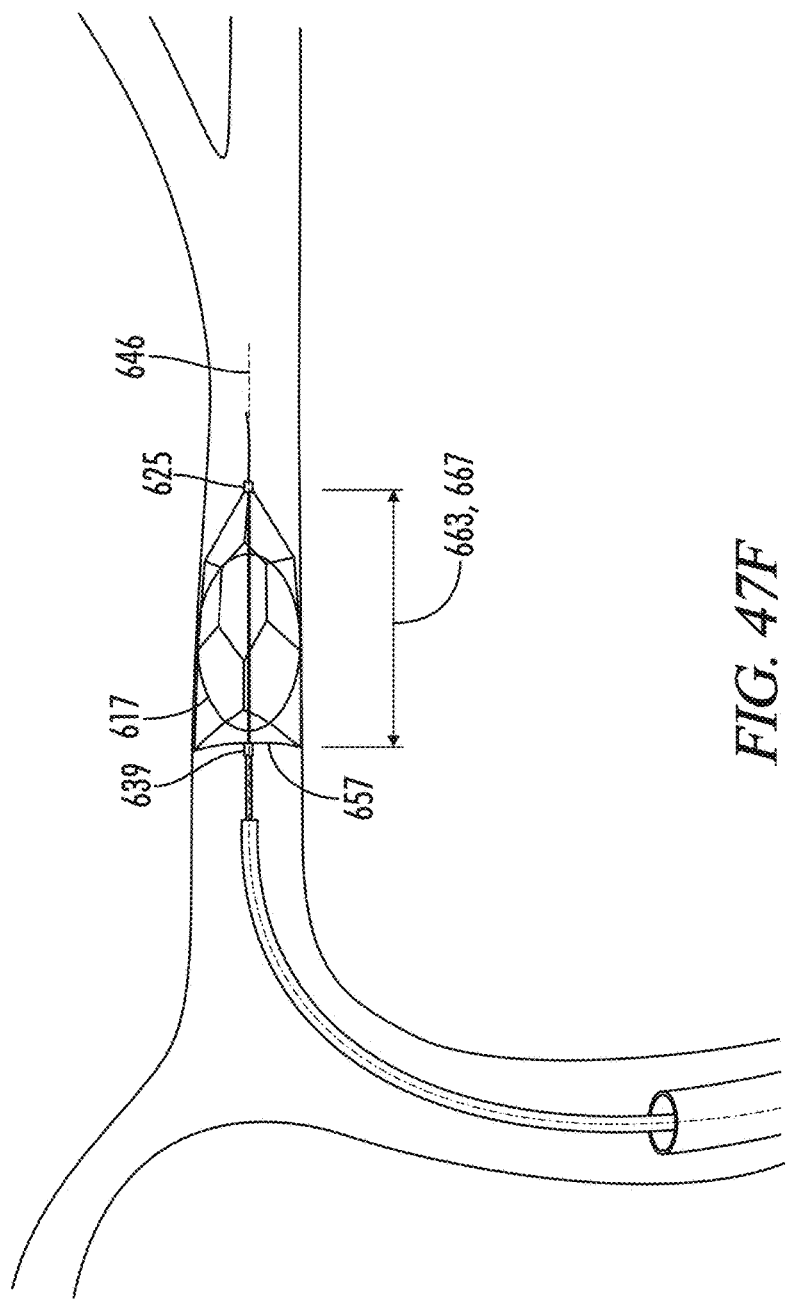

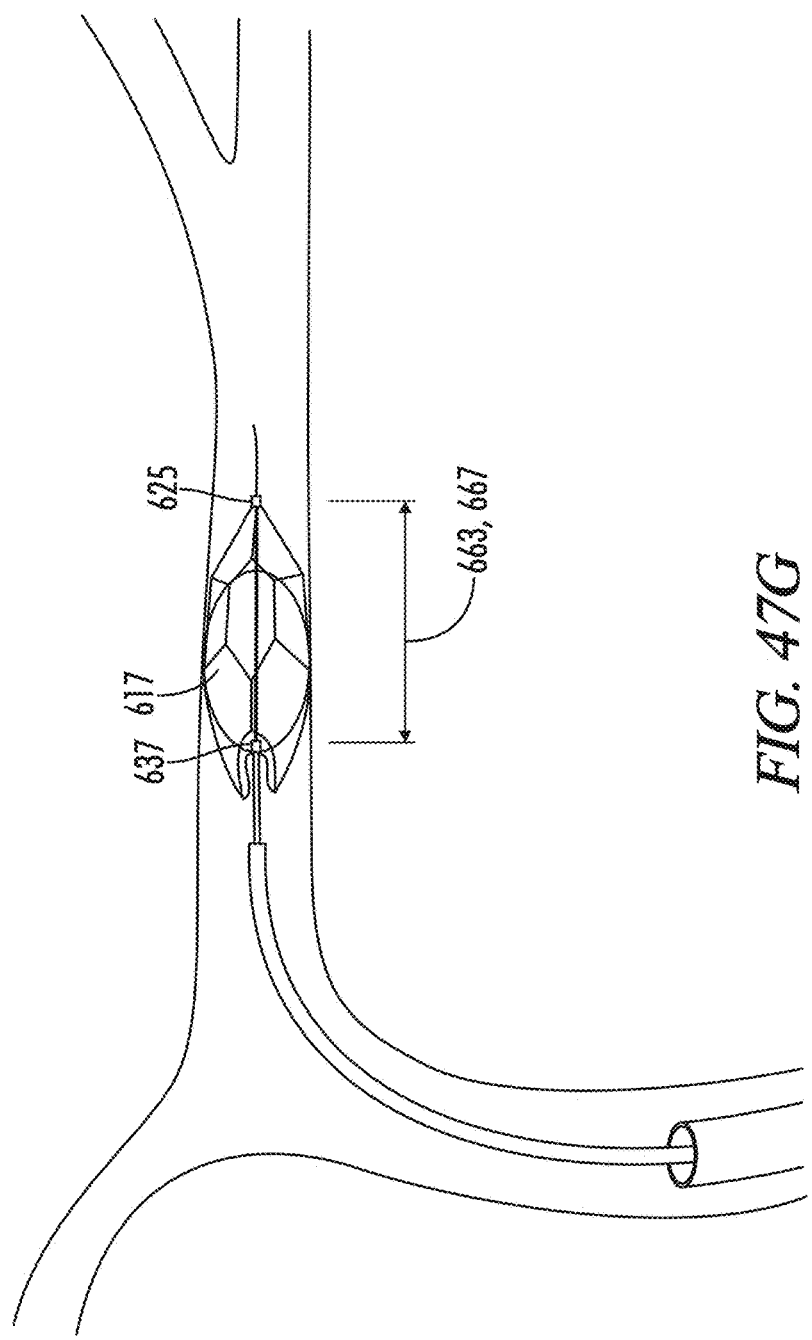

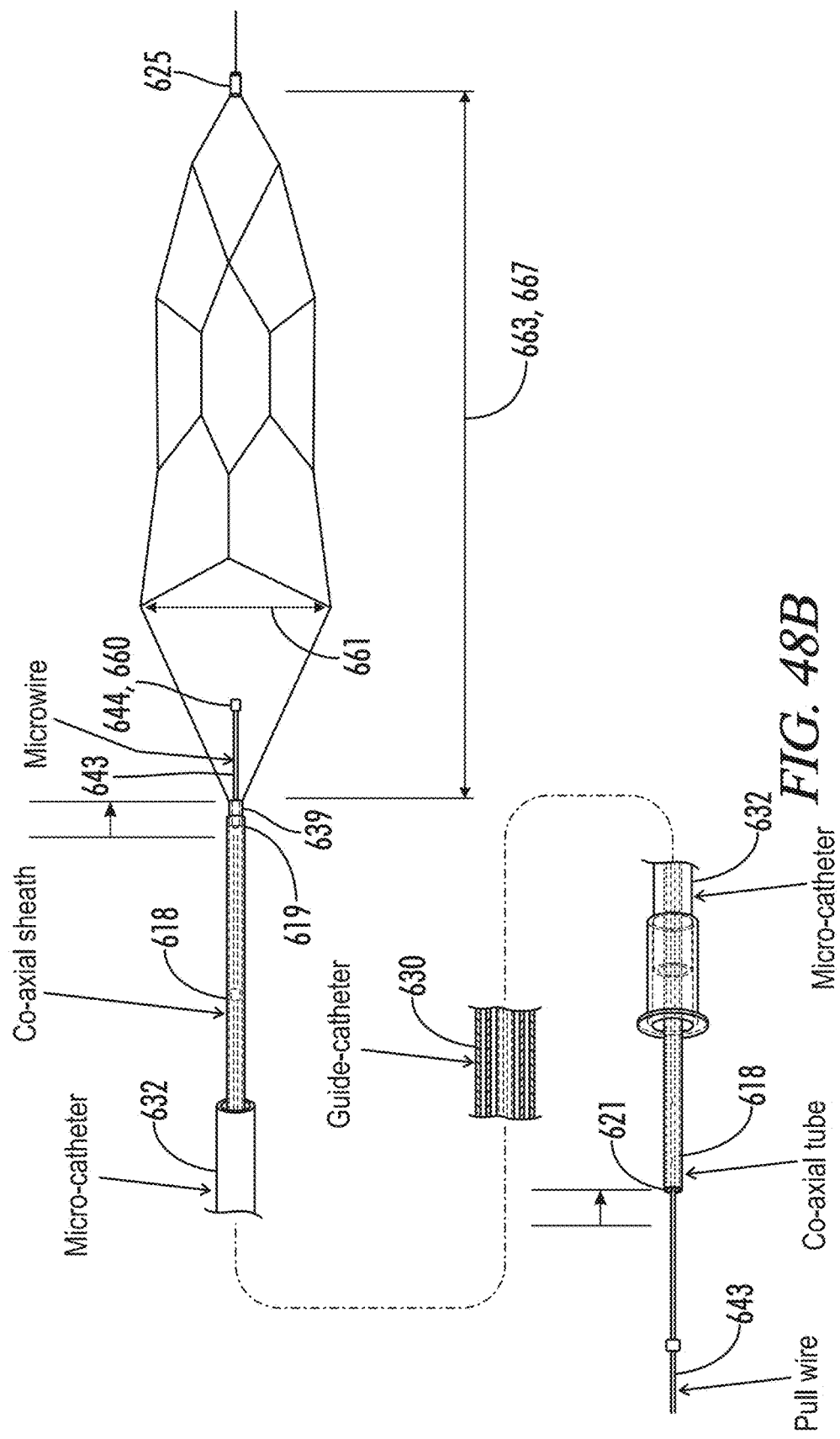

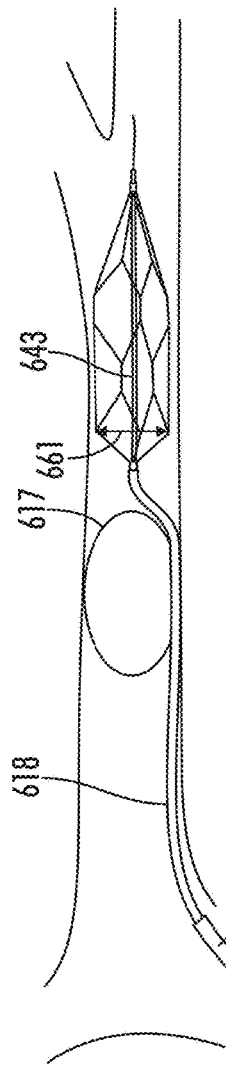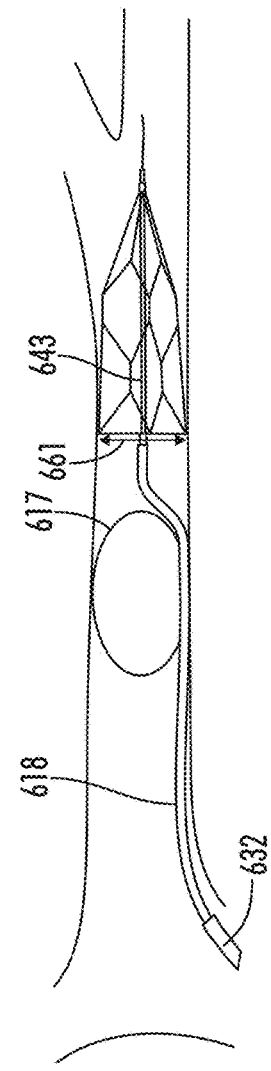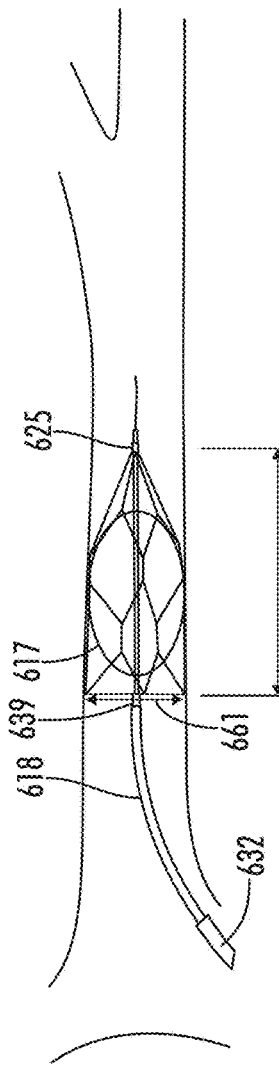

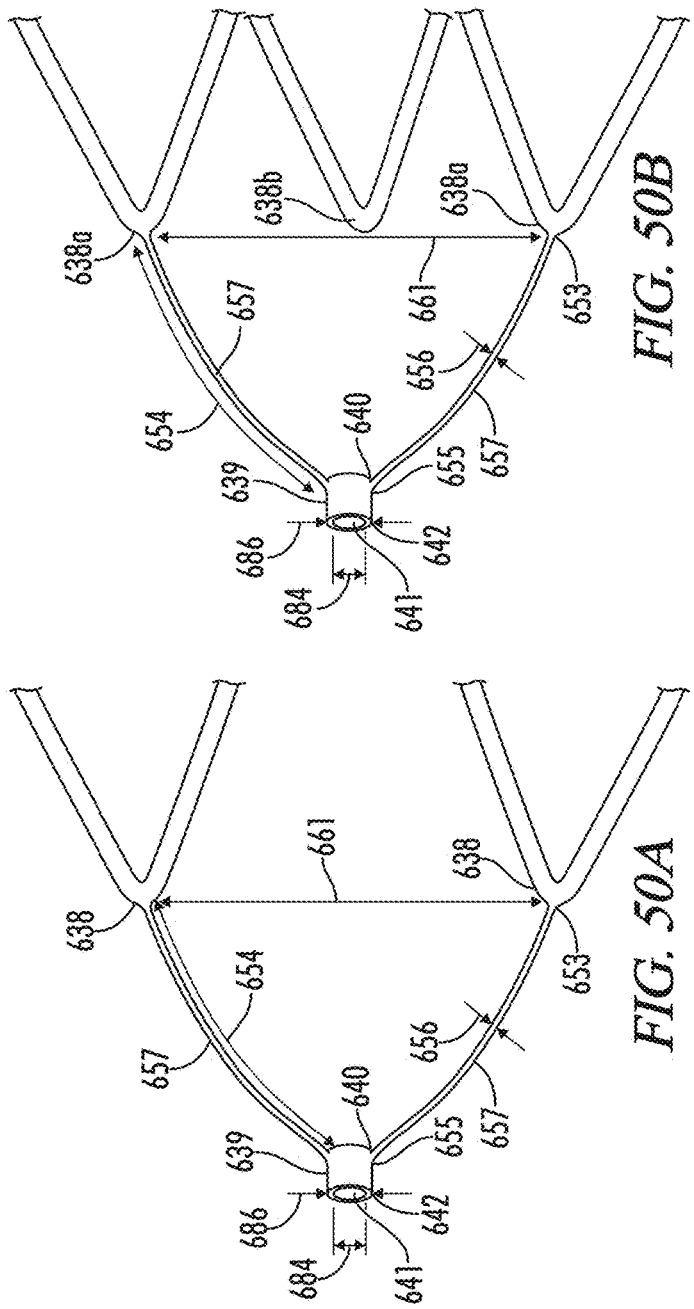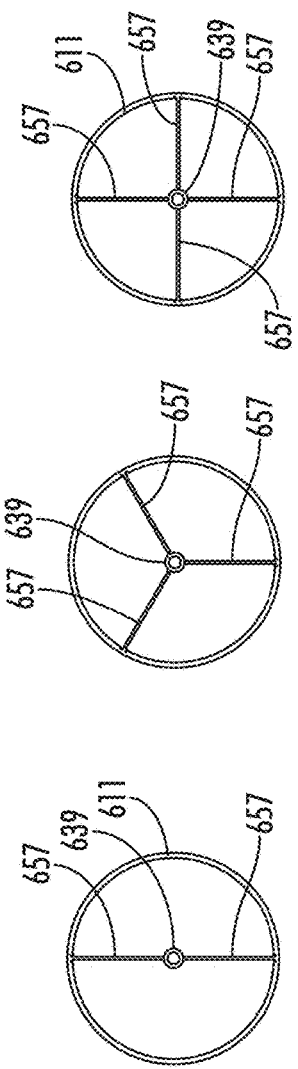

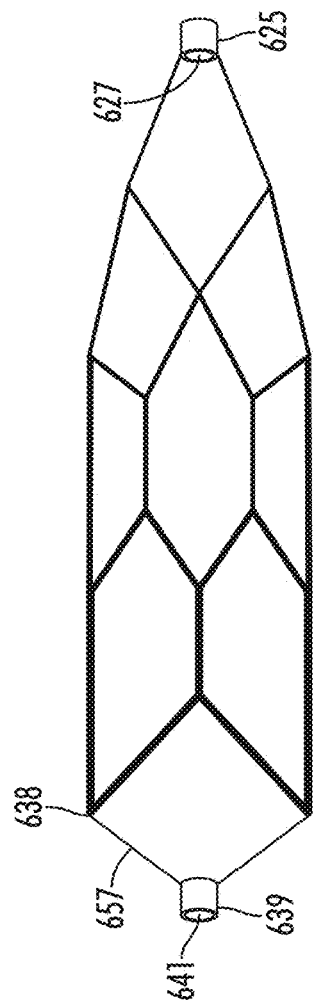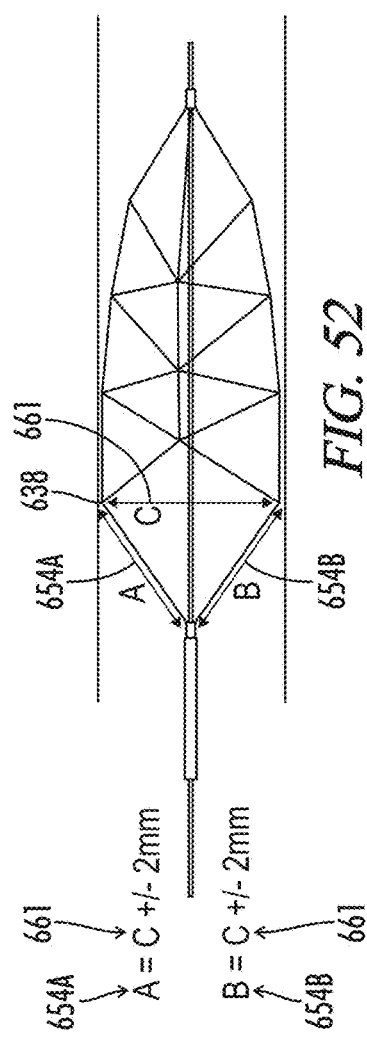

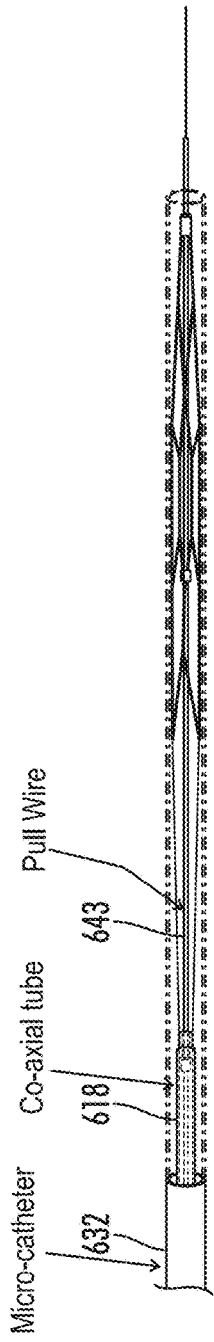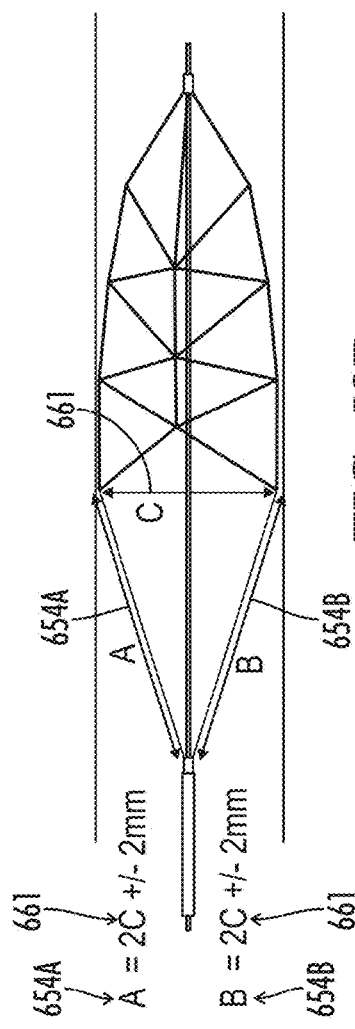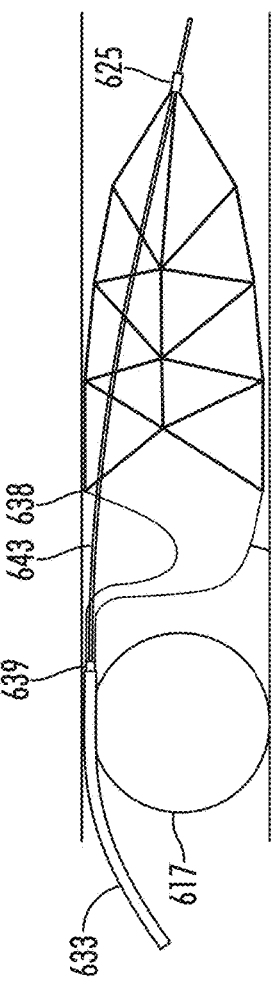

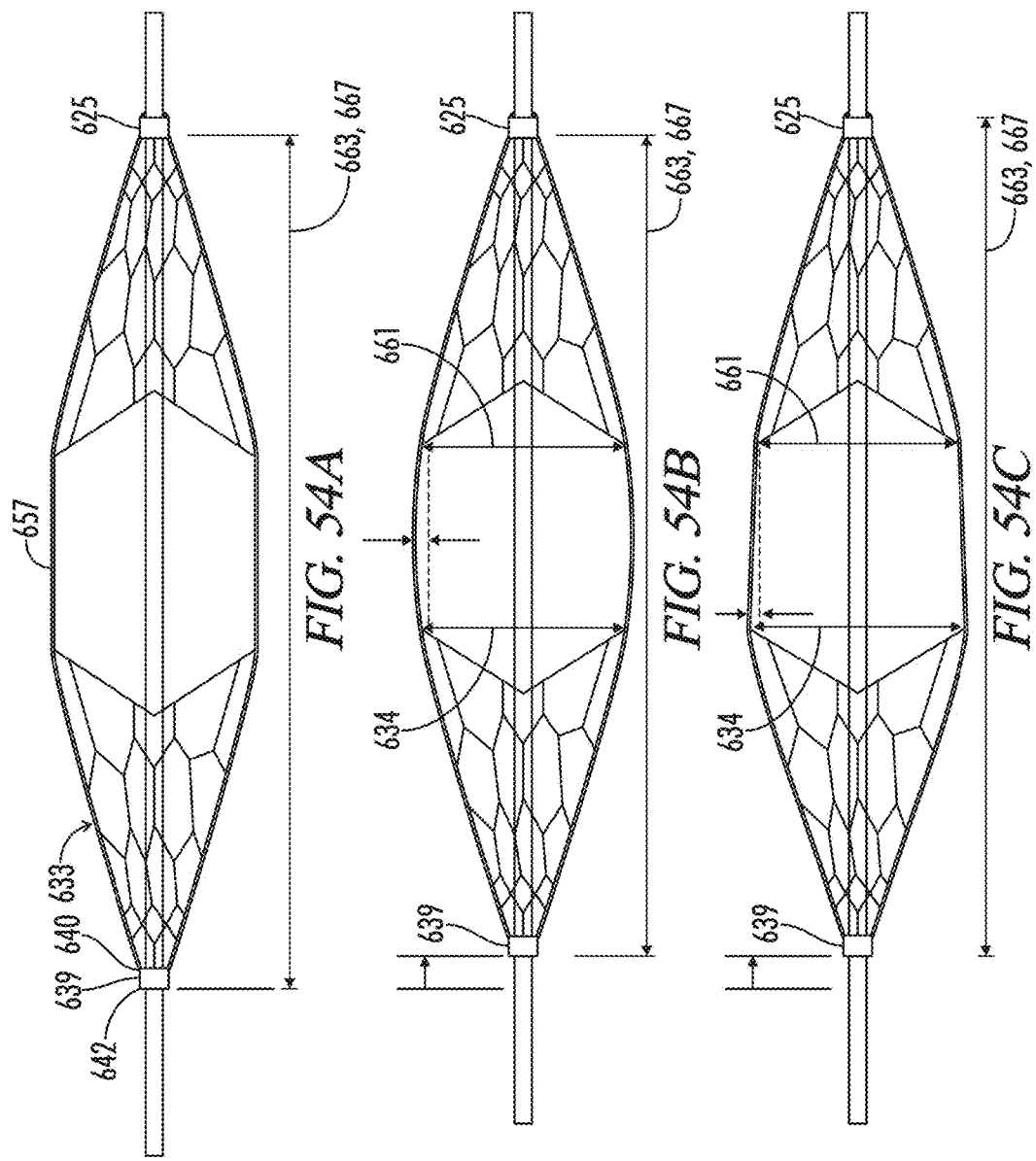

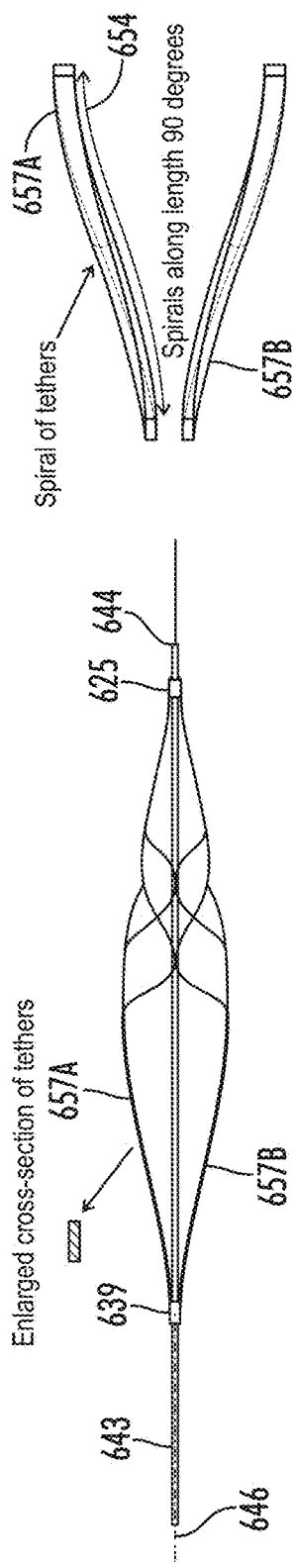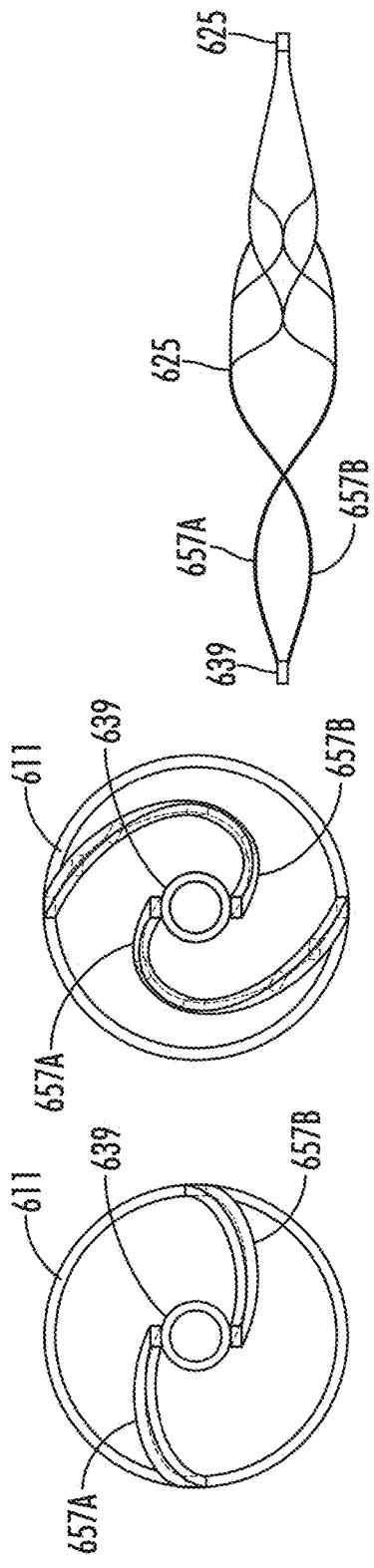

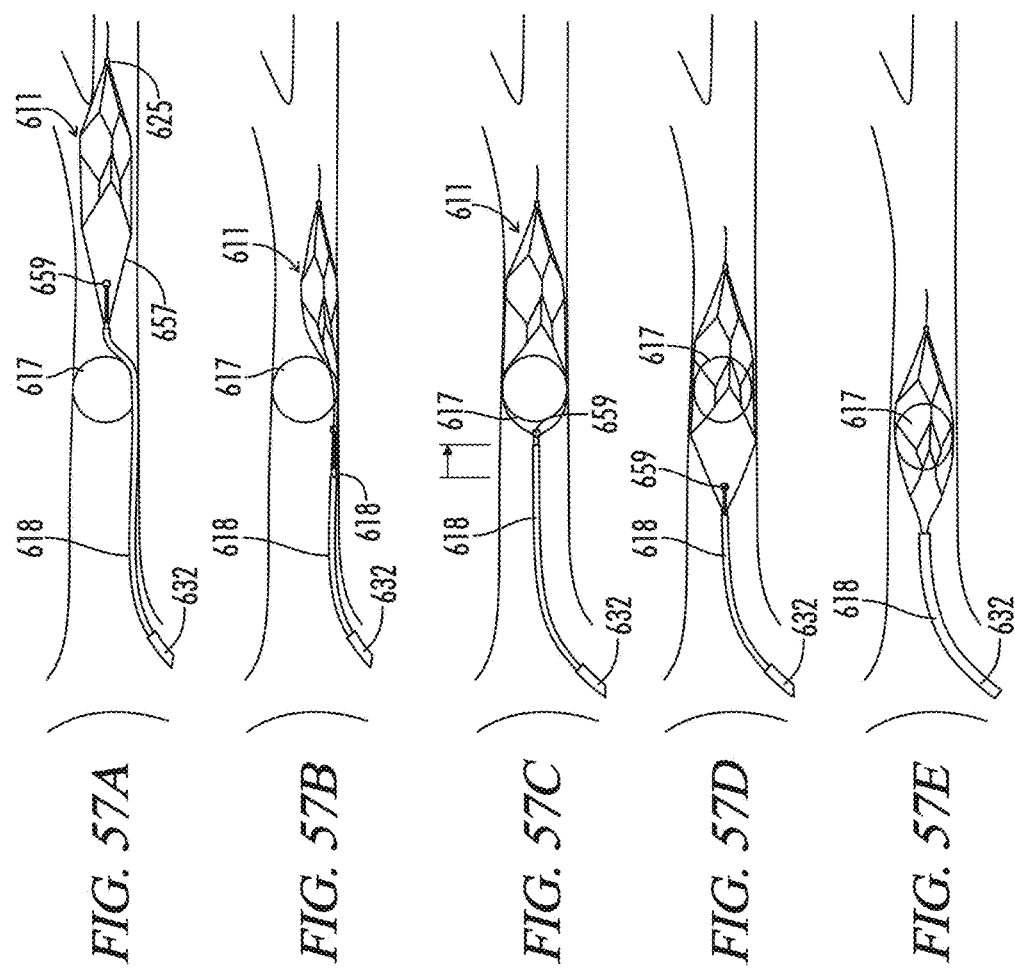

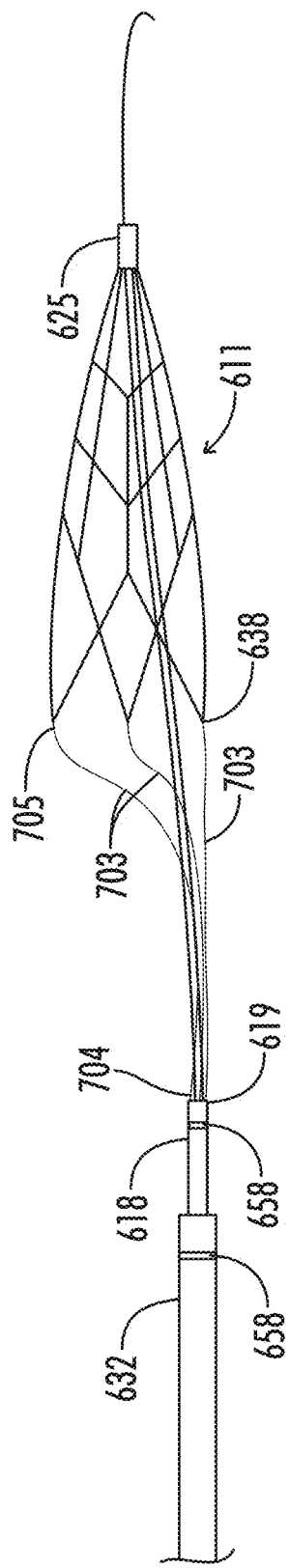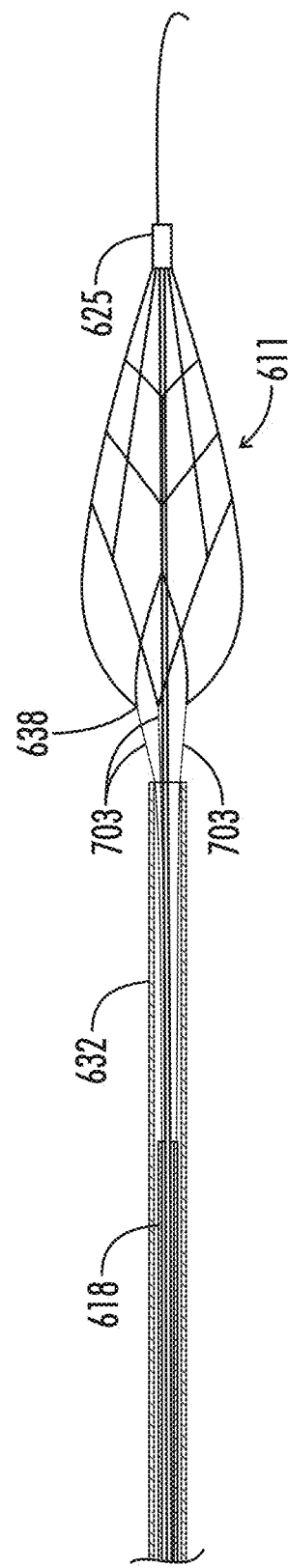
FIG. 58A
FIG. 58B

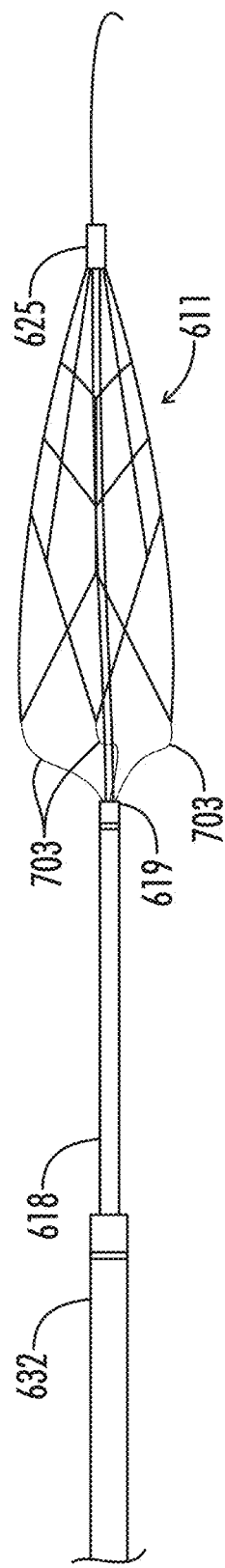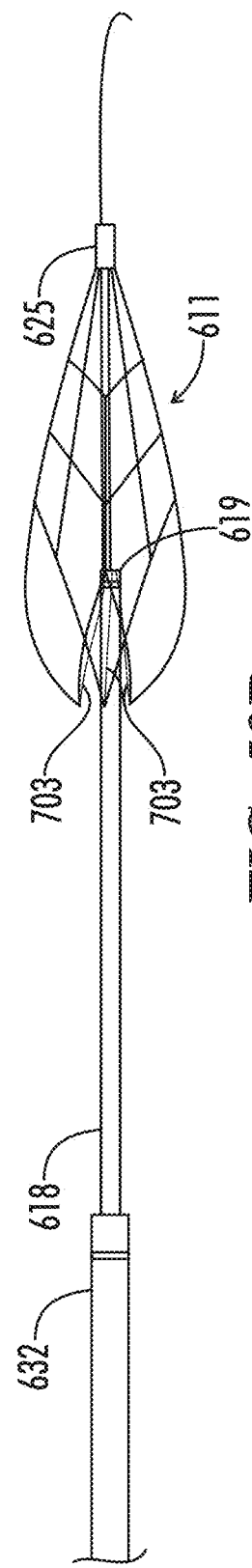
FIG. 59A
FIG. 59B

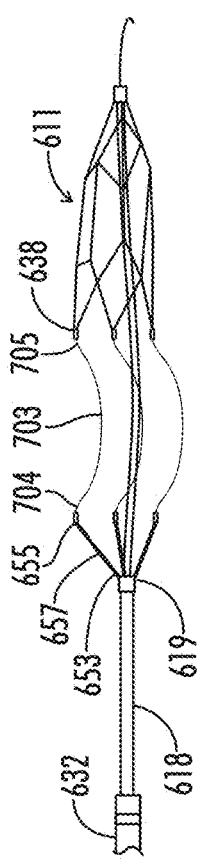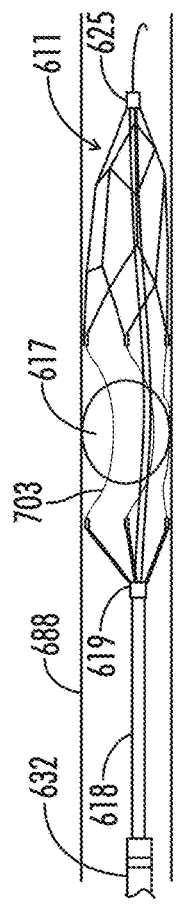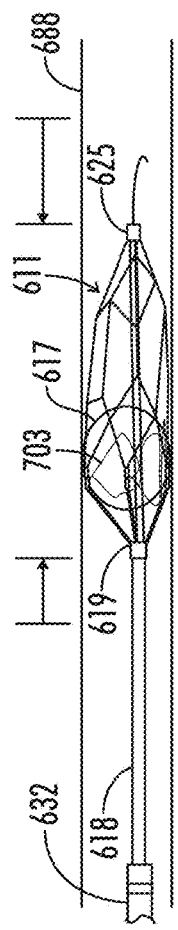

CLOT RETRIEVAL SYSTEM

RELATED APPLICATIONS

This application is a continuation-in-part of U.S. patent application Ser. No. 14/558,712, filed Dec. 2, 2014 and entitled "CLOT RETRIEVAL SYSTEM, which is a continuation of U.S. patent application Ser. No. 14/558,705, filed Dec. 2, 2014 and entitled "CLOT RETRIEVAL SYSTEM", which is a continuation-in-part of U.S. patent application Ser. No. 14/147,491 (now U.S. Pat. No. 8,900,265), entitled "CLOT RETRIEVAL SYSTEM" and filed Jan. 3, 2014. U.S. patent application Ser. No. 14/558,705 further claims priority under 35 U.S.C. § 119 to U.S. Provisional Patent Application Ser. No. 61/994,934, filed May 18, 2014 and entitled "ARTICULATING CLOT RETRIEVAL SYSTEM". The entire contents of all of the above patent applications are hereby incorporated by reference.

This application is also a continuation-in-part of International Patent Application No. PCT/US15/10178, entitled "CLOT RETRIEVAL SYSTEM" and filed Jan. 5, 2015, which is a continuation-in-part of U.S. patent application Ser. No. 14/558,712, filed Dec. 2, 2014 and entitled "CLOT RETRIEVAL SYSTEM", which is a continuation of U.S. patent application Ser. No. 14/558,705, filed Dec. 2, 2014 and entitled "CLOT RETRIEVAL SYSTEM." U.S. patent application Ser. No. 14/558,705 is a continuation-in-part of U.S. patent application Ser. No. 14/147,491 (now U.S. Pat. No. 8,900,265), entitled "CLOT RETRIEVAL SYSTEM" and filed Jan. 3, 2014, and further claims priority under 35 U.S.C. § 119 to U.S. Provisional Patent Application Ser. No. 61/994,934, filed May 18, 2014 and entitled "ARTICULATING CLOT RETRIEVAL SYSTEM". International Patent Application No. PCT/US15/10178 further claims priority under 35 U.S.C. § 119 to U.S. Patent Application No. 61/994,919, filed May 18, 2014 and entitled "CLOT RETRIEVAL SYSTEM." The entire contents of all of the above patent applications are hereby incorporated by reference.

This application is also a continuation-in-part of International Patent Application No. PCT/US15/31447, entitled "CLOT RETRIEVAL SYSTEM" and filed May 18, 2015. The entire contents of all of the above patent applications are hereby incorporated by reference.

BACKGROUND

Technical Field

The present invention relates to a deployable system for removing a blood clot or other object from a lumen of an animal.

Background of the Invention

Acute ischemic strokes develop when a blood clot (thrombus) blocks an artery supplying blood to the brain. Needless to say, when a blood clot creates such a blockage, time in removing the clot is critical.

The removal of intracranial obstructions is limited by several factors, such as the distance of the intracranial obstruction from the femoral access site, the tortuosity (twists and turns in the artery as it enters the base of the skull) of the cervical and proximal intracranial vasculature, the small size of the vessels and the extremely thin walls of intracranial vessels, which lack a significant muscular layer. These limitations require a device to be small and flexible enough to navigate through tortuous vessels within a guide catheter and microcatheter, expand after delivery at the site of occlusion and be retrievable into the microcatheter and yet be strong enough to dislodge strongly adherent thrombus from the vessel wall. In addition, the device should distally entrap or encase the thrombus to prevent embolization to other vessels and to completely remove the occlusion. The device should be retrievable without the need for proximal occlusion of the vessel, which carries risk of further ischemia and risk of vessel injury. The device should be simple to use and be capable of multi-use within the same patient treatment. The device should not be abrasive and should not have sharp corners exposed to the endothelial layer of the vessel wall.

Currently available intravascular thrombus and foreign body removal devices lack several of these features. Currently available devices include the MERCI™ RETRIEVER clot retriever device marketed by Concentric Medical, Inc. (Mountainview, Calif.), the PENUMBRA™ system marketed by Penumbra Inc. (Alameda, Calif.) to retrieve clots, and the newer stent retrieval devices TREVO™ (Stryker, Kalamazoo, Mich.) and SOLITAIRE™ (eV3 Endovascular Inc., Plymouth, Mass., which is a subsidiary of Covidien). All the devices are ineffectual at removing organized hard thrombus that embolize to the brain from the heart and from atherosclerotic proximal vessels. These "hard" thrombi constitute the majority of strokes which are refractory to medical treatment and are therefore referred for removal by mechanical means through an endovascular approach. The MERCI retrieval system is comprised of coiled spring-like metal and associated suture material. The method of use is deployment distal to the thrombus and by withdrawing the device through the thrombus, the thrombus becomes entangled in the coil and mesh and then is retrieved. The MERCI system requires occlusion of the proximal vessel with a balloon catheter and simultaneous aspiration of blood while the thrombus is being removed. Most of the time, the device fails to dislodge the thrombus from the wall of the vessel and often, even when successfully dislodging the thrombus, the thrombus embolizes into another or the same vessel due to the open ended nature of the device.

The next attempt at a thrombus removal system was the PENUMBRA. The PENUMBRA is a suction catheter with a separator that macerates the thrombus which is then removed by suction. The device is ineffective at removing hard, organized thrombus which has embolized from the heart, cholesterol plaque from proximal feeding arteries and other foreign bodies.

The SOLITAIRE and TREVO systems are self-expanding non-detachable stents. The devices are delivered across the thrombus which is then supposed to become entwined in the mesh of the stent and which is then removed in a manner similar to the MERCI system. Again, these devices are ineffectual at treating hard thrombus. In fact, the thrombus is often compressed against the vessel wall by the stent which temporarily opens the vessel by outwardly pressing the clot against the vessel wall. Upon retrieval of the devices, the clot remains or is broken up into several pieces which embolize to vessels further along the vessel.

Thus, there is a need for new, easy-to-use, easy-to-manufacture, safe surgical devices for removing obstructions, such as blood clots, from internal lumens of humans and other animals in a timely manner.

BRIEF SUMMARY

The present disclosure provides several systems for removing obstructions and other objects within a blood vessel or other lumen of an animal. The system may be deployed in the lumen from a distal end of a catheter and, in some embodiments, includes a pull wire having a proximal end and a distal end; a distal body attached to the pull wire, the distal body comprising an interior, an exterior, a proximal end, a distal end, a plurality of proximal memory metal strips located at the proximal end, a proximal hub/junction located in the distal body interior, and a distal hub/junction located distal relative to the proximal hub/junction. The distal body has a relaxed state wherein the distal body has a first height and width and a collapsed state wherein the distal body has a second height and width, the second height less than said first height, the second width less than the first width. The system further includes a catheter having an interior, a proximal end leading to the interior and a distal end leading to the interior, the catheter comprised of a biocompatible material and configured to envelope the distal body when the distal body is in the collapsed state. Each of the proximal memory metal strips has a proximal end and a distal end and preferably, in the relaxed state, each of the proximal ends of the proximal memory metal strips is located proximal relative to the proximal hub/junction. Preferably, in the relaxed state, the proximal ends of the proximal memory metal strips are configured to move towards each other and towards the pull wire when an operator moves the proximal hub/junction distally and closer to the stationary distal hub/junction (i.e., when the operator decreases the distance between the hubs/junctions). Preferably, in the relaxed state, the proximal ends of the proximal memory metal strips are configured to move away from each other and away from the pull wire by moving the proximal hub/junction proximally away from the stationary distal hub/junction (i.e., when the operator increases the distance between the hubs/junctions).

Optionally, the system further includes a plurality of memory metal connector strips, the plurality of memory metal connector strips each having a proximal end attached to a proximal memory metal strip and a distal end attached to the proximal hub/junction. Optionally, the connector strips are integral with the proximal hub/junction (i.e., optionally, the connector strips and the proximal hub/junction are formed from the same piece of memory metal). Optionally, the proximal hub/junction is a tube having an aperture and the pull wire passes through the aperture. Optionally, in the relaxed state, the proximal hub/junction is slideable along the pull wire (i.e., at least a segment of the pull wire). Optionally, in the relaxed state, the proximal memory metal strips are distributed substantially evenly about a perimeter of the distal body. Optionally, the distal hub/junction is a tube having an aperture. Optionally, the distal hub/junction is attached to the pull wire such that the distal hub/junction is not slideable along the pull wire. Optionally, the distal body further comprises a lead wire extending distally from the distal hub/junction. Optionally, the distal body comprises a basket comprised of a plurality of memory metal strips distal relative to the proximal memory metal strips. Optionally, the distal hub/junction, the proximal hub/junction, and the distal basket are comprised of a nitinol having the same material composition. Optionally, the distal body further comprises an x-ray marker. Optionally, the proximal memory metal strips form a claw, the claw having a closeable proximal end formed by the proximal ends of the proximal memory metal strips. Optionally, between 2 and 4 proximal memory metal strips form the claw. Optionally, the distal body, in the relaxed state, has a tapered shape in which the distal body height and width decrease from the proximal end to the distal end. Optionally, the distal body, in the relaxed state, has a bullet shape.

Optionally, the proximal hub/junction and the distal hub/junction are generally cylindrical in shape and each has an outer diameter and an inner diameter that forms the apertures of the proximal and distal hub/junctions, the outer diameters of the proximal and distal hub/junctions are substantially the same size, and the inner diameters of the proximal and distal hubs/junctions are substantially the same size. Optionally, the outer diameters of the proximal and distal hubs/junctions are from about 0.011 inches to about 0.054 inches, and the inner diameters of the proximal and distal hubs are from about 0.008 inches to about 0.051 inches. Optionally, the pull wire is generally cylindrical and the diameter of the pull wire is between about 0.008 inches and about 0.051 inches. Optionally, the proximal memory metal strips have a length of between about 10 and about 60 millimeters. Optionally, the first height and first width of the distal body are between about 2 millimeters (mm) and about 6 millimeters. Optionally, the proximal memory metal strips are configured to a separate a clot from a blood vessel wall.

The present invention also provides a method of removing an object from an interior lumen of an animal, the lumen having an interior wall forming the lumen. In some embodiments, the method includes:

a) providing a system comprising: i) a pull wire having a proximal end and a distal end; ii) a distal body attached to the pull wire, the distal body comprising a proximal end, a distal end, and a claw, the claw comprised of a plurality of memory metal strips, the distal body having a relaxed state wherein the distal body has a first height and width and a collapsed state wherein the distal body has a second height and width, the second height less than said first height, the second width less than said first width; and iii) a catheter having an interior, a proximal end leading to the interior and a distal end leading to the interior, the catheter comprised of a biocompatible material and configured to envelope the distal body when said distal body is in said collapsed state;

b) positioning the system in the lumen;

c) deploying the distal body from the distal end of the catheter;

d) allowing the height and width of said distal body to increase; and e) moving the memory metal strips towards each other and the pull wire so as to capture the obstruction. Optionally, the claw and the memory metal strips are located at the proximal end of said distal body and the distal body is deployed distal to said object. Optionally, the proximal memory metal strips have a proximal end forming the proximal end of the claw and a distal end, and the method includes moving the proximal ends of the memory metal strips towards each other and the pull wire so as to capture the obstruction. Optionally, the distal body further comprises a proximal hub/junction located in the distal body interior, and a distal hub/junction located distal relative to the proximal hub/junction, each of the memory metal strips has a proximal end and a distal end, each of the proximal ends of the memory metal strips is located proximal relative to the proximal hub/junction, and the proximal ends of the memory metal strips are configured to move towards each other and towards the pull wire by moving the proximal hub/junction distally and closer to the distal hub/junction, and the proximal ends of the memory metal strips are configured to move away from each other and away from the pull wire by moving the proximal hub/junction proximally and away from the distal hub/junction, and the method further comprises moving the proximal hub/junction distally and closer to the distal hub/junction so as to capture the obstruction in the claw. Optionally, the interior lumen is an intracranial artery and the obstruction is a blood clot.

Optionally, the method further comprises using the clot to move the proximal hub/junction toward the distal hub/junction and exert tension on the proximal memory metal strips. Optionally, the method further comprises using a tube to move the proximal hub/junction toward the distal hub/junction and exert tension on the proximal memory metal strips.

The present invention also provides a method of manufacturing a system for removing objects within an interior lumen of an animal. In some embodiments, the method includes:

a) providing a single tube comprised of a memory metal, the single tube having an exterior, a hollow interior, a wall separating the exterior from the hollow interior, a proximal portion comprising an aperture leading to the hollow interior, a distal portion comprising an aperture leading to the hollow interior, and a middle portion between the proximal portion and the distal portion;

b) cutting the wall of the middle portion with a laser;

c) removing the pieces of the middle portion cut by the laser to form a proximal tube, a middle portion comprising a plurality of memory metal strips attached to the proximal tube and a distal tube;

d) altering the shape of the middle portion;

e) allowing the middle portion to expand relative to the distal tube and the proximal tube;

f) cutting the memory metal strips to form a first segment comprising the proximal tube and a proximal segment of the memory metal strips, and a second segment comprising the distal tube and a distal segment of the memory metal strips; and g) joining the proximal segments to the distal segments such that the distal segments form the proximal end of a distal body, such that the proximal tube is located inside an interior of said distal body, and such that the proximal tube is located distal relative to the proximal end.

Optionally, the method further includes placing a pull wire through the proximal tube such that the proximal tube is slideable along at least a segment of the pull wire. Optionally, the method further includes attaching the pull wire to the distal tube. Optionally, the step of joining the proximal segments to the distal segments comprises welding or soldering the proximal segments to the distal segments. Optionally, after the step of joining the proximal segments to the distal segments, the proximal end forms a claw comprised of between 2 and 4 memory metal strips, the claw memory metal strips configured to move towards each by moving said proximal tube distally and closer to the distal tube, and the claw memory metal strips configured to move away from each other by moving the proximal tube proximally and away from said distal tube. Optionally, the method further includes not altering the shape of the proximal and distal portions while altering the shape of the middle portion. Optionally, the method further includes cooling the proximal portion, the middle portion, and the distal portion after step D) and, after cooling, the proximal and distal portions have substantially the same size as the proximal and distal portions had prior to step A). Optionally, the method of allowing said middle portion to expand comprises heating the middle portion. Optionally, the method of altering the shape of the middle portion comprises using a mandrel. Optionally, the mandrel is tapered. Optionally, the proximal portion and the distal portion are not cut by the laser. Optionally, prior to cutting the memory metal tube, the memory metal tube has an outer diameter that is from about 0.011 inches to about 0.054 inches and an inner diameter that is from about 0.008 inches to about 0.051 inches.

In an alternate embodiment, the present disclosure provides a system for removing objects from an interior lumen of an animal that includes:

a pull wire having a proximal end and a distal end;

a distal body attached to the pull wire, the distal body comprising an interior, a proximal end, a distal end, a distal body length extending from the proximal end to the distal end, a proximal hub/junction (preferably in the form of a tube) forming the proximal end of the distal body, a basket comprised of a plurality of cells formed by a plurality of basket strips, a plurality of proximal strips, and, optionally a distal hub/junction (preferably in the form of a tube) forming a distal end of the basket, the basket comprising a basket interior, each proximal strip having a proximal end attached to the proximal hub/junction, and a distal end attached to a cell, the distal body having a relaxed state wherein the distal body has a first height and a first width, and a collapsed state wherein the distal body has a second height and a second width, the second height less than the first height, the second width less than the first width; and a catheter having an interior, a proximal end leading to the interior and a distal end leading to the interior, the catheter comprised of a biocompatible material and configured to envelope the distal body when the distal body is in the collapsed state, wherein, in the relaxed state, the basket comprises a first pair of distal crowns not attached to another cell of the basket and pointing generally in the distal direction, the first pair of distal crowns located approximately the same distance from the proximal hub/junction and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub/junction and further wherein each of the distal crowns in the first and second pair of distal crowns comprises an x-ray marker, the x-ray maker more visible under x-ray as compared to the basket strips when the distal body is located in a cranial blood vessel inside the body of a human and the x-ray is taken from outside the human's body. When it is said that the first pair of distal crowns are located approximately the same distance from the proximal hub/junction, it will be understood that if one of the first pair of distal crowns is located X distance from the proximal hub/junction, the other of the first pair of distal crowns is located X distance plus or minus (+/−) 3 mm from the proximal hub/junction, more preferably X distance plus or minus (+/−) 0.5 mm from the proximal hub/junction. Similarly, when it is said that the second pair of distal crowns are located approximately the same distance from the proximal hub/junction, it will be understood that if one of the second pair of distal crowns is located Y distance from the proximal hub/junction, the other of the first pair of distal crowns is located Y distance plus or minus (+/−) 3 mm from the proximal hub/junction, more preferably Y distance plus or minus (+/−) 0.5 mm from the proximal hub/junction. Optionally, instead of a distal hub/junction, the basket includes an open distal end.

Optionally, the x-ray markers are comprised of a material different than the material forming the basket strips. Optionally, in the relaxed state, the basket interior is substantially hollow. Optionally, in the relaxed state, the distal body does not have another x-ray marker that is located approximately the same distance from the proximal hub/junction as the first pair of x-ray markers and the distal body does not have another x-ray marker that is located approximately the same distance from the proximal hub/junction as the second pair of x-ray markers. In other words, the first and second pair of x-ray markers are the only markers their respective distances from the proximal hub/junction. Optionally, each distal crown in the first and second pair of distal crowns forms part of an enlarged cell and further wherein the surface area of each enlarged cell in the relaxed state is greater than the surface area of each of the other individual cells of the basket and further wherein the enlarged cells are configured to allow a thrombus to pass therethrough and into the basket interior. Optionally, in the relaxed state, the distal body does not have another free distal-pointing crown that is located approximately the same distance from the proximal hub/junction as the first pair of distal crowns and the distal body does not have another free distal-pointing crown that is located approximately the same distance from the proximal hub/junction as the second pair of distal crowns. Optionally, the basket strips are comprised of a memory metal. Optionally, each of the distal crowns in the first pair and second pair of distal crowns curve radially inward toward the basket interior in the relaxed state, wherein the distal crowns of the first pair of distal crowns are configured to contact each other when an exterior, external compressive force (such as a thrombus) is exerted on a distal crown of the first pair of distal crowns when the distal body is in the relaxed state, and further wherein the distal crowns of the second pair of distal crowns are configured to contact each other when an exterior, external compressive force (such as a thrombus) is exerted on a distal crown of the second pair of distal crowns when the distal body is in the relaxed state. Optionally, the proximal hub/junction is located approximately in the center of the first height and first width in the relaxed state. For example, preferably the proximal hub/junction is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub/junction (e.g., within about 0 and about 4 mm of the proximal hub/junction). Optionally, each distal crown forms part of a cell that further comprises a proximal crown pointing generally in the proximal direction and connected to a memory metal strip (e.g., a proximal strip comprised of a memory metal or a basket strip comprised of a memory metal). In other words, the proximal crowns are not free. Optionally, the basket, the proximal hub/junction and the proximal strips are comprised of a memory metal, wherein the proximal hub/junction comprises a proximal end and a distal end, and further wherein the proximal strips are integral with the distal end of the proximal hub/junction.

Optionally, the length of the distal body from the proximal hub/junction to the distal hub/junction (not including any lead wire) is from about 20 mm to about 65 mm. Optionally, the system is used in a method of removing a blood clot from a blood vessel of an animal the method comprising the steps of:

a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles. Optionally, at least one x-ray marker attached to the distal crowns is distal to the clot when the distal body is deployed from the distal end of the catheter. Optionally, the method further comprises applying contrast dye proximally and distally to the clot. Optionally, the method further comprises providing a suction catheter having a proximal end and a distal end, and attaching the distal end of the suction catheter to the clot by applying suction to the suction catheter. Optionally, the method further comprises aspirating by hand a pre-determined volume of fluid from the suction catheter using a syringe and then locking the syringe at the pre-determined volume. Optionally, the method further comprises delivering the suction catheter adjacent to the clot by advancing the catheter over the pull wire.

In yet another embodiment, the system includes:
a pull wire having a proximal end and a distal end;
a distal body attached to the pull wire, the distal body comprising an interior, a proximal end, a distal end, a distal body length extending from the proximal end to the distal end, a proximal hub/junction (preferably in the form of a tube) forming the proximal end of the distal body, a basket comprised of a plurality of cells formed by a plurality of basket strips, a plurality of proximal strips, and optionally a distal hub/junction (preferably in the form of a tube) forming a distal end of the basket, the basket comprising a basket interior, each proximal strip having a proximal end attached to the proximal hub/junction, and a distal end attached to a cell, the distal body having a relaxed state wherein the distal body has a first height and a first width, and a collapsed state wherein the distal body has a second height and a second width, the second height less than the first height, the second width less than the first width; and
a catheter having an interior, a proximal end leading to the interior and a distal end leading to the interior, the catheter comprised of a biocompatible material and configured to envelope the distal body when the distal body is in the collapsed state,
wherein, in the relaxed state, the basket comprises a first pair of distal crowns not attached to another cell of the basket and pointing generally in the distal direction, the first pair of distal crowns located approximately the same distance from the proximal hub/junction and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub/junction, wherein each distal crown of the first and second pair of distal crowns form a cell, each cell further comprising a proximal crown pointing generally in the proximal direction and connected to a memory metal strip, wherein each of the distal crowns in the first pair and second pair of distal crowns curve radially inward toward the basket interior in the relaxed state, wherein the distal crowns of the first pair of distal crowns are configured to contact each other when an exterior, external compressive force (e.g., a thrombus) is exerted on a distal crown of the first pair of distal crowns when the distal body is in the relaxed state, and further wherein the distal crowns of the second pair of distal crowns are configured to contact each other when an exterior, external compressive force (e.g., a thrombus) is exerted on a distal crown of the second pair of distal crowns when the distal body is in the relaxed state. When it is said that a proximal crown pointing generally in the proximal direction and is connected to a memory metal strip, it is meant that the proximal crown is either connected to a basket strip or a proximal strip comprised of a memory metal (e.g., nitinol). When it is said that the first pair of distal crowns are located approximately the same distance from the proximal hub/junction, it will be understood that if one of the first pair of distal crowns is located X distance from the proximal hub/junction, the other of the first pair of distal crowns is located X distance plus or minus (+/−) 0.5 mm from the proximal hub/junction. Similarly, when it is said that the second pair of distal crowns are located approximately the same distance from the proximal hub/junction, it will be understood that if one of the second pair of distal crowns is located Y distance from the proximal hub/junction, the other of the first pair of distal crowns is located Y distance plus or minus (+/−) 0.5 mm from the proximal hub/junction. Optionally, instead of a distal hub/junction, the basket includes an open distal end.

Optionally, the proximal hub/junction is located approximately in the center of the first height and first width in the relaxed state. For example, preferably the proximal hub/junction is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, in the relaxed state, the basket interior is substantially hollow. Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub/junction (e.g., within about 0 mm and about 4 mm of the proximal hub/junction). Optionally, each distal crown in the first and second pair of distal crowns forms part of an enlarged cell and further wherein the surface area of each enlarged cell in the relaxed state is at least twice as large as the surface area of each other individual cell of the basket and further wherein the enlarged cells are configured to allow a thrombus to pass therethrough and into the basket interior. Optionally, the pull wire is attached to the proximal hub/junction.

Optionally, the basket, the proximal hub/junction and the proximal strips are comprised of a memory metal, wherein the proximal hub/junction comprises a proximal end and a distal end, and further wherein the proximal strips are integral with the distal end of the proximal hub/junction. Optionally, the distal body further comprises a lead wire extending distally from the distal hub/junction, the lead wire having a length of from about 3 mm to about 10 mm. Optionally, the distal hub/junction, the proximal hub/junction, and the basket are comprised of a nitinol having the same material composition and further wherein the proximal and the distal hubs/junctions are tubular and generally cylindrical in shape and each has an outer diameter and an inner diameter, the inner diameter forming apertures of the proximal and distal hubs/junctions and further wherein the outer diameters of the proximal and distal hubs/junctions are substantially the same size and further wherein the inner diameters of the proximal and distal hubs/junctions are substantially the same size. Optionally, the length of the distal body from the proximal hub/junction to the distal hub/junction (not including any lead wire) is from about 20 mm to about 65 mm.

Optionally, the system is used in a method of removing a blood clot from a blood vessel of an animal the method comprising the steps of:
a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles.

In other embodiments the present disclosure provides a system for removing objects within an interior lumen of an animal, the system comprising:

a pull wire having a proximal end, a distal end and a pull wire longitudinal axis extending from the proximal end to the distal end;

a coaxial sheath having a hollow interior, an open proximal end leading to the interior, and an open distal end leading to the interior, the coaxial sheath enveloping the pull wire, the coaxial sheath slideable along at least a segment of the pull wire;

a distal basket comprising an interior, a proximal end, a distal end, a distal basket length extending from the distal basket proximal end to the distal basket distal end, a distal basket height perpendicular to the distal basket length, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, and a plurality of distal cells distal to the proximal cells;

a plurality of proximal strips, each proximal strip having a proximal end extending from the coaxial sheath, a distal end attached to a proximal crown of a proximal cell and a length extending from the proximal end to the distal end; and a catheter having a hollow interior, a proximal end leading to the interior and a distal end leading to the interior, the catheter comprised of a biocompatible material, the distal basket comprised of a memory metal and having:

a relaxed state in which the distal end of the coaxial sheath is located at a first position along the pull wire, the first position located a first distance proximal to the proximal crowns, and in which the distal basket, as measured at the proximal-most crown, has a first height, a proximal collapsed state in which the distal end of the coaxial sheath is located at a second position along the pull wire, the second position located a second distance proximal to the proximal crowns, and in which the distal basket, as measured at the proximal-most crown, has a second height, the second distance greater than the first distance, the second height less than the first height, and a distal collapsed state in which the distal end of the coaxial sheath is located at a third position along the pull wire, the third position distal to the proximal crowns and located in the basket interior, and in which the distal basket, as measured at the proximal-most crown, has a third height, the third height less than the first height, wherein the catheter is configured to envelope the distal basket when the distal basket is in the proximal collapsed state;

wherein the distal basket is configured to move from the relaxed state to the proximal collapsed state by moving the distal end of the coaxial sheath proximally to the second position while keeping the distal basket at a fixed location along the pull wire; and wherein the distal basket is configured to move from the relaxed state to the distal collapsed state by moving the distal end of the coaxial sheath distally to the third position while keeping the distal basket at a fixed location along the pull wire.

Optionally, each proximal crown comprises a proximal tip and further wherein each proximal strip is configured to cover a proximal tip when the distal basket is in the distal collapsed state. Optionally, each proximal crown comprises an eyelet and further wherein each proximal strip passes through an eyelet. Optionally, the distal end of each proximal strip comprises a loop attaching the proximal strip to an eyelet. Optionally, each proximal crown has an interior surface facing the distal basket interior and an exterior surface opposite the interior surface and further wherein each proximal strip contacts an exterior surface of a proximal crown in the proximal collapsed state and in the distal collapsed state. Optionally, the pull wire extends through the distal basket interior and further wherein the proximal crowns are configured to move towards each other and towards the pull wire when the distal basket moves from the relaxed state to the distal collapsed state and when the distal basket moves from the relaxed state to the proximal collapsed state. Optionally, the proximal crowns are configured to remain a fixed distance from the distal end of the distal basket when the distal basket moves from the relaxed state to the distal collapsed state. Optionally, the coaxial sheath is a braided catheter comprised of a plurality of braids, and further wherein the proximal segments of the braids are wound together to form the braided catheter and further wherein an unwound distal segment of each braid forms a proximal strip. Optionally, at least one proximal crown further comprises an x-ray marker. Optionally, the proximal ends of the proximal strips are integral with the coaxial sheath. Optionally, the proximal ends of the proximal strips are attached to the coaxial sheath. Optionally, the system comprises between two and four proximal strips and the proximal strips are spaced substantially evenly apart. Optionally, the proximal strips have a length of from about 5 millimeters to about 40 millimeters in the relaxed state.

Optionally, the pull wire extends through the basket interior from the distal basket proximal end to the distal basket distal end. Optionally, the coaxial sheath interior has a size and shape, and further wherein the size and shape of the coaxial sheath interior are configured to prevent a segment of the pull wire located in the basket interior and distal relative to the distal end of the coaxial sheath from moving through the coaxial sheath interior. Optionally, the distal end of the distal basket comprises a distal tube having an open proximal end and an open distal end, the distal tube comprised of a memory metal. Optionally, the distal basket and the distal were prepared from the same memory metal tube. Optionally, the second and third position along the pull wire each comprise an x-ray marker. Optionally, the distal tube is attached to the pull wire such that the distal tube is not slideable along the pull wire. Optionally, all proximal crowns of the proximal cells are attached to a proximal strip. Optionally, the distal basket further comprises a lead wire extending distally from the distal basket. Optionally, the proximal strips and the distal basket have a different material composition. Optionally, the proximal strips are comprised of a polymer. Optionally, the polymer is selected from the group consisting of fluorinated ethylene propylene, polytetrafluoroethylene, and tetrafluoroethylene. Optionally, the proximal strips are comprised of a material selected from the group consisting of plastic, rubber, nylon, suture material, and braided catheter material.

Optionally, the system is used in a method of removing a clot from a blood vessel of an animal, the blood vessel having an interior wall forming the blood vessel, the method comprising the steps of:

a) providing the system, wherein the coaxial sheath is located in the catheter interior and the distal basket is located in the catheter interior in a collapsed state;

b) positioning the catheter in the blood vessel;

c) deploying the distal basket from the distal end of the catheter so that the proximal crowns of the proximal cells are distal to the clot;

d) allowing the distal basket to move to the relaxed state:

e) holding the coaxial sheath in the user's hand and moving the coaxial sheath distally to a fourth position (i.e., the surgeon interventionalist moves the coaxial sheath with his/her hands), the fourth position located distally beyond the proximal crowns and in the basket interior but proximal to the third position (this third position is not sufficiently distal to the proximal crowns to place tension on the proximal strips; thus, the crowns do not begin to move towards each other and the pull wire);

f) capturing the clot in the distal basket interior;

g) holding the coaxial sheath in a user's hand and moving the coaxial sheath further distally into the basket interior (i.e., to or near) the third position (i.e., the surgeon interventionalist moves the coaxial sheath with his/her hands) so that the distal basket height, as measured at the proximal-most crown, decreases and the proximal crowns move toward each other and the pull wire; and h) moving the system proximally out of the blood vessel.

In still further embodiments, the present disclosure provides a system for removing objects within an interior lumen of an animal, the system comprising:

a pull wire having a proximal end, a distal end and a pull wire longitudinal axis extending from the proximal end to the distal end;

a coaxial sheath having an open proximal end and an open distal end, the coaxial sheath enveloping the pull wire, the coaxial sheath slideable along at least a segment of the pull wire;

a distal basket comprising an interior, a proximal end, a distal end, a distal basket length extending from the distal basket proximal end to the distal end, a distal basket height perpendicular to the distal basket length, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, and a plurality of distal cells distal to the proximal cells;

a plurality of proximal strips, each proximal strip having a proximal end extending from the coaxial sheath, a distal end attached to a crown of a proximal cell and a length extending from the proximal end to the distal end; and a catheter having a hollow interior, a proximal end leading to the interior and a distal end leading to the interior, the catheter comprised of a biocompatible material, the distal basket comprised of a memory metal, wherein each proximal crown of each proximal cell comprises an eyelet and further wherein each proximal strip passes through an eyelet.

The present disclosure also provides additional modular, easy-to-manufacture platform of systems for retrieving hard clots and other objects in animal lumens. In some embodiments, the system includes a proximal tube, a distal tube, and a plurality of memory metal strips between the proximal and distal tubes. The plurality of memory metal strips form a wide range of basket designs. Preferably, the proximal tube, memory metal strips, and distal tube are derived from a standard, off-the-shelf single tube of memory metal (e.g., a memory metal alloy such as nitinol), with the proximal tube and distal tube having the same inner diameter and outer diameter as the native tube from which they were derived and with the basket formed by cutting the middle portion of the native tube and expanding and shape-setting this cut portion. Preferably, the proximal tube and distal tube have an outer diameter that is from about 0.02 inches to about 0.03 inches (e.g., about 0.027 inches) so that the device fits inside a standard microcatheter and an inner diameter that is from about 0.01 inches to about 0.02 inches. Preferably, there are no welded or soldered parts between the proximal tube and distal tube, which makes the system easy and cheap to reliably manufacture. The system also includes one or more catheters for deploying the system, a pull wire that passes through the hollow interior of the proximal tube, and a coaxial tube. Preferably, the system includes two catheters—a guide catheter and a microcatheter. The coaxial tube envelopes the pull wire, is slideable along at least a segment of the pull wire, and is attached to the proximal hub/junction. The coaxial tube allows a user to move the proximal hub/junction toward and away from the distal hub/junction while keeping the distal hub/junction stationary. Movement of the proximal hub/junction toward and away from the distal hub/junction causes conformational changes in the basket, including (depending on the basket design and the location of the proximal tube), collapsing the basket, expanding the basket, strengthening the basket, and moving the basket around the clot. The plurality of memory metal strips attached to the proximal hub/junction include a plurality of proximal tether memory metal strips, which have a proximal end attached to the distal end of the proximal tube. The length and thickness of the proximal tether memory metal strips vary in the different embodiments described herein, which allows the surgical user to select from the various embodiments in the platform based on the features needed for the particular operation (e.g., vessel anatomy and hardness of the clot).

In some embodiments, the present disclosure provides a method of manufacturing a system for removing objects within an interior lumen of an animal that includes:

a) providing a single tube comprised of a memory metal, the single tube having an exterior, a hollow interior, a wall separating the exterior from the hollow interior, a proximal portion comprising an aperture leading to the hollow interior, a distal portion comprising an aperture leading to the hollow interior, and a middle portion between the proximal portion and the distal portion;

b) cutting the wall of the middle portion with a laser;

c) removing the pieces of the middle portion cut by the laser to form a basket system comprising a proximal tube comprising a hollow interior extending through said proximal tube, said proximal tube having a proximal end and a distal end, a distal tube comprising a hollow interior extending through said distal tube, and a middle portion located between said proximal tube and said distal tube and comprising a plurality of proximal tether memory metal strips, each proximal tether memory metal strip having a proximal end attached to the distal end of the proximal tube and a distal end;

d) altering the shape of the middle portion;

e) allowing the middle portion to expand relative to the distal tube and the proximal tube to form a basket that includes a plurality of cells;

f) optionally, inserting a pull wire through said proximal tube interior so that said proximal tube is slideable along at least a portion of said pull wire, said pull wire having a proximal end and a distal end; and g) optionally, attaching said pull wire to said distal hub/junction.

In other embodiments, instead of steps f) and g) noted above, the method includes inserting a pull wire comprising a proximal end, a distal end, a stop located adjacent to said distal end, through said proximal tube interior, said stop having a width and/or height that is greater than said proximal tube interior, said stop located distal relative to said proximal tube interior, so that said proximal tube is slideable distally until the proximal hub/junction reaches said stop, said pull wire not contacting said distal tube. In such embodiments, the pull wire does not contact the distal hub/junction. Rather in these embodiments, the method further includes attaching a leader wire to said distal tube In some embodiments, either of the above methods further include h) providing a coaxial tube, said coaxial tube comprising a hollow interior receiving said pull wire, a proximal end, and a distal end, and i) attaching said distal end of said coaxial tube to said proximal tube. In some embodiments, the method of attaching said distal end of said coaxial tube to said proximal tube comprises welding or soldering said distal end of said coaxial tube to said proximal tube. In other embodiments, the method of attaching said distal end of said coaxial tube to said proximal tube comprises shrink wrapping said distal end of said coaxial tube to said proximal tube. In other embodiments, the method of attaching said distal end of said coaxial tube to said proximal tube comprises gluing said distal end of said coaxial tube to said proximal tube.

Optionally, after step e, the basket further comprises a row of proximal cells, each proximal cell defined by a plurality of memory metal strips and comprising a proximal crown located at a proximal end of the cell and pointing in the proximal direction and a distal crown located at a distal end of the cell and pointing in the distal direction and further wherein each of said proximal crowns of said proximal cells is attached to a distal end of a proximal tether memory metal strip. Optionally, after step e, the basket further comprises a row of distal cells located distal to said proximal cells and connected to said distal crowns of said proximal cells, each distal cell defined by a plurality of memory metal strips and comprising a proximal crown located at a proximal end of the cell and pointing in the proximal direction and a distal crown located at a distal end of the cell and pointing in the distal direction, and further wherein the number of distal cells is twice the number of proximal cells. Optionally, after step e, the basket further comprises a row of distal crowns distal to said proximal crowns and pointing in the distal direction and further wherein the number of distal crowns in said row is twice the number of proximal crowns attached to said proximal tether memory metal strip.

Optionally, after step e, the basket system further comprises a row of strut memory metal strips, each strut memory metal strip having a proximal end attached to a distal crown of a proximal cell and a distal end attached to a proximal crown of a distal cell. Optionally, the basket comprises no welded or soldered components and said proximal tether memory metal strips are integral with said proximal cell crowns.

Optionally, after step e, the basket system comprises between two and four proximal tether memory metal strips. Optionally, the method further comprises not altering the shape of the proximal and distal portions while altering the shape of the middle portion. Optionally, the method further comprises cooling the proximal portion, the middle portion, and the distal portion after step D) and, after cooling, the proximal and distal portions have substantially the same size as the proximal and distal portions had prior to step A). Optionally, the method of allowing said middle portion to expand comprises heating the middle portion. Optionally, the method of altering the shape of the middle portion comprises using a mandrel. Optionally, the mandrel is tapered. Optionally, the proximal portion and the distal portion are not cut by the laser. Optionally, prior to cutting the memory metal tube, the memory metal tube has an outer diameter that is from about 0.011 inches to about 0.054 inches and an inner diameter that is from about 0.008 inches to about 0.051 inches. Optionally, after step e), the proximal tube and distal tube have an outer diameter that is from about 0.02 inches to about 0.03 inches and an inner diameter that is from about 0.01 inches to about 0.02 inches. Optionally, the method further includes placing said basket inside a catheter comprised of a biocompatible material. Optionally, the method further includes the steps of placing the basket inside a lumen of an animal and using the basket to retrieve an object located inside said lumen.

The present disclosure also provides several systems for removing objects within an interior lumen of an animal. In some embodiments, the system includes:

a pull wire having a proximal end, a distal end and a pull wire longitudinal axis extending from said proximal end to said distal end;

a distal basket attached to said pull wire, said distal basket comprising a proximal end, a distal end, a distal basket length extending from said distal basket proximal end to said distal end, a distal basket height perpendicular to said distal basket length and said pull wire longitudinal axis, a proximal hub/junction located at said proximal end of the distal basket, said proximal hub/junction comprising a hollow interior, said pull wire passing through said proximal hub/junction hollow interior, said proximal hub/junction slideable along at least a segment of the pull wire, a plurality of proximal tether memory metal strips, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, each proximal tether memory metal strip having a proximal end attached to said proximal hub/junction, a distal end attached to a crown of a proximal cell and a length extending from said proximal end to said distal end, a plurality of distal cells distal to the proximal cells, and a distal hub/junction located at said distal end of said distal basket and comprising a hollow interior, said distal basket having a relaxed state in which said proximal hub/junction is located a first distance proximal to said proximal crowns and wherein said distal basket has a first height, as measured at the proximal-most crown, a gaping state in which said proximal hub/junction is located a second distance from said proximal crowns and wherein has a second height, as measured at the proximal-most crown, said second height greater than said first height, said second distance less than said first distance, a proximal collapsed state in which said proximal hub/junction is located a third distance proximal to said proximal crowns and wherein said distal basket has a third height, as measured at the proximal-most crown, said third distance greater than said first distance, said third height less than said first height, a catheter having a hollow interior, a proximal end leading to said interior and a distal end leading to said interior, said catheter comprised of a biocompatible material and configured to envelope said distal basket when said distal basket is in said proximal collapsed state;

wherein said distal basket is configured to move from said relaxed state to said gaping state by moving said proximal hub/junction distally relative to said distal hub/junction; and wherein said distal basket is configured to move from said expanded state to said proximal collapsed state by moving said proximal hub/junction proximally relative to said distal hub/junction.

In some embodiments, the proximal tether memory metal strips have a thickness of between about 25% and 75% of the memory metal strips forming the proximal cell of the distal basket. In these embodiments, translation of the proximal hub/junction toward the stationary distal hub/junction deforms the tethers instead of the distal basket. In other embodiments, the proximal tether memory metal strips are as thick or thicker than the memory metal strips forming the proximal cells of the distal basket (e.g., between about 100% and 175% of the thickness of the memory metal strips forming the proximal cells of the basket). In these embodiments with thicker proximal tether memory metal strips, the proximal tether memory metal strips resist deforming when the proximal hub/junction is translated distally toward the stationary distal hub/junction and instead the proximal tether memory metal strips are bowed out laterally, dissecting through or around the clot and centering, buttressing and strengthening the opening of the basket. Generally, in both embodiments, moving the proximal hub/junction towards the distal hub/junction when the basket is in the relaxed state causes the proximal crowns of the proximal cells to move apart from each other, thereby expanding the opening of the distal basket. Preferably, in the embodiments with the thin tethers, in the relaxed state, the tethers have a length of from about 3 mm to about 10 mm, and in the embodiments with the thick tethers, the tethers have a length of from about 10 mm to about 20 mm.

Optionally, the distal basket further comprises a distal collapsed state in which said proximal hub/junction is located distal to said proximal crowns and wherein said distal basket has a fourth height, as measured at the proximal-most crown, said fourth height less than said first height and, wherein said catheter is configured to envelope said distal basket when said distal basket is in said distal collapsed state, and further wherein said distal basket is configured to move from said gaping state to said distal collapsed state by moving said proximal hub/junction distally relative to said distal hub/junction. Optionally, the system further includes a coaxial tube, said coaxial tube configured to be received in said catheter, said coaxial tube having a proximal end, a distal end attached to said proximal hub/junction, and a hollow interior, said pull wire passing through said coaxial tube hollow interior, said coaxial tube slideable along at least a segment of said pull wire. In some embodiments with the thin proximal memory metal strips, the combined length of two of said proximal tether memory metal strips is within about 2 mm of said second height. In other embodiments with the thin proximal memory metal strips, the combined length of two of said proximal tether memory metal strips is within about 2 mm of said second height multiplied by a factor of two. Optionally, said pull wire extends from said distal basket proximal end to said distal basket distal end. Optionally, said pull wire is not in contact with said distal hub/junction. Optionally, in said gaping state, said proximal hub/junction is located parallel to said proximal crown. Optionally, said pull wire and said proximal hub/junction are offset from the center of the distal basket height, as measured at the proximal-most crown. Optionally, all proximal crowns of said proximal cells are attached to a proximal tether memory metal strip. In other embodiments, the system has four proximal cells, each proximal cell having a proximal crown, and not all (e.g., only two) of the proximal crowns are attached to a proximal tether memory metal strip. Optionally, said distal basket further comprises a plurality of strut memory metal strips and plurality of distal cells defined by a plurality of distal memory metal strips, said distal cells comprising a proximal crown located at a proximal end of said distal cells and a distal crown located at a distal end of said distal cells, said strut memory metal strips having a proximal end attached to a distal crown of a proximal cell and a distal end attached to a proximal crown of a distal cell. Optionally, the distal basket comprises between two and four proximal tether memory metal strips. Optionally, said proximal memory metal strips are integral with said proximal hub/junction. Optionally, said proximal hub/junction is a tube, wherein said interior of said proximal hub/junction has a size and shape, and further wherein said size and shape of said proximal hub/junction interior are configured to prevent a segment of said pull wire distal relative to said proximal hub/junction from moving through proximal hub/junction interior. Optionally, said distal hub/junction is a tube. Optionally, said distal hub/junction is attached to said pull wire such that said distal hub/junction is not slideable along said pull wire. Optionally, said distal basket further comprises a lead wire extending distally from said distal hub/junction. Optionally, said distal hub/junction, said proximal hub/junction, and said distal basket are comprised of a nitinol having the same material composition. Optionally, said distal basket further comprises an x-ray marker. Optionally, said proximal and said distal hubs/junctions are generally cylindrical in shape and each has an outer diameter and an inner diameter, the inner diameter forming apertures of the proximal and distal hubs/junctions and further wherein the outer diameters of the proximal and distal hubs/junctions are substantially the same size and further wherein the inner diameters of the proximal and distal hubs/junctions are substantially the same size. Optionally, the outer diameters of the proximal and distal hubs/junctions are from about 0.011 inches to about 0.054 inches, and further wherein the inner diameters of the proximal and distal hubs/junctions are from about 0.008 inches to about 0.051 inches. Optionally, the proximal tube and distal tube have an outer diameter that is from about 0.02 inches to about 0.03 inches and an inner diameter that is from about 0.01 inches to about 0.02 inches. Optionally, the pull wire is generally cylindrical and further wherein the diameter of the pull wire is between about 0.008 inches and about 0.051 inches. Optionally, the first height of the distal basket is between about 2 millimeters and about 8 millimeters. Optionally, said proximal tether memory metal strips rotate about said pull wire longitudinal axis such that a distal end of a proximal tether memory metal strip is located between about 90 and about 270 degrees relative to said proximal end of the same proximal tether memory metal strip.

The present disclosure also provides a method of removing an object from an interior lumen of an animal, said lumen having an interior wall forming said lumen. In some embodiments, the method includes:

a) providing the system described above;
b) positioning the system in said lumen, said basket located in said catheter in a collapsed state;
c) deploying said distal basket from said distal end of said catheter so that said proximal crowns of said proximal cells are distal to said obstruction:
d) allowing said distal basket to move to said relaxed state;
e) moving said proximal hub/junction distally relative to said distal hub/junction so that said distal basket height, as measured at the proximal-most crown, increase;
f) moving said distal basket over said obstruction; and
g) removing said distal basket and said obstruction from said lumen.

Optionally, the interior lumen is an intracranial artery and said obstruction is a blood clot. Optionally, the method further comprises using said blood clot to move said proximal hub/junction distally relative to said distal hub/junction and allow said distal basket to move to said gaping state. Optionally, the method further comprises using a coaxial tube to push said proximal hub/junction distally relative to said distal hub/junction and allow said distal basket to move to said gaping state. Optionally, the method further includes, after step e, moving said proximal hub/junction relative to said distal hub/junction so that said distal basket height, as measured at the proximal-most crown, decrease. Optionally, after step e, said pull wire and said proximal hub/junction are offset with respect to the center of said distal basket height, as measured at the proximal-most crown, as measured at the proximal-most crown, and the center of said lumen.

The present disclosure also provides a system for removing objects within an interior lumen of an animal, the system comprising:

a pull wire having a proximal end, a distal end and a pull wire longitudinal axis extending from said proximal end to said distal end;

a proximal basket attached to said pull wire, said proximal basket comprising a proximal end, a distal end, a proximal basket length extending from said proximal basket proximal end to said distal end, a proximal basket height perpendicular to said proximal basket length and said pull wire longitudinal axis, a proximal tube located at said proximal end of the proximal basket, said proximal tube comprising a hollow interior, said pull wire passing through said hollow interior and said proximal tube slideable along at least a segment of said pull wire, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction, a distal basket attached to said pull wire, said distal basket comprising a proximal end, a distal end, a distal basket length extending from said distal basket proximal end to said distal end, a distal basket height perpendicular to said distal basket length and said pull wire longitudinal axis, a distal tube located at said distal end of the distal basket, said distal tube comprising a hollow interior, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction, a plurality of tether memory metal strips, each tether memory metal strip having a proximal end attached to a distal crown of a cell located at the distal end of said proximal basket and a distal end attached to a proximal crown of a cell located at the proximal end of said distal basket, said proximal basket having
a relaxed state wherein said proximal basket has a first height, as measured at the distal-most crown, and said proximal hub/junction is located a first distance proximal to said distal hub/junction;
a collapsed state wherein said proximal basket has a second height, as measured at the distal-most crown, said second height less than said first height;
a gaping state wherein said proximal basket has a third height, as measured at the distal-most crown, and said proximal hub/junction is located a second distance proximal to said distal hub/junction, said third height greater than said first height and said second distance less than said first distance,
said proximal basket configured to move from said expanded state to said gaping state by pushing said proximal tube distally relative to said distal tube;
said distal basket having
a relaxed state wherein said distal basket has a first height and
a collapsed state wherein said distal basket has a second height, said second height less than said first height, and
a catheter having an interior, a proximal end leading to said interior and a distal end leading to said interior, said catheter comprised of a biocompatible material and configured to envelope said distal and said proximal basket when said baskets are in said collapsed state.

Optionally, said proximal tether memory metal strips rotate about said pull wire longitudinal axis such that a distal end of a proximal tether memory metal strip is located between about 90 and about 270 degrees relative to said proximal end of the same proximal tether memory metal strip.

In some embodiments, the system does not include a proximal hub/junction and the system includes soft cords in place of or in addition to the proximal memory metal strips.

For example, in one embodiment, the system includes:
a pull wire having a proximal end, a distal end and a pull wire longitudinal axis extending from said proximal end to said distal end;
a coaxial tube having a proximal end, a distal end and a hollow interior, said pull wire passing through said coaxial tube hollow interior, said coaxial tube slideable along at least a segment of said pull wire;
a distal basket attached to said pull wire and said coaxial tube, said distal basket comprising a proximal end, a distal end, a distal basket length extending from said distal basket proximal end to said distal end, a distal basket height perpendicular to said distal basket length and said pull wire longitudinal axis, a plurality of cords, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, each cord having a proximal end attached to said coaxial tube, a distal end attached to a crown of a proximal cell and a length extending from said proximal end to said distal end, a plurality of distal cells distal to the proximal cells, and a distal hub/junction located at said distal end of said distal basket and comprising a hollow interior,
said distal basket having
a relaxed state in which said coaxial tube is located a first distance proximal to said proximal crowns and wherein said distal basket, as measured at the proximal-most crown, has a first height,
a proximal collapsed state in which said coaxial tube is located a second distance proximal to said proximal crowns and wherein said distal basket, as measured at the proximal-most crown, has a second height, said second distance greater than said first distance, said second height less than said first height,
a catheter having a hollow interior, a proximal end leading to said interior and a distal end leading to said interior, said catheter comprised of a biocompatible material and configured to envelope said coaxial tube and said distal basket when said distal basket is in said proximal collapsed state;
wherein said distal basket is configured to move from said relaxed state to said proximal collapsed state by moving said coaxial tube proximally relative to said distal hub/junction.

Optionally, the distal basket further comprises a distal collapsed state in which said coaxial tube is located distal to said proximal crowns and wherein said distal basket, as measured at the proximal-most crown, has a third height, said third height less than said first height, wherein said catheter is configured to envelope said distal basket when said distal basket is in said distal collapsed state, and further wherein said distal basket is configured to move from said relaxed state to said distal collapsed state by moving said coaxial tub distally relative to said distal hub/junction. Optionally said cord is comprised of a material selected from the group consisting of plastic, rubber, nylon, suture material, braided catheter material, platinum coils, and ultrafine nitinol. Optionally, said cords are integral with said coaxial sheath. Optionally, said cords are glued to said coaxial sheath. Optionally, said cords are shrink wrapped to said coaxial sheath. Optionally, said cords have a thickness of about 0.004 to about 0.1 inches (more preferably, from about 0.004 to 0.018 inches). Optionally, said cords in said relaxed state, have a length of about 3 to about 20 mm.

Optionally, said pull wire extends from said distal basket proximal end to said distal basket distal end and said pull wire is attached to said distal hub/junction. Optionally, all proximal crowns of said proximal cells are attached to a cord. Optionally, the basket comprises four proximal cells, each proximal cell having a proximal crown, and not all (e.g., only two) of the proximal crowns are attached to a cord. Optionally, said distal basket further comprises a plurality of strut memory metal strips and plurality of distal cells defined by a plurality of distal memory metal strips, said distal cells comprising a proximal crown located at a proximal end of said distal cells and a distal crown located at a distal end of said distal cells, said strut memory metal strips having a proximal end attached to a distal crown of a proximal cell and a distal end attached to a proximal crown of a distal cell. Optionally, the distal basket comprises between two and four cords. Optionally, said distal hub/junction is attached to said pull wire such that said distal hub/junction is not slideable along said pull wire. Optionally, said distal basket further comprises a lead wire extending distally from said distal hub/junction. Optionally, said distal hub/junction and said basket are comprised of a nitinol having the same material composition. Optionally, said distal basket and/or said coaxial tube further comprises an x-ray marker. Optionally, said distal hub/junction is generally cylindrical in shape and has an outer diameter and an inner diameter, the inner diameter forming the aperture of the distal hub/junction and further wherein the outer diameter of the distal hub/junction from about 0.011 inches to about 0.054 inches, and further wherein the inner diameter of the distal hub/junction is from about 0.008 inches to about 0.051 inches. Optionally, the distal tube has an outer diameter that is from about 0.02 inches to about 0.03 inches and an inner diameter that is from about 0.01 inches to about 0.02 inches. Optionally, the pull wire is generally cylindrical and further wherein the diameter of the pull wire is between about 0.008 inches and about 0.051 inches. Optionally, the first height of the distal basket, as measured at the proximal-most crown, is between about 2 millimeters and about 8 millimeters. Optionally, said cords are soft.

In some embodiments, the present disclosure provides a method of removing an object from an interior lumen of an animal, said lumen having an interior wall forming said lumen, the method comprising the steps of:
a) providing the system described above;
b) positioning the system in said lumen, said basket located in said catheter in a collapsed state;
c) deploying said distal basket from said distal end of said catheter so that said proximal crowns of said proximal cells are distal to said obstruction;
d) allowing said distal basket to move to said relaxed state;
e) moving said coaxial tube distally relative to said distal hub/junction so that said coaxial tube moves distally to the proximal-most crown;
f) moving said distal basket, said pull wire and said coaxial tube proximally so that said distal basket moves over said obstruction;
g) moving said coaxial sheath distally relative to said distal hub/junction so that said distal basket height, as measured at the proximal-most crown, decreases and said coaxial tube is closer to said distal hub/junction as compared to the proximal-most crown; and
h) removing said distal basket and said obstruction from said lumen.

In other embodiments, the method includes
a) providing the system described above;
b) positioning the system in said lumen, said basket located in said catheter in a collapsed state;
c) deploying said distal basket from said distal end of said catheter so that said proximal crowns of said proximal cells are distal to said obstruction;
d) allowing said distal basket to move to said relaxed state;
e) moving said coaxial tube distally relative to said distal hub/junction so that said coaxial tube moves distally to the proximal-most crown;
f) moving said distal basket, said pull wire and said coaxial tube proximally so that said distal basket moves over said obstruction;
g) moving said coaxial sheath proximally relative to said distal hub/junction so that said distal basket height, as measured at the proximal-most crown, decreases;
h) moving said catheter distally relative to said distal hub/junction so that said catheter re-sheaths said coaxial sheath and partially re-sheaths said cords, thereby decreasing said distal basket height, as measured at the proximal-most crown;
i) removing said distal basket and said obstruction from said lumen.

Optionally, said interior lumen is an intracranial artery and said obstruction is a blood clot.

In other embodiments that do not include a proximal hub/junction, the system includes
a pull wire having a proximal end, a distal end and a pull wire longitudinal axis extending from said proximal end to said distal end;
a coaxial tube having a proximal end, a distal end and a hollow interior, said pull wire passing through said coaxial tube hollow interior, said coaxial tube slideable along at least a segment of said pull wire;
a distal basket attached to said pull wire and said coaxial tube, said distal basket comprising a proximal end, a distal end, a distal basket length extending from said distal basket proximal end to said distal end, a distal basket height perpendicular to said distal basket length and said pull wire longitudinal axis, a plurality of proximal tether memory metal strips, a plurality of cords, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, each proximal tether memory metal strip having a proximal end attached to said coaxial tube and a distal end, each cord having a proximal end attached to a distal end of a proximal tether memory metal strip and a distal end attached to a crown of a proximal cell and a length extending from said proximal end to said distal end, and a plurality of distal cells distal to the proximal cells, and a distal hub/junction located at said distal end of said distal basket and comprising a hollow interior,
said distal basket having
a relaxed state in which said distal basket, as measured at the proximal-most crown, has a first height,
a collapsed state in which said distal basket, as measured at the proximal-most crown, has a second height, said second height less than said first height, a catheter having a hollow interior, a proximal end leading to said interior and a distal end leading to said interior, said catheter comprised of a biocompatible material and configured to envelope said coaxial tube and said distal basket when said distal basket is in said collapsed state.

Optionally, said cord is comprised of a material selected from the group consisting of plastic, rubber, nylon, suture material, braided catheter material, platinum coils and ultrafine nitinol. Optionally, said proximal tether memory metal strips are integral with said coaxial sheath. Optionally, said cords are glued to said proximal tether memory metal strips. Optionally, said cords are shrink wrapped to said proximal tether memory metal strips. Optionally, said cords have a thickness of from about 0.004 and about 0.1 inches (more preferably about 0.004 to about 0.018 inches) and said cords have a length of from about 3 mm to about 10 mm in said relaxed state. Optionally, said pull wire extends from said distal basket proximal end to said distal basket distal end and said pull wire is attached to said distal hub/junction. Optionally, all proximal crowns of said proximal cells are attached to a cord. Optionally, the basket comprises four proximal cells, each proximal cell having a proximal crown, and not all (e.g., only two) of the proximal crowns are attached to a cord. Optionally, said distal basket further comprises a plurality of strut memory metal strips and plurality of distal cells defined by a plurality of distal memory metal strips, said distal cells comprising a proximal crown located at a proximal end of said distal cells and a distal crown located at a distal end of said distal cells, said strut memory metal strips having a proximal end attached to a distal crown of a proximal cell and a distal end attached to a proximal crown of a distal cell. Optionally, the distal basket comprises between two and four cords. Optionally, said distal hub/junction is attached to said pull wire such that said distal hub/junction is not slideable along said pull wire. Optionally, said distal basket further comprises a lead wire extending distally from said distal hub/junction. Optionally, said distal hub/junction and said basket are comprised of a nitinol having the same material composition. Optionally, said distal basket and/or said coaxial tube further comprises an x-ray marker. Optionally, said distal hub/junction is generally cylindrical in shape and has an outer diameter and an inner diameter, the inner diameter forming the aperture of the distal hub/junction and further wherein the outer diameter of the distal hub/junction is from about 0.011 inches to about 0.054 inches, and further wherein the inner diameter of the distal hub/junction is from about 0.008 inches to about 0.051 inches. Optionally, the distal tube has an outer diameter that is from about 0.02 inches to about 0.03 inches and an inner diameter that is from about 0.01 inches to about 0.02 inches. Optionally the pull wire is generally cylindrical and further wherein the diameter of the pull wire is between about 0.008 inches and about 0.051 inches. Optionally, the first height of the distal basket, as measured at the proximal-most crown, is between about 2 millimeters and about 8 millimeters. Optionally, the cords are soft.

In some embodiments, the above system is used in a method of removing an object from an interior lumen of an animal, said lumen having an interior wall forming said lumen that includes
a) providing the above system;
b) positioning the system in said lumen, said basket located in said catheter in a collapsed state;
c) deploying said distal basket from said distal end of said catheter so that said proximal crowns of said proximal cells are distal to said obstruction, said coaxial sheath is proximal to said obstruction, said proximal tether memory metal strips are proximal to said obstruction, and said cords are adjacent to said obstruction;
d) allowing said distal basket to move to said relaxed state;
e) moving said coaxial tube distally relative to said distal hub/junction so that said proximal tether memory metal strips move distally relative to the proximal-most crown and said obstruction is sandwiched between said proximal tether memory metal strips and said proximal crowns of said proximal cells;
f) removing said distal basket and said obstruction from said lumen.

Optionally said interior lumen is an intracranial artery and said obstruction is a blood clot.

In still further embodiments, the system includes a first wire that is attached to the proximal tube (but not the distal tube) and a second wire that is attached to the distal tube (but not the proximal tube). Preferably, in such embodiments, the system includes two catheters—a guide catheter and a microcatheter. The plurality of memory metal strips attached to the proximal hub/junction include a plurality of proximal tether memory metal strips, which have a proximal end attached to the distal end of the proximal tube. In some embodiments, the present disclosure provides a method of manufacturing a system for removing objects within an interior lumen of an animal comprising:
a) providing a single tube comprised of a memory metal, the single tube having an exterior, a hollow interior, a wall separating the exterior from the hollow interior, a proximal portion comprising an aperture leading to the hollow interior, a distal portion comprising an aperture leading to the hollow interior, and a middle portion between the proximal portion and the distal portion;
b) cutting the wall of the middle portion with a laser;
c) removing the pieces of the middle portion cut by the laser to form a basket system comprising a proximal tube comprising a proximal end, a distal end, and a hollow interior extending through said proximal tube, a distal tube comprising a hollow interior extending through said distal tube, and a middle portion located between said proximal tube and said distal tube and comprising a plurality of proximal memory metal tether strips, each proximal memory metal tether strip having a proximal end attached to the distal end of said proximal tube and a distal end,
d) altering the shape of the middle portion;
e) allowing the middle portion to expand relative to the distal tube and the proximal tube;
f) attaching a first wire to the proximal tube; and
g) attaching a second wire to the distal tube.

Optionally, after step e, the basket system further comprises a row of proximal cells, each proximal cell defined by a plurality of memory metal strips and comprising a proximal crown located at a proximal end of the cell and pointing in the proximal direction and a distal crown located at a distal end of the cell and pointing in the distal direction and further wherein each of said proximal crowns of said proximal cells is attached to a distal end of a proximal tether memory metal strip.

Optionally, after step e, the basket system further comprises a row of distal cells located distal to said proximal cells and connected to said distal crowns of said proximal cells, each distal cell defined by a plurality of memory metal strips and comprising a proximal crown located at a proximal end of the cell and pointing in the proximal direction and a distal crown located at a distal end of the cell and pointing in the distal direction, and further wherein the number of distal cells is twice the number of proximal cells.

Optionally, after step e, the basket system further comprises a row of strut memory metal strips, each strut having a proximal end attached to a distal crown of a proximal cell and a distal end attached to a proximal crown of a distal cell. Optionally, after step e, the basket system further comprises a row of distal crowns located distal to said proximal crowns and pointing in the distal direction, and further wherein the number of distal crowns in said row is twice the number of proximal crowns attached to said proximal tether memory metal strips. Optionally, the step of attaching said first wire to said proximal tube comprises placing said first wire inside said aperture of said proximal tube and gluing said first wire to said proximal tube. Optionally, the step of attaching said first wire to said proximal tube comprises placing said first wire inside said aperture of said proximal tube and welding or soldering said first wire to said proximal tube. Optionally, the step of attaching said first wire to said proximal tube comprises shrink wrapping said first wire to said proximal tube. Optionally, after step e, the basket system comprises between two and four proximal tether memory metal strips. Optionally, the method further comprises not altering the shape of the proximal and distal portions while altering the shape of the middle portion. Optionally, the method further comprises cooling the proximal portion, the middle portion, and the distal portion after step D) and, after cooling, the proximal and distal portions have substantially the same size as the proximal and distal portions had prior to step A). Optionally, the method of allowing said middle portion to expand comprises heating the middle portion. Optionally, the method of altering the shape of the middle portion comprises using a mandrel. Optionally, the mandrel is tapered. Optionally, the proximal portion and the distal portion are not cut by the laser. Optionally, prior to cutting the memory metal tube, the memory metal tube has an outer diameter that is from about 0.011 inches to about 0.054 inches and an inner diameter that is from about 0.008 inches to about 0.051 inches. Optionally, after step e), the proximal tube and distal tube have an outer diameter that is from about 0.02 inches to about 0.03 inches and an inner diameter that is from about 0.01 inches to about 0.02 inches. Optionally, the method further includes placing said basket inside a catheter comprised of a biocompatible material.

The present disclosure also provides a system for removing objects within an interior lumen of an animal. In some embodiments, the system includes
a pull wire having a proximal end, a distal end and a pull wire longitudinal axis extending from said proximal end to said distal end;
a distal basket attached to said pull wire, said distal basket comprising a proximal end, a distal end, a distal basket length extending from said distal basket proximal end to said distal end, a distal basket height perpendicular to said distal basket length and said pull wire longitudinal axis, a proximal tube located at said proximal end of the distal basket, said proximal tube comprising a hollow interior, a plurality of proximal tether memory metal strips, a row of proximal cells defined by a plurality of proximal cell memory metal strips, each proximal cell comprising a proximal crown located at the proximal end of the proximal cell and pointing generally in the proximal direction, each proximal tether memory metal strip having a proximal end attached to said proximal tube, a distal end attached to a crown of a proximal cell and a length extending from said proximal end to said distal end, a row of distal crowns located distal to said proximal cells pointing in the distal direction, and further wherein the number of distal crowns in said row is twice the number of proximal crowns attached to said proximal tether memory metal strips, and a distal tube located at said distal end of said distal basket,
said distal basket having
a relaxed state wherein said distal basket has a first height and
a collapsed state wherein said distal basket has a second height, said second height less than said first height, and
a catheter having an interior, a proximal end leading to said interior and a distal end leading to said interior, said catheter comprised of a biocompatible material and configured to envelope said distal body when said distal basket is in said collapsed state.

Optionally, said proximal tether memory metal strips rotate about said pull wire longitudinal axis such that a distal end of a proximal tether memory metal strip is located between about 90 and about 270 degrees relative to said proximal end of the same proximal tether memory metal strip. Optionally, said proximal tether memory metal strips and said proximal cell memory metal strips each have a thickness and further wherein said thickness of said proximal tether memory metal strips is between about 100 to about 175 percent of the thickness of the proximal cell memory metal strips. Optionally, the length of said proximal tether memory metal strips is about 10 mm to about 20 mm in the relaxed (and the length of the remainder of the basket is about 10 to about 20 mm in the relaxed state so that the total basket length is between about 20 to about 40 mm in the relaxed state). Optionally, said distal end of said pull wire is attached to said proximal tube. Some or all of the proximal crowns of said proximal cells may be attached to a proximal tether memory metal strip. Optionally, said distal basket further comprises a row of strut memory metal strips, each strut memory metal strip having a proximal end attached to a distal crown of a proximal cell and a distal end attached to a proximal crown of a distal cell. Optionally, the distal basket comprises between two and four proximal tether memory metal strips. Optionally, said proximal tether memory metal strips are integral with said proximal tube. Optionally, said distal body further comprises a lead wire extending distally from said distal tube. Optionally, said distal tube, said proximal tube, and said basket are comprised of a nitinol having the same material composition. Optionally, said distal body further comprises an x-ray marker. Optionally, said proximal and said distal tubes are generally cylindrical in shape and each has an outer diameter and an inner diameter, the inner diameter forming the apertures of the proximal and distal tubes and further wherein the outer diameters of the proximal and distal tubes are substantially the same size and further wherein the inner diameters of the proximal and distal tubes are substantially the same size. Optionally, the outer diameters of the proximal and distal tubes are from about 0.011 inches to about 0.054 inches, and further wherein the inner diameters of the proximal and distal tubes are from about 0.008 inches to about 0.051 inches. Optionally, the pull wire is generally cylindrical and further wherein the diameter of the pull wire is between about 0.008 inches and about 0.051 inches. Optionally, the first height is between about 2 millimeters and about 8 millimeters.

The present disclosure also provides a method of removing an object from an interior lumen of an animal, said lumen having an interior wall forming said lumen, the method comprising the steps of:
a) providing the system described above:
b) positioning the system in said lumen, said basket located in said catheter in said collapsed state;

c) deploying said distal basket from said distal end of said catheter so that said proximal crowns of said proximal cells are distal to said obstruction;
d) allowing said distal basket to move to said relaxed state;
e) moving said distal basket over said obstruction; and
f) removing said distal basket and said obstruction from said lumen.

Optionally, said interior lumen is an intracranial artery and said obstruction is a blood clot.

In other embodiments, the system includes:
a pull wire having a proximal end, a distal end and a pull wire longitudinal axis extending from said proximal end to said distal end;
a proximal basket attached to said pull wire, said proximal basket comprising an interior, an exterior, a proximal end, a distal end, a proximal basket length extending from said proximal basket proximal end to said distal end, a proximal basket height perpendicular to said proximal basket length and said pull wire longitudinal axis, a proximal tube located at said proximal end of the proximal basket, said proximal tube comprising a hollow interior, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction,
a distal basket attached to said pull wire, said distal basket comprising an interior, an exterior, a proximal end, a distal end, a distal basket length extending from said distal basket proximal end to said distal end, a distal basket height perpendicular to said distal basket length and said pull wire longitudinal axis, a distal tube located at said distal end of the distal basket, said distal tube comprising a distal tube aperture, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction,
a plurality of tether memory metal strips, each tether memory metal strip having a proximal end attached to a distal crown of a cell located at the distal end of said proximal basket and a distal end attached to a proximal crown of a cell located at the proximal end of said distal basket,
said proximal basket having
a relaxed state wherein said proximal basket has a first height and
a collapsed state wherein said proximal basket has a second height, said second height less than said first height and said second width less than said first width,
said distal basket having
a relaxed state wherein said distal basket has a first height and a first width and
a collapsed state wherein said distal basket has a second height and a second width, said second height less than said first height, and
a catheter having an interior, a proximal end leading to said interior and a distal end leading to said interior, said catheter comprised of a biocompatible material and configured to envelope said distal and said proximal basket when said baskets are in said collapsed state.

Optionally, said tether memory metal strips rotate about said pull wire longitudinal axis such that a distal end of a tether memory metal strip is located between about 90 and about 270 degrees relative to said proximal end of the same proximal tether memory metal strip.

BRIEF DESCRIPTION OF THE DRAWINGS

in FIG. 2A, the tube is shown as though it were flat for purposes of illustrating the cut pattern only.

in FIG. 2C, the tube is rotated as compared to FIG. 2B.

FIGS. 3A-3H illustrate a method of manufacturing a distal body of one embodiment of the present invention using the laser cut memory metal tube of FIGS. 1 and 2; in FIGS. 3A-3H, the basket portion of the distal body is not shown for simplicity of illustration.

in FIGS. 4A-4D, the basket portion of the distal body is not shown for simplicity of illustration.

FIGS. 5 and 6 illustrate different locations that connector strips may be welded to the proximal memory metal strips.

FIG. 7 illustrates a side, elevation view of a catheter and the distal body of FIG. 6.

FIG. 8 illustrates a side, elevation view of a deployable system of one embodiment of the present invention being used to capture a blood clot; in FIG. 8, the basket portion of the distal body is not shown for simplicity of illustration.

in FIG. 9, the basket portion of the distal body is not shown for simplicity of illustration.

in FIG. 10, the basket portion of the distal body is not shown for simplicity of illustration.

FIG. 11 illustrates a first, perspective view of a distal body of an alternate embodiment of the present invention; the distal body is in what is referred to herein as "Orientation 1".

FIG. 12A illustrates a second, perspective view of the distal body of FIG. 11; the distal body is in what is referred to herein as "Orientation 2".

FIG. 12B illustrates a proximal, elevation view of the proximal strips of the distal body of FIG. 11.

in FIG. 26, the user has locked the syringe lever at the desired volume.

in FIG. 27, the suction catheter has partially sucked the distal body and clot into the suction catheter.

in FIG. 28, the suction catheter has completely sucked the distal body and clot into the suction catheter.

FIG. 30A illustrates a front, perspective view of a system of another embodiment of the present invention that includes a delivery catheter, a coaxial tube slideable along a pull wire, and proximal strips that extend from the distal end of the coaxial tube and are attached to a distal basket; in FIG. 30A, the distal basket is in the relaxed state.

FIG. 30B illustrates a front, perspective view of the system of FIG. 30A; in FIG. 30B, the system is in a partially collapsed state due to distal movement of the catheter.

FIG. 31A illustrates a front, perspective view of the system of FIG. 30A; in FIG. 31A, the system is between the proximal collapsed state and the relaxed state.

FIG. 31B illustrates a front, perspective view of the system of FIG. 30A; in FIG. 31A, the system is in the distal collapsed state.

FIG. 33 illustrates a front, perspective view of an alternate embodiment of the system of FIGS. 31-32 in which the proximal ends of the proximal strips are attached to the distal end of the coaxial sheath.

FIG. 34 illustrates a front, perspective view of an alternate embodiment of the system in which the coaxial sheath is a braided catheter comprised of a plurality of braids and further wherein the distal segment of each braid forms a proximal strip.

FIG. 35A-C illustrate a front, perspective view of an embodiment of the system of FIGS. 30-34 in which the proximal strips cover the proximal tip of the proximal crowns; in particular, FIG. 35A is an exploded view, FIG. 35B shows the proximal strip attached to the proximal crown via a loop and an eyelet, and FIG. 35C shows how the proximal strips bend backwards to cover the proximal tips when the distal body is in the distal collapsed state.

FIGS. 37A-37B illustrate a side, perspective view of stepwise deployment and use of a basket system with proximal tether memory metal strips that are about the same length as the rest of the basket (as measured from the proximal-most crown to the distal tube).

FIGS. 38A-38E illustrate a side, perspective view of stepwise deployment and use of the basket system of FIGS. 37A-37B in a blood vessel to retrieve a clot.

FIG. 39A illustrates a side, perspective view of the basket system of FIGS. 37A and 37B; as shown, all proximal crowns of the proximal cells are attached to a proximal tether memory metal strip.

FIG. 39B illustrates an alternative embodiment in which one proximal crown of a proximal cell is not attached to a proximal tether memory metal strip.

FIGS. 43A-43B illustrate a side, perspective view of a basket system in which the proximal tether memory metal strips rotate 90 degrees about both the longitudinal axis of the proximal tether memory metal strips and about the longitudinal axis of the pull wire.

FIG. 43C illustrates a front, elevation view of the basket system of FIGS. 43A-43B.

FIGS. 43D and 43E illustrate a front, elevation view and a side, perspective view of a basket system in which the proximal tether memory metal strips rotate 180 degrees about both the longitudinal axis of the proximal tether memory metal strips and about the longitudinal axis of the pull wire.

FIGS. 44A-44E illustrate a side, perspective view of stepwise deployment and use of a basket system with a proximal basket and a distal basket in a blood vessel to retrieve a clot.

FIGS. 47A-47H illustrate a side, perspective view of stepwise deployment and use of the basket system of FIGS. 46A-46E in a blood vessel to retrieve a clot.

FIGS. 48A-48B illustrate a side, perspective view of stepwise deployment and use of a basket system with relatively thick and short proximal tether memory metal strips.

FIGS. 49A-49C illustrate a side, perspective view of stepwise deployment and use of a basket system with three relatively thin and short proximal tether memory metal strips; the system is deployed in a blood vessel to retrieve a clot.

FIG. 50A illustrates a side, perspective view of a basket system with relatively thin and short proximal tether memory metal strips; in FIG. 50A, all proximal crowns of the proximal cells are attached to a proximal tether memory metal strip.

FIG. 50B illustrates a side, perspective view of a basket system with relatively thin and short proximal tether memory metal strips; in FIG. 50B, one proximal crowns of a proximal cell is not attached to a proximal tether memory metal strip.

FIG. 50C illustrates a front view of a basket system with two proximal tether memory metal strips.

FIG. 50D illustrates a front view of a basket system with three proximal tether memory metal strips.

FIG. 50E illustrates a front view of a basket system with four proximal tether memory metal strips.

FIG. 51 illustrates a side, perspective view of a basket system with relatively thin and short proximal tether memory metal strips; in this FIG. 51, as shown, the proximal tether memory metal strips are not as thick as the memory metal strips forming the proximal-most crown; further, the thickness of the memory metal strips gradually decreases from the proximal-most crown along the basket length to the distal hub/junction.

FIG. 52 illustrates a side, perspective view of a basket system with relatively thin, short proximal tether memory metal strips.

FIGS. 53A-53C illustrate a side, perspective view of stepwise deployment and use of a basket system with relatively long and thin proximal tether memory metal strips; the system is used in a blood vessel to retrieve a clot.

FIGS. 54A-54C illustrate a side, perspective view of a basket system with a proximal basket connected to a distal basket by proximal tether memory metal strips.

FIGS. 55A-55B illustrate a side, perspective view of a basket system in which the proximal tether memory metal strips rotate 90 degrees about both the longitudinal axis of the proximal tether memory metal strips and about the longitudinal axis of the pull wire.

FIG. 55C illustrates a front, elevation view of the basket system of FIGS. 55A-55B.

FIGS. 55D and 55E illustrate a front, elevation view and a side, perspective view of a basket system in which the proximal tether memory metal strips rotate 180 degrees about both the longitudinal axis of the proximal tether memory metal strips and about the longitudinal axis of the pull wire.

FIG. 57A-E illustrates a side perspective view of deployment a basket system in which the proximal tether memory metal strips are thicker than the memory metal strips forming the proximal cells of the distal basket.

FIGS. 58A-58B illustrates a side perspective view of a basket system with relatively long cords, instead of proximal tether memory metal strips.

FIGS. 59A-59B illustrates a side perspective view of a basket system with relatively short cords, instead of proximal tether memory metal strips.

FIG. 61 illustrates a side perspective view of a basket system with cords and proximal tether memory metal strips.

FIGS. 62A-62C illustrate a perspective view of deployment of the basket system of FIG. 61.

DETAILED DESCRIPTION

Figure 1A:
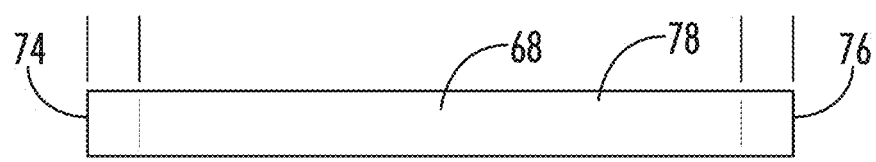
FIG. 1A illustrates a side, elevation view of a memory metal tube prior to being cut by a laser.

With reference to FIGS. 1-10, the present disclosure provides a deployable system, generally designated by the numeral 10, for removing an obstruction such as a blood clot 12 or other object from a blood vessel 14 or other interior lumen of an animal. In addition to a blood clot 12, the obstruction may be, for example, extruded coils during aneurysm treatment, intravascular embolic material such as onyx or other obstructions requiring mechanical intravascular removal from small distal vessels. In the drawings, not all reference numbers are included in each drawing for the sake of clarity.

Referring further to FIGS. 1-10, the deployable system 10 includes a pull wire 16 that has a proximal end (not shown) and a distal end 20. Optionally, the diameter of the pull wire is between about 0.008 inches and about 0.051 inches. Preferably, the pull wire 16 is comprised of a biocompatible metallic material.

The system 10 further includes a distal body 22, which is attached to the pull wire 16. The distal body 22 has a proximal end 24, a distal end 26, an interior 28, and an exterior 30. The distal body 22 has a collapsed state, wherein the distal body 22 has a first height and width and is configured to fit into a catheter 50 (see FIG. 10A), and a relaxed state wherein the distal body 22 has a different height 32 and width and is configured to expand to about the height and width of a human blood vessel 14 when the distal body 22 is deployed from the catheter 50 (see FIGS. 10B-G). The distal body 22 further includes a proximal hub/junction 74 and a distal hub/junction 76 that is located distal relative to the proximal hub/junction 74. In some embodiments, the distal body 22 includes a plurality of strips 40 comprised of a memory metal (e.g., a memory metal alloy such as nitinol) that form the proximal end 24 of the distal body 22. Optionally, the proximal memory metal strips 40 each have a distal end 44 and a proximal end 42 that forms an openable and closeable claw 46. Optionally, the proximal memory metal strips 40 are attached to the proximal hub/junction 74 through connector memory metal strips 48. In such embodiments, the proximal hub/junction 74 may be slideable along at least a segment of the pull wire 16, in contrast to the distal hub/junction 76, which is optionally fixed to the pull wire 16 and not slideable along the pull wire 16. Moving the proximal hub/junction 74 distally and closer to the distal hub/junction 76 (i.e., shortening the distance 88 between the proximal hub/junction 74 and distal hub/junction 76 by moving the proximal hub/junction 74 distally while keeping the distal hub/junction 76 stationary) exerts tension on the connector memory metal strips 48 and, in turn, the proximal memory metal strips 40. This tension, in turn, causes the proximal ends 42 of the proximal memory metal strips 40 to move radially toward each other and the pull wire 16. As the proximal ends 42 of the proximal memory metal strips 40 move radially toward each other and the pull wire 16, the claw 46 (formed by the proximal memory metal strips 40) is brought from the open position to at least a partially closed position, which in turn, separates the obstruction 12 from the wall of the human lumen 14 and captures the obstruction 12. See FIG. 3H, FIG. 8, FIG. 9F, and FIGS. 10F and 10G. Conversely, preferably, movement of the proximal hub/junction 74 proximally and away from the distal hub/junction 76 (i.e., increasing the distance 88 between the hubs/junctions 74 and 76) releases the tension in the proximal memory metal strips 40, which in turn, causes the proximal ends 42 of the proximal memory metal strips 40 to move away from each other and the pull wire 16, opening the claw 46. The claw 46 and proximal hub/junction 74 form several functions. First, as described, closing of the claw 46 captures the obstruction 12. Second, closing the claw 46 retracts the claw 46 from the wall of the lumen 14 so that the claw 46 does not scrape against (and damage) the lumen wall while capturing the obstruction 12. Third, closing the claw 46 reduces the height and width of the distal body 22, which allows the distal body 22 to be re-sheathed in the catheter 50, which may be desired, for example, if the operator seeks to re-deploy the distal body 22 in another location in the body (which may be the case if the operator originally deploys the distal body 22 in the wrong location in the lumen 14). For purposes of the present invention, "closing the claw" embraces both partially closing the claw 46 (where the proximal ends 42 of the proximal memory metal strips 40 do not contact the pull wire 16) and fully closing the claw 46 (where the proximal ends 42 contact the pull wire 16).

The claw 46 may be comprised of any number of proximal memory metal strips 40. Preferably, however, between 2 and 4 proximal memory metal strips 40 comprise the claw 46 (it being understood that the connector strips 48, if present, merely serve to tether the claw 46 to the proximal hub/junction 74). Preferably, the proximal memory metal strips 40 have a length of between about 10 and about 60 millimeters. The proximal memory metal strips 40 can be thought of as arms of the claw 46.

In some embodiments, the connector strips 48 are integral with the proximal hub/junction 74 (i.e., formed from the same piece of memory metal). In other embodiments, the proximal hub/junction 74 may be welded or soldered to the connector strips 48. Optionally, in the relaxed state, the proximal memory metal strips 42 are distributed substantially evenly about a perimeter of the distal body 22.

Optionally, the distal body 22 includes a lead wire 52 extending distally from the distal body 22. Optionally, the lead wire 52 extends distally from the distal hub/junction 76. If present, the lead wire 52 may be used to facilitate movement of the system 10 in the lumen 14.

Figure 2A:
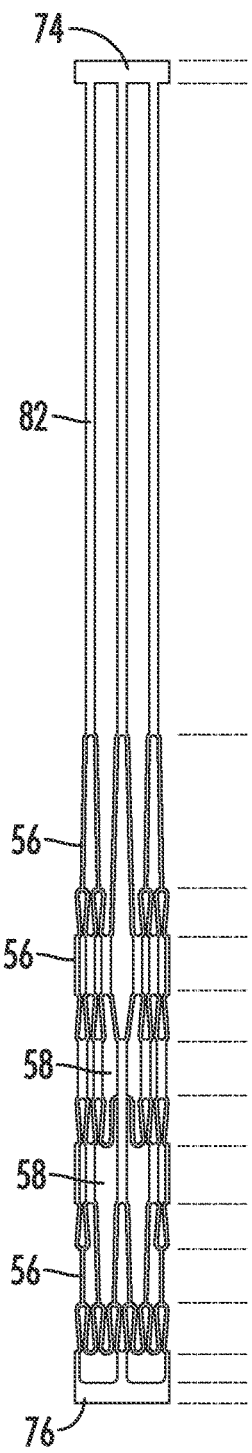
FIG. 2A illustrates a side, elevation view of the memory metal tube of FIG. 1B after being cut by a laser.
Figure 2B:
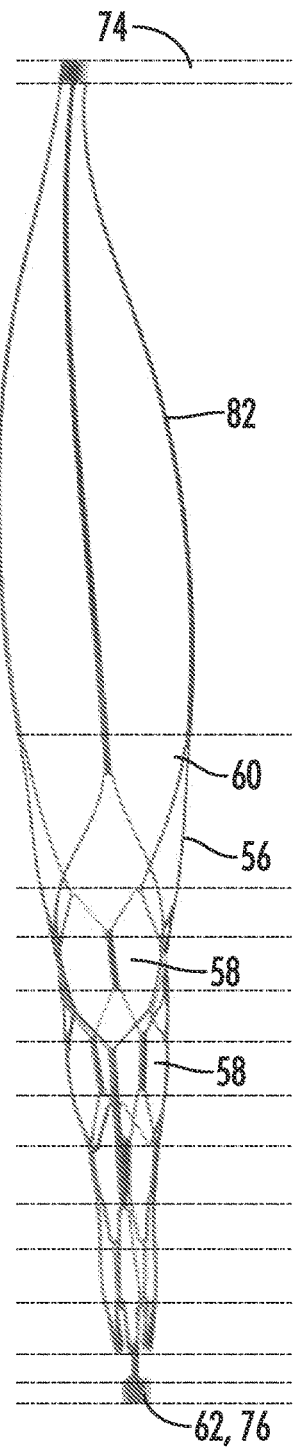
FIG. 2B illustrates a side, perspective view of the memory metal tube of FIG. 1B after being cut by a laser.
Figure 2C:
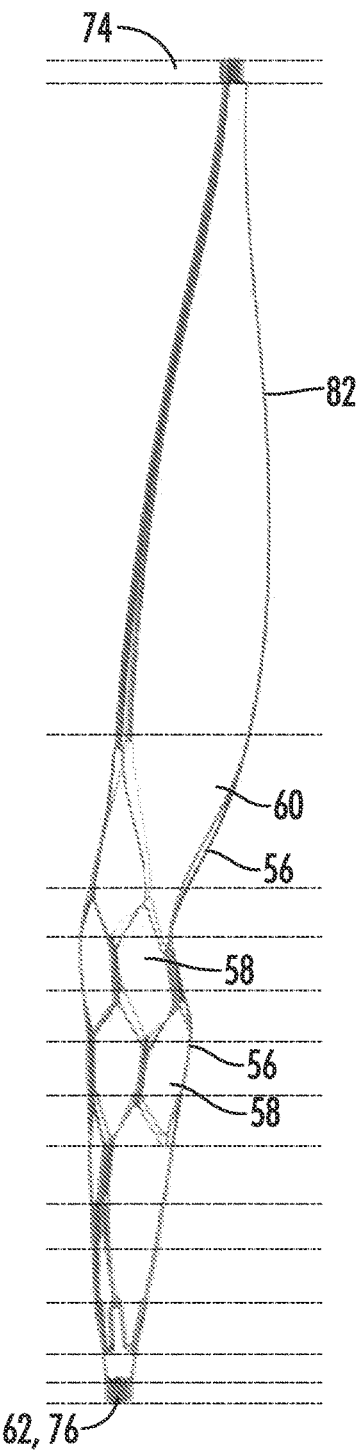
FIG. 2C illustrates another side, perspective view of the memory metal tube of FIG. 1B after being cut by a laser.
Figure 4A:
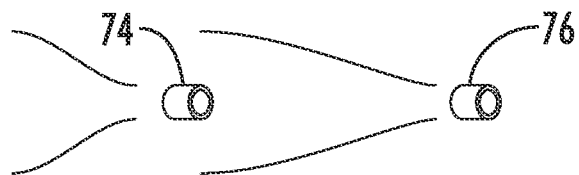
FIGS. 4A-4D illustrate the welding steps of the method of manufacturing shown in FIG. 3.
Figure 4B:
Figure 4C:
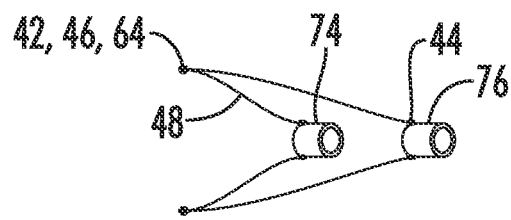
Figure 4D:
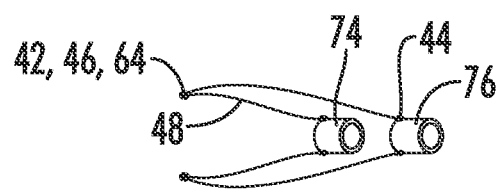
Figure 9:
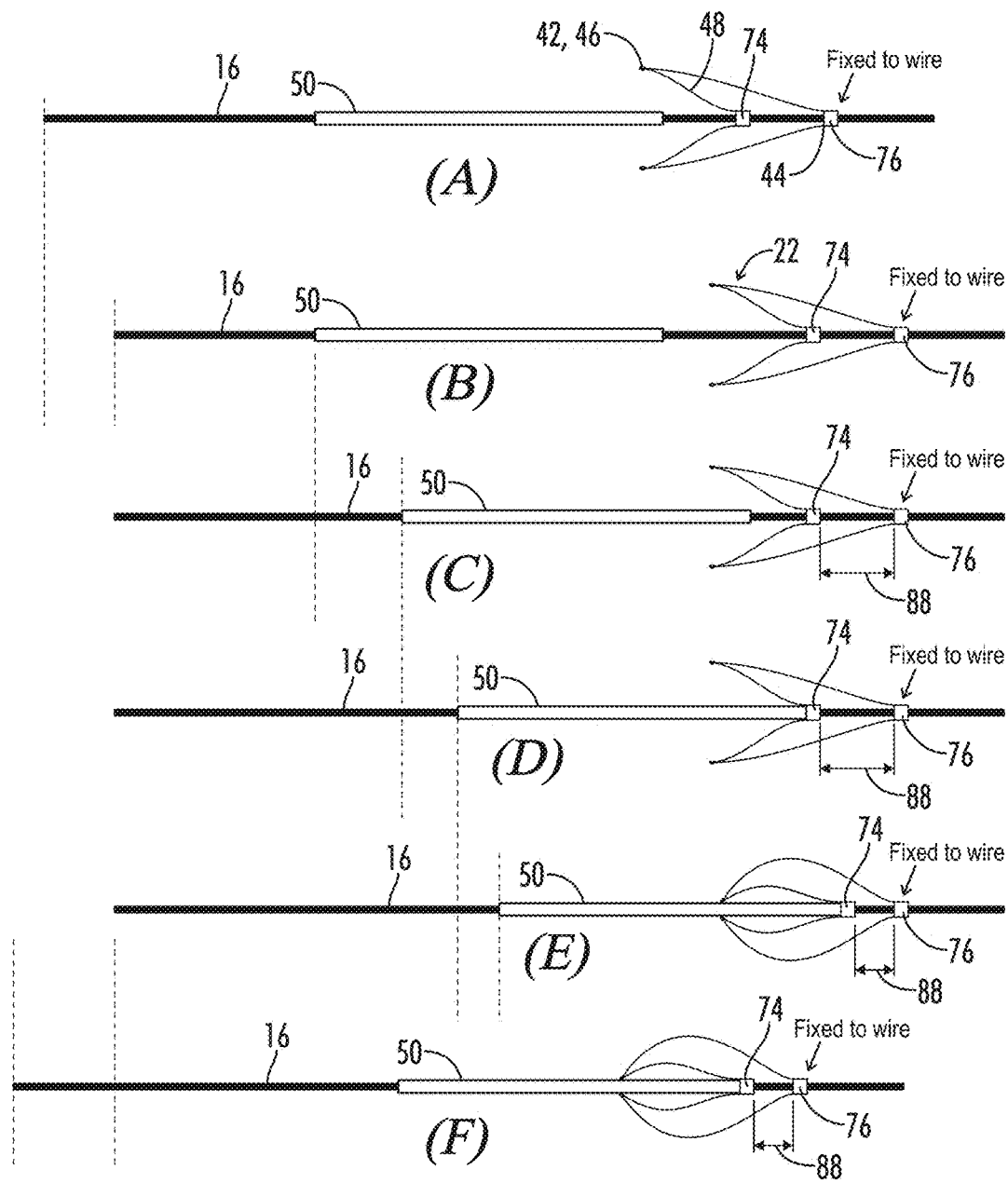
FIG. 9 illustrates a side, elevation view of a claw of one embodiment of the present invention being closed by a claw actuator tube.
Figure 10:
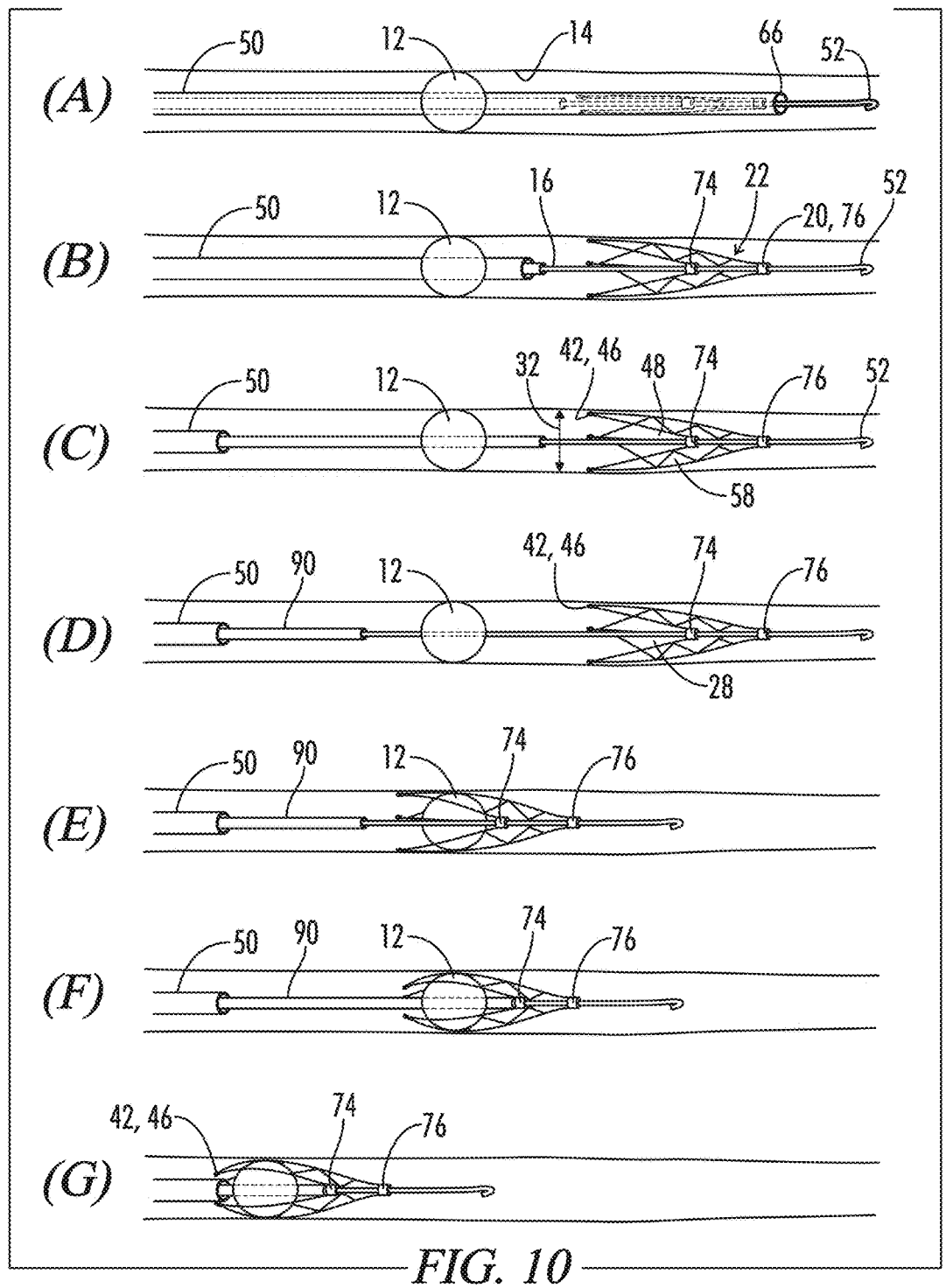
FIG. 10 illustrates a side, elevation view of a deployable system of one embodiment of the present invention being used to capture a blood clot.

Optionally, the distal body 22 includes a basket 54 distal to the proximal memory metal strips 40, the basket 54 comprised of a plurality of memory metal strips 56 distal relative to the proximal memory metal strips 40. The distal memory metal strips 56 may, for example, form a basket 54 with a plurality of mesh openings 58. Optionally, the size of the mesh openings 58 in the basket 54 when the distal body 22 is in its relaxed state is less (preferably significantly less) than the diameter of an average-sized ischemic blood clot 12 so that the blood clot 12 does not escape from the distal basket 54 after being captured by the distal body 22. Optionally, the basket 54 has an open proximal end 60 and a substantially closed distal end 62, which is formed by distal tube 76. Optionally, the distal and proximal hubs/junctions 74 and 76 and the distal basket 54 are comprised of a nitinol having the same material composition. Optionally, the size of the mesh openings 58 decreases from the proximal end 60 of the basket 54 to the distal end 62. The distal basket 54 is best seen in FIG. 2 and can be comprised of a different number of cell patterns. The distal basket 54 is not shown in FIGS. 3-10 for ease of illustrating the other components in the system 10.

Optionally, the proximal hub/junction 74 and the distal hub/junction 76 are cylindrical tubes comprising substantially circular apertures that span the length of the hubs/junctions 74 and 76 and the hubs/junctions 74 and 76 have approximately the same inner diameter 72 and the same outer diameter 70. Preferably, the inner diameter 72 is at least slightly larger than the diameter of the pull wire 16 so that the pull wire 16 can slide through the proximal hub/junction 74. In some embodiments, the outer diameters 70 of the proximal and distal hubs/junctions 74 and 76 may be from about 0.011 inches to about 0.054 inches and the inner diameters 72 of the proximal and distal hubs/junctions 74 and 76 may be from about 0.008 inches to about 0.051 inches.

Optionally, the distal body 22 further comprises an x-ray marker 64 that is more visible under x-ray as compared to the proximal memory metal strips 40 when the distal body 22 is located in a cranial blood vessel inside the body of a human and the x-ray is taken from outside the human's body. If the connector strips 48 are welded or soldered to the proximal memory metal strips 40, the x-ray markers 64 may be, for example, located at the welding or soldering site. In some cases, the increased thickness at the welding or soldering site may in of itself comprise the x-ray marker 64. Preferably, the x-ray marker 64 is comprised of a radiopaque material. Some examples of radiopaque materials can include, but are not limited to, gold, platinum, palladium, tantalum, tungsten alloy, polymer material loaded with radiopaque filler, and the like. Preferably, the proximal memory metal strips 40 are comprised of nitinol and the x-ray marker 64 is comprised of a material having a density greater than the nitinol.

A catheter 50 with an open proximal end (not shown) and an open distal end 66 initially envelopes the system 10. As used herein, the term "catheter" generally refers to any suitable tube through which the system 10 can be deployed. Preferably, the catheter 50 is sterile and comprised of a biocompatible material (i.e., a material that does not irritate the human body during the course of a 45 minute operation that involves using the system 10 to remove a clot 12 from an intracranial blood vessel 14). The catheter 50 can be any suitable shape, including but not limited to generally cylindrical. Preferably, the catheter 50 is a microcatheter. For purposes of the present invention, when it is said that the catheter 50 envelopes the system 10, it will be understood that the catheter 50 envelopes at least one component of the system 10 (preferably, the distal body 22, the lead wire 52, and the pull wire 16). In some embodiments, the catheter 50 is about 2.5 French in diameter. Optionally, the catheter 50 is delivered to the region of the lumen 14 that has the obstruction 12 as follows: a guide wire is delivered to the obstruction region past the obstruction 12; the catheter 50 is delivered over the guide wire; the guide wire is removed; and the system 10 is delivered with its pull wire 16 and lead wire 52 through the catheter 50. Optionally, the pull wire 16 is used to push the system 10 through the catheter 50 as well as to retrieve the distal body 22 after capturing the obstruction 14 as described below. The system 10 may utilize a plurality of catheters 50, such as, for example, a wider catheter that travels to the brain and a very flexible, smaller diameter microcatheter that is delivered from the first catheter and travels through the small arteries of the brain. Preferably, the catheter 50 is comprised of a biocompatible, polymeric material (i.e., one or more polymeric materials such as silicone, PVC, latex rubber or braided nylon).

Optionally, in the relaxed, opened-claw state, the distal body 22 or optionally just the distal basket 54 has a tapered shape (e.g., substantially conical or bullet in shape) so that the distal body 22 or just the distal basket 54 tapers from the distal body 22 or the distal basket's 54 proximal end to the distal end.

The proximal end of the system 10 is shown at the left end of FIGS. 1 and 3-10 and the distal end of the system 10 is shown at the right end of FIGS. 1 and 3-10 because a principal use of the system 10 is to remove a blood clot 12 from a human intracranial artery 14, in which case the system 10 generally will enter the artery 14 at its proximal end by the surgeon entering the patient's body near the groin and pushing the catheter 50 towards the brain. The diameter of human arteries 14 generally decrease from their proximal end to their distal end. However, when used in other types of lumens, the distal body 22 may be located proximally relative to the catheter 50 as the term proximally and distally are used in that lumen.

The surgeon may deploy the distal body 22 by, for example, moving the catheter 50 proximally so as to unsheathe the distal body 22 or by pushing the distal body 22 out of the catheter 50.

Use of the system 10 will now be described to remove a blood clot 12 from an intracranial artery 14 of a human ischemic stroke patient, however, it will be appreciated that the system 10 may be used to remove other objects from other interior lumens.

A catheter 50, which contains the collapsed distal body 22 is positioned in the lumen 14 distal to the clot 12. See FIG. 10A.

The distal body 22 is deployed from the catheter 50 and the height and width of the distal body 22 expand to about the height and width of the blood vessel 14. See FIG. 10B.

The catheter 50 is pulled proximally and a claw-actuator tube 90 is deployed into the blood vessel 14. See FIG. 10C.

The distal body 22 is moved proximally so that the clot 12 is located in the interior 28 of the distal body 22. See FIGS. 10D and 10E.

The claw-actuator tube 90 is moved distally, which pushes the proximal hub/junction 74 distally so that the distance 88 between the proximal hub/junction 74 and the distal hub/junction 76 (which is fixed to the pull wire 16 and kept stationary) decreases. Distal movement of the proximal hub/junction 74 exerts tension on the connector and proximal memory metal strips 40 and 48, which in turn, closes the claw 46. See FIG. 10F. (The claw actuator tube 90 should float on the pull wire 16—i.e., have an aperture extending the tube's length that has a diameter larger than the diameter of the pull wire 16—and the aperture of the claw actuator tube 90 should be smaller than the diameter of the proximal hub/junction 74 so that the claw actuator tube 90 pushes the proximal hub/junction 74).

The system 10 is withdrawn proximally and removed from the body. See FIG. 10G.

To test the efficacy of the system 10, a distal body 22 with a distal basket 54, proximal and distal hubs/junctions 74 and 76, and a claw 46 comprised of three proximal memory metal strips 42 was tested in a flow model that included a tube and a moist cotton ball located in the tube. The cotton ball was used to simulate a blood clot. The system 10 was deployed distal to the cotton ball. The claw 46 was closed by moving the proximal hub/junction 74 distally to capture the cotton ball. The system 10 and cotton ball were withdrawn proximally in the tube.

Figure 1B:
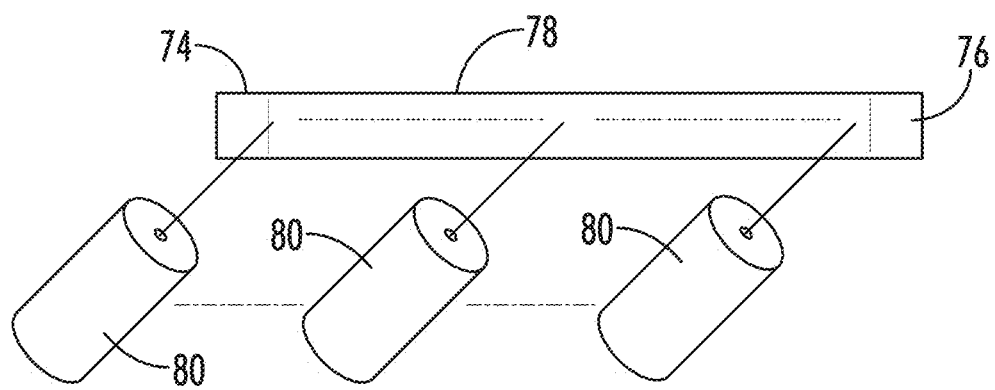
FIG. 1B illustrates a side, elevation view of the memory metal tube of FIG. 1A being cut by a laser.

In some embodiments, the distal body 22 is prepared by a process that includes one or more of the following steps, as illustrated in FIGS. 1-4 a) providing a single tube 68 comprised of a memory metal such as nitinol, the single tube 68 having an exterior, a substantially hollow interior, a wall separating the exterior from the substantially hollow interior, an open proximal end 74, an open distal end 76, a middle portion 78 between the open proximal end 74 and the open distal end 76 (see FIG. 1A);

b) cutting the wall of the middle portion 78 with a laser 80 (see FIG. 1B);

c) removing the pieces of the middle portion 78 cut by the laser 80 to form a proximal tube 74, a distal tube 76 and a middle portion 78 comprising a plurality of memory metal strips 82 attached to the proximal tube 74;

d) altering the shape of the middle portion 78 using a mandrel and allowing the middle portion 78 to expand relative to the distal tube 76 and proximal tube 74 to form the distal basket 54;

e) quenching the middle portion 78 at room temperature;

f) removing the mandrel from the middle portion 78 (see FIGS. 2 and 3A);

g) mechanically or chemically electropolishing the middle portion 78 to remove oxides;

h) cutting the memory metal strips 82 to form a first segment 84 comprising the proximal tube 74 and a proximal segment of the memory metal strips 82 and a second segment 86 comprising the distal tube 76 and a distal segment of the memory metal strips 82 (see FIG. 3B); and i) joining the proximal segments to the distal segments such that the distal segments form the proximal end 24 of the distal body 22, such that the proximal tube 74 is located inside the interior 28 of the distal body 22, and such the proximal tube 74 is located distal relative to the distal body proximal end 24 (see FIGS. 3C-3E).

In some embodiments, the method further includes placing the pull wire 16 through the proximal tube 74 so that the proximal tube 74 is slideable along at least a segment of the pull wire 16.

In some embodiments, the method further includes attaching the pull wire 16 to the distal tube 76 so that the distal tube 76 is not slideable along the pull wire 16 but instead the distal tube 76 moves with the pull wire 16.

In some embodiments, after step i, the proximal end 24 of the distal body 22 forms a claw 46 comprised of between 2 to 4 proximal memory metal strips 40, the claw proximal memory metal strips 40 configured to move towards each other and the pull wire 16 by moving the proximal tube 74 distally and toward the distal tube 76 (i.e., decreasing the distance 88 between the tubes 74 and 76) and the claw memory metal strips 40 configured to move away from each other and away from the pull wire (i.e., increasing the distance 88 between the tubes 74 and 76) by moving the proximal tube 76 proximally and away from the distal tube 76 (as described previously).

In some embodiments, the middle portion 78 is expanded by heating the mandrel and the middle portion 78 by, for example, placing the mandrel and the middle portion 78 in a fluidized sand bath at about 500° C. for about 3 to about 7 minutes. As the middle portion 78 is heated, the heating causes the crystalline structure of the memory metal tube 68 to realign. Preferably, the mandrel is tapered (e.g., substantially conical or bullet in shape) so that the distal basket 54 formed from the middle portion 78 tapers from the proximal end 60 to the distal end 62. Preferably, the proximal and distal ends of the tube 74 and 76 are not shape set by the mandrel and are not cut by the laser 80 so that the proximal and distal ends 74 and 76 do not change in shape and only slightly expand in size under heating and return to the size of the native tube 68 after the heat is removed. Preferably, the laser cuts are programmed via a computer. To ensure that the laser cuts only one surface of the tube wall at the time (and not the surface directly opposite the desired cutting surface), the laser 80 is preferably focused between the inner and outer diameter of the desired cutting surface and a coolant is passed through the memory metal tube 68 so that the laser 80 cools before reaching the surface directly opposite the desired cutting surface.

The portions of the wall not cut by the laser 80 create the distal basket 53, proximal and distal tubes 74 and 76, and memory metal strips 40, 48 and 56, as described.

Preferably, the memory metal selected for the native tube 68 has a heat of transformation below average human body temperature (37° C.) so that the distal body 22 has sufficient spring and flexibility after deployment from the catheter 50 in the human blood vessel 14.

In some embodiments, the native tube 68 (and hence the distal and proximal tubes 74 and 76) have an outer diameter of less than about 4 French, e.g., a diameter of about 1 to about 4 French. In some embodiments, the diameter of the pull wire 16 is between about 0.008 inches and about 0.051, as noted above, and in such embodiments, the diameter of the pull wire 16 may be approximately equal to the inner diameter 72 of the native nitinol tube 68.

Without being bound by any particular theory, it is believed that manufacturing the distal body 22 from a single memory metal tube 68 provides ease of manufacturing and safety from mechanical failure and provides tensile strength necessary for the system 10 to remove hard thrombus 12 and other obstructions.

The Embodiments of FIGS. 11-29

FIGS. 11-29 illustrate an alternate embodiment 200 that includes one or more of the following additional features, as described below: twisting proximal strips/tethers 252, unattached/free distal-pointing crowns 258 that optionally curve inward and have x-ray markers 244, and enlarged openings/drop zones 262 in the basket 246 immediately distal to the unattached, distal-pointing crowns 258 that allow the obstruction or other object 270 to enter the distal basket interior 222.

More specifically, as shown in FIGS. 11-29, the system 200 may include a pull wire 202 having a proximal end 204 and a distal end 206, as described above, a distal body 216 attached to the pull wire 202, the distal body 216 comprising an interior 222, a proximal end 218, a distal end 220, a distal body length 226 extending from the proximal end 218 to the distal end 220, a distal body height 224, a proximal hub/junction 228 (preferably in the form of a tube and which has a proximal end 230 and a distal end 232) forming the proximal end 218 of the distal body 216, a basket 246 comprised of a plurality of cells/openings 248 formed by a plurality of basket strips 291 that preferably are comprised of a memory metal, optionally a distal hub/junction 236 that forms the distal end 220 of the basket 246 (preferably in the form of a tube that has a proximal end 238 and a distal end 240), and a plurality of proximal strips 252 (preferably the proximal strips 252 are comprised of a memory metal), each proximal strip 252 having a proximal end 254 attached to the proximal hub/junction/tube 228, and a distal end 256 attached to a cell 248 (more specifically a proximal-pointing crown of a cell 248 located at the proximal end of the basket 246), the basket comprising a basket interior 292, the distal body 216 having a relaxed state wherein the distal body 216 has a first height and width, a collapsed state wherein the distal body 216 has a second height and width, the second height less than the first height, the second width less than the first width; and a delivery catheter 208 for delivering the distal body 216, as described above, having an interior 210, a proximal end 212 leading to the interior 210 and a distal end 214 leading to the interior 210, the delivery catheter 208 comprised of a biocompatible (preferably polymeric) material and configured to envelope the distal body 216 when the distal body 216 is in the collapsed state. Optionally, the basket interior 292 is substantially hollow—i.e., unlike U.S. Patent Publication No. 2013/0345739, the basket interior 292 does not contain an inner elongate body. Optionally, instead of a distal hub/junction 236, the basket 246 includes an open distal end. Optionally, at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246. In other words, the distal crowns 258 of at least two cells 250 are free floating and are not attached to any strip except for the strips forming part of the at least two cells 250; such distal crowns 258 are referred to below as unattached, distal-pointing crowns 258. Preferably, the distal tips of the unattached, distal-pointing crowns 258 terminate at an x-ray marker 244. (Cells labeled with the numerals 250, 250A, 250B, 250C, and 250D refer to the at least two cells that include a proximal crown 260 pointing generally in the proximal direction and an unattached, distal-pointing crown 258, cells labeled with the numerals 262, 262A, 262B, 262C, and 262D refer to the enlarged cells/drop zones adjacent to (preferably immediately distal to) an unattached, distal-pointing crown 258, and cells designated with numeral 248 refer to generally the cells of the basket 246). (When it is said that the enlarged cells/drop zones 262 are preferably immediately distal to an unattached, distal-pointing crown 258, it will be understood that at least a portion of an enlarged cell/drop zone 262 is immediately distal to an unattached, distal-pointing crown 258, and that a portion of the enlarged cell/drop zone 262 may be proximal to an unattached, distal-pointing crown 258, as shown in FIGS. 11-12 due to the shape of the enlarged cells/drop zones 262). It will be understood that part number 250 refers generally to one or more of the at least two cells, whereas part numbers 250A, 250B, 250C, and 250D refer to a specific one of the at least two cells. Similarly, it will be understood that part number 262 refers generally to one or more of the enlarged cells/drop zones, whereas part numbers 262A, 262B, 262C, and 262D refer to a specific one of the enlarged cells/drop zones. Similarly, it will be understood that part number 258 refers generally to one or more of the unattached, distal-pointing crowns, whereas part numbers 258A, 258B, 258C, and 258D refer to a specific one of the unattached, distal-pointing crowns.

Optionally, at least two of the unattached, distal-pointing crowns 258 are located approximately 180 degrees (e.g., about 150 to about 180 degrees) relative to each other and approximately the same distance from the proximal hub/junction/tube 228, as best seen in FIG. 12A. Optionally, the basket 246 comprises a first pair of unattached, distal-pointing crowns 258A and 258B, each of the first pair of unattached, distal-pointing crowns 258A and 258B is located approximately the same distance from the proximal hub/junction/tube 228 and approximately 180 degrees relative to each other, and the basket 246 further comprises a second pair of unattached, distal-pointing crowns 258C and 258D located distally relative to, and approximately 90 degrees (e.g., between about 60 and about 90 degrees) relative to, the first pair of unattached, distal-pointing crowns 258A and 258B. Optionally, the second pair of unattached, distal-pointing crowns 258C and 258D form cells 250C and 250D that are adjacent to, but offset from, the cells 250A and 250B formed by the first pair of unattached, distal-pointing crowns 258A and 258B. (In other words, optionally, the center of cell 250A is about 90 degrees relative to the centers of cells 250C and 250D and optionally the center of cell 250B is also about 90 degrees relative to the centers of cells 250C and 250D). Optionally, at least one of (and preferably all) the unattached, distal-pointing crowns 258A, 258B, 258C or 258D comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the x-ray markers 244 comprise a heavy metal welded or soldered to the unattached, distal-pointing crowns 258. Optionally, the unattached, distal-pointing crowns 258 curve subtly towards the interior 222 of the distal basket 246, which decreases the likelihood that the unattached, distal-pointing crowns 258 will rub against and damage the vessel wall 268. Optionally, the basket 246 comprises at least two cells proximal to the at least two cells 250 that include the unattached, distal-pointing crowns 258. Optionally, the unattached, distal-pointing distal crowns 258 are located about at least 5 mm (e.g., about 5 to about 30 mm) from the proximal hub/junction/tube 228. Optionally, the unattached, distal-pointing crowns 258 are located at least about 5 mm from the distal hub/junction/tube 236. Optionally, the unattached, distal-pointing crowns 258 of the at least two cells 250 also each form part (namely a portion of the proximal boundary) of an enlarged cell 262 (which is the entry point of hard thrombus 270B into the basket interior 222) and further wherein the surface area of the enlarged cells 262 in the relaxed state is greater than the surface area of the other cells of the basket 246 in the relaxed state. Optionally, the unattached, distal-pointing crowns 258 serve several functions: 1) they form flex points of the basket 246, which makes it easier for the system 200 to navigate the curves of the blood vessels 266 of the brains; 2) through the use of x-ray markers 244 on the unattached, distal-pointing crowns 258, they allow the operator to locate the enlarged cells 262 of the basket 246 that form the point at which hard thrombuses 270B enter the basket 246; and 3) they allow the operator to ratchet or force the object 270 into the basket 246 by moving the unattached, distal-pointing crowns 258 proximally and distally relative to the object 270. (As explained below, the numeral 270 refers to clots/thrombuses and other objects generally, and 270A refers to a soft clot, 270B refers to a hard clot and 270C refers to a deformable, cohesive, adherent clot). Optionally, the proximal end 254 of a proximal strip 252 is located about 65-180 degrees (preferably approximately 180 degrees) relative to the distal end 256 of the same proximal strip 252, as best seen in FIG. 12B. In other words, preferably the proximal end 254 of a first proximal strip 252 is attached to the 12 o'clock position on the proximal tube 228 and the distal end 256 of the first proximal strip 252 (which terminates at a proximal cell 248 of the basket 246) is located at the 6 o'clock position (i.e., 180 degrees from the start position), and the proximal end 254 of a second proximal strip 252 is attached to the 6 o'clock position on the proximal tube 228 and the distal end 254 (which terminates at a cell 248 of the basket 246) of the second proximal strip 252 is located at the 12 o'clock position (i.e., 180 degrees from the start position). This twisting feature serves two functions: 1) it allows the proximal strips 252 to surround the object 270; and 2) it allows the manufacturer to insert a mandrel into the basket 246 during the shape-setting procedure. Optionally, the pull wire 202 is attached to the proximal tube 228 (e.g., by gluing, welding, soldering or the like). Preferably, the pull wire 202 does not extend through the distal basket interior 222. Optionally, the proximal strips 252 are integral with the distal end 232 of the proximal tube 228 and the entire distal body 216 is created from a single tube 264 of a memory metal. Optionally, the proximal crowns 260 of the at least two cells 250 that include the unattached, distal pointing-crowns 258 are each attached to another cell 248 of the basket 246. In other words, preferably the basket 246 does not have any free-floating proximal-pointing crowns, as free-floating proximal-pointing crowns could damage the vessel 266 when the distal body 216 is pulled proximally. Optionally, the system 200 further comprises a lead wire 286 extending distally from the distal tube 236, the lead wire 286 having a length of from about 3 mm to about 10 mm. Optionally, the distal hub/junction/tube 236, the proximal hub/junction/tube 228, and the basket 246 are comprised of a nitinol having the same material composition. In other words, as with the prior embodiment of FIGS. 1-10, optionally the entire distal body 216 is manufactured from a single tube of nitinol 264. Optionally, the proximal and distal hubs/junctions/tubes 228 and 236 comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the proximal and distal hubs/junctions/tube interiors 234 and 242 may comprise tantalum welded or otherwise attached to the interior 234 and 242 of the proximal and distal hubs/junctions/tubes 228 and 236. Optionally, the proximal and the distal tubes 228 and 236 are generally cylindrical in shape and each has an outer diameter and an inner diameter, the inner diameter forming apertures of the proximal and distal tubes 228 and 236 and further wherein the outer diameters of the proximal and distal tubes 228 and 236 are substantially the same size and further wherein the inner diameters of the proximal and distal tubes 228 and 236 are substantially the same size. Optionally, the outer diameters of the proximal and distal tubes 228 and 236 are from about 0.011 inches to about 0.054 inches, and further wherein the inner diameters of the proximal and distal tubes 228 and 236 are from about 0.008 inches to about 0.051 inches. Optionally, the pull wire 202 is generally cylindrical and further wherein the diameter of the pull wire 202 is between about 0.008 inches and about 0.051 inches. Optionally, the distal body 216 has a length of between about 10 and about 60 millimeters. Optionally, the first height 224 and first width 226 of the distal body 216 are between about 2 millimeters and about 6 millimeters.

The present disclosure also provides a method of removing a clot or other object 270 from an interior lumen 266 of an animal, the method comprising the steps of:

a) providing the system 200 of FIGS. 11-29, wherein at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246 (i.e., free-floating), and further wherein at least one of the unattached, distal-pointing crowns 258 comprises an x-ray marker 244;

b) positioning the system 200 in the lumen 266;

c) deploying the distal body 216 from the distal end 214 of the delivery catheter 208;

d) allowing the height and width 224 and 226 of the distal body 216 to increase:

e) irradiating the x-ray marker 244 with x-ray radiation and f) moving the object 270 into the distal basket interior 222.

Optionally, the object 270 enters the distal basket interior 222 adjacent to (preferably adjacent and immediately distal to) at least one of the unattached, distal-pointing crowns 258—i.e., in the enlarged cells/drop zones 262. In some embodiments, the distal body 216 is deployed so that at least one (e.g., preferably the two proximal 258A and 258B) of the unattached, distal-pointing crowns 258 is distal to the object 270. As explained below, the x-ray markers 244 of the unattached, distal-pointing crowns 258 are used to locate the distal body 216 relative to the clot or other object 270. It will be appreciated that clots 270 can generally be located in blood vessels 266 by injecting a contrast dye, for example, into the blood vessel 266 proximal and distal to the believed area of obstruction and viewing on an x-ray where the fluid stops moving in the blood vessel 266. It will also appreciated that if the object 270 is not a blood clot but is a radio-opaque object, the object 270 may be viewed on an x-ray.

Figure 13:
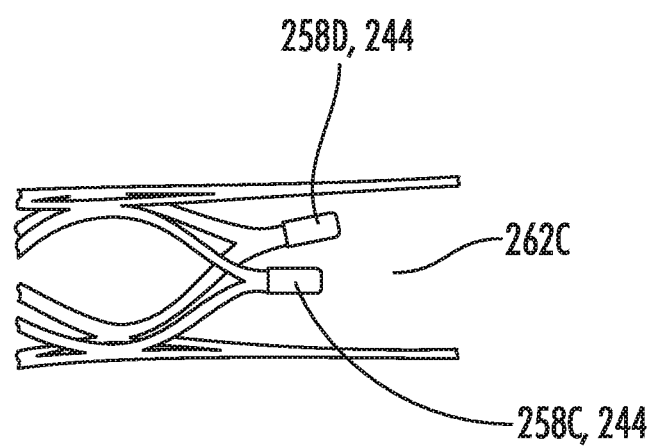
FIG. 13 illustrates a close-up, perspective view of two unattached distal-pointing crowns of the distal body of FIG. 11.
Figure 14A:
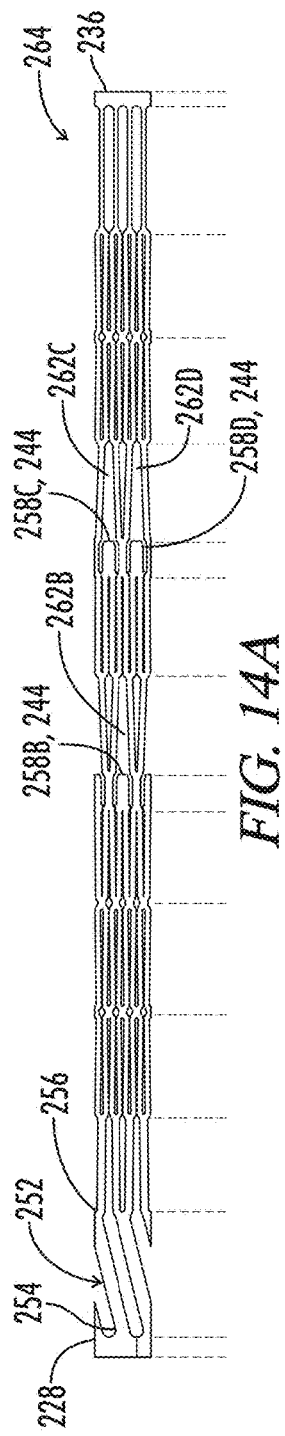
FIG. 14A illustrates a native memory metal tube used to manufacture the distal body of FIG. 11; the native tube has been rolled out flat and the lines in the tube indicate where the tube has been cut by a laser.
Figure 14B:
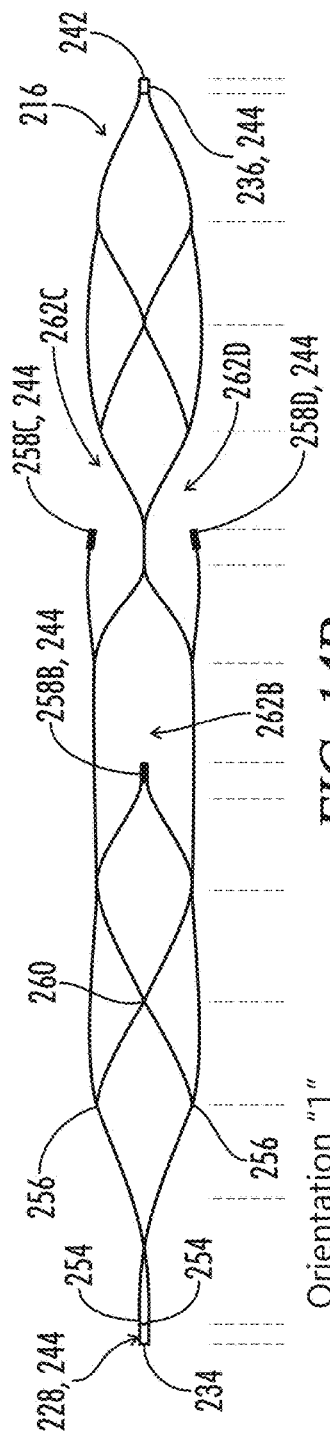
FIG. 14B illustrates a first, perspective view of the distal body manufactured from the native tube of FIG. 14A; the distal body is in Orientation 1.
Figure 14C:
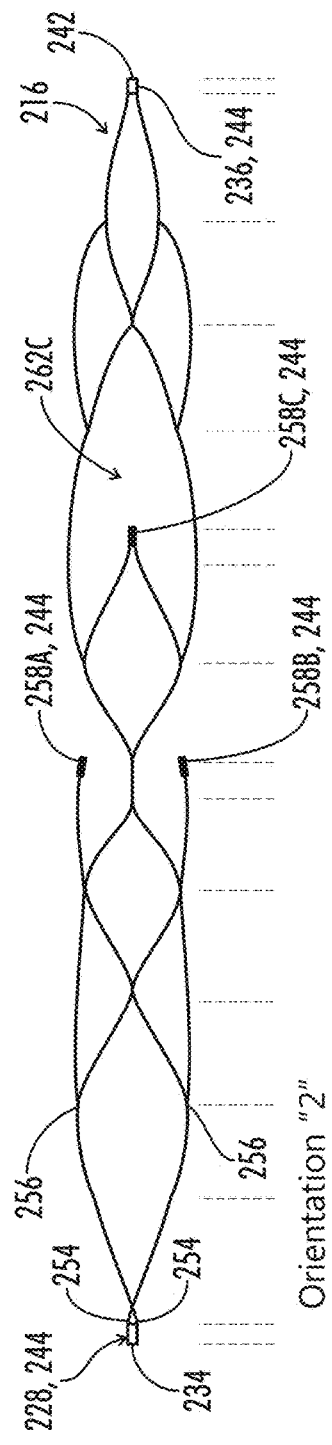
FIG. 14C illustrates a second, perspective view of the distal body manufactured from the native tube of FIG. 14A; the distal body is in Orientation 2.
Figure 63:
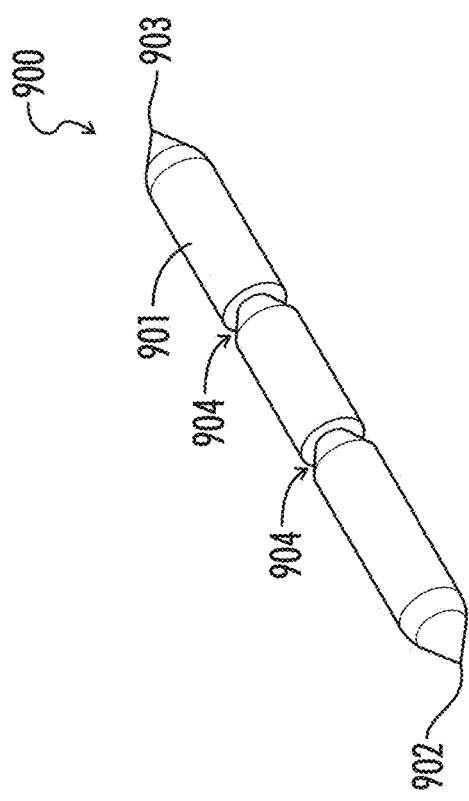
FIG. 63 illustrates a right side perspective view of a mandrel used to prepare unattached distal-pointing crowns that curve radially toward the basket interior.
Figure 64:
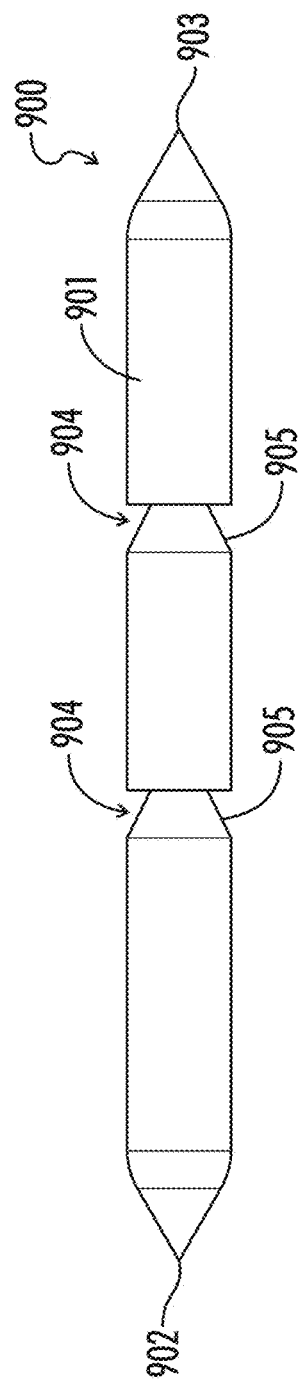
FIG. 64 illustrates a right side elevation view of the mandrel of FIG. 63.

FIGS. 11 and 14B illustrate a first, perspective view of one embodiment of a distal body 216 with twisting proximal strips 252, unattached distal-pointing crowns 258 that subtly curve inward and have x-ray markers 244, and enlarged openings/drop zones 262 in the basket 246 that allow the obstruction or other object 270 to enter. In FIGS. 11 and 14B, the distal body 216 is in Orientation 1. (To prepare a basket 246 with unattached distal-pointing crowns 258 that curve inward toward the basket interior 292, a mandrel 900 such as that illustrated in FIGS. 63 and 64 may be used. The mandrel 900 includes a generally cylindrical body 901 with tapered proximal and distal ends 902 and 903 that slope like the ends of a pencil. The cylindrical body 901 includes two grooves 904 that extend around the circumference of the cylindrical body 901. The grooves 904 include tapered portions 905 that slope towards the distal end 903, which are designed to shape the unattached distal-pointing crowns 258. The grooves 904 are generally in the shape of a truncated cone, as shown in FIGS. 63-64). The two proximal, unattached distal-pointing crowns 258A and 258B are located approximately the same distance from the proximal hub/junction/tube 228 and are oriented approximately 180 degrees relative to each other. The two distal, unattached distal-pointing crowns 258C and 258D are located approximately the same distance from the proximal hub/junction/tube 228 as each other (and distal to the two proximal, unattached distal-pointing crowns 258A and 258B) and are oriented approximately 180 degrees relative to each other and approximately 90 degrees to the proximal, unattached distal-pointing crowns 258A and 258B. The two proximal enlarged openings/drop zones 262A and 262B distal to the proximal, unattached distal pointing crowns 258A and 258B are located approximately the same distance from the proximal hub/junction/tube 228 and the centers of the two proximal enlarged openings/drop zones 262A and 262B are oriented approximately 180 degrees relative to each other. (As noted above, preferably, the proximal, unattached distal-pointing crowns 258A and 258B form part of the proximal boundary of the proximal, enlarged cells/drop zones 262A and 262B, and the distal, unattached distal-pointing crowns 258C and 258C form part of the proximal boundary of the distal, enlarged cells/drop zones 262C and 262D). The two distal, enlarged openings/drop zones 262C and 262D distal to the distal, unattached distal pointing crowns 258C and 258D are located approximately the same distance from the proximal hub/junction/tube 228 and the centers of the distal, enlarged openings/drop zones 262C and 262D are oriented approximately 180 degrees relative to each other and approximately 90 degrees relative to the proximal enlarged openings/drop zones 262A and 262B. FIGS. 12A and 14C illustrate a second view of the distal body 216 of FIG. 11 (Orientation 2). FIG. 13 is a close-up view of two unattached, distal-pointing crowns 262. The lines in FIG. 14 show how a nitinol tube 264 is cut with a laser to create the distal body 216 shown in FIG. 14B and FIG. 14C. It will be appreciated that FIG. 14B is a simplified view of the distal body 216 and orientation shown in FIG. 11 and FIG. 14C is a simplified view of the distal body 216 and orientation shown in FIG. 12A.

As described below, FIGS. 15-19 describe how the distal body 216 is used to retrieve, soft clots 270A, hard clots 270B, and deformable, cohesive adhesive clots 270C in a human intracranial artery 266. (In FIGS. 15-19, the center of the artery 266 is denominated by the dashed line). As explained below, the distal body 216 has four rows of x-ray markers namely, 1) a first row of one x-ray marker, which is located inside the proximal tube denominated by the numeral 228, 244; 2) a second row of two x-ray markers, which are located at the two proximal, unattached distal-pointing crowns (the two markers are oriented 180 degrees relative to each other) denominated by the numerals 258A, 244 and 258B, 244; 3) a third row of two x-ray markers, which are located at the two distal, unattached distal-pointing crowns (these two markers are oriented 180 degrees relative to each other and 90 degrees relative to the two proximal, unattached distal-pointing crowns) denominated by the numerals 258C, 244 and 258D, 244; and 4) a fourth row of one x-ray marker, which is located inside the distal tube denominated by the numeral 236, 244. (It will be appreciated that the first number in the sequence describes the position of the x-ray marker and the second number. 244, represents the fact that the item is an x-ray marker). As explained below, upon deploying the distal body 216 so that the two proximal, unattached distal-pointing crowns 258A, 244 and 258B, 244 are immediately distal to the clot 270, the surgeon interventionalist (i.e., operator of the distal body 216) detects the four rows of x-ray markers using x-ray radiation from a first vantage point and from a second vantage point that is offset from the first vantage point (e.g. 90 degrees). Next, the surgeon moves the distal body 216 proximally relative to the clot 270 and takes additional x-rays from the first and second vantage points. As explained in greater detail below, the surgeon uses the x-ray markers of the proximal and distal, unattached distal-pointing crowns, namely 258A, 244; 258B, 244; 258C, 244; and 258D, 244 (more specifically, the convergence or lack thereof of the proximal and distal, unattached distal-pointing crowns 258A, 244; 258B, 244; 258C, 244; and 258D, 244 as shown on the x-ray) to determine whether the clot 270 is located inside the distal body interior 222 or whether the clot 270 is collapsing the distal body 216.

Figure 15A:
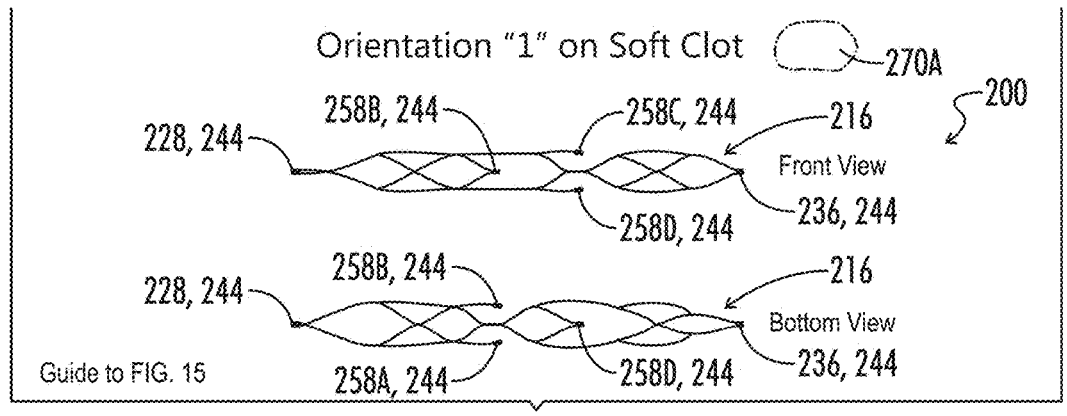
FIGS. 15A-G illustrate stepwise use of the distal body of FIG. 11 in retrieving a soft clot; the distal body is in Orientation 1.
Figure 15B:
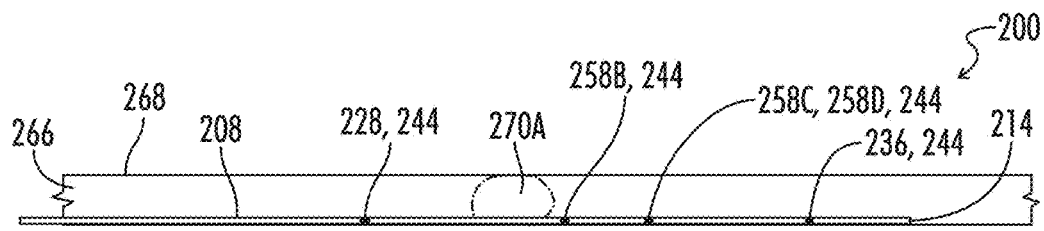
Figure 15C:
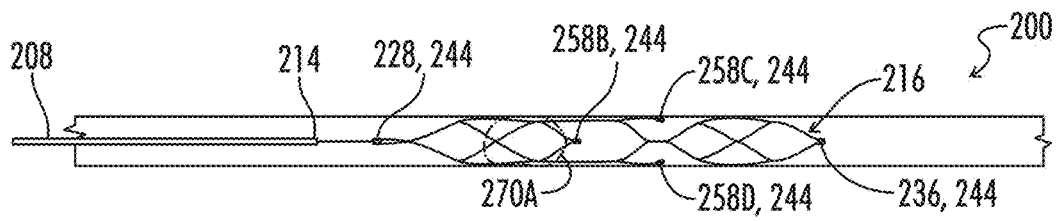
Figure 15D:
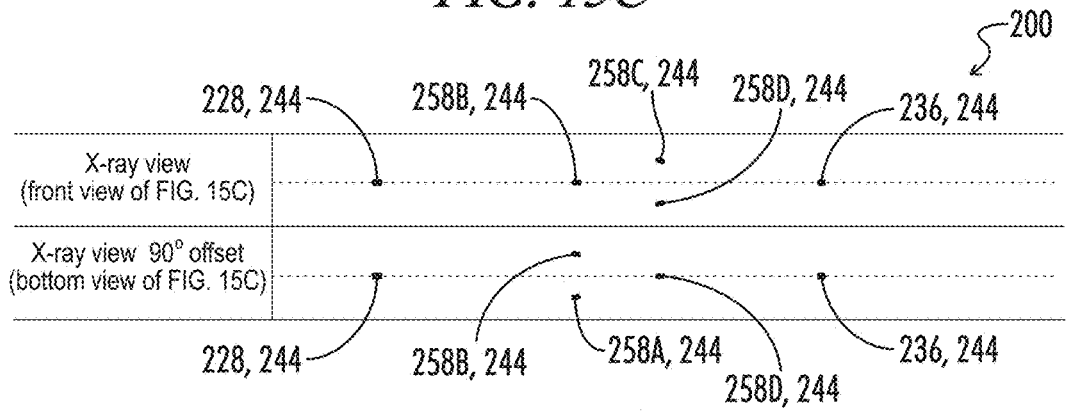
Figure 15E:
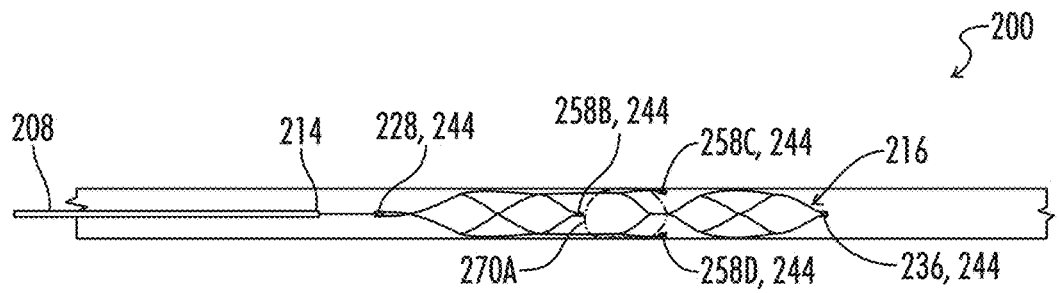
Figure 15F:
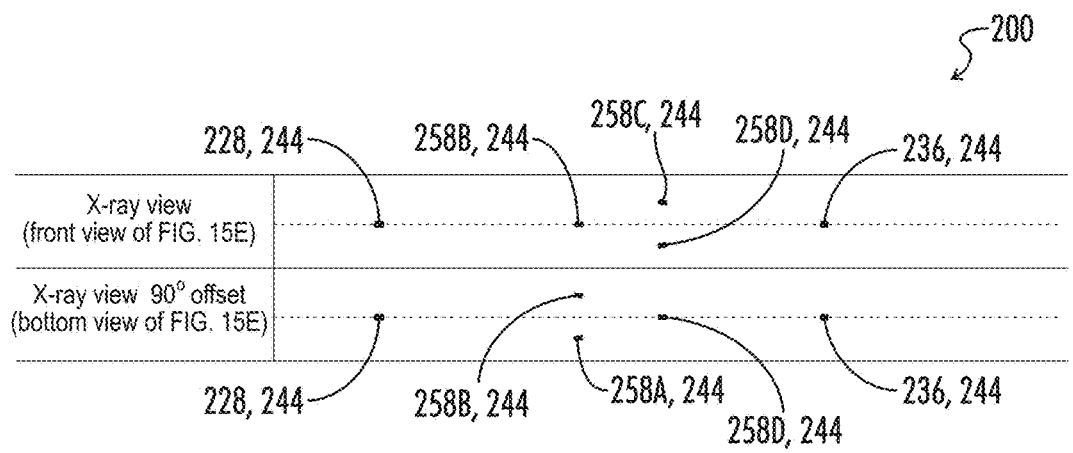
Figure 15G:
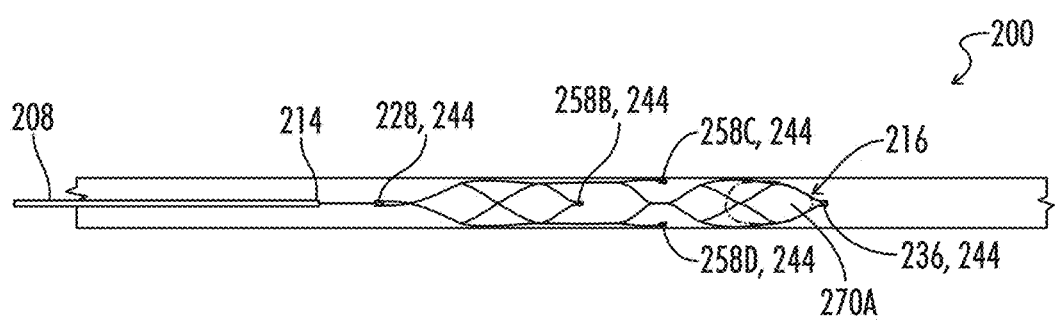

More specifically, FIGS. 15A-G illustrate stepwise use of the distal body 216 in retrieving a soft clot 270A in a human intracranial artery 266. (The distal body 216 in FIGS. 15A-15G is in Orientation 1). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 15B. The distal body 216 is then deployed from the delivery catheter 208 by moving the catheter 208 proximally. The soft clot 270A, which is unable to collapse the distal body 216, then enters the distal body interior 222. See FIG. 15C. However, at this time, the surgeon is unaware that the clot 270A has entered into the distal body interior 222. Thus, without moving the distal body 216, the surgeon irradiates the four rows of x-ray markers at a first vantage point (i.e., from the front of the distal body 216 in the orientation shown in FIGS. 15A-G; i.e., into the page). As shown in FIG. 15D, the first vantage point shows four rows of x-ray markers. The first row is a single point, which represents the x-ray marker located in the proximal tube 228, 244; the proximal tube x-ray marker 228, 244 always appears as a single point. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row 258C, 244 and 258D, 244 is hidden from view on the x-ray at this angle—rather, one marker 258C, 244 is located above the other marker 258D, 244—and as shown in FIG. 15C, the distal body 216 is not collapsed at the distal, unattached distal-pointing crowns 258C, 244 and 258D, 244. The fourth row is a single point, which represents the x-ray marker located in the distal tube 236, 244; the distal tube x-ray marker 236, 244 always appears as a single point. Without moving the distal body 216, the surgeon then irradiates the four rows of x-ray markers from a second vantage point 90 degrees offset from the first vantage point (i.e., from the bottom of the distal body 216 in the orientation shown in FIG. 15A). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker 258A, 244 and 258B, 244 in the second row is hidden from view on the x-ray at this offset angle—rather, one marker 258B, 244 is located above the other marker 258A, 244—and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the x-ray markers at the second row 258A, 244 and 258B, 244 nor the x-ray markers at the third row 258C, 244 and 258D, 244 (i.e., the x-ray markers at both the proximal and distal unattached distal pointing-crowns) have converged. As shown in FIG. 15E, the surgeon then moves the distal body 216 proximally relative to the soft clot 270A so that the distal, unattached distal-pointing crowns 258C, 244 and 258D, 244 are immediately distal to the clot 270A and then the surgeon irradiates the four rows of x-ray markers again from the first vantage point and the second vantage point. As shown in FIG. 15F, the results are the same as FIG. 15D. With the results from FIGS. 15D and 15F, the surgeon concludes that neither x-ray markers at the second row 258A, 244 and 258B, 244 nor the x-ray markers at the third row 258C, 244 and 258D, 244 (i.e., the x-ray markers at both the proximal and distal unattached distal pointing-crowns) converged at either the original position of the distal body 216 (FIGS. 15C and 15D) or the position after moving the distal body 216 proximally (FIGS. 15E and 15F), and, thus, the distal body 216 was expanded in the vessel 266 in both positions. Thus, the surgeon concludes that the clot is a soft clot 270A that has entered into the distal body interior 222 and the surgeon removes the distal body 216 and the soft clot 270A, captured by the distal body 216, by moving the distal body 216 proximally out of the vessel 266, as shown in FIG. 15G.

Figure 16A:
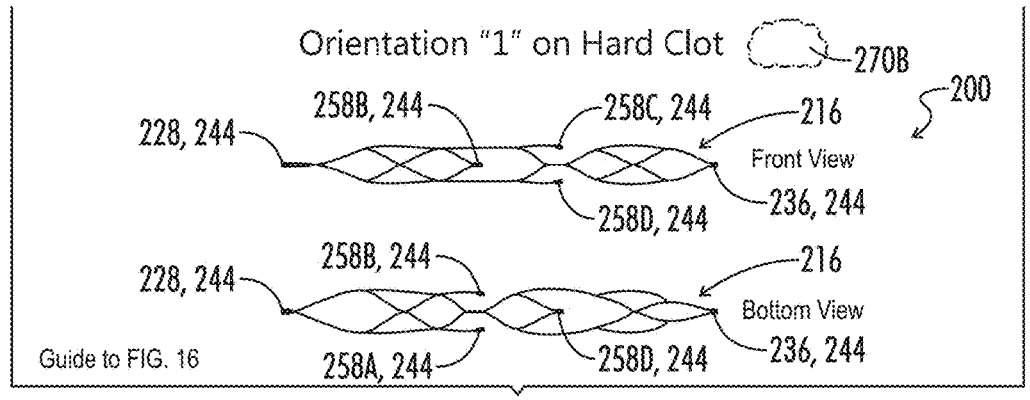
FIGS. 16A-H illustrate stepwise use of the distal body of FIG. 11 in retrieving a hard clot; the distal body is in Orientation 1.
Figure 16B:
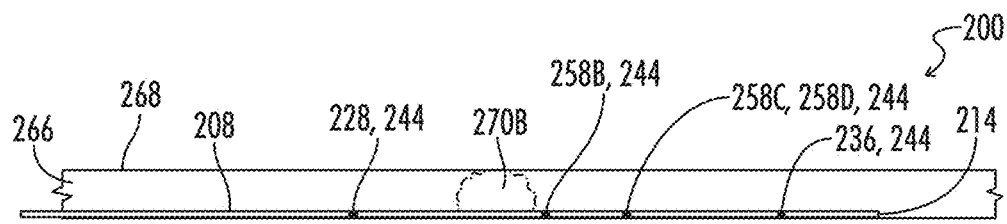
Figure 16C:
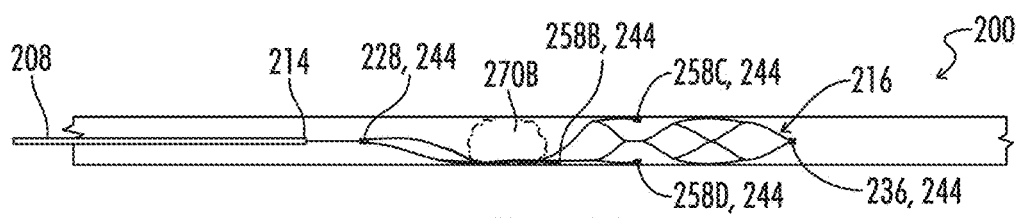
Figure 16D:
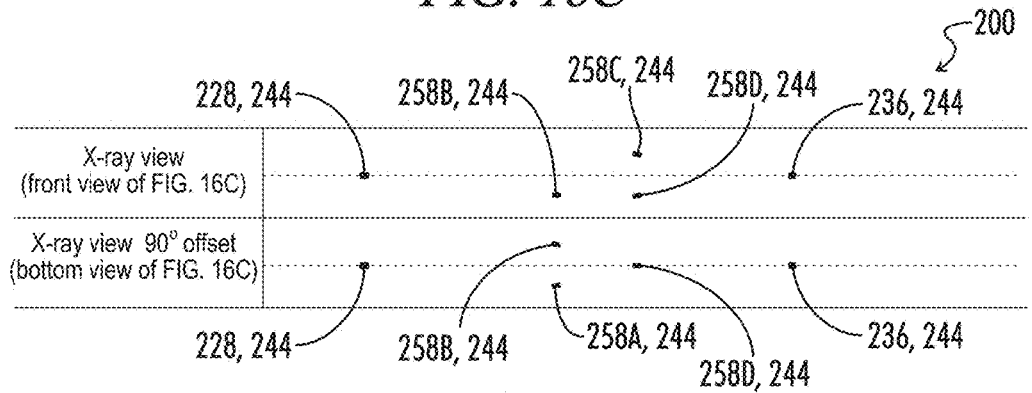
Figure 16E:
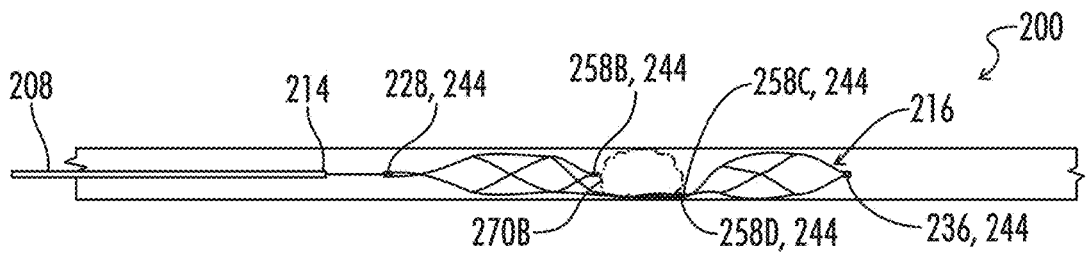
Figure 16F:
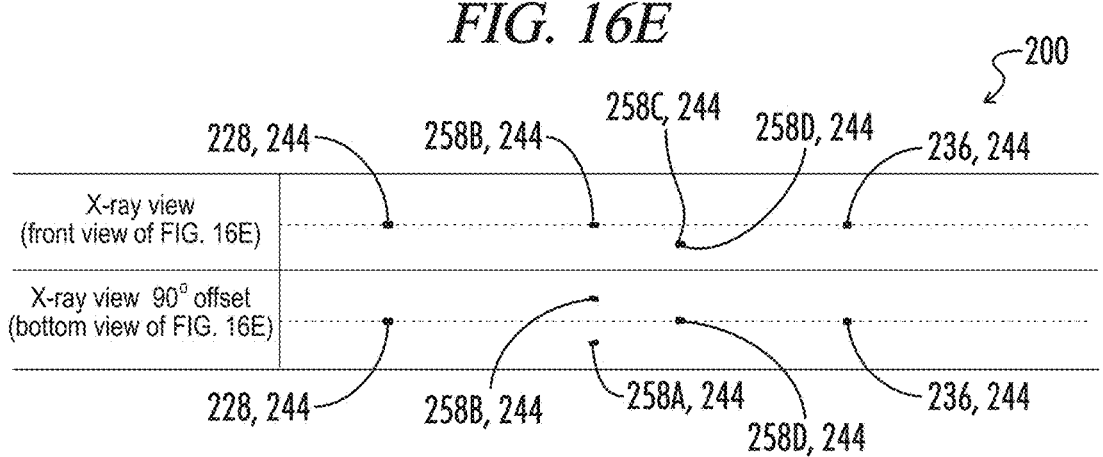
Figure 16G:
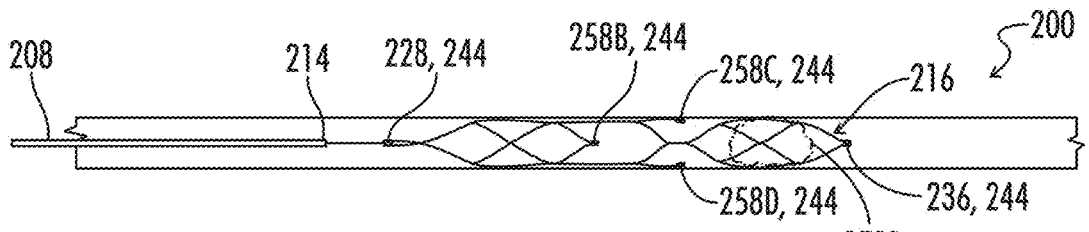
Figure 16H:
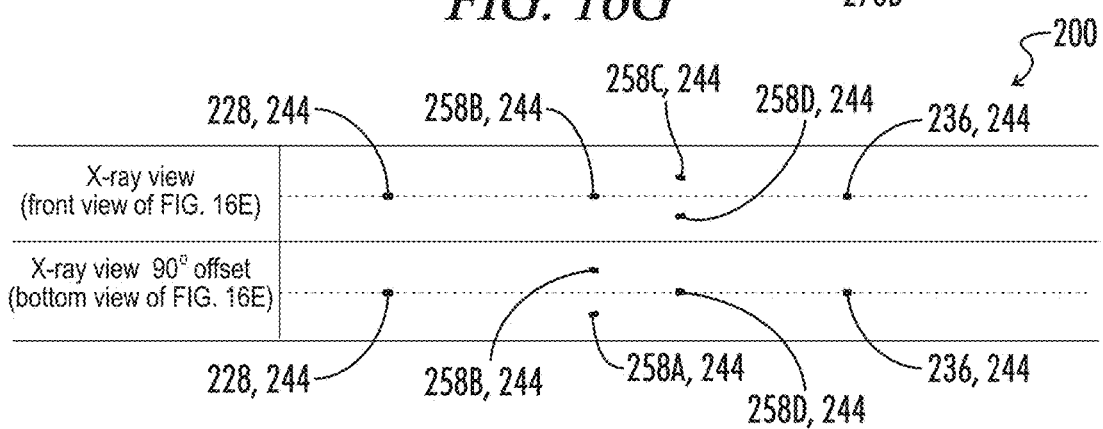

FIGS. 16A-H illustrate stepwise use of the distal body 216 in retrieving a hard clot 270B in a human intracranial artery 266. (In FIGS. 16A-H, the distal body 216 is in Orientation 1). First, as always, the surgeon determines the location of the clot 270B in the vessel 266 using, for example, a contrast dye injected proximal and distal to the clot 270B. Next, the delivery catheter 208, which is enveloping the distal body 216, is positioned in the blood vessel 266 so that the two proximal, unattached distal-pointing crowns 258A and 258B are immediately distal to the clot 270B. See FIG. 16B. The distal body 216 is then deployed from the delivery catheter 208 by moving the catheter 208 proximally. The hard clot 270B, which is located above the distal body 216, collapses the distal body 216, as shown in FIG. 16C. However, at this time, the surgeon is unaware that the clot 270B has collapsed the distal body 216. Thus, without moving the distal body 216, the surgeon irradiates the x-ray markers at a first vantage point (i.e., from the front of the distal body 216; i.e., into the page). As shown in FIG. 16D, the first vantage point shows four rows of x-ray markers. The first row is, as always, a single point, representing the x-ray marker located in the proximal tube—i.e., 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row is hidden from view on the x-ray at this angle—rather, one marker 258C, 244 is located above the other marker 258D, 244—and as shown in FIG. 16C, the distal body 216 is not collapsed at the distal, unattached distal-pointing crowns 258C, 244 and 258D, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has two points, which represents the two x-ray markers located at the proximal, unattached distal-pointing crowns 258A, 244 and 258B, 244; the reason that this second row of markers shows up as two points is that neither marker in the second row is hidden from view on the x-ray at this offset angle—rather, one marker 258B, 244 is located above the other marker 258A, 244—and although the distal body 216 is collapsed at the proximal, unattached distal-pointing crowns as shown in FIG. 16C, the second row of x-ray markers have not converged because the clot 270B is on top of the second row of x-ray markers. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the second row 258A, 244 and 258B, 244 nor the third row 258C, 244 and 258D, 244 of x-ray markers (i.e., the x-ray markers at both the proximal and distal unattached distal pointing-crowns) has converged. As shown in FIG. 16E, the surgeon then moves the distal body 216 proximally so that the distal, unattached distal-pointing crowns 258C, 244 and 258D, 244 are immediately distal to the clot 270B and the surgeon then irradiates the x-markers again from the first vantage point. As shown in FIG. 16F, the first row is, as always, a single point, representing the x-ray marker located in the proximal tube 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has only one point because the clot 270B, which is on top of the third row of x-ray markers 258C, 244 and 258D, 244 (i.e., the markers at the distal, unattached distal-pointing crowns), has pushed the third row of x-ray markers 258C, 244 and 258D, 244 together. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker in the second row is hidden from view on the x-ray at this offset angle and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the bottom x-ray marker of the third row 258D, 244 is directly in front of the top x-ray marker of the third row 258C, 244, and thus, the top x-ray marker of the third row 258C, 244 is hidden from view. The fourth row is, as always, a single point, which represents the x-ray marker located in the distal tube 236, 244. Knowing that the distal, unattached distal-pointing crowns 258C, 244 and 258D, 244 have converged as shown in FIG. 16F, the surgeon moves the distal body 216 proximally and the hard clot 270B falls into the distal body interior 222 in the enlarged cell/drop zone 262C immediately distal to the top, distal, unattached distal-pointing crown 258C. See FIG. 16G. To confirm that the hard clot 270B has entered the distal body interior 222, the surgeon takes x-rays from the first and second vantage points. The results are shown in FIG. 16H. As compared to 16F, the front x-ray view of FIG. 16H shows that the distal, unattached distal-pointing crowns 258C, 244 and 258D, 244 are not converged, and, thus, the surgeon concludes that the hard clot 270B has entered the distal body interior 222. The surgeon then removes the distal body 216 and the hard clot 270B, captured by the distal body 216, by moving the distal body 216 proximally out of the vessel 266.

Figure 17A:
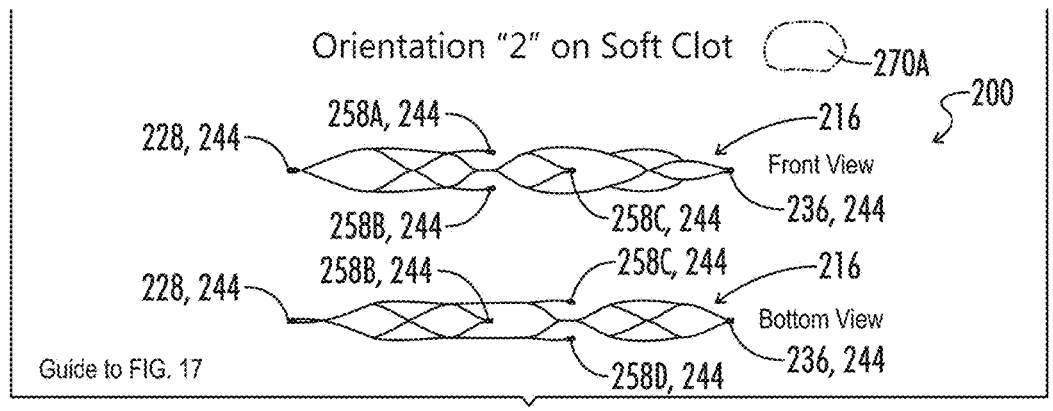
FIGS. 17A-G illustrate stepwise use of the distal body of FIG. 11 in retrieving a soft clot; the distal body is in Orientation 2.
Figure 17B:
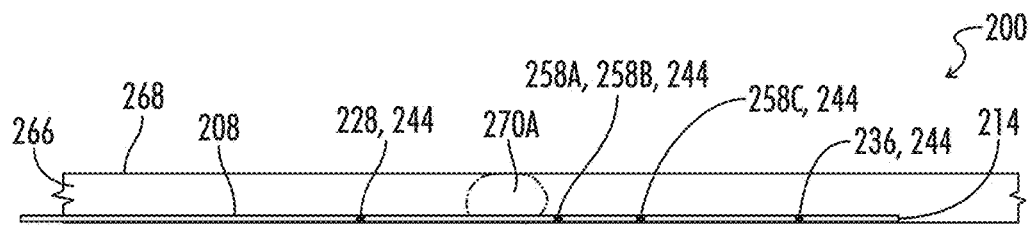
Figure 17C:
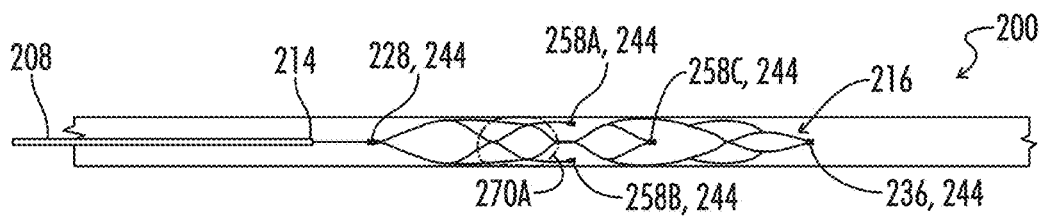
Figure 17D:
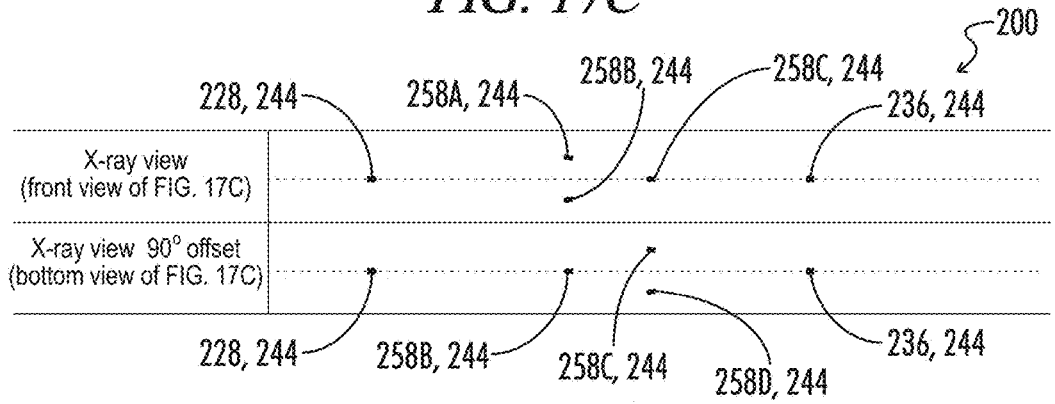
Figure 17E:
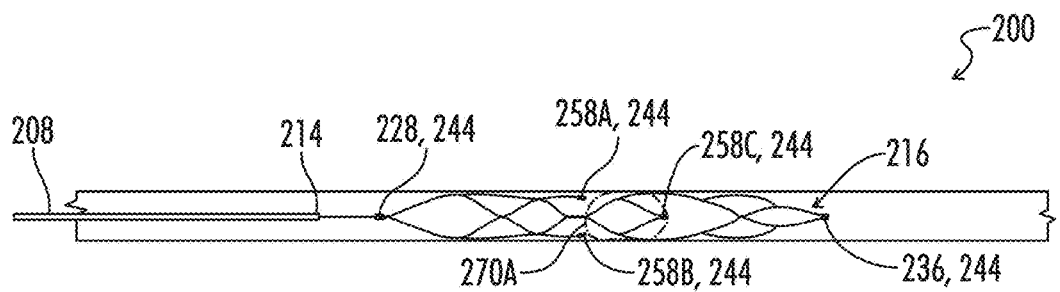
Figure 17F:
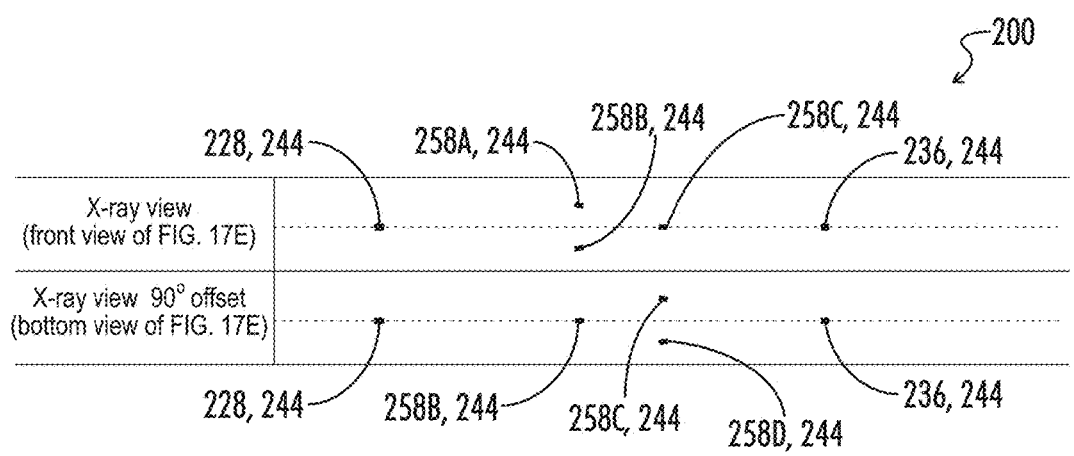
Figure 17G:
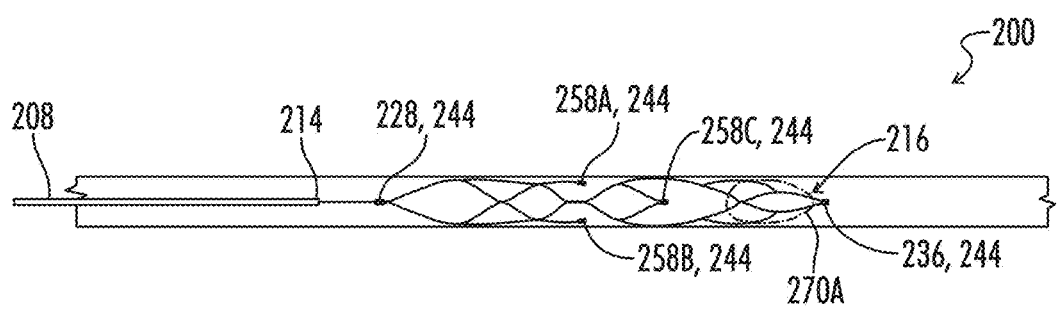

FIGS. 17A-G illustrate stepwise use of the distal body 216 in retrieving a soft clot 270A in a human intracranial artery 266. (In FIGS. 17A-G, the distal body 216 is in Orientation 2). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 17B. The distal body 216 is then deployed from the catheter 208 by moving the catheter 208 proximally. The soft clot 270A, which is unable to collapse the distal body 216, then enters the distal body interior 222. See FIG. 17C. However, at this time, the surgeon is unaware that the clot 270A has entered into the distal body interior 222. Thus, without moving the distal body 216, the surgeon irradiates the x-ray markers at a first vantage point (i.e., from the front of the distal body; into the page). As shown in FIG. 17D, the first vantage point shows four rows of x-ray markers. The first row is, as always, a single point, representing the x-ray marker located in the proximal tube 228, 244. The second row has two points, which represents the two x-ray markers located at the proximal, unattached distal-pointing crowns 258A, 244 and 258B, 244; the reason that this second row of markers has two points is that neither marker in the second row is hidden from view on the x-ray at this angle—rather, one marker 258A, 244 is located above the other marker 258B, 244—and as shown in FIG. 17C, the distal body 216 is not collapsed at the proximal, unattached distal-pointing crowns 258A, 244 and 258B, 244. The third row has a single point, which represents the x-ray marker located at the front (in Orientation 2), distal, unattached distal-pointing crown 258C, 244; the reason that this third row of markers is a single point is that the rear (in Orientation 2) x-ray marker 258D, 244 of the third row is hidden from view because it is directly behind the front x-ray marker 258C, 244 of the third row. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body, as shown in this view). As shown, the first row is, as always, a single point, which represents the x-ray marker located in the proximal tube 228, 244. The second row is a single point, which represents the x-ray marker located at the bottom (in Orientation 2), proximal, unattached distal-pointing crown 258B, 244; the reason that this second row of markers is a single point is that the top (in Orientation 2) x-ray marker of the second row 258A, 244 is directly behind the bottom x-ray marker of the second row 258B, 244, and thus, hidden from view. The third row has two points, which represents the two x-ray markers located at the distal, unattached distal-pointing crowns 258C, 244 and 258D, 244; the reason that this third row of markers shows up as two points is that neither marker in the third row is hidden from view on the x-ray at this offset angle and the distal body 216 is not collapsed at the distal, unattached distal-pointing crowns 258C, 244 and 258D, 244. The fourth row is, as always, a single point, which represents the x-ray marker located in the distal tube 236, 244. The surgeon, thus, concludes that neither the second row 258A, 244 and 258B, 244 nor the third row of x-ray markers 258C, 244 and 258D, 244 (i.e., the x-ray markers at both the proximal and distal unattached distal pointing-crowns) has converged. As shown in FIG. 17E, the surgeon then moves the distal body 216 proximally relative to the clot 270A so that the distal, unattached distal-pointing crowns 258C, 244 and 258D, 244 are immediately distal to the clot 270A and then the surgeon irradiates the x-markers again from the first vantage point and the second vantage point. As shown in FIG. 17F, the results are the same as FIG. 17D. With the results from FIGS. 17D and 17F, the surgeon concludes that neither the second row 258A, 244 and 258B, 244 nor the third row of x-ray markers 258C, 244 and 258D, 244 (i.e., the x-ray markers at both the proximal and distal unattached distal pointing-crowns) were converged at either the original position of the distal body 216 (FIGS. 17C and 17D) or the position after moving the distal body 216 proximally (FIGS. 17E and 17F), and, thus, the distal body 216 was expanded in the vessel 266 in both positions. Thus, the surgeon concludes that the clot 270A is a soft clot 270A that has entered into the distal body interior 222 and the surgeon removes the distal body 216 and the soft clot 270A, captured by the distal body 216, by moving the distal body 216 proximally out of the vessel 266, as shown in FIG. 17G.

Figure 18A:
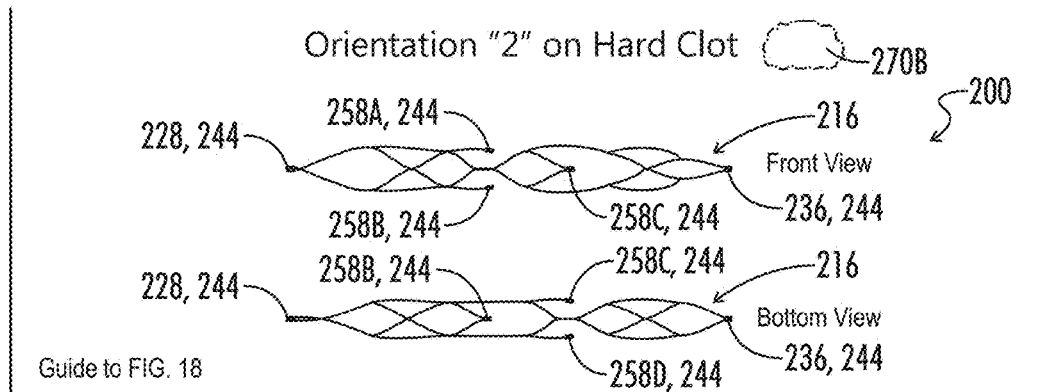
FIGS. 18A-G illustrate stepwise use of the distal body of FIG. 11 in retrieving a hard clot; the distal body is in Orientation 2.
Figure 18B:
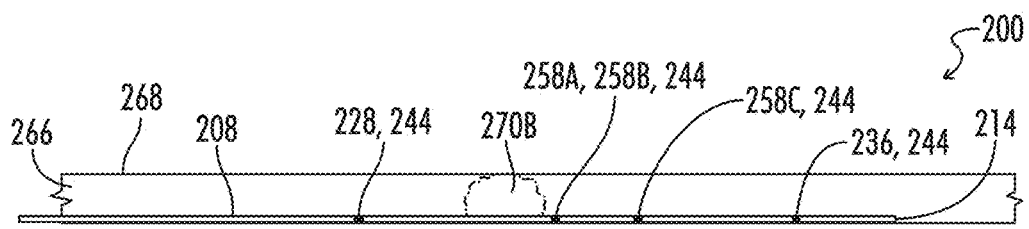
Figure 18C:
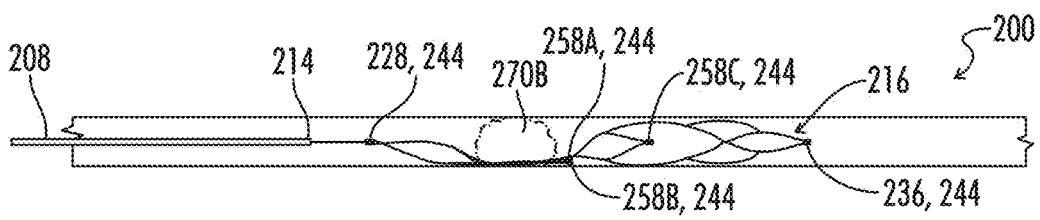
Figure 18D:
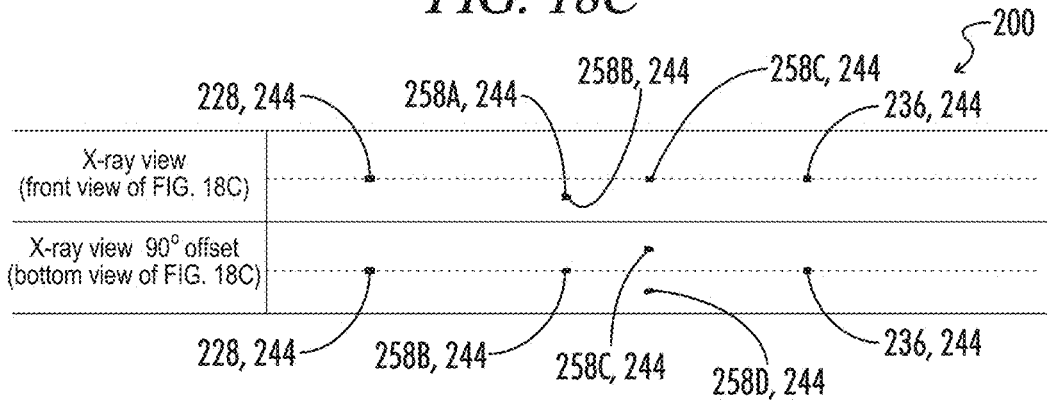
Figure 18E:
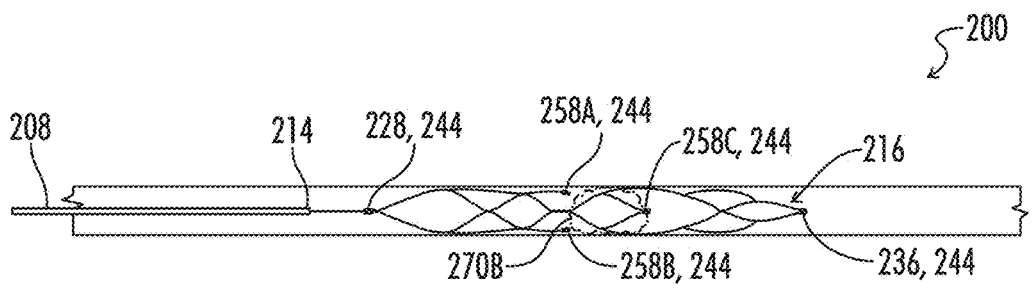
Figure 18F:
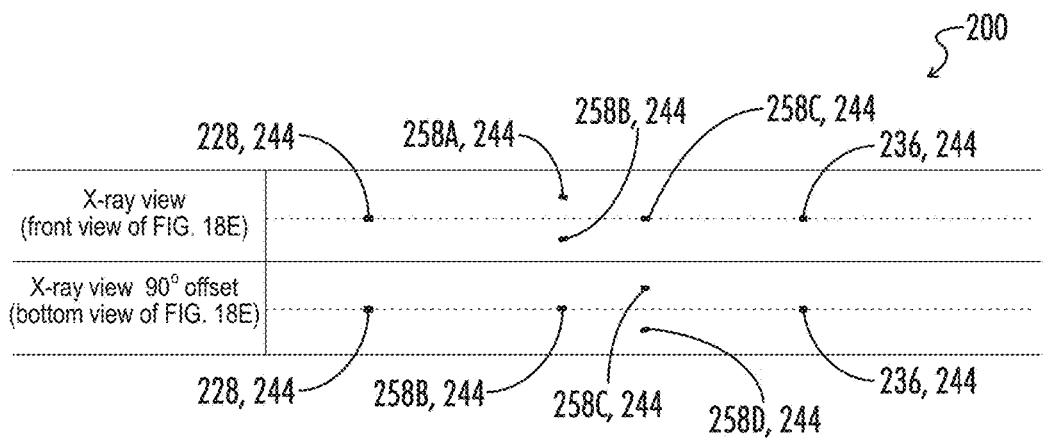
Figure 18G:
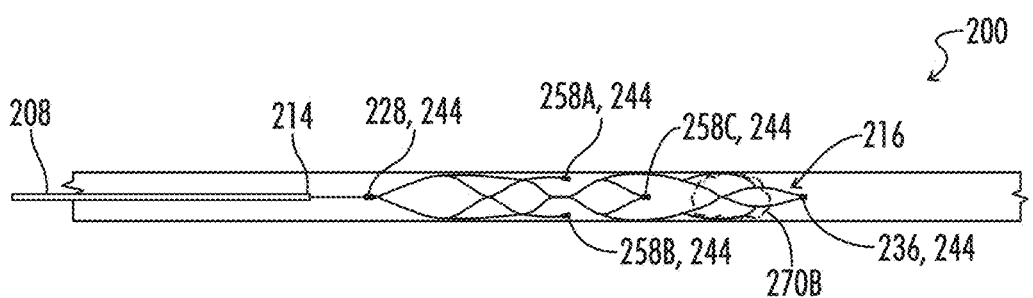

FIGS. 18A-G illustrate stepwise use of the distal body 216 in retrieving a hard clot 270B in a human intracranial artery 266. (In FIGS. 18A-G, the distal body 216 is in Orientation 2). (As described below, the primary differences between FIGS. 18A-G and FIGS. 16A-G is that the clot 270B enters the distal body interior 222 in an enlarged cell/drop zone 262A immediately distal to one of the proximal, unattached distal-pointing crowns 258A in FIGS. 18A-G, as compared to FIGS. 16A-G where the clot 270B enters the distal body interior 222 in an enlarged cell/drop zone 262C immediately distal to one of the distal, unattached distal-pointing crowns 258C). First, as always, the surgeon determines the location of the clot 270B in the vessel 266 using, for example, a contrast dye injected proximal and distal to the clot 270B. Next, the delivery catheter 208, which is enveloping the distal body 216, is positioned in the blood vessel 266 so that the two proximal, unattached distal-pointing crowns 258A and 258B are immediately distal to the clot 270B. See FIG. 18B. The distal body 216 is then deployed from the catheter 208 by moving the catheter 208 proximally. The hard clot 270B, which is located above the distal body 216, collapses the distal body 216, as shown in FIG. 18C. However, at this time, the surgeon is unaware that the clot 270B has collapsed the distal body 216. Thus, without moving the distal body 216, the surgeon irradiates the x-ray markers at a first vantage point (i.e., from the front of the distal body in Orientation 2; into the page). As shown in FIG. 18D, the first vantage point shows four rows of x-ray markers. The first row is, as always, a single point, representing the x-ray marker located in the proximal tube 228, 244. The second row has only one point because the clot 270B, which is on top of the second row of x-ray markers 258A, 244 and 258B, 244 (i.e., the markers at the proximal, unattached distal-pointing crowns), has pushed them together. The third row has only one point, which represents the x-ray marker located at the front (in Orientation 2), proximal, unattached distal-pointing crown 258C, 244; the reason that this third row of markers is a single point is that the rear (in this view) x-ray marker of the third row 258D, 244 is hidden from view because it is directly behind the front x-ray marker of the third row 258C, 244. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the top (in Orientation 2) x-ray marker of the second row 258A, 244 is located behind the bottom (in Orientation 2) x-ray marker 258B, 244 and thus, the top x-ray marker of the second row 258A, 244 is hidden from view. The third row has two points, which represents the x-ray markers located at the distal, unattached distal-pointing crowns 258C, 244 and 258D, 244; in this x-ray view neither of the x-ray markers of the third row is hidden view. The fourth row is, as always, a single point, which represents the x-ray marker located in the distal tube 236, 244. The surgeon, thus, concludes that the second row of x-ray markers 258A, 244 and 258B, 244 (i.e., the x-ray markers at the proximal, unattached distal pointing-crowns) has converged. As shown in FIG. 18E, the surgeon then moves the distal body 216 proximally so that the distal, unattached distal-pointing crowns 258C, 244 and 258D, 244 are immediately distal to the clot 270B. Unbeknownst to the surgeon, the clot 270B enters the distal body interior 222 immediately distal to the top (in Orientation 2), proximal unattached distal-pointing crown 258A and the distal body 216 is no longer collapsed. The surgeon then irradiates the x-markers again from the first vantage point. As shown in FIG. 18F, the first row is, as always, a single point, representing the x-ray marker located in the proximal tube 228, 244. The second row has two x-ray markers because the distal body 216 is not collapsed and neither the top (in Orientation 2) 258A, 244 nor the bottom 258B, 244 (in Orientation 2) x-ray marker of the second row (i.e., the marker at the proximal, unattached distal-pointing crowns) is hidden from view. The third row has only one point because the rear (in Orientation 2), distal unattached distal-pointing crown 258D, 244 is hidden behind the front (in Orientation 2), distal, unattached distal pointing-crown 258C, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the x-ray marker at the top (in Orientation 2), proximal, unattached distal-pointing crown 258A, 244 is hidden behind the bottom (in Orientation 2), proximal, unattached-distal pointing crown 258B, 244. The third row has two points because neither the front nor the rear x-ray markers at the distal, unattached, distal-pointing crowns 258C, 244 and 258D, 244 is hidden from view. The fourth row is, as always, a single point, which represents the x-ray marker located in the distal tube 236, 244. Based on the information from FIGS. 18D and 18F, the surgeon concludes that the clot 270B has entered into the distal body interior 222. The surgeon then removes the distal body 216 and the hard clot 270B, captured by the distal body 216, by moving the distal body 216 proximally out of the vessel 266, as shown in FIG. 18G. Upon comparing FIGS. 16A-G and FIGS. 18A-G it will be appreciated that the orientation of the enlarged cells/drop zone 262A-D relative to the orientation of a hard clot 270B determine which enlarged cell/drop zone 262A, 262B, 262C, or 262D, the hard clot 270 enters the distal body interior 222 through. For example, in FIG. 16C, the hard clot 270B is located above the distal body 216, and thus, the hard clot 270B must enter through the enlarged cell/drop zone located at the top of the distal body, which in the orientation of the distal body shown in FIGS. 16A-G, is the enlarged cell/drop zone 262C immediately distal to the top, distal, unattached, distal-pointing crown 258C. In FIG. 18C, the hard clot 270B is again located above the distal body and, thus, the hard clot 270B must enter through the enlarged cell/drop zone located at the top of the distal body. However, in FIG. 18C, the enlarged cell/drop zone located at the top of the distal body 216, in the orientation of the distal body 216 shown in FIGS. 18A-G, is the enlarged cell/drop zone 262A immediately distal to the top, proximal, unattached, distal-pointing crown 258A.

Figure 19A:
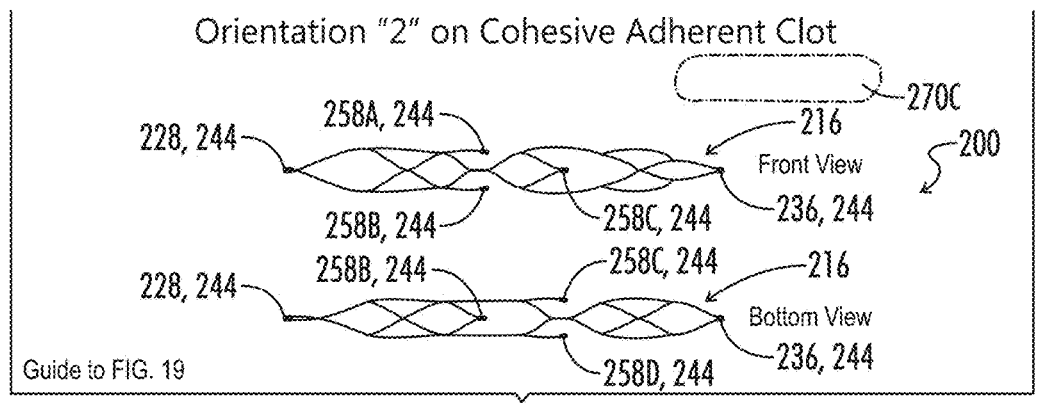
FIGS. 19A-N illustrate stepwise use of the distal body of FIG. 11 in retrieving a deformable, cohesive adherent clot; the distal body is in Orientation 2.
Figure 19B:
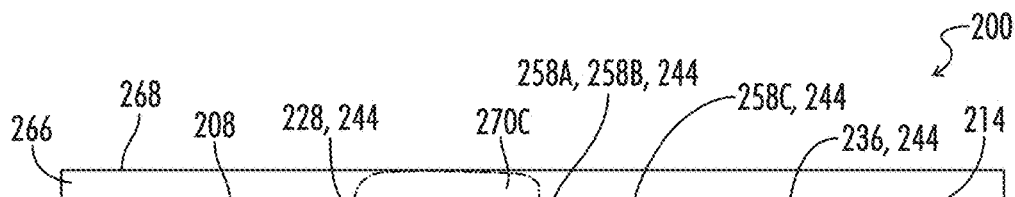
Figure 19C:
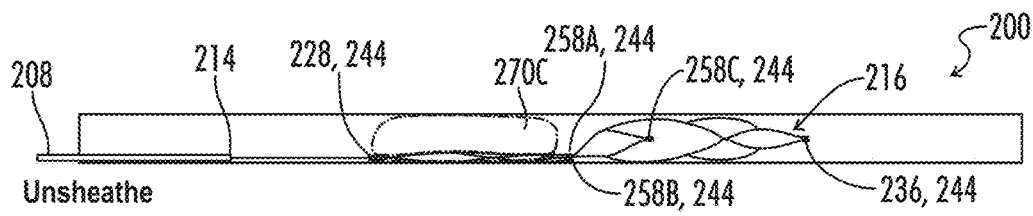
Figure 19D:
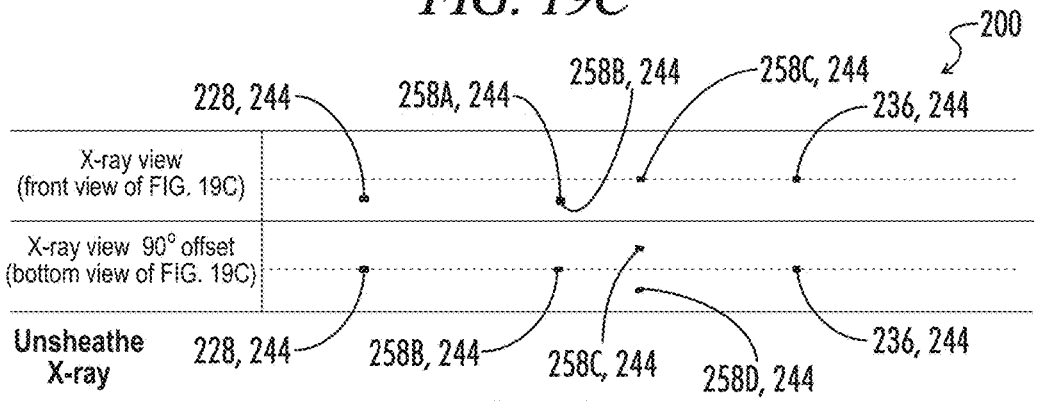
Figure 19E:
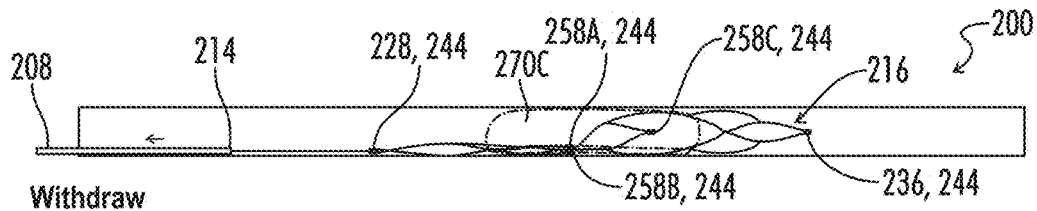
Figure 19F:
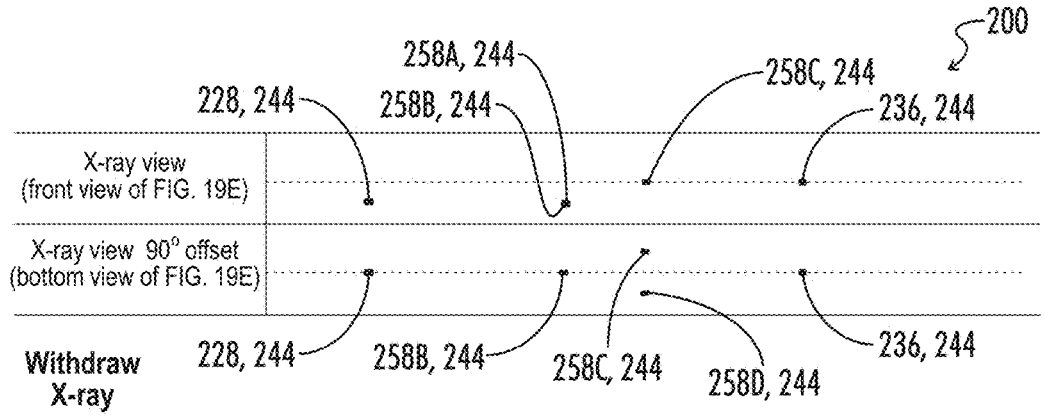
Figure 19G:
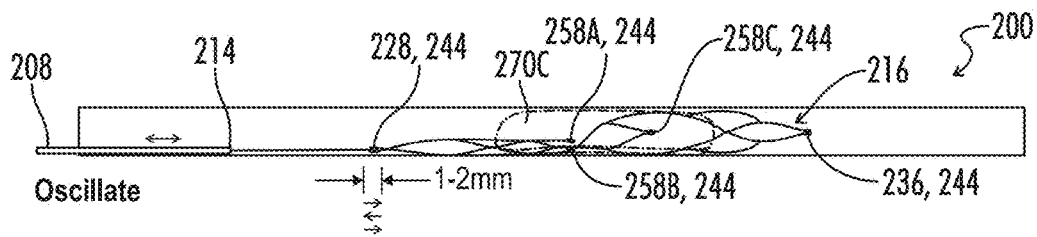
Figure 19H:
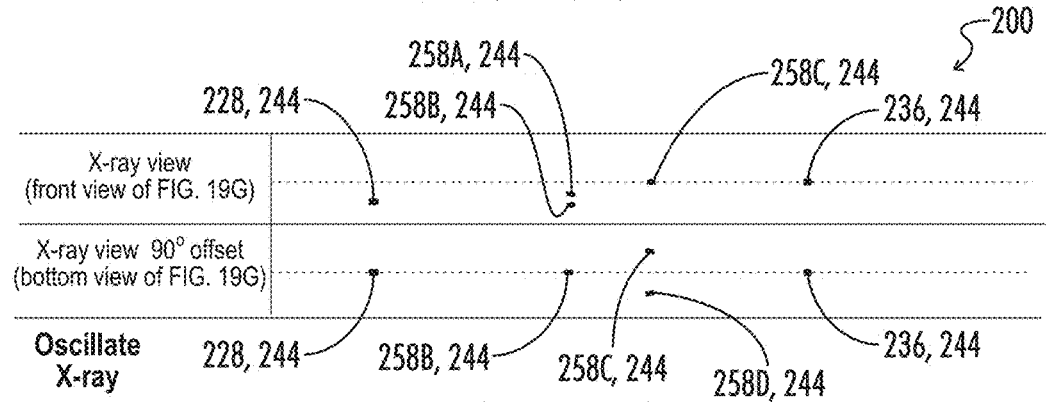
Figure 19I:
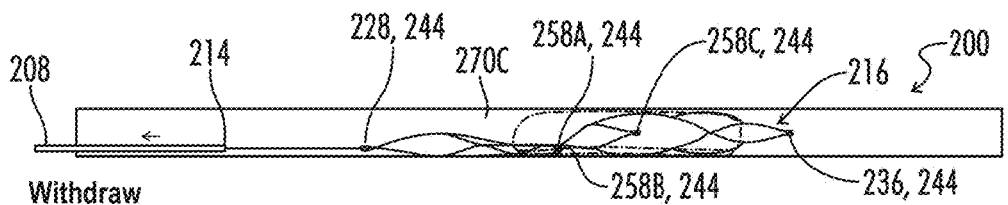
Figure 19J:
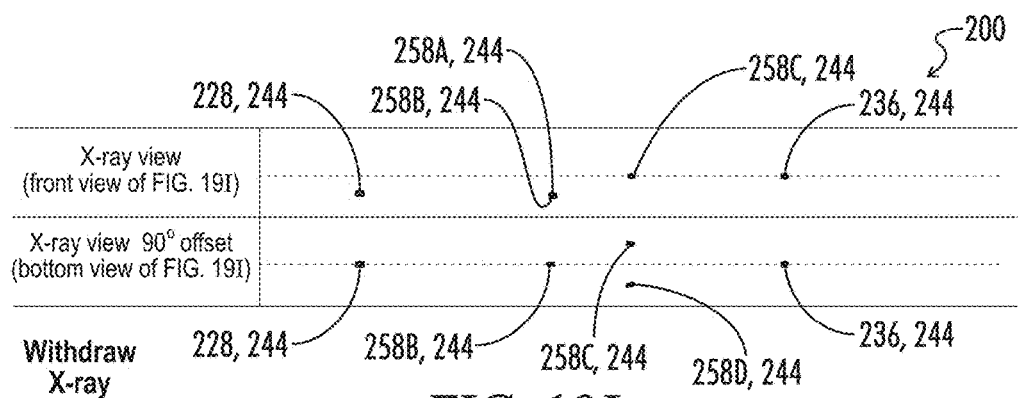
Figure 19K:
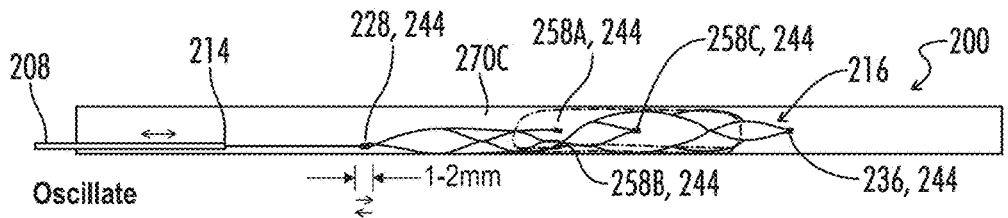
Figure 19L:
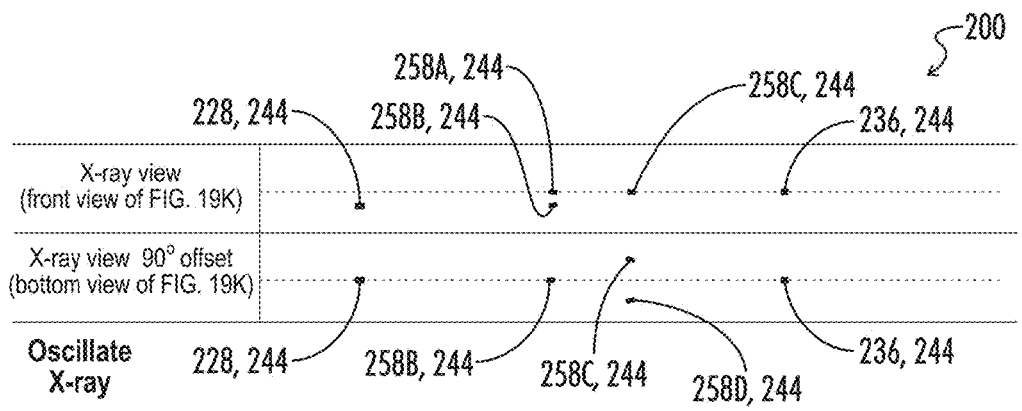
Figure 19M:
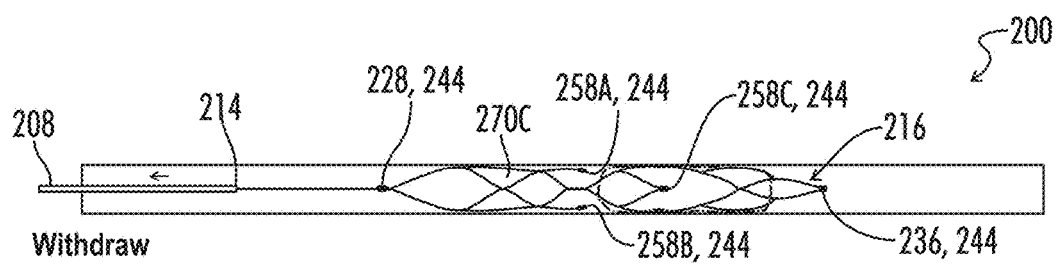
Figure 19N:
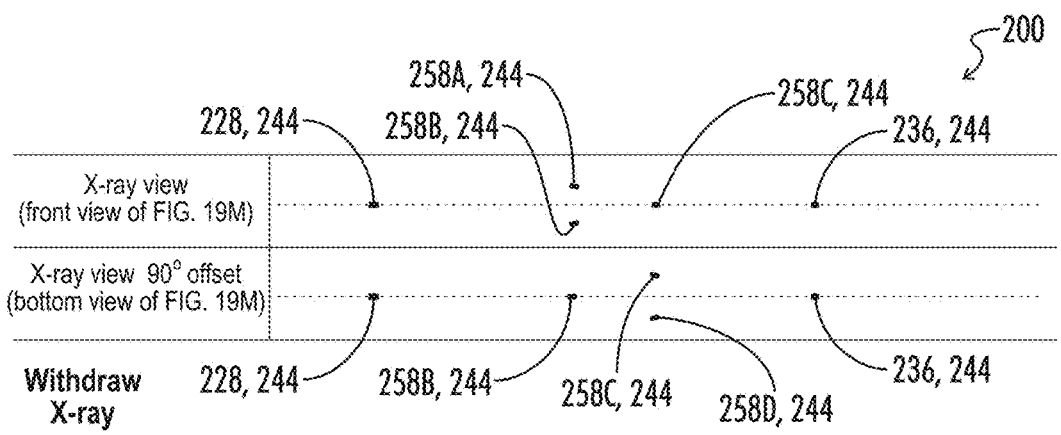

FIGS. 19A-N illustrate stepwise use of the distal body 216 in retrieving a deformable cohesive, adherent clot 270C—i.e., a clot that is difficult to break up and is tightly adhered to the vessel wall 268—in a human intracranial artery 266. (In FIGS. 19A-N, the distal body 216 is in Orientation 2). First, as always, the surgeon determines the location of the clot 270C in the vessel 266 using, for example, a contrast dye injected proximal and distal to the clot 270C. Next, the delivery catheter 208, which is enveloping the distal body 216, is positioned in the blood vessel 266 so that the two proximal, unattached distal-pointing crowns 258A and 258B are immediately distal to the clot 270C. See FIG. 19B. The distal body 216 is then deployed from the catheter 208 by moving the catheter 208 proximally. The deformable, cohesive adherent clot 270C, which is located above the distal body 216, collapses the distal body 216, as shown in FIG. 19C. However, at this time, the surgeon is unaware that the clot 270C has collapsed the distal body 216. Thus, without moving the distal body 216, the surgeon irradiates the x-ray markers at a first vantage point (i.e., from the front of the distal body; i.e., into the page). As shown in FIG. 19D, the first vantage point shows four rows of x-ray markers. The first row is, as always, a single point, representing the x-ray marker located in the proximal tube 228, 244. The second row has a single point, corresponding to the top (in Orientation 2) and bottom (in Orientation 2), proximal, unattached distal-pointing crowns 258A, 244 and 258B, 244, which have converged because the clot 270C is collapsing the distal body 216. The third row has a single point, which represents the x-ray marker located at the front (in Orientation 2), distal, unattached distal-pointing crown 258C, 244; the x-ray marker located at the rear, distal, unattached distal-pointing crown 258D, 244 is hidden from view. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has a single point, which corresponds to the bottom (in Orientation 2), proximal, unattached distal-pointing crown 258B, 244; the top (in Orientation 2), proximal, unattached distal-pointing crown 258A, 244 is located behind the bottom, proximal, unattached distal-pointing crown 258B, 244 and hidden from view. The third row has two points, which correspond to the front (in Orientation 2) 258C, 244 and rear 258D, 244 (in Orientation 2), distal, unattached distal-pointing crowns, neither of which is blocked in this view. The fourth row is, as always, a single point, which represents the x-ray marker located in the distal tube 236, 244. As shown in FIG. 19E, the surgeon then moves the distal body 216 proximally (i.e., slightly withdraws the distal body 216). The surgeon then irradiates the x-markers again from the first and second vantage points. As shown in FIG. 19F, the results are exactly the same as in FIG. 19D. Based on the observation that the proximal, unattached distal-pointing crowns 258A, 244 and 258B, 244 have converged at both the original position (FIGS. 19C and 19D in which the proximal, unattached distal-pointing crowns 258A, 244 and 258B, 244 are immediately distal to the clot 270C) and the second position (FIGS. 19E and 19F), the surgeon concludes that the clot 270C is a deformable cohesive, adherent clot 270C. The surgeon then oscillates the distal body 216 proximally and distally a small distance (e.g., about 1 mm to about 2 mm) in the vessel 266, and the clot 270C begins to enter the distal body 216, as shown in FIG. 19G. The surgeon then irradiates the x-markers again from the first and second vantage points. As shown in FIG. 19H, the results are exactly the same as in FIG. 19D and FIG. 19F except that the second row of markers 258A, 244 and 258B, 244 (at the proximal, unattached distal-pointing crowns) are beginning to move apart. The surgeon then moves the distal body 216 proximally again, as shown in FIG. 19I. The surgeon then irradiates the x-markers again from the first and second vantage points. As shown in FIG. 19J, the results are exactly the same as in FIGS. 19D and 19F, as the clot 270C has caused the second row of markers 258A, 244 and 258B, 244 to re-converge. The surgeon then oscillates the distal body 216 proximally and distally a small distance (e.g., about 1 mm to about 2 mm) in the vessel 266, and the clot 270C begins to further enter the distal body interior 222, as shown in FIG. 19K. The surgeon then irradiates the x-markers again from the first and second vantage points. As shown in FIG. 19L, the results are the same as in FIG. 19H. The surgeon then moves the distal body 216 again proximally, and, instead of collapsing the second row of markers 258A, 244 and 258B, 244, the clot 270C fully enters the distal body interior 222, as shown in FIG. 19M. The surgeon then irradiates the x-markers again from the first and second vantage points. As shown in FIG. 19N, the results show that the second row of markers 258A, 244 and 258B, 244 (at the proximal, unattached distal-pointing crowns) have moved apart. Satisfied that the x-ray markers in the second row 258A, 244 and 258B, 244 (at the proximal, unattached distal-pointing crowns) are sufficiently far apart and that the x-ray markers in the third row (at the distal, unattached distal-pointing crowns) 258C, 244 and 258D, 244 have stayed far apart, the surgeon concludes that the deformable cohesive, adherent clot 270C has been sufficiently captured by the distal body 216 and the surgeon then removes the distal body 216 and the clot 270C, captured by the distal body 216, by moving the distal body 216 proximally out of the vessel 266.

Several observations can be made from FIGS. 15-19, as indicated above. For example, the x-ray markers at the proximal and distal, unattached distal-pointing crowns 258A-D, 244 provide the surgeon feedback concerning the interaction between the distal body 216 and the clot 270 in the blood vessel 266. In addition, the guiding principle of a soft clot 270A is that the soft clot 270A does not collapse the distal body 216, and thus, x-ray markers at the proximal and distal, unattached distal-pointing crowns 258A-D, 244 always appear as two points except when a marker is hidden behind another marker (due to the view). When it comes to a hard clot 270B, the hard clot 270B is generally able to enter the distal body interior 222 without needing to oscillate the distal body 216 proximally and distally (unlike a deformable cohesive, adherent clot 270C). However, to capture the hard clot 270B, the hard clot 270B must be oriented properly relative to the enlarged cell/drop zones 262A, 262B, 262C, or 262D. (This is the reason that the distal body 216 has four enlarged cells/drop zones: one enlarged cells/drop zone at 0 degrees 262B, one enlarged cells/drop zone at 90 degrees 262C, one enlarged cells/drop zone at 180 degrees 262A and one enlarged cells/drop zone at 270 degrees 262D). As a guiding principle, an enlarged cell/drop zone 262A, 262B, 262C, or 262D is properly oriented to the clot 270B when the x-ray markers at the proximal, unattached distal-pointing crowns 258A, 244 and 258B, 244 or the distal, unattached distal pointing crowns 258C, 244 and 258D, 244 are together at both a first x-ray view and a second x-ray view 90 degrees relative to the first x-ray view, and the hard clot 270B can enter the enlarged cell/drop zone 262A, 262B, 262C, or 262D by moving the distal body 216 proximally. See FIGS. 16F and 18D. Finally, the guiding principal of retrieval of deformable cohesive, adherent clots 270C is that oscillation of the distal body 216 causes the deformable cohesive, adherent clots 270C to gradually enter the distal basket interior 222 over time.

Figure 20A:
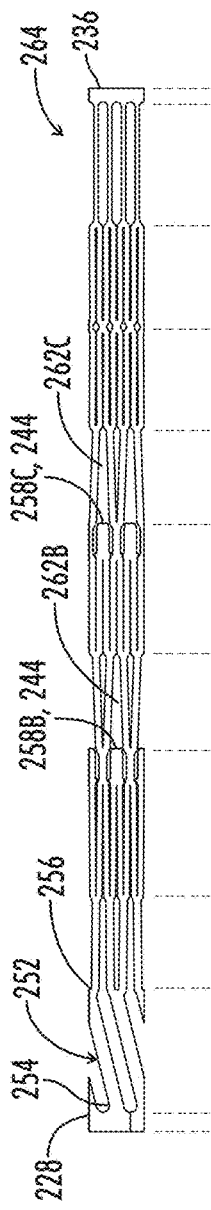
FIG. 20A illustrates a view of a native memory metal tube used to manufacture a distal body of yet another embodiment of the present invention; the native tube has been rolled out flat, the lines in the tube indicate where the tube has been cut by a laser, and the distal body of FIGS. 20A-20C is slightly shorter than the distal body of FIGS. 11-19 and is meant for use in tortuous blood vessels.
Figure 20B:
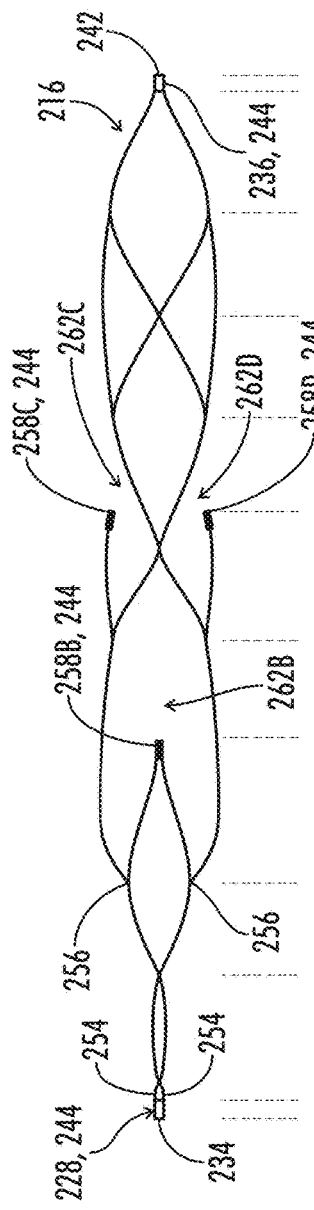
FIG. 20B illustrates a first, perspective view of the distal body manufactured from the native tube of FIG. 20A; the distal body is in Orientation 1.
Figure 20C:
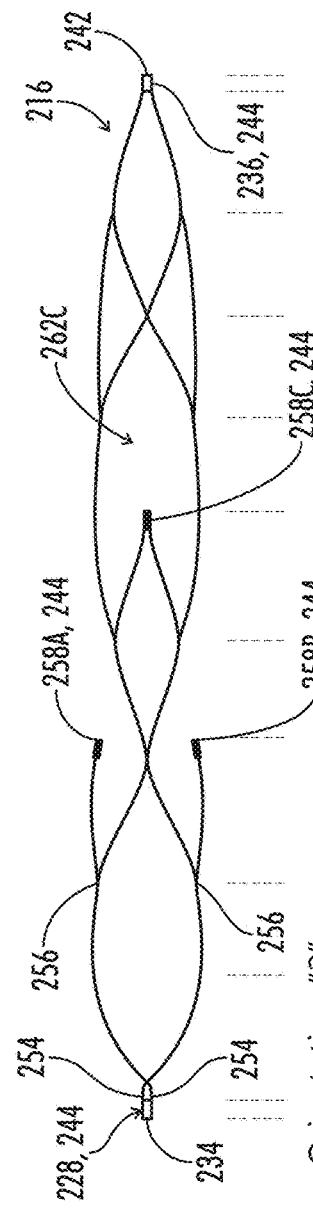
FIG. 20C illustrates a second, perspective view of the distal body manufactured from the native tube of FIG. 20A; the distal body is in Orientation 2.
Figure 21:
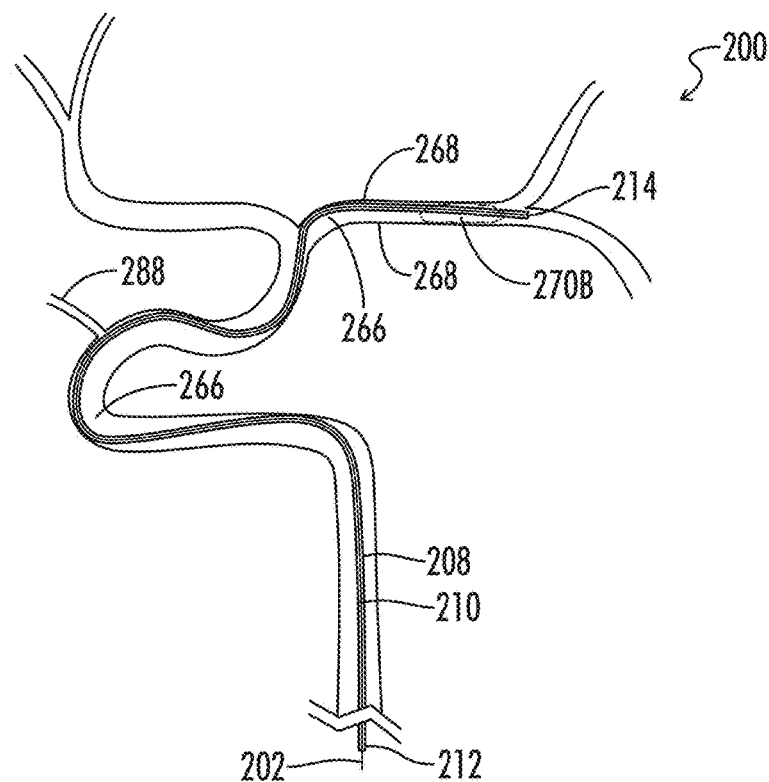
FIG. 21 shows a perspective view of a clot retrieval system that includes the distal body of FIGS. 20B-C being delivered in a blood vessel using a delivery catheter.
Figure 22:
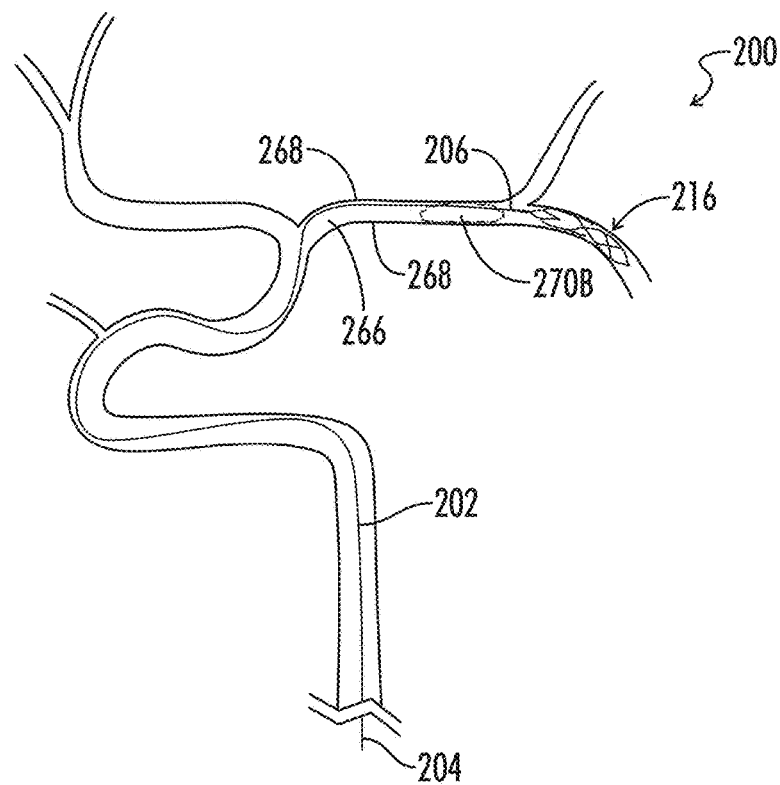
FIG. 22 shows a perspective view of the distal body of FIG. 21, after deployment of the distal body and retraction of the delivery catheter, in a blood vessel.
Figure 23:
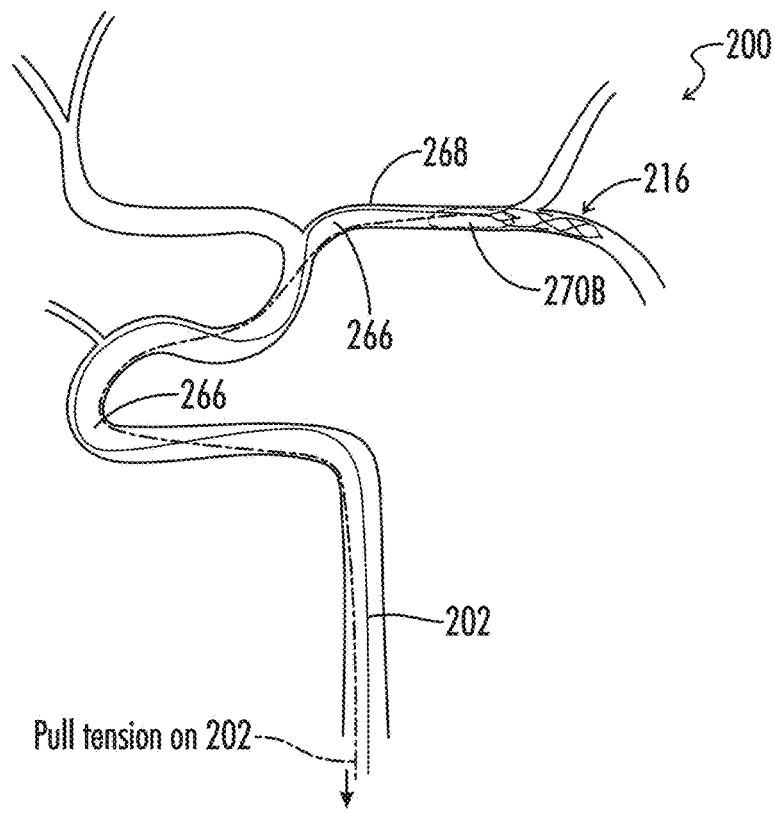
FIG. 23 shows a perspective view of the distal body of FIG. 21; as compared to FIG. 22, the distal body has been moved proximally and tension has been exerted on the pull wire.
Figure 24:
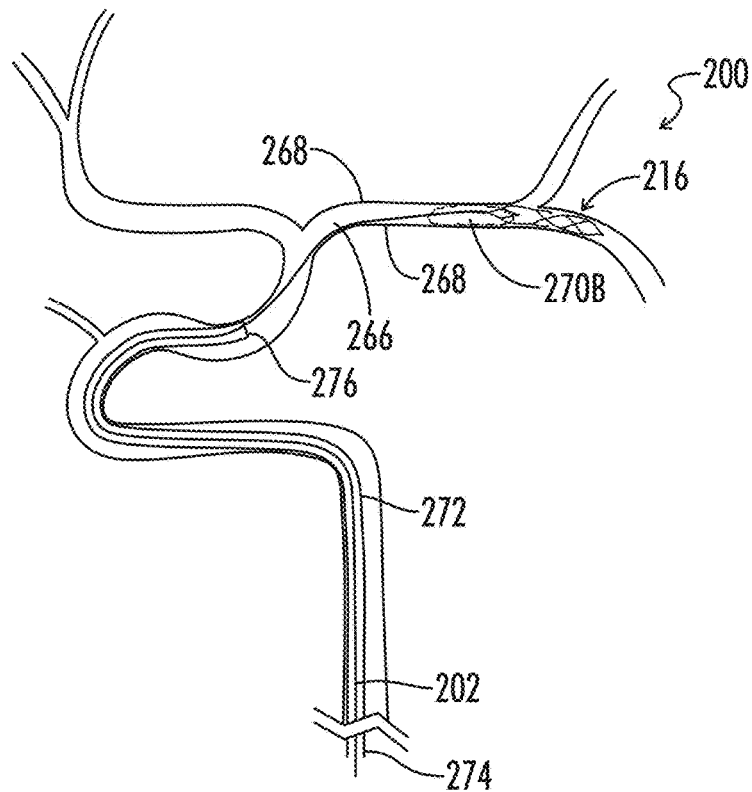
FIG. 24 shows a perspective view of a suction catheter that is being delivered over the pull wire of the system of FIG. 21.
Figure 25:
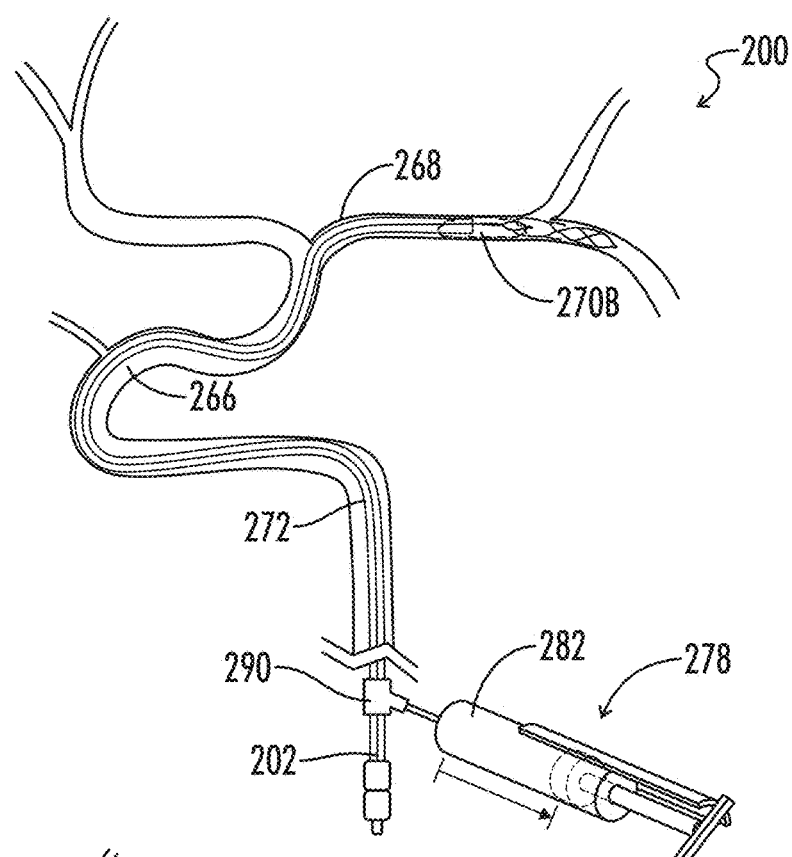
FIG. 25 shows a perspective view of the distal end of the suction catheter of FIG. 24 being pushed into a clot; a syringe is sucking the clot to the suction catheter because the user has pulled back on the lever of the syringe.
Figure 26:
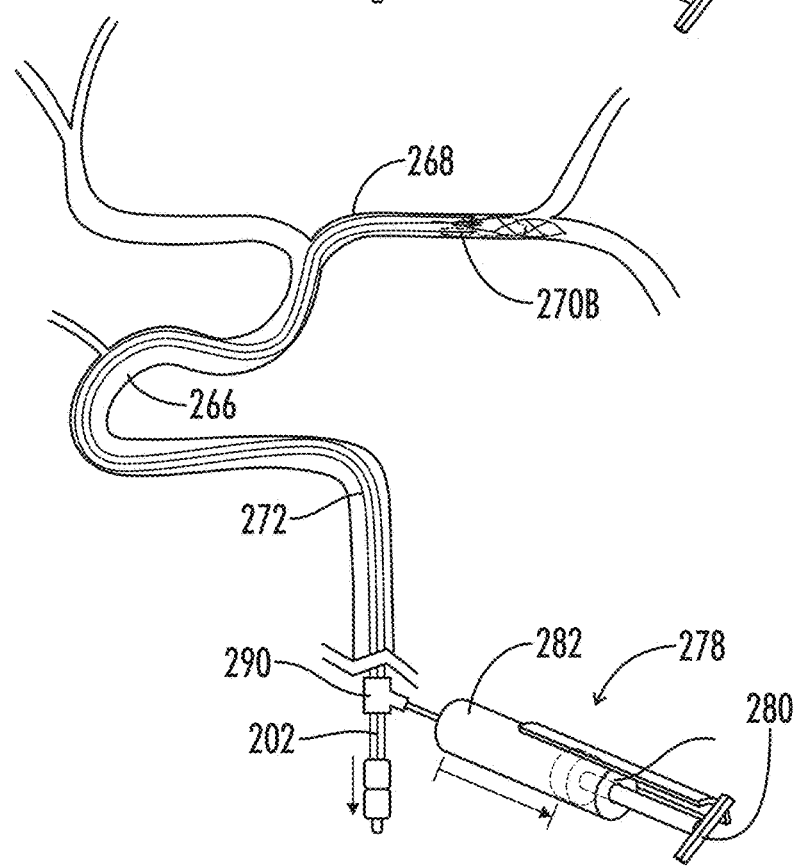
FIG. 26 shows a perspective view of the distal end of the suction catheter of FIG. 24 being pushed into a clot.
Figure 27:
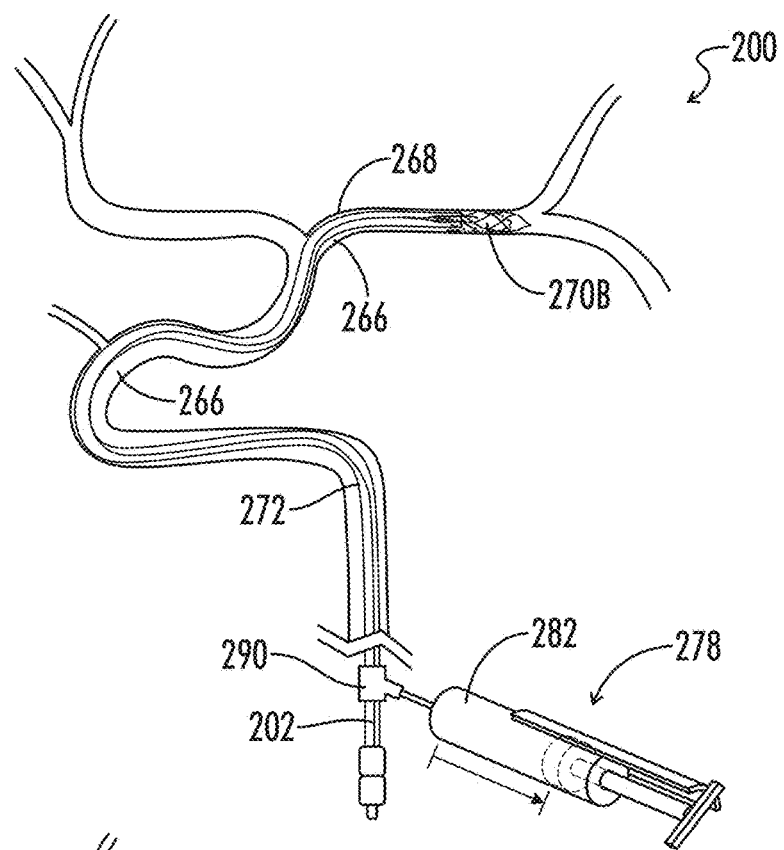
FIG. 27 shows a perspective view of the system of FIG. 24.
Figure 28:
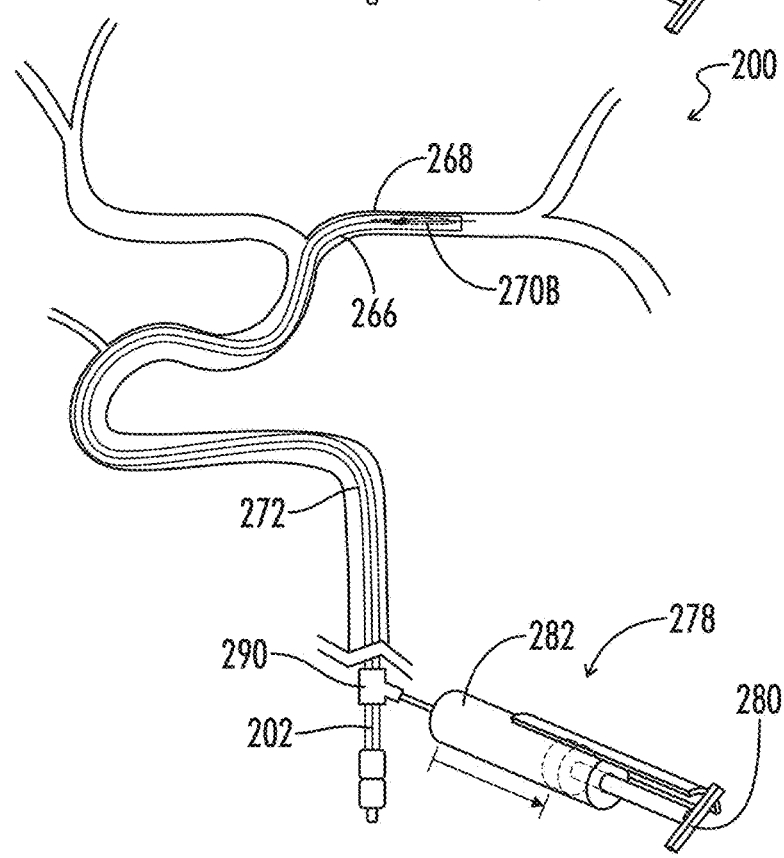
FIG. 28 shows a perspective view of the system of FIG. 24.
Figure 29:
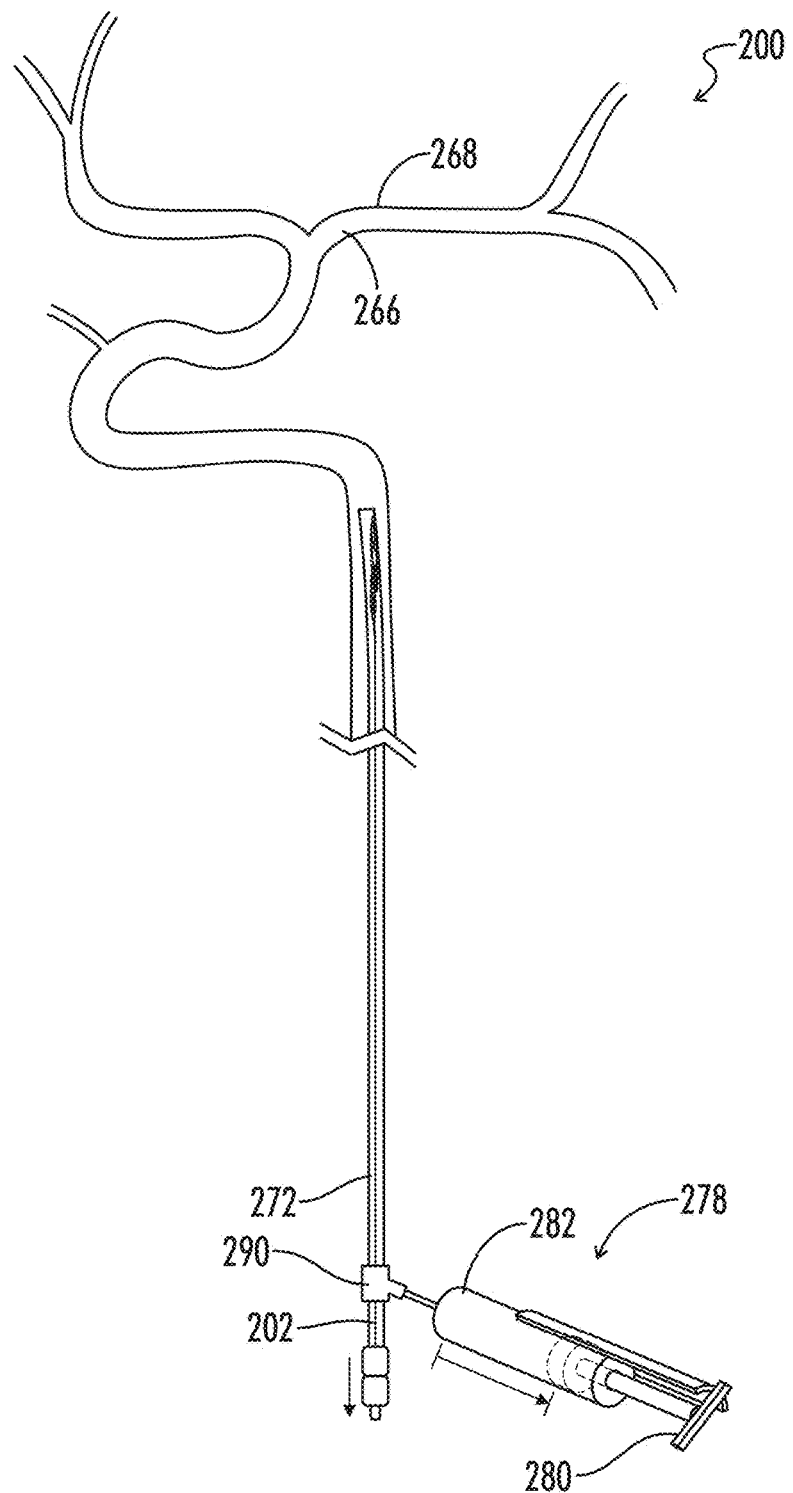
FIG. 29 shows a perspective view of the system of FIG. 24; the system, and captured clot, is being removed proximally from the vessel.

FIGS. 20A, 20B and 20C show a distal body 216 that is similar to the distal body 216 of FIGS. 14A, 14B and 14C except that the distal body 216 of FIGS. 20A, 20B and 20C is slightly shorter and its unattached, distal-pointing crowns 258A, 258B, 258C, and 258D are closer to the proximal tube 228. The shortened distal body 216 of FIGS. 20A, 20B and 20C is particularly adapted for tortuous blood vessels 266. FIG. 21-29 show stepwise deployment of the distal body 216 of FIGS. 20A, 20B and 20C in use with a manual (i.e., hand-operated), volume-dependent (i.e. volume locked) suction catheter 272 that is locked at between about 10 to about 60 cubic centimeters (cc). Optionally, the suction catheter 272 has an outer diameter of between about 0.05 inches and about 0.09 inches and its outer diameter is substantially larger than the outer diameter of the delivery catheter 208. The clot 270 is located in the vessel 266 through the use of, for example, contrast dye injected proximal and distal to the clot 270. As shown in FIG. 21, a delivery catheter 208 containing the distal body 216 of FIGS. 20A, 20B and 20C is positioned in the tortuous vessel 266 distal to the clot 270. The delivery catheter 208 is withdrawn, deploying the distal body 216. See FIG. 22. The distal body 216 is moved proximally relative to the clot 270 and tension is exerted on pull wire 202. See FIG. 23. While maintaining tension on the pull wire 202, a suction catheter 272 having a proximal end 274 and a distal end 276 is delivered over the pull wire 202 that is attached to the distal body 216. See FIG. 24. (The reason for exerting tension on the pull wire 202 is that the pull wire 202 serves as the guide/track for the movement of the suction catheter 272 and without tension, the suction catheter 272 and pull wire 202 could end up in the ophthalmic artery 288). The distal end 276 of the suction catheter 272 is positioned against the clot 270. A syringe 278 is attached to the suction catheter 272 using a rotating hemostatic valve 290, which allows the surgeon to aspirate while a pull wire 202 is in the system. The surgeon aspirates the syringe 278 by pulling back on the lever 280 to a mark on the base 282 corresponding to between about 10 and about 60 cubic centimeters of fluid. The surgeon then locks the lever 280 (and attached plunger) into place, leaving the suction catheter 272 under suction. The surgeon captures the clot 270 in the distal body 216 using the techniques described in FIGS. 15-19. The distal body 216 and clot 270 become captured by the suction catheter 272. See FIGS. 27 and 28. The surgeon then removes the suction catheter 272 and the distal body 216 and the clot 270, captured by the suction catheter 272, by moving the suction catheter 272 proximally out of the vessel 266. See FIG. 29. It is believed that the suction catheter 272 would be helpful in the event that a small portion of the clot 270 breaks off when retrieving the clot 270 using the distal body 216.

To examine effectiveness of the systems 200, the systems 200 of FIGS. 11-20, without the use of a suction catheter 272, were used to retrieve soft and hard clots 270A and 270B induced in a pig weighing between 30 to 50 kg. The weight of the pig was chosen so that the size of its vessels 266 would be approximate to the size of a human vessel. The pig was anesthetized. Several hard clots 270B were prepared by mixing pig blood and barium and incubating the mixture for 2 hours. Several soft clots 270A were prepared by mixing pig blood, thrombin and barium and incubating the mixture for 1 hour. The clots 270A and 270B, each of which had a width of 4 to 6 mm and a length of 10 to 40 mm, were then inserted into a vessel 266 having a diameter of 2 to 4 mm. (Only one clot 270A and 270B was located in the vessel 266 at a time). Angiograms were then performed to confirm occlusion. After waiting ten minutes after confirming occlusion, the distal bodies 216 of FIGS. 11-20 were then delivered distal to the clots 270A and 270B as described above and were used to retrieve the clots 270A and 270B as described in FIGS. 11-19. In each case, the distal bodies 216 were successful in retrieving the clots 270A and 270B. As shown, the distal body height in the relaxed state tapers/decreases as the proximal strips 252 approach the proximal hub/junction/tube 228 and also tapers/decreases as the basket strips 291 located at the distal end 220 of the basket 246 converge at the distal hub/junction/tube 236.

Figure 65:
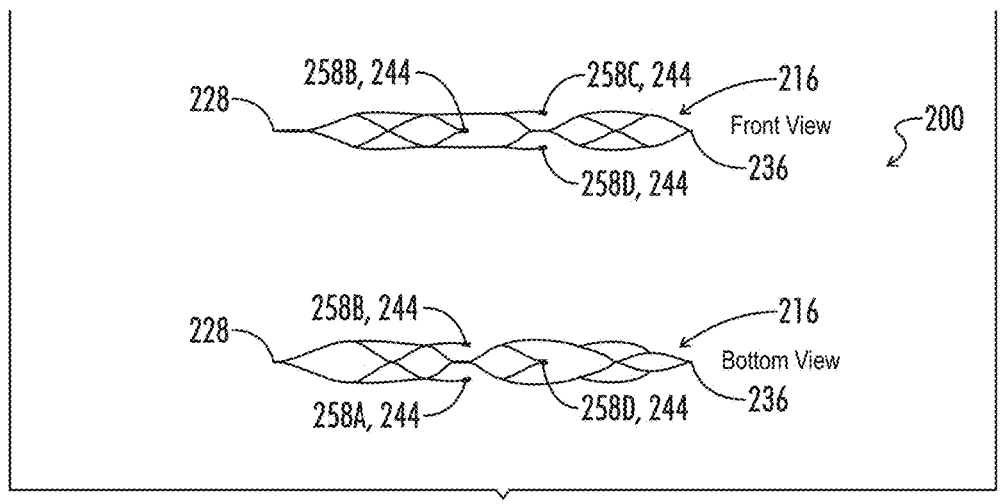
FIG. 65 illustrates an alternate embodiment of a distal body; in the distal body of FIG. 65, the proximal strips converge and are soldered or welded at the proximal hub/junction and the basket strips located at the distal end of the basket converge and are soldered or welded at the distal hub/junction.

The Alternate Embodiment of FIG. 65

FIG. 65 shows a distal body 216 in which the proximal strips proximal ends 254 converge and are soldered or welded at the proximal hub/junction 228 and the basket strips 291 located at the distal end 220 of the basket 246 converge and are soldered or welded at the distal hub/junction 236. To create such an embodiment, the distal body 216 may be prepared from a single tube, as described above, and the proximal and distal tubes may be clipped and the proximal ends 254 of the proximal strips 252 soldered or welded together (and optionally to the pull wire 202) and the basket strips 291 located at the distal end 220 of the basket 246 may also be welded or soldered or welded together. Optionally, the proximal and distal hubs/junctions 228 and 236 may include x-ray markers 244 as described above.

The Embodiments of FIGS. 30-35

FIGS. 30-35 illustrate additional embodiments of object retrieval system. Optionally, the system 300 of FIGS. 30-35 includes:

a pull wire 308 having a proximal end 310, a distal end 312 and a pull wire longitudinal axis 314 extending from the proximal end 310 to the distal end 312;

a coaxial sheath/tube 316 having a hollow interior, an open proximal end 318 leading to the hollow interior, and an open distal end 320 leading to the hollow interior, the coaxial sheath 316 enveloping the pull wire 308, the coaxial sheath 316 slideable along at least a segment of the pull wire 308;

a distal basket 322 comprising an interior 324, a proximal end 326, a distal end 328, a distal basket length 330 extending from the distal basket proximal end 326 to the distal basket distal end 328, a distal basket height 332 perpendicular to the distal basket length 330, a plurality of proximal cells 336 defined by a plurality of proximal cell memory metal strips 338, each proximal cell 336 comprising a proximal crown 340 located at the proximal end of the proximal cell 336 and pointing generally in the proximal direction and a distal crown 342 located at the distal end of the proximal cell 336 and pointing generally in the distal direction, and a plurality of distal cells 350 distal to the proximal cells 336;

a plurality of proximal strips 352, each proximal strip 352 having a proximal end 354 extending from the coaxial sheath distal end 320, a distal end 356 attached to a proximal crown 340 of a proximal cell 336 and a length 358 extending from the proximal end 354 to the distal end 356; and a delivery catheter 360, as described above, and having a hollow interior 366, a proximal end 362 leading to the interior 366 and a distal end 364 leading to the interior 366, the delivery catheter 360 comprised of a biocompatible material.

Optionally, the distal basket 322 is comprised of a memory metal and has:

a relaxed state in which the distal end 320 of the coaxial sheath 316 is located a first distance proximal to the proximal crowns 336 and wherein the distal basket 322, as measured at the proximal-most crown 336, has a first height, a proximal collapsed state in which the distal end 320 of the coaxial sheath 316 is located a second distance proximal to the proximal crowns 336 and wherein the distal basket 322, as measured at the proximal-most crown 336, has a second height, the second distance greater than the first distance, the second height less than the first height, and a distal collapsed state in which the distal end 320 of the coaxial sheath 316 is located distal to the proximal crowns 336 and in the basket interior 324 and wherein the distal basket 322, as measured at the proximal-most crown 336, has a third height, the third height less than the first height, wherein the delivery catheter 366 is configured to envelope the distal basket 322 when the distal basket 322 is in the proximal collapsed state;

wherein the distal basket 322 is configured to move from the relaxed state to the proximal collapsed state by moving the distal end 320 of the coaxial sheath 316 proximally relative to the proximal crowns 336; and wherein the distal basket 322 is configured to move from the relaxed state to the distal collapsed state by moving the distal end 320 of the coaxial sheath 316 distally beyond the proximal crowns 336 and into the distal basket interior 324.

Figure 30C:
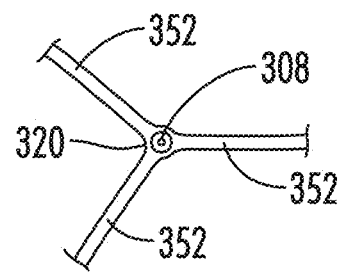
FIG. 30C illustrates a proximal, elevation view of the proximal strips of the system of FIG. 30A.
Figure 30D:
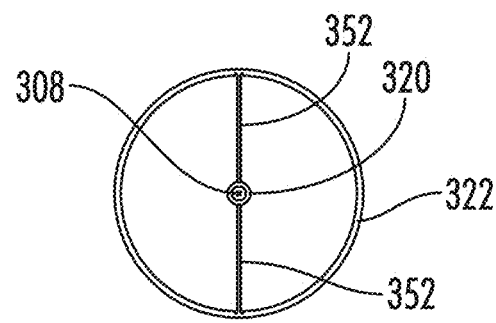
FIG. 30D illustrates a proximal, elevation view of an alternate embodiment of FIGS. 30A and 30B that includes two proximal strips.
Figure 30E:
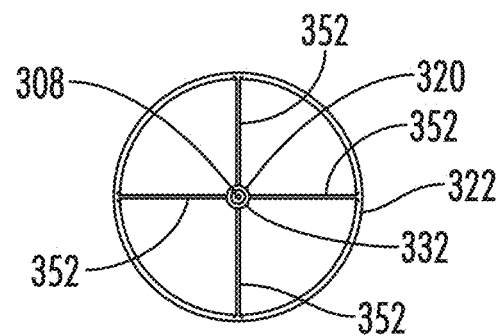
FIG. 30E illustrates a proximal, elevation view of an alternate embodiment of FIGS. 30A and 30B that includes four proximal strips.

Optionally, each proximal crown 340 comprises a proximal tip 344 and further wherein each proximal strip 352 is configured to cover a proximal tip 344 when the distal basket 322 is in the distal collapsed state. See FIG. 35C, where the proximal strip 352 is folding back on itself to cover the proximal tip 344. Optionally, each proximal crown 340 comprises an eyelet 370 and further wherein each proximal strip 352 passes through an eyelet 370. Optionally, the distal end 356 of each proximal strip 352 comprises a loop 372 attaching the proximal strip 352 to an eyelet 370. Optionally, each proximal crown 340 has an interior surface 348 facing the distal basket interior 324 and an exterior surface 350 opposite the interior surface 348 and further wherein each proximal strip 352 contacts an exterior surface 350 of a proximal crown 340 in the proximal collapsed state and the distal collapsed states, as best seen in FIGS. 35A-C. Without being bound to any particular theory, it is believed that threading the proximal strips 352 through the eyelets 370 as shown in FIGS. 35A-35C, helps protect the proximal crowns 340 (in particular, the proximal tips 344 of the proximal crowns 340) from damaging the vessel wall 306 when the proximal crowns 340 move towards each other and the pull wire 308 when the distal basket 322 moves to the distal collapsed state and the proximal collapsed state. Optionally, the pull wire 308 extends through the distal basket interior 324 and further wherein the proximal crowns 340 are configured to move towards each other and towards the pull wire 308 when the distal basket 322 moves from the gaping state to the distal collapsed state. Optionally, the proximal crowns 340 are configured to remain a fixed distance from the distal end 328 of the distal basket 322 when the distal basket 322 moves from the relaxed state to the distal collapsed state. In other words, preferably, the distal basket length 330 does not change when the distal basket 322 moves from the distal basket relaxed state to the distal basket. Optionally, the coaxial sheath 316 is a braided catheter comprised of a plurality of braids and further wherein the proximal segments of the braids are wound/woven together to form the braided catheter and further wherein an unwound/unwoven distal segment of each braid forms a proximal strip 352, as shown in FIG. 34. Optionally, at least one component of the system 300 (e.g., the proximal crown 340 or the distal tube 334) comprises an x-ray marker 374 that is more visible under x-ray as compared to the other components when the distal basket 322 is located in a cranial blood vessel 304 inside the body of a human and the x-ray is taken from outside the human's body. Preferably, the x-ray marker 374 is a radiopaque material. Some examples of radiopaque materials can include, but are not limited to, gold, platinum, palladium, tantalum, tungsten alloy, polymer material loaded with radiopaque filler, and the like. Preferably, the non x-ray marker components are comprised of nitinol and the x-ray marker 374 is comprised of a material having a density greater than the nitinol. In some embodiments, as shown in FIGS. 30A, 30B, 31A, 31B, 32A-F, the proximal ends 354 of the proximal strips 352 are integral with the coaxial sheath 316. In other embodiments, as shown in FIG. 33, the proximal ends 354 of the proximal strips 352 are attached to the coaxial sheath 316. Optionally, the system 300 comprises between two and four proximal strips 352 and the proximal strips 352 are spaced substantially evenly apart (e.g., if there are two proximal strips 252, the strips are located about 180 degrees relative to each other, as shown in FIG. 30D; if there are three proximal strips 252, the strips are located about 120 degrees relative to each other, as shown in FIG. 30C; and if there are four proximal strips 252, the strips are located about 1200 degrees relative to each other, as shown in FIG. 30E). Optionally, the proximal strips 352 have a length 358 of from about 5 mm to about 40 mm in the relaxed state. Optionally, the pull wire 308 extends through the basket interior 324 from the distal basket proximal end 326 to the distal basket distal end 328. Optionally, the coaxial sheath interior has a size and shape, and further wherein the size and shape of the coaxial sheath interior are configured to prevent a segment 376 of the pull wire 308 located in the basket interior 322 and distal relative to the distal end 320 of the coaxial sheath 316 from moving through the coaxial sheath interior. In other words, optionally the pull wire 308 has a stop 376 that consists of a knot or other enlargement. Optionally, the distal end 328 of the distal basket 322 comprises a distal tube 334 having an open proximal end and an open distal end, the distal tube 334 comprised of a memory metal. Optionally, the distal tube 334 is attached to the pull wire 308 so that the distal tube 334 is not slideable along the pull wire 308. This allows the entire distal basket 322 to be fixed to (i.e., not slideable along) the pull wire 308. Optionally, wherein all proximal crowns 340 of the proximal cells 336 are attached to a proximal strip 352, which is designed to minimize damage to the vessel wall 306. Optionally, the distal basket 322 further comprises a lead wire 378 extending distally from the distal basket 322. Optionally, the proximal strips 352 and the distal basket 322 have a different material composition. In other words, whereas the proximal strips 352 are designed to be soft, preferably, the distal basket 322 is comprised of a memory metal such as nitinol. Optionally, the proximal strips 352 are comprised of a polymer, which as used herein includes a co-polymer. Optionally, the polymer is selected from the group consisting of fluorinated ethylene propylene, polytetrafluoroethylene, and tetrafluoroethylene. Optionally, the proximal strips 352 are comprised of a material selected from the group consisting of plastic, rubber, nylon, suture material, and braided catheter material.

Figure 32A:
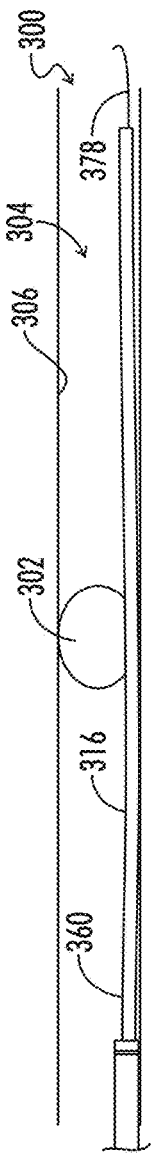
FIG. 32A-F illustrates a front, perspective view of the system of FIG. 30A and stepwise use of the system in retrieving a clot in a human intracranial artery.
Figure 32B:
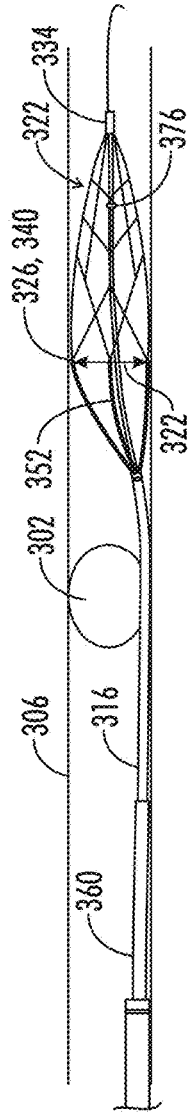
Figure 32C:
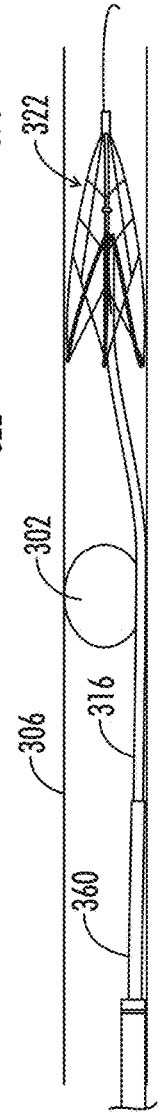
Figure 32D:
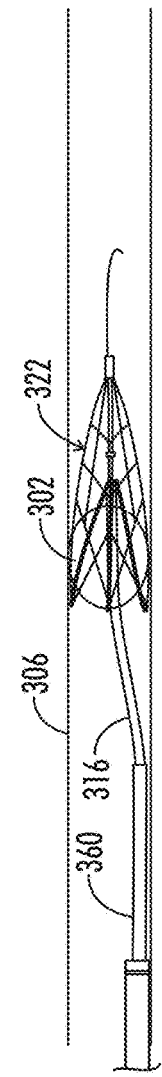
Figure 32E:
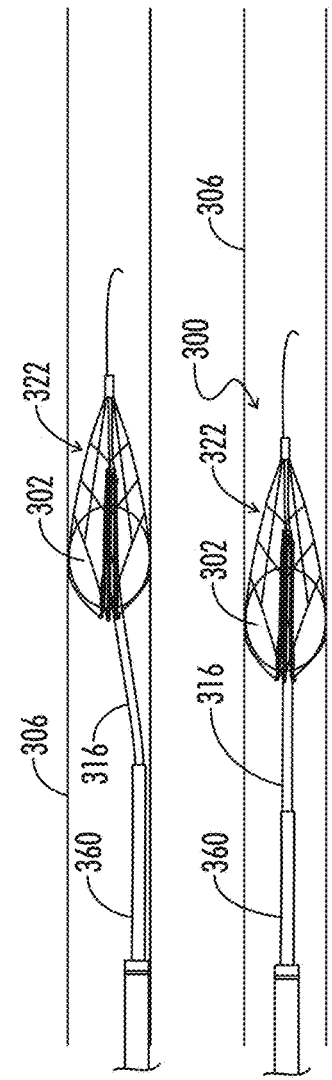
Figure 32F:

Optionally, as illustrated in FIGS. 32A-32F, the system 300 is used in method of removing a clot 302 from a blood vessel 304 of an animal, the blood vessel 304 having an interior wall 306 forming the blood vessel 304, the method comprising the steps of:

a) providing the system 300, wherein the coaxial sheath 316 is located in the catheter interior 366 and the distal basket 322 is located in the catheter interior 366 in a collapsed state;

b) positioning the catheter 360 in the blood vessel 304 (see FIG. 32A):

c) deploying the distal basket 322 from the distal end 364 of the catheter 360 so that the proximal crowns 340 of the proximal cells 336 are distal to the clot 302;

d) allowing the distal basket 322 to move to the relaxed state (see FIG. 32B; the coaxial sheath 316 is in the first position along the pull wire 308);

e) moving the distal end 320 of the coaxial sheath 316 distally along the pull wire 308 to the fourth position (see FIG. 32C; note that the proximal crowns 340 have remained in the same location and that the distal basket height 332, as measured at the proximal-most crown 340, has not decreased yet; preferably, an x-ray marker 374 on the pull wire 308 allows the surgeon to locate the fourth position);

f) moving the distal basket 322 and the coaxial sheath 316 proximally and capturing the clot 302 in the distal basket interior 324 (see FIG. 32D);

g) moving the coaxial sheath 316 further distally along the pull wire (i.e., at or near the third position; preferably, an x-ray marker 374 on the pull wire 308 allows the surgeon to locate the third position) so that the distal basket height 332, as measured at the proximal-most crown 340, decreases and the proximal crowns 340 move toward each other and towards the pull wire 308 (see FIGS. 32D and 32E; it will be appreciated that the proximal crowns 340 collapse like a claw in FIGS. 31B, 32D and 32E due to tension exerted on the crowns 340 by the proximal strips 352, similar to the mechanism described in FIGS. 3-10); and h) moving the system 300 proximally out of the blood vessel 304.

The coaxial sheath 316 optionally has a length of at least 50 centimeters (cm), e.g., about 50 cm to about 300 cm, so that the coaxial sheath 316 can be moved by the surgeon outside of the patient's body. The coaxial sheath 316 can be formed of several parts that are fused together to form the coaxial sheath 316.

The Embodiments of FIGS. 36-44

FIGS. 36-44 further illustrate other embodiments of a modular, easy-to-manufacture platform of systems for retrieving hard clots and other objects in animal lumens. In some embodiments, the system includes a proximal tube, a distal tube, and a plurality of memory metal strips between the proximal and distal tubes. The plurality of memory metal strips form a wide range of basket designs. Preferably, the proximal tube, memory metal strips, and distal tube are derived from a standard, off-the-shelf single tube of memory metal (e.g., nitinol), with the proximal tube and distal tube having the same inner diameter and outer diameter as the native tube from which they were derived and with the basket formed by cutting the middle portion of the native tube and expanding and shape-setting this cut portion.

Preferably, the proximal tube and distal tube have an outer diameter that is from about 0.02 inches to about 0.03 inches (e.g., about 0.027 inches) so that the device fits inside a standard microcatheter and an inner diameter that is from about 0.01 inches to about 0.02 inches. Preferably, there are no welded or soldered parts between the proximal tube and distal tube, which makes the system easy and cheap to reliably manufacture. The system also includes one or more catheters for deploying the system, and a first wire that is attached to the proximal tube and a second wire that is attached to the distal tube. Preferably, the system includes two catheters—a guide catheter and a microcatheter. The plurality of memory metal strips attached to the proximal hub/junction include a plurality of proximal tether memory metal strips, which have a proximal end attached to the distal end of the proximal tube.

The present disclosure also provides a system for removing objects within an interior lumen of an animal. In some embodiments, the system includes a pull wire having a proximal end, a distal end and a pull wire longitudinal axis extending from said proximal end to said distal end;

a distal basket attached to said pull wire, said distal basket comprising a proximal end, a distal end, a distal basket length extending from said distal basket proximal end to said distal end, a distal basket height perpendicular to said distal basket length and said pull wire longitudinal axis, a proximal tube located at said proximal end of the distal basket, said proximal tube comprising a hollow interior, a plurality of proximal tether memory metal strips, a row of proximal cells defined by a plurality of proximal cell memory metal strips, each proximal cell comprising a proximal crown located at the proximal end of the proximal cell and pointing generally in the proximal direction, each proximal tether memory metal strip having a proximal end attached to said proximal tube, a distal end attached to a crown of a proximal cell and a length extending from said proximal end to said distal end, a row of distal crowns located distal to said proximal cells pointing in the distal direction, and further wherein the number of distal crowns in said row is twice the number of proximal crowns attached to said proximal tether memory metal strips, and a distal tube located at said distal end of said distal basket, said distal basket having a relaxed state wherein said distal basket has a first height and a collapsed state wherein said distal basket has a second height, said second height less than said first height, and a catheter having an interior, a proximal end leading to said interior and a distal end leading to said interior, said catheter comprised of a biocompatible material and configured to envelope said distal body when said distal basket is in said collapsed state.

Optionally, said proximal tether memory metal strips rotate about said pull wire longitudinal axis such that a distal end of a proximal tether memory metal strip is located between about 90 and about 270 degrees relative to said proximal end of the same proximal tether memory metal strip. Optionally, said proximal tether memory metal strips and said proximal cell memory metal strips each have a thickness and further wherein said thickness of said proximal tether memory metal strips is between about 100 to about 175 percent of the thickness of the proximal cell memory metal strips. Optionally, the length of said proximal tether memory metal strips is about 10 mm to about 20 mm in the relaxed state (and the length of the remainder of the basket is about 10 to about 20 mm in the relaxed state so that the total basket length is between about 20 to about 40 mm in the relaxed state). Optionally, said distal end of said pull wire is attached to said proximal tube. Some or all of the proximal crowns of said proximal cells may be attached to a proximal tether memory metal strip. Optionally, said distal basket further comprises a row of strut memory metal strips, each strut memory metal strip having a proximal end attached to a distal crown of a proximal cell and a distal end attached to a proximal crown of a distal cell. Optionally, the distal basket comprises between two and four proximal tether memory metal strips. Optionally, said proximal tether memory metal strips are integral with said proximal tube. Optionally, said distal body further comprises a lead wire extending distally from said distal tube. Optionally, said distal tube, said proximal tube, and said basket are comprised of a nitinol having the same material composition. Optionally, said distal body further comprises an x-ray marker. Optionally, said proximal and said distal tubes are generally cylindrical in shape and each has an outer diameter and an inner diameter, the inner diameter forming the apertures of the proximal and distal tubes and further wherein the outer diameters of the proximal and distal tubes are substantially the same size and further wherein the inner diameters of the proximal and distal tubes are substantially the same size. Optionally, the outer diameters of the proximal and distal tubes are from about 0.011 inches to about 0.054 inches, and further wherein the inner diameters of the proximal and distal tubes are from about 0.008 inches to about 0.051 inches. Optionally, the pull wire is generally cylindrical and further wherein the diameter of the pull wire is between about 0.008 inches and about 0.051 inches. Optionally, the first height is between about 2 millimeters and about 8 millimeters.

The present disclosure also provides a method of removing an object from an interior lumen of an animal, said lumen having an interior wall forming said lumen, the method comprising the steps of:

a) providing the system described above;
b) positioning the system in said lumen, said basket located in said catheter in said collapsed state;
c) deploying said distal basket from said distal end of said catheter so that said proximal crowns of said proximal cells are distal to said obstruction;
d) allowing said distal basket to move to said relaxed state;
e) moving said distal basket over said obstruction; and
f) removing said distal basket and said obstruction from said lumen.

Optionally, said interior lumen is an intracranial artery and said obstruction is a blood clot.

In further embodiments, the system includes:

a pull wire having a proximal end, a distal end and a pull wire longitudinal axis extending from said proximal end to said distal end;

a proximal basket attached to said pull wire, said proximal basket comprising an interior, an exterior, a proximal end, a distal end, a proximal basket length extending from said proximal basket proximal end to said distal end, a proximal basket height perpendicular to said proximal basket length and said pull wire longitudinal axis, a proximal tube located at said proximal end of the proximal basket, said proximal tube comprising a hollow interior, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction, a distal basket attached to said pull wire, said distal basket comprising an interior, an exterior, a proximal end, a distal end, a distal basket length extending from said distal basket proximal end to said distal end, a distal basket height perpendicular to said distal basket length and said pull wire longitudinal axis, a distal tube located at said distal end of the distal basket, said distal tube comprising a distal tube aperture, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction, a plurality of tether memory metal strips, each tether memory metal strip having a proximal end attached to a distal crown of a cell located at the distal end of said proximal basket and a distal end attached to a proximal crown of a cell located at the proximal end of said distal basket, said proximal basket having a relaxed state wherein said proximal basket has a first height and a collapsed state wherein said proximal basket has a second height, said second height less than said first height and said second width less than said first width, said distal basket having a relaxed state wherein said distal basket has a first height and a first width and a collapsed state wherein said distal basket has a second height and a second width, said second height less than said first height, and a catheter having an interior, a proximal end leading to said interior and a distal end leading to said interior, said catheter comprised of a biocompatible material and configured to envelope said distal and said proximal basket when said baskets are in said collapsed state.

Optionally, said tether memory metal strips rotate about said pull wire longitudinal axis such that a distal end of a tether memory metal strip is located between about 90 and about 270 degrees relative to said proximal end of the same proximal tether memory metal strip.

More particularly, with reference to FIGS. 36-44 the present disclosure provides a deployable system, generally designated by the numeral 410, for removing an obstruction such as a blood clot 417 or other object from a blood vessel 488 or other interior lumen of an animal. In addition to a blood clot 417, the obstruction may be, for example, extruded coils during aneurysm treatment, intravascular embolic material such as onyx or other obstructions requiring mechanical intravascular removal from small distal vessels. In the drawings, not all reference numbers are included in each drawing for the sake of clarity.

One example of a deployable basket system 410 is shown in FIGS. 37A-37B, 38A-E and 39A. As shown in FIGS. 31A-31E, 32G-32H and 35A, the system 410 includes a pull wire 443 having a proximal end 445, a distal end 444 and a pull wire longitudinal axis 446 extending from said proximal end 445 to said distal end 444. Optionally, the diameter of the pull wire 443 is between about 0.008 inches and about 0.051 inches.

The system 410 further includes a distal basket 411 attached to said pull wire 443, said distal basket 411 comprising a proximal end 469, a distal end 465, a distal basket length 467 extending from said distal basket proximal end 469 to said distal end 465, a distal basket height 461 perpendicular to said distal basket length 467 and said pull wire longitudinal axis 446, a proximal hub/junction 439 located at said proximal end 469 of the distal basket 411 and comprising a hollow interior 441, said distal end 444 of said pull wire 443 attached to said proximal hub/junction 439, a plurality of proximal tether memory metal strips 457, a plurality of proximal cells 436 defined by a plurality of proximal cell memory metal strips 466, each proximal cell 436 comprising a proximal crown 438 located at the proximal end of the proximal cell 436 and pointing generally in the proximal direction and a distal crown 424 located at the distal end of the proximal cell 436 and pointing generally in the distal direction, each proximal tether memory metal strip 457 having a proximal end 455 attached to said proximal hub/junction 439 (preferably said proximal hub/junction distal end 440), a distal end 453 attached to a crown of a proximal cell 438 and a length 455 extending from said proximal end 455 to said distal end 453, a plurality of distal cells 422 distal to the proximal cells 436, and a distal hub/junction 425 located at said distal end 465 of said distal basket, comprising a hollow interior 427 and attached to a proximal end of a leader wire 431. Preferably, the proximal hub/junction 439 and distal hub/junction 425 are hollow tubes formed from the same tube of memory metal, as described below. In some embodiments, the basket 411 includes a first row of two crowns (i.e., the proximal crowns 438 of the proximal cells 436) and then subsequent repeating rows of twice as many crowns as compared to the number of proximal crowns 438 (i.e., four crowns) along the basket length 467.

The system further includes a guide catheter 430 and a microcatheter 432, which is wider and shorter than the guide catheter 430, so that the microcatheter 432 can fit inside the guide catheter 430. The microcatheter 432 has a hollow interior 415, a proximal end 416 leading to said interior 415 and a distal end 414 leading to said interior 415. The microcatheter 432 is comprised of a biocompatible material. For purposes of FIGS. 36-44, the terms "guide catheter", "microcatheter" and "catheter" generally refers to any suitable tube through which the system 410 can be deployed. Preferably, the catheters are sterile and comprised of a biocompatible material (i.e., a material that does not irritate the human body during the course of a 45 minute operation that involves using the system 410 to remove a clot 417 from an intracranial blood vessel 488). The catheter can be any suitable shape, including but not limited to generally cylindrical. For purposes of the present invention, when it is said that the catheter envelopes the system 410, it will be understood that the catheter envelopes at least one component of the system 410 (preferably, the distal basket 411, the lead wire 431, which is a wire that extends distally from the pull wire 443, and the pull wire 443). In some embodiments, the microcatheter 32 is about 2.5 French in diameter. Optionally, the catheter is delivered to the region of the lumen that has the obstruction 417 as follows: a guide wire is delivered to the obstruction region past the obstruction 417; the catheter is delivered over the guide wire; the guide wire is removed; and the system 410 is delivered with its pull wire 443 and lead wire 431 through the catheter. Optionally, the pull wire 443 is used to push the system 410 through the catheter as well as to retrieve the distal basket 411 after capturing the obstruction 417 as described below. The system 410 may utilize a plurality of catheters as described above, such as, for example, a wider catheter that travels to the brain and a very flexible, smaller diameter microcatheter that is delivered from the first catheter and travels through the small arteries of the brain.

Figure 36A:
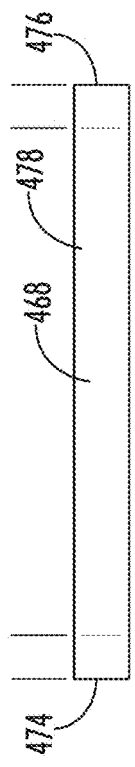
FIGS. 36A-36D illustrate a side, perspective view of a stepwise sequence of making an embodiment of the basket system of the present invention.
Figure 36B:
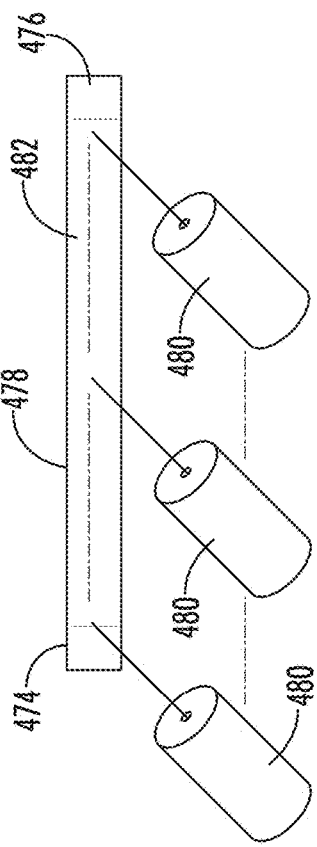
Figure 36C:
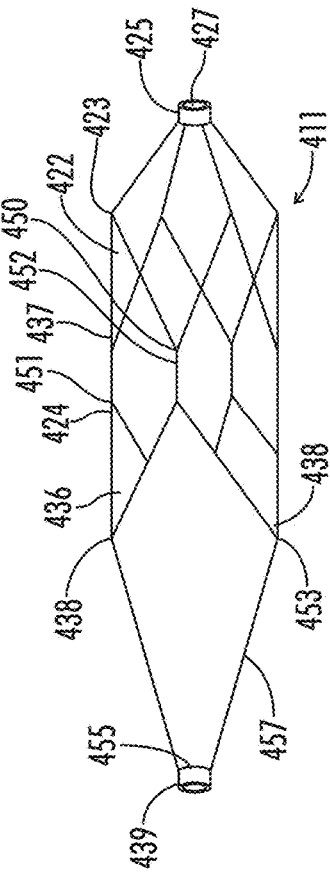
Figure 36D:
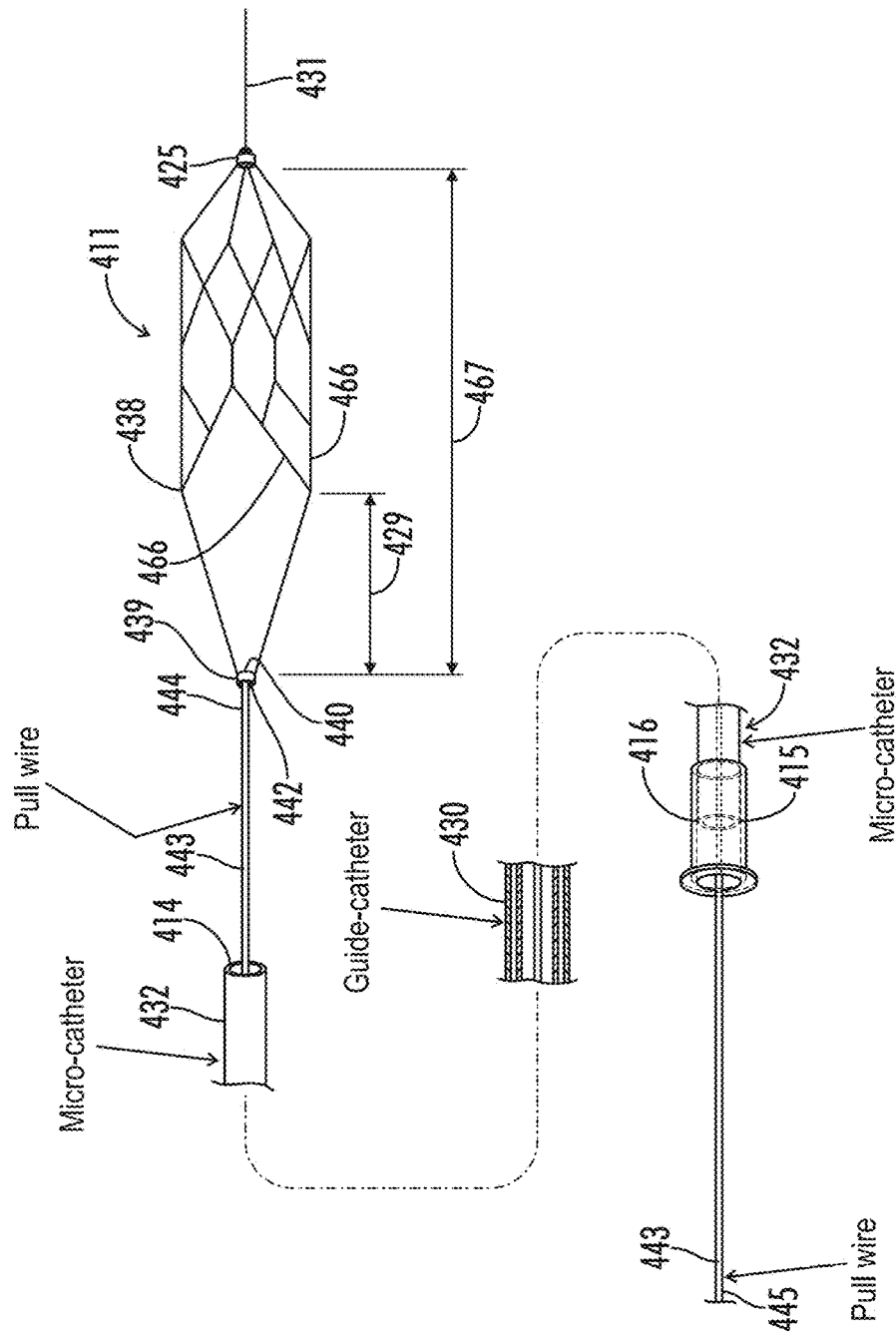
Figure 37A:
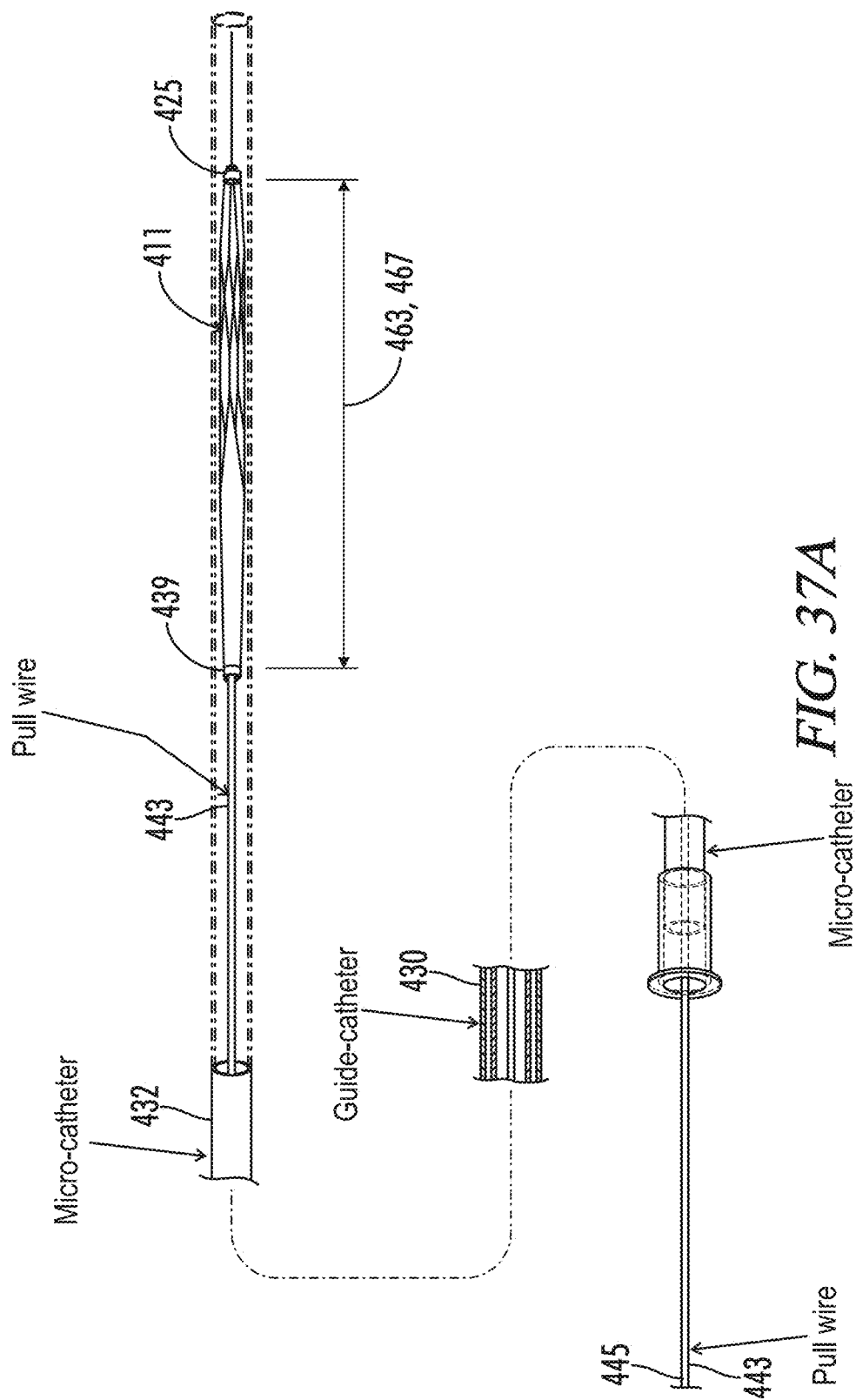

FIG. 37A shows the distal basket 411 collapsed inside a microcatheter 432. The distal basket 411 is in what's referred to as the collapsed state. In this state, the system 410 is able to be located inside the microcatheter 432 and the basket height 461 is collapsed. For purposes of FIGS. 36-44, the basket height 461 generally refers to the height at a particular location (e.g., at the proximal-most crown 438 of the distal basket 411 or the distal-most crown 500 of the proximal basket 433), it being understood that the height of the distal basket 411 and proximal basket 433 may vary along the distal basket length 467 and the length of the proximal basket 433.

As shown in FIGS. 36-44, the distance 463 between the proximal hub/junction 439 and distal hub/junction 425 (i.e., the basket length 467) is generally longer in the collapsed state, as compared to the relaxed state.

FIG. 37B shows the same basket system as FIG. 37A, except that the basket 411 has been deployed from the distal end 414 of the microcatheter 432 by pulling the microcatheter 432 proximally. As shown in FIG. 37B, the basket 411 is now in a relaxed state and the basket height 461 has increased. In the relaxed state exemplified, the basket length 467 and the distance 463 between the proximal and distal hubs/junctions 439 and 425 has decreased slightly as the basket 411 has relaxed. Optionally, the length of said proximal basket 467 is between about 20 and about 40 mm and the length 454 of said proximal tether memory metal strips 457 are between about 10 and about 20 mm in the relaxed state.

Figure 38A:
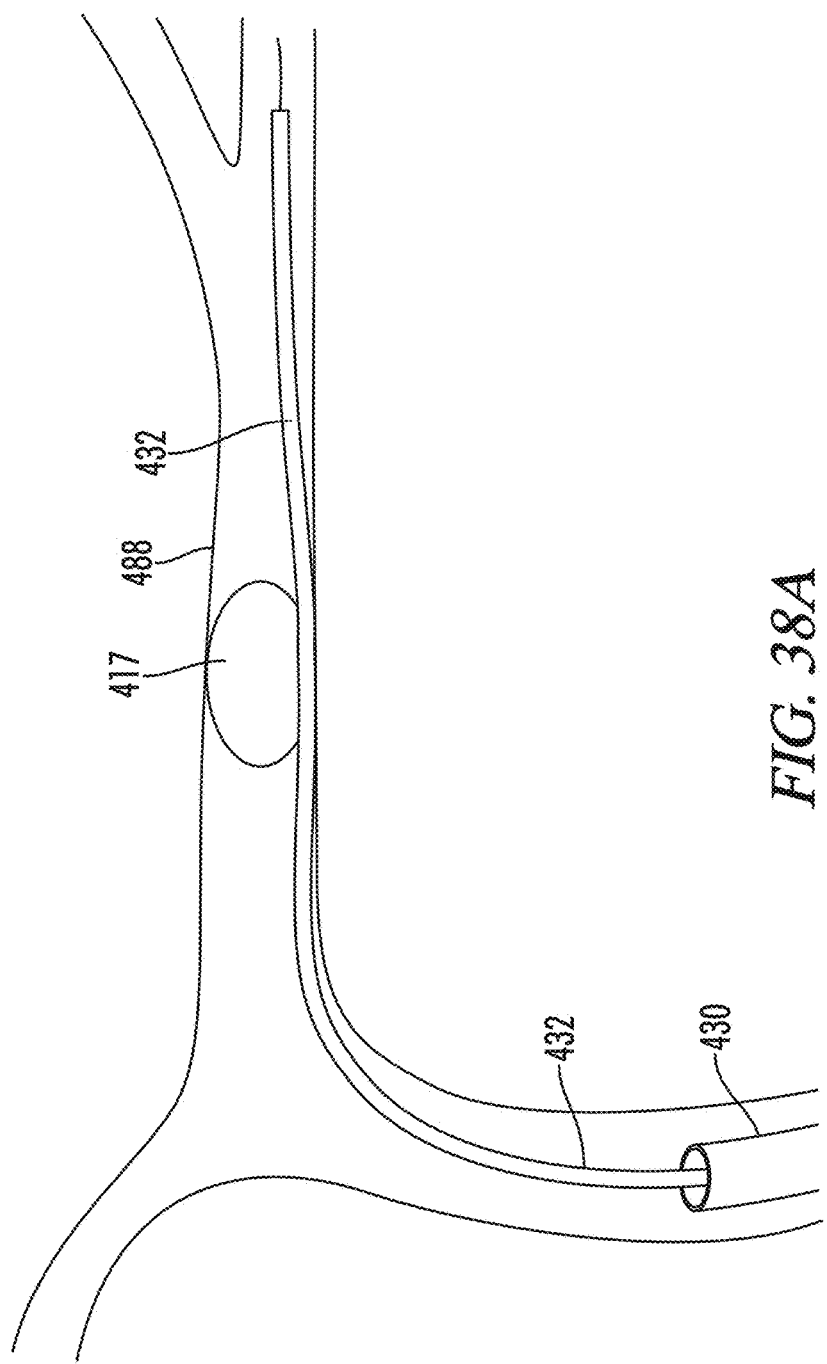
Figure 38B:
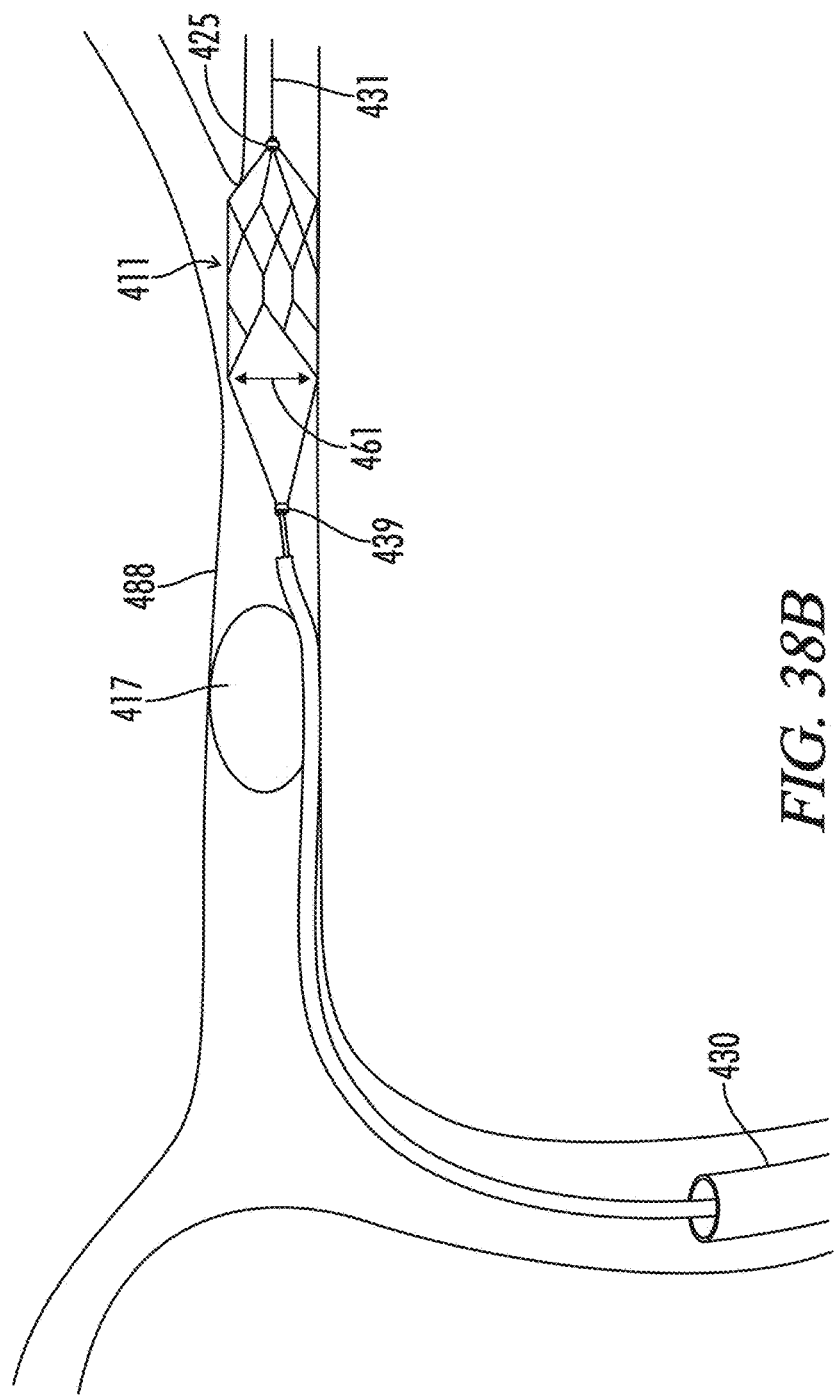
Figure 38C:
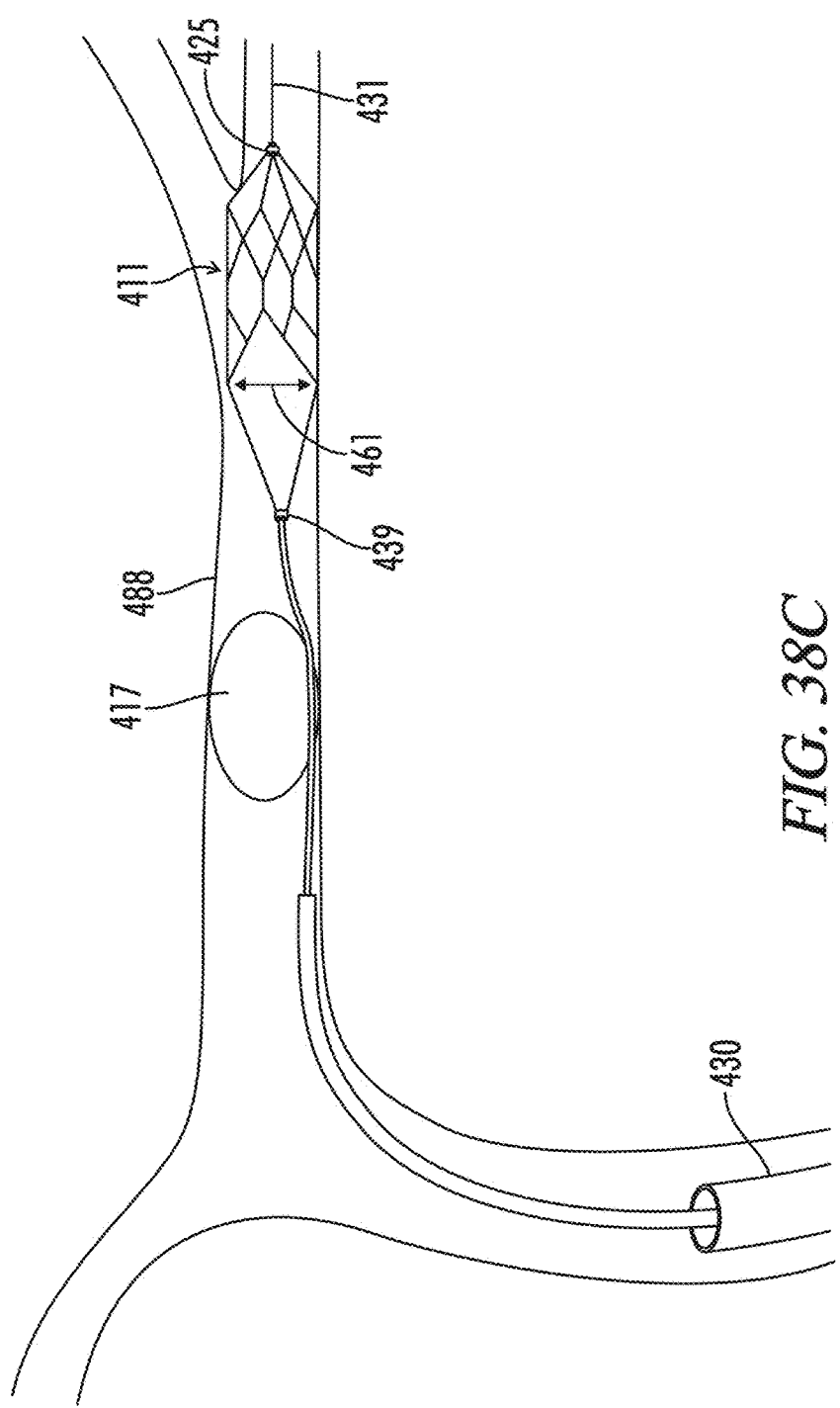

FIG. 38 illustrates use of the basket system shown in FIG. 37 in an intracranial artery 488. As shown in FIG. 38A, first the guide catheter 430 is deployed proximal to the clot 417. The microcatheter 432 is then advanced distally beyond the clot 417. The basket 411 is collapsed inside the microcatheter 432. Next, as shown in FIG. 38B, the microcatheter 432 is moved proximally to deploy the basket 411 so that the proximal tether memory metal strips 457 are distal to the clot 417. The basket 411 is now in the relaxed state. Next, as shown in FIG. 38C, the user moves the basket 411 proximally over the clot 417.

FIG. 39A shows a close-up view of the proximal end of the basket 411, including the proximal tube interior 441, the attachment of the proximal tether memory metal strips 457 at the distal end 455 of the proximal hub/junction 439, and the proximal crowns 438 of the proximal cells 436. In FIG. 39A, all proximal crowns 438 of the proximal cells 436 are attached to a proximal tether memory metal strip 457. FIG. 39B illustrates an alternative embodiment in which two proximal crowns 438*a* of a proximal cell 436 (the top and bottom crowns 438*a*) are attached to a proximal tether memory metal strip 457 and one proximal crown 438*b* of a proximal cell 436 is not attached to a proximal tether memory metal strip 457.

Figure 40:
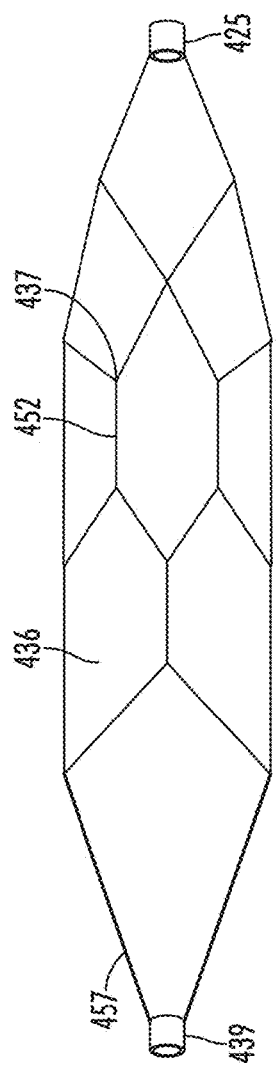
FIG. 40 illustrates a side, perspective view of a basket system with relatively thick proximal tether memory metal strips; in this FIG. 40, as shown, the proximal tether memory metal strips are thicker than the memory metal strips forming the proximal-most crown.

FIG. 40 illustrates a similar to basket system 410 to the above systems. In FIG. 40, the proximal tether memory metal strips 457 are relatively thick (e.g., about 150% of the thickness of the proximal cell memory metal strips 466).

It will be noted that the proximal end of the system 410 is shown at the bottom end of FIGS. 36-44 and the distal end of the system 410 is shown at the top end of FIGS. 36-44 because a principal use of the system 410 is to remove a blood clot 417 from a human intracranial artery 488, in which case the system 410 generally will enter the artery 488 at its proximal end by the surgeon entering the patient's body near the groin and pushing the catheter 432 towards the brain. The diameter of human arteries 488 generally decrease from their proximal end to their distal end. However, when used in other types of lumens, the distal basket 411 may be located proximally relative to the catheter 432 as the term proximally and distally are used in that lumen.

Figure 41:
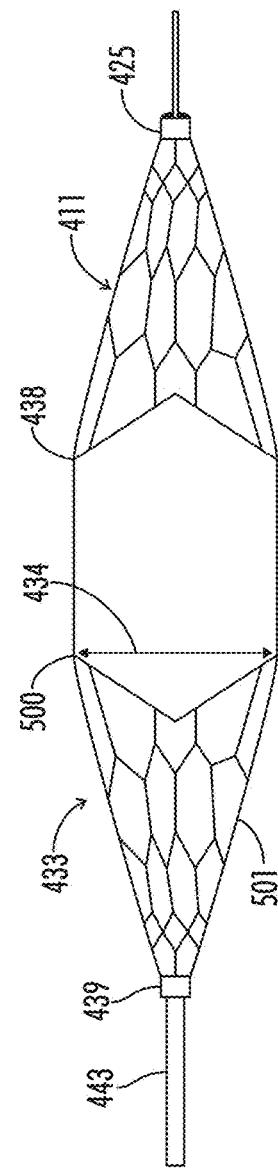
FIG. 41 illustrates a side, perspective view of a basket system with a proximal basket and a distal basket.

FIG. 41 illustrates another embodiment of a basket system 411 with a proximal basket 433 and a distal basket 411. In this embodiment, the system 411 includes a proximal hub/junction 439 (similar to the prior embodiments). The difference is that the tether memory metal strips 457 actually join the proximal basket 433 and the distal basket 411. More particularly, the proximal basket 433 is comprised of a plurality of proximal cells 436 attached to the proximal hub/junction 439 and a plurality of distal cells 422 and the distal basket is comprised of a plurality of proximal cells 436 attached to the proximal hub/junction 439 (preferably to the proximal end 499 of the distal hub/junction 425) and a plurality of distal cells 422 and the tether memory metal strips 457 join a distal crown 423 of a distal cell 422 of the distal basket 411 with a proximal crown 438 of a proximal cell 436 of the proximal basket 433.

Figure 42:
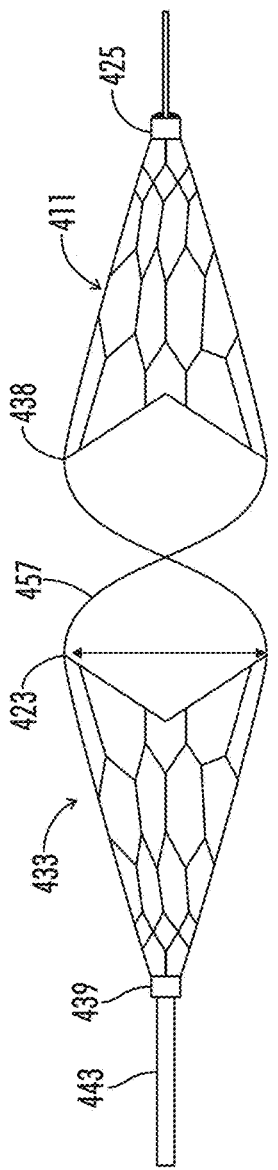
FIG. 42 illustrates a side, perspective view of a basket system with a proximal basket and a distal basket in which the proximal tether memory metal strips rotate 180 degrees about both the longitudinal axis of the proximal tether memory metal strips and about the longitudinal axis of the pull wire.

FIG. 42 illustrate an embodiment of the tether memory metal strips 457 rotating about said pull wire longitudinal axis 446 such that the distal end 453 of a proximal tether memory metal strip 457 is located between about 90 and about 270 degrees relative to said proximal end 455 of the same proximal tether memory metal strip 457. In addition, the proximal tether memory metal strips 457 may rotate around their longitudinal axis 454 such that a distal end 453 of a proximal tether memory metal strip 457 rotates about 90 degrees around this tether longitudinal axis 454 from the distal end 453 to the proximal end 455 of the same proximal memory metal strip 457. FIGS. 43B and 43C illustrates an exemplary embodiment, where the proximal end 455A of the first proximal tether memory metal strip 457A is located attached to the proximal tube 439 at the 12 o'clock position and the distal end 453A of the same proximal tether memory metal strip 457A is attached to a proximal-most crown 439 at the 9 o'clock position. In addition, the second proximal tether memory metal strip 457B is located attached to the proximal tube 439 at the 6 o'clock position and the distal end 453B of the same proximal tether memory metal strip 457B is attached to the other proximal-most crown 439 at the 3 o'clock position. FIGS. 43D and 43E illustrate an exemplary embodiment of 180 degree rotation, where the proximal end 455A of the first proximal tether memory metal strip 457A is located attached to the proximal tube 439 at the 12 o'clock position and the distal end 453A of the same proximal tether memory metal strip 457A is attached to a proximal-most crown 439 at the 6 o'clock position. In addition, the second proximal tether memory metal strip 457B is located attached to the proximal tube 439 at the 6 o'clock position and the distal end 453B of the same proximal tether memory metal strip 457*b* is attached to the other proximal-most crown 439 at the 12 o'clock position.

FIGS. 44A-44E illustrate a side, perspective view of stepwise deployment and use of a basket system 410 with a proximal basket 433 and a distal basket 411 in a blood vessel to retrieve a clot 417. As shown, the distal basket 411 is deployed proximal to said clot 417 and said proximal basket 433 is deployed at said clot 417 so that said proximal basket 433 is at level of the clot. After allowing some time for clot debris to penetrate the proximal basket 433, the basket system 433 is moved proximally toward said microcatheter 432. See FIGS. 44B and 44C. As shown in FIG. 44D, the clot 417 falls moves medially into the void or space 498 between the proximal basket 433 and distal basket 411. The system 410 continues to move proximally. The clot 477 is then located inside the distal basket 411. See FIG. 44E. The proximal basket 433 optionally has a length in the relaxed state of preferably from about 10 to about 20 mm, as measured from the proximal-most crown to the distal-most crown.

The proximal basket 433 is used to deploy the system 411 across the obstruction 417 and is the initial site where the clot 417 enters through the struts 452. As the basket system 411 is pulled/dragged proximally, the site of the proximal tether memory metal strip 457 gives a relative "open" area 498 for the clot 417 to fall into in the lumen of the vessel 488. The distal basket 411 captures the clot 417 that has entered into the system 410 either through the basket cell openings or at the level of proximal tether memory metal strips 457 and prevents embolization into distal vessels 480. Preferably, the proximal basket 433 has two distal crowns 500 at the distal end of the proximal basket 433 that are attached to the proximal end 455 of the proximal tether memory metal strips 457 and then one or more rows of proximal cells 501, with four cells in each row.

In some embodiments, the basket system 410 is prepared by a process that includes one or more of the following steps, as illustrated in FIG. 36:

a) providing a single tube 468 comprised of a memory metal such as nitinol, the single tube 468 having an exterior, a substantially hollow interior, a wall 482 separating the exterior from the substantially hollow interior, an open proximal end 474, an open distal end 476, a middle portion 478 between the open proximal end 474 and the open distal end 476 (see FIG. 36A);
b) cutting the wall of the middle portion 478 with a laser 480 (see FIG. 36B);
c) removing the pieces of the middle portion cut by the laser 480 to form a basket system 410 comprising a proximal tube 439 comprising a hollow interior 441 extending through said proximal tube 439, said proximal tube having a proximal end 442 and a distal end 440, a distal tube 425 comprising a hollow interior 441 extending through said distal tube 425, and a middle portion 478 located between said proximal tube 439 and said distal tube 425 and comprising a plurality of proximal tether memory metal strips 457, each proximal tether memory metal strip 457 having a proximal end 455 attached to the distal end 440 of the proximal tube 439 and a distal end 453;
d) altering the shape of the middle portion 478 using a mandrel and allowing the middle portion 478 to expand relative to the distal tube 476 and proximal tube 474 to form a distal basket 411 that includes a plurality of cells 422 and 436;
e) quenching the middle portion 478 at room temperature;
f) removing the mandrel from the middle portion 478;
g) mechanically or chemically electropolishing the middle portion 478 to remove oxides (see FIG. 36C);
h) inserting a pull wire 443 to said proximal tube 439; and
i) attaching a leader wire 431 to said distal hub/junction 425 (see FIG. 36D).

In some embodiments, the middle portion 478 is expanded by heating the mandrel and the middle portion 478 by, for example, placing the mandrel and the middle portion 478 in a fluidized sand bath at about 500° C. for about 3 to about 7 minutes. As the middle portion 478 is heated, the heating causes the crystalline structure of the memory metal tube 468 to realign. Preferably, the mandrel is tapered (e.g., substantially conical or bullet in shape) so that the portion of the distal basket 411 formed from the middle portion 478 tapers from the proximal-most crown 438 to the distal end 466. Preferably, the proximal and distal ends of the tube 474 and 476 are not shape set by the mandrel and are not cut by the laser 480 so that the proximal and distal ends 474 and 476 do not change in shape and only slightly expand in size under heating and return to the size of the native tube 468 after the heat is removed. Preferably, the laser cuts are programmed via a computer. To ensure that the laser cuts only one surface of the tube wall at the time (and not the surface directly opposite the desired cutting surface), the laser 480 is preferably focused between the inner and outer diameter of the desired cutting surface and a coolant is passed through the memory metal tube 468 so that the laser 480 cools before reaching the surface directly opposite the desired cutting surface.

The portions of the wall not cut by the laser 480 create the proximal and distal tubes 474 and 476 as well as the other components of the distal basket 411, and memory metal strips 457 and 466, as described.

Preferably, the memory metal selected for the native tube 468 has a heat of transformation below average human body temperature (37° C.) so that the distal basket 411 has sufficient spring and flexibility after deployment from the catheter 432 in the human blood vessel 88.

In some embodiments, the native tube 468 (and hence the distal and proximal tubes 474 and 476) have an outer diameter of less than about 4 French, e.g., a diameter of about 1 to about 4 French. In some embodiments, the diameter of the pull wire 443 is between about 0.008 inches and about 0.051, as noted above, and in such embodiments, the diameter of the pull wire 443 may be approximately equal to the inner diameter 472 of the native nitinol tube 468.

Without being bound by any particular theory, it is believed that manufacturing the distal basket 411 from a single memory metal tube 468 provides ease of manufacturing and safety from mechanical failure and provides tensile strength necessary for the system 410 to remove hard thrombus 417 and other obstructions.

Optionally, after step e, the basket 411 further comprises a row 448 of proximal cells 436, each proximal cell 436 defined by a plurality of memory metal strips 466 and comprising a proximal crown 438 located at a proximal end of the cell 436 and pointing in the proximal direction and a distal crown 424 located at a distal end of the cell and pointing in the distal direction and further wherein each of said proximal crowns 438 of said proximal cells 436 is attached to a distal end 453 of a proximal tether memory metal strip 457. Optionally, after step e, the basket 410 further comprises a row 447 of distal cells 422 located distal to said proximal cells 436 and connected to said distal crowns 424 of said proximal cells 436, each distal cell 422 defined by a plurality of memory metal strips 466 and comprising a proximal crown 437 located at a proximal end of the cell 422 and pointing in the proximal direction and a distal crown 423 located at a distal end of the cell 422 and pointing in the distal direction, and further wherein the number of distal cells 422 is twice the number of proximal cells 436. Optionally, after step e, the basket system 410 further comprises a row 449 of strut memory metal strips 452, each strut memory metal strip 452 having a proximal end 451 attached to a distal crown 424 of a proximal cell 436 and a distal end 450 attached to a proximal crown 437 of a distal cell 422. Optionally, the basket 411 comprises no welded or soldered components and said proximal tether memory metal strips 457 are integral with said proximal cell crowns 438.

Optionally, after step e, the basket system 411 comprises between two and four proximal tether memory metal strips 457. Optionally, prior to cutting the memory metal tube 468, the memory metal tub 468 has an outer diameter 486 that is from about 0.011 inches to about 0.054 inches and an inner diameter 484 that is from about 0.008 inches to about 0.051 inches. Optionally, after step e), the proximal tube 439 and distal tube 425 have an outer diameter that is from about 0.02 inches to about 0.03 inches and an inner diameter that is from about 0.01 inches to about 0.02 inches. Optionally, the method further includes placing said basket 411 inside a catheter 432 comprised of a biocompatible material. Optionally, the method further includes the steps of placing the basket 411 inside a lumen 488 of an animal and using the basket to retrieve an object 417 located inside said lumen 488.

The Embodiments of FIGS. 45-62

FIGS. 45-62 illustrate additional embodiments of a modular, easy-to-manufacture platform of systems for retrieving hard clots and other objects in animal lumens. In some embodiments, the system includes a proximal tube, a distal tube, and a plurality of memory metal strips between the proximal and distal tubes. The plurality of memory metal strips form a wide range of basket designs. Preferably, the proximal tube, memory metal strips, and distal tube are derived from a standard, off-the-shelf single tube of memory metal (e.g., nitinol), with the proximal tube and distal tube having the same inner diameter and outer diameter as the native tube from which they were derived and with the basket formed by cutting the middle portion of the native tube and expanding and shape-setting this cut portion. Preferably, the proximal tube and distal tube have an outer diameter that is from about 0.02 inches to about 0.03 inches (e.g., about 0.027 inches) so that the device fits inside a standard microcatheter and an inner diameter that is from about 0.01 inches to about 0.02 inches. Preferably, there are no welded or soldered parts between the proximal tube and distal tube, which makes the system easy and cheap to reliably manufacture. The system also includes one or more catheters for deploying the system, a pull wire that passes through the hollow interior of the proximal tube, and a coaxial tube. Preferably, the system includes two catheters—a guide catheter and a microcatheter. The coaxial tube envelopes the pull wire, is slideable along at least a segment of the pull wire, and is attached to the proximal hub/junction. The coaxial tube allows a user to move the proximal hub/junction toward and away from the distal hub/junction while keeping the distal hub/junction stationary. Movement of the proximal hub/junction toward and away from the distal hub/junction causes conformational changes in the basket, including (depending on the basket design and the location of the proximal tube), collapsing the basket, expanding the basket, strengthening the basket, and moving the basket around the clot. The plurality of memory metal strips attached to the proximal hub/junction include a plurality of proximal tether memory metal strips, which have a proximal end attached to the distal end of the proximal tube. The length and thickness of the proximal tether memory metal strips vary in the different embodiments described herein, which allows the surgical user to select from the various embodiments in the platform based on the features needed for the particular operation (e.g., vessel anatomy and hardness of the clot).

In some embodiments, the disclosure provides a system for removing objects within an interior lumen of an animal that includes a pull wire having a proximal end, a distal end and a pull wire longitudinal axis extending from said proximal end to said distal end;

a distal basket attached to said pull wire, said distal basket comprising a proximal end, a distal end, a distal basket length extending from said distal basket proximal end to said distal end, a distal basket height perpendicular to said distal basket length and said pull wire longitudinal axis, a proximal hub/junction located at said proximal end of the distal basket, said proximal hub/junction comprising a hollow interior, said pull wire passing through said proximal hub/junction hollow interior, said proximal hub/junction slideable along at least a segment of the pull wire, a plurality of proximal tether memory metal strips, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, each proximal tether memory metal strip having a proximal end attached to said proximal hub/junction, a distal end attached to a crown of a proximal cell and a length extending from said proximal end to said distal end, a plurality of distal cells distal to the proximal cells, and a distal hub/junction located at said distal end of said distal basket and comprising a hollow interior, said distal basket having a relaxed state in which said proximal hub/junction is located a first distance proximal to said proximal crowns and wherein said distal basket has a first height, as measured at the proximal-most crown, a gaping state in which said proximal hub/junction is located a second distance from said proximal crowns and wherein has a second height, as measured at the proximal-most crown, said second height greater than said first height, said second distance less than said first distance, a proximal collapsed state in which said proximal hub/junction is located a third distance proximal to said proximal crowns and wherein said distal basket has a third height and a third width, as measured at the proximal-most crown, said third distance greater than said first distance, said third height less than said first height, a catheter having a hollow interior, a proximal end leading to said interior and a distal end leading to said interior, said catheter comprised of a biocompatible material and configured to envelope said distal basket when said distal basket is in said proximal collapsed state; wherein said distal basket is configured to move from said relaxed state to said gaping state by moving said proximal hub/junction distally relative to said distal hub/junction; and wherein said distal basket is configured to move from said expanded state to said proximal collapsed state by moving said proximal hub/junction proximally relative to said distal hub/junction.

Optionally, the distal basket further comprises a distal collapsed state in which said proximal hub/junction is located distal to said proximal crowns and wherein said distal basket has a fourth height, as measured at the proximal-most crown, said fourth height less than said first height, wherein said catheter is configured to envelope said distal basket when said distal basket is in said distal collapsed state, and further wherein said distal basket is configured to move from said gaping state to said distal collapsed state by moving said proximal hub/junction distally relative to said distal hub/junction. Optionally, the system further includes a coaxial tube, said coaxial tube configured to be received in said catheter, said coaxial tube having a proximal end, a distal end attached to said proximal hub/junction, and a hollow interior, said pull wire passing through said coaxial tube hollow interior, said coaxial tube slideable along at least a segment of said pull wire. In some embodiments, said proximal tether memory metal strips and said proximal cell memory metal strips each have a thickness and further wherein said thickness of said proximal tether memory metal strips is between about 25 to about 75 percent of the thickness of the proximal cell memory metal strips. In such embodiments, the length of the proximal tether memory metal strips is between about 3 mm to about 10 mm in the relaxed state. In some embodiments with thin proximal tether memory metal strips, the combined length of two of said proximal tether memory metal strips is within about 2 mm of said second height. In other embodiments with thin proximal tether memory metal strips, the combined length of two of said proximal tether memory metal strips is within about 2 mm of said second height multiplied by a factor of two.

In other embodiments, the proximal tether memory metal strips are as thick or thicker than the memory metal strips forming the proximal cells and in such embodiments, the length of the proximal tether memory metal strips may be between about 10 mm and about 20 mm in the relaxed state.

Optionally, said pull wire extends from said distal basket proximal end to said distal basket distal end. Optionally, said pull wire is not in contact with said distal hub/junction. Optionally, in said gaping state, said proximal hub/junction is located parallel to said proximal crown. Optionally, said pull wire and said proximal hub/junction are offset from the center of the distal basket height, as measured at the proximal-most crown. Optionally, all proximal crowns of said proximal cells are attached to a proximal tether memory metal strip. Optionally, said distal basket further comprises a plurality of strut memory metal strips and plurality of distal cells defined by a plurality of distal memory metal strips, said distal cells comprising a proximal crown located at a proximal end of said distal cells and a distal crown located at a distal end of said distal cells, said strut memory metal strips having a proximal end attached to a distal crown of a proximal cell and a distal end attached to a proximal crown of a distal cell. Optionally, the distal basket comprises between two and four proximal tether memory metal strips. Optionally, said proximal memory metal strips are integral with said proximal hub/junction. Optionally, said proximal hub/junction is a tube, wherein said interior of said proximal hub/junction has a size and shape, and further wherein said size and shape of said proximal hub/junction interior are configured to prevent a segment of said pull wire distal relative to said proximal hub/junction from moving through proximal hub/junction interior. Optionally, said distal hub/junction is a tube. Optionally, said distal hub/junction is attached to said pull wire such that said distal hub/junction is not slideable along said pull wire. Optionally, said distal basket further comprises a lead wire extending distally from said distal hub/junction. Optionally, said distal hub/junction, said proximal hub/junction, and said basket are comprised of a nitinol having the same material composition. Optionally, said distal basket further comprises an x-ray marker that is more visible under x-ray as compared to the other components when the distal basket is located in a cranial blood vessel inside the body of a human and the x-ray is taken from outside the human's body. Preferably, the x-ray marker is a radiopaque material. Some examples of radiopaque materials can include, but are not limited to, gold, platinum, palladium, tantalum, tungsten alloy, polymer material loaded with radiopaque filler, and the like. Preferably, the components are comprised of nitinol and the x-ray marker is comprised of a material having a density greater than the nitinol. Optionally, said proximal and said distal hubs/junctions are generally cylindrical in shape and each has an outer diameter and an inner diameter, the inner diameter forming apertures of the proximal and distal hubs/junctions and further wherein the outer diameters of the proximal and distal hubs/junctions are substantially the same size and further wherein the inner diameters of the proximal and distal hubs/junctions are substantially the same size. Optionally, the outer diameters of the proximal and distal hubs/junctions are from about 0.011 inches to about 0.054 inches, and further wherein the inner diameters of the proximal and distal hubs/junctions are from about 0.008 inches to about 0.051 inches. Optionally, the proximal tube and distal tube have an outer diameter that is from about 0.02 inches to about 0.03 inches and an inner diameter that is from about 0.01 inches to about 0.02 inches. Optionally, the pull wire is generally cylindrical and further wherein the diameter of the pull wire is between about 0.008 inches and about 0.051 inches. Optionally, the first height is between about 2 millimeters and about 8 millimeters. Optionally, said proximal tether memory metal strips rotate about said pull wire longitudinal axis such that a distal end of a proximal tether memory metal strip is located between about 90 and about 270 degrees relative to said proximal end of the same proximal tether memory metal strip.

The present disclosure also provides a method of removing an object from an interior lumen of an animal, said lumen having an interior wall forming said lumen. In some embodiments, the method includes:

a) providing the system described above;

b) positioning the system in said lumen, said basket located in said catheter in a collapsed state:

c) deploying said distal basket from said distal end of said catheter so that said proximal crowns of said proximal cells are distal to said obstruction;

d) allowing said distal basket to move to said relaxed state;

e) moving said proximal hub/junction distally relative to said distal hub/junction so that said distal basket height, as measured at the proximal-most crown, increase;

f) moving said distal basket over said obstruction; and g) removing said distal basket and said obstruction from said lumen.

Optionally, the interior lumen is an intracranial artery and said obstruction is a blood clot. Optionally, the method further comprises using said blood clot to move said proximal hub/junction distally relative to said distal hub/junction and allow said distal basket to move to said gaping state. Optionally, the method further comprises using a coaxial tube to push said proximal hub/junction distally relative to said distal hub/junction and allow said distal basket to move to said gaping state. Optionally, the method further includes, after step e, moving said proximal hub/junction relative to said distal hub/junction so that said distal basket height, as measured at the proximal-most crown, decrease. Optionally, after step e, said pull wire and said proximal hub/junction are offset with respect to the center of said distal basket height, as measured at the proximal-most crown, as measured at the proximal-most crown, and the center of said lumen.

The present disclosure also provides a system for removing objects within an interior lumen of an animal, the system comprising:

a pull wire having a proximal end, a distal end and a pull wire longitudinal axis extending from said proximal end to said distal end;

a proximal basket attached to said pull wire, said proximal basket comprising a proximal end, a distal end, a proximal basket length extending from said proximal basket proximal end to said distal end, a proximal basket height perpendicular to said proximal basket length and said pull wire longitudinal axis, a proximal tube located at said proximal end of the proximal basket, said proximal tube comprising a hollow interior, said pull wire passing through said hollow interior and said proximal tube slideable along at least a segment of said pull wire, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction, a distal basket attached to said pull wire, said distal basket comprising a proximal end, a distal end, a distal basket length extending from said distal basket proximal end to said distal end, a distal basket height perpendicular to said distal basket length and said pull wire longitudinal axis, a distal tube located at said distal end of the distal basket, said distal tube comprising a hollow interior, a plurality of rows of cells, each cell defined by a plurality of memory metal strips, each cell comprising a proximal crown located at the proximal end of the proximal cell and pointing generally in the proximal direction and a distal crown located at the distal end of the proximal cell and pointing generally in the distal direction, a plurality of tether memory metal strips, each tether memory metal strip having a proximal end attached to a distal crown of a cell located at the distal end of said proximal basket and a distal end attached to a proximal crown of a cell located at the proximal end of said distal basket, said proximal basket having a relaxed state wherein said proximal basket has a first height as measured at the distal-most crown, and said proximal hub/junction is located a first distance proximal to said distal hub/junction:

a collapsed state wherein said proximal basket has a second height, as measured at the distal-most crown, said second height less than said first height;

a gaping state wherein said proximal basket has a third height, as measured at the distal-most crown, and said proximal hub/junction is located a second distance proximal to said distal hub/junction, said third height greater than said first height and said second distance less than said first distance, said proximal basket configured to move from said expanded state to said gaping state by pushing said proximal tube distally relative to said distal tube;

said distal basket having a relaxed state wherein said distal basket has a first height and a collapsed state wherein said distal basket has a second height, said second height less than said first height, and a catheter having an interior, a proximal end leading to said interior and a distal end leading to said interior, said catheter comprised of a biocompatible material and configured to envelope said distal and said proximal basket when said baskets are in said collapsed state.

Optionally, said proximal tether memory metal strips rotate about said pull wire longitudinal axis such that a distal end of a proximal tether memory metal strip is located between about 90 and about 270 degrees relative to said proximal end of the same proximal tether memory metal strip.

In some embodiments, the system does not include a proximal hub/junction and the system includes soft cords in place of or in addition to the proximal memory metal strips.

For example, in one embodiment, the system includes:

a pull wire having a proximal end, a distal end and a pull wire longitudinal axis extending from said proximal end to said distal end;

a coaxial tube having a proximal end, a distal end and a hollow interior, said pull wire passing through said coaxial tube hollow interior, said coaxial tube slideable along at least a segment of said pull wire;

a distal basket attached to said pull wire and said coaxial tube, said distal basket comprising a proximal end, a distal end, a distal basket length extending from said distal basket proximal end to said distal end, a distal basket height perpendicular to said distal basket length and said pull wire longitudinal axis, a plurality of cords, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, each cord having a proximal end attached to said coaxial tube, a distal end attached to a crown of a proximal cell and a length extending from said proximal end to said distal end, a plurality of distal cells distal to the proximal cells, and a distal hub/junction located at said distal end of said distal basket and comprising a hollow interior, said distal basket having a relaxed state in which said coaxial tube is located a first distance proximal to said proximal crowns and wherein said distal basket, as measured at the proximal-most crown, has a first height, a proximal collapsed state in which said coaxial tube is located a second distance proximal to said proximal crowns and wherein said distal basket, as measured at the proximal-most crown, has a second height, said second distance greater than said first distance, said second height less than said first height, a catheter having a hollow interior, a proximal end leading to said interior and a distal end leading to said interior, said catheter comprised of a biocompatible material and configured to envelope said coaxial tube and said distal basket when said distal basket is in said proximal collapsed state;

wherein said distal basket is configured to move from said relaxed state to said proximal collapsed state by moving said coaxial tube proximally relative to said distal hub/junction.

Optionally, the distal basket further comprises a distal collapsed state in which said coaxial tube is located distal to said proximal crowns and wherein said distal basket, as measured at the proximal-most crown, has a third height, said third height less than said first height, wherein said catheter is configured to envelope said distal basket when said distal basket is in said distal collapsed state, and further wherein said distal basket is configured to move from said relaxed state to said distal collapsed state by moving said coaxial tub distally relative to said distal hub/junction. Optionally said cord is comprised of a material selected from the group consisting of plastic, rubber, nylon, suture material, and braided catheter material. Optionally, said cords are integral with said coaxial sheath. Optionally, said cords are glued to said coaxial sheath. Optionally, said cords are shrink wrapped to said coaxial sheath. Optionally, said cords have a thickness of from about 0.001 to about 0.1 inches (more preferably about 0.004 to about 0.018 inches) and have a length of from about 3 mm to about 20 mm in said relaxed state. Optionally, said pull wire extends from said distal basket proximal end to said distal basket distal end and said pull wire is attached to said distal hub/junction. Optionally, all proximal crowns of said proximal cells are attached to a cord. Optionally, the basket comprises four proximal cells, each proximal cell having a proximal crown, and not all (e.g., only two) of the proximal crowns are attached to a cord. Optionally, said distal basket further comprises a plurality of strut memory metal strips and plurality of distal cells defined by a plurality of distal memory metal strips, said distal cells comprising a proximal crown located at a proximal end of said distal cells and a distal crown located at a distal end of said distal cells, said strut memory metal strips having a proximal end attached to a distal crown of a proximal cell and a distal end attached to a proximal crown of a distal cell. Optionally, the distal basket comprises between two and four cords. Optionally, said distal hub/junction is attached to said pull wire such that said distal hub/junction is not slideable along said pull wire. Optionally, said distal basket further comprises a lead wire extending distally from said distal hub/junction. Optionally, said distal hub/junction and said basket are comprised of a nitinol having the same material composition. Optionally, said distal basket and/or said coaxial tube further comprises an x-ray marker that is more visible under x-ray as compared to the other components when the distal basket is located in a cranial blood vessel inside the body of a human and the x-ray is taken from outside the human's body. Preferably, the x-ray marker is a radiopaque material. Some examples of radiopaque materials can include, but are not limited to, gold, platinum, palladium, tantalum, tungsten alloy, polymer material loaded with radiopaque filler, and the like. Preferably, the components are comprised of nitinol and the x-ray marker is comprised of a material having a density greater than the nitinol. Optionally, said distal hub/junction is generally cylindrical in shape and has an outer diameter and an inner diameter, the inner diameter forming the aperture of the distal hub/junction and further wherein the outer diameter of the distal hub/junction from about 0.011 inches to about 0.054 inches, and further wherein the inner diameter of the distal hub/junction is from about 0.008 inches to about 0.051 inches. Optionally, the distal tube has an outer diameter that is from about 0.02 inches to about 0.03 inches and an inner diameter that is from about 0.01 inches to about 0.02 inches. Optionally, the pull wire is generally cylindrical and further wherein the diameter of the pull wire is between about 0.008 inches and about 0.051 inches. Optionally, the first height of the distal basket, as measured at the proximal-most crown, is between about 2 millimeters and about 8 millimeters. Optionally, said cords are soft.

In some embodiments, the present disclosure provides a method of removing an object from an interior lumen of an animal, said lumen having an interior wall forming said lumen, the method comprising the steps of:

a) providing the system described above;

b) positioning the system in said lumen, said basket located in said catheter in a collapsed state;

c) deploying said distal basket from said distal end of said catheter so that said proximal crowns of said proximal cells are distal to said obstruction:

d) allowing said distal basket to move to said relaxed state;

e) moving said coaxial tube distally relative to said distal hub/junction so that said coaxial tube moves distally to the proximal-most crown;

f) moving said distal basket, said pull wire and said coaxial tube proximally so that said distal basket moves over said obstruction;

g) moving said coaxial sheath distally relative to said distal hub/junction so that said distal basket height, as measured at the proximal-most crown, decreases and said coaxial tube is closer to said distal hub/junction as compared to the proximal-most crown; and i) removing said distal basket and said obstruction from said lumen.

In other embodiments, the method includes a) providing the system described above;

b) positioning the system in said lumen, said basket located in said catheter in a collapsed state:

c) deploying said distal basket from said distal end of said catheter so that said proximal crowns of said proximal cells are distal to said obstruction;

d) allowing said distal basket to move to said relaxed state;

e) moving said coaxial tube distally relative to said distal hub/junction so that said coaxial tube moves distally to the proximal-most crown;

f) moving said distal basket, said pull wire and said coaxial tube proximally so that said distal basket moves over said obstruction:

g) moving said coaxial sheath proximally relative to said distal hub/junction so that said distal basket height, as measured at the proximal-most crown, decreases;

h) moving said catheter distally relative to said distal hub/junction so that said catheter re-sheaths said coaxial sheath and partially re-sheaths said cords, thereby decreasing said distal basket height, as measured at the proximal-most crown;

i) removing said distal basket and said obstruction from said lumen.

Optionally, said interior lumen is an intracranial artery and said obstruction is a blood clot.

In other embodiments that do not include a proximal hub/junction, the system includes a pull wire having a proximal end, a distal end and a pull wire longitudinal axis extending from said proximal end to said distal end;

a coaxial tube having a proximal end, a distal end and a hollow interior, said pull wire passing through said coaxial tube hollow interior, said coaxial tube slideable along at least a segment of said pull wire;

a distal basket attached to said pull wire and said coaxial tube, said distal basket comprising a proximal end, a distal end, a distal basket length extending from said distal basket proximal end to said distal end, a distal basket height perpendicular to said distal basket length and said pull wire longitudinal axis, a plurality of proximal tether memory metal strips, a plurality of cords, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, each proximal tether memory metal strip having a proximal end attached to said coaxial tube and a distal end, each cord having a proximal end attached to a distal end of a proximal tether memory metal strip and a distal end attached to a crown of a proximal cell and a length extending from said proximal end to said distal end, and a plurality of distal cells distal to the proximal cells, and a distal hub/junction located at said distal end of said distal basket and comprising a hollow interior, said distal basket having a relaxed state in which said distal basket, as measured at the proximal-most crown, has a first height, a collapsed state in which said distal basket, as measured at the proximal-most crown, has a second height, said second height less than said first height, a catheter having a hollow interior, a proximal end leading to said interior and a distal end leading to said interior, said catheter comprised of a biocompatible material and configured to envelope said coaxial tube and said distal basket when said distal basket is in said collapsed state.

Optionally, said cord is comprised of a material selected from the group consisting of plastic, rubber, nylon, suture material, and braided catheter material. Optionally, said proximal tether memory metal strips are integral with said coaxial sheath. Optionally, said cords are glued to said proximal tether memory metal strips. Optionally, said cords are shrink wrapped to said proximal tether memory metal strips. Optionally, said cords have a thickness of from about 0.004 to about 0.1 inches (more preferably about 0.004 inches to about 0.018 inches) and further wherein said cords have a length of from about 3 mm to about 20 mm in said relaxed state. Optionally, said pull wire extends from said distal basket proximal end to said distal basket distal end and said pull wire is attached to said distal hub/junction. Optionally, all proximal crowns of said proximal cells are attached to a cord. Optionally, the basket comprises four proximal cells, each proximal cell having a proximal crown, and not all (e.g., only two) of the proximal crowns are attached to a cord. Optionally, said distal basket further comprises a plurality of strut memory metal strips and plurality of distal cells defined by a plurality of distal memory metal strips, said distal cells comprising a proximal crown located at a proximal end of said distal cells and a distal crown located at a distal end of said distal cells, said strut memory metal strips having a proximal end attached to a distal crown of a proximal cell and a distal end attached to a proximal crown of a distal cell. Optionally, the distal basket comprises between two and four cords. Optionally, said distal hub/junction is attached to said pull wire such that said distal hub/junction is not slideable along said pull wire. Optionally, said distal basket further comprises a lead wire extending distally from said distal hub/junction. Optionally, said distal hub/junction and said basket are comprised of a nitinol having the same material composition. Optionally, said distal basket and/or said coaxial tube further comprises an x-ray marker that is more visible under x-ray as compared to the other components when the distal basket is located in a cranial blood vessel inside the body of a human and the x-ray is taken from outside the human's body. Preferably, the x-ray marker is a radiopaque material. Some examples of radiopaque materials can include, but are not limited to, gold, platinum, palladium, tantalum, tungsten alloy, polymer material loaded with radiopaque filler, and the like. Preferably, the components are comprised of nitinol and the x-ray marker is comprised of a material having a density greater than the nitinol. Optionally, said distal hub/junction is generally cylindrical in shape and has an outer diameter and an inner diameter, the inner diameter forming the aperture of the distal hub/junction and further wherein the outer diameter of the distal hub/junction from about 0.011 inches to about 0.054 inches, and further wherein the inner diameter of the distal hub/junction is from about 0.008 inches to about 0.051 inches. Optionally, the distal tube has an outer diameter that is from about 0.02 inches to about 0.03 inches and an inner diameter that is from about 0.01 inches to about 0.02 inches. Optionally the pull wire is generally cylindrical and further wherein the diameter of the pull wire is between about 0.008 inches and about 0.051 inches. Optionally, the first height of the distal basket, as measured at the proximal-most crown, is between about 2 millimeters and about 8 millimeters. Optionally, the cords are soft.

In some embodiments, the above system is used in a method of removing an object from an interior lumen of an animal, said lumen having an interior wall forming said lumen that includes a) providing the above system;

b) positioning the system in said lumen, said basket located in said catheter in a collapsed state:

c) deploying said distal basket from said distal end of said catheter so that said proximal crowns of said proximal cells are distal to said obstruction, said coaxial sheath is proximal to said obstruction, said proximal tether memory metal strips are proximal to said obstruction, and said cords are adjacent to said obstruction;

d) allowing said distal basket to move to said relaxed state, e) moving said coaxial tube distally relative to said distal hub/junction so that said proximal tether memory metal strips move distally relative to the proximal-most crown and said obstruction is sandwiched between said proximal tether memory metal strips and said proximal crowns of said proximal cells:

f) removing said distal basket and said obstruction from said lumen.

Optionally said interior lumen is an intracranial artery and said obstruction is a blood clot.

With reference to FIGS. 45-62 the present disclosure provides a deployable system, generally designated by the numeral 610, for removing an obstruction such as a blood clot 617 or other object from a blood vessel 688 or other interior lumen of an animal. In addition to a blood clot 617, the obstruction may be, for example, extruded coils during aneurysm treatment, intravascular embolic material such as onyx or other obstructions requiring mechanical intravascular removal from small distal vessels. In the drawings, not all reference numbers are included in each drawing for the sake of clarity.

One example of a deployable basket system 610 is shown in FIGS. 46A-46E, 47G-47H and 50A. As shown in FIGS. 46A-46E, 47G-47H and 50A, the system 610 includes a pull wire 643 having a proximal end 645, a distal end 644 and a pull wire longitudinal axis 646 extending from said proximal end 645 to said distal end 644. Optionally, the diameter of the pull wire 643 is between about 0.008 inches and about 0.051 inches.

The system 610 further includes a distal basket 611 attached to said pull wire 643, said distal basket 611 comprising a proximal end 669, a distal end 665, a distal basket length 667 extending from said distal basket proximal end 669 to said distal end 665, a distal basket height 661 perpendicular to said distal basket length 667 and said pull wire longitudinal axis 646, a proximal hub/junction 639 located at said proximal end 669 of the distal basket 611, said proximal hub/junction 639 comprising a hollow interior 641, said pull wire 643 passing through said proximal hub/junction hollow interior 641, said proximal hub/junction 639 slideable along at least a segment of the pull wire 643, a plurality of proximal tether memory metal strips 657, a plurality of proximal cells 636 defined by a plurality of proximal cell memory metal strips 666, each proximal cell 636 comprising a proximal crown 638 located at the proximal end of the proximal cell 636 and pointing generally in the proximal direction and a distal crown 624 located at the distal end of the proximal cell 636 and pointing generally in the distal direction, each proximal tether memory metal strip 657 having a proximal end 655 attached to said proximal hub/junction 639, a distal end 663 attached to a crown of a proximal cell 638 and a length 655 extending from said proximal end 655 to said distal end 653, a plurality of distal cells 622 distal to the proximal cells 636, and a distal hub/junction 625 located at said distal end 665 of said distal basket and comprising a hollow interior 627. Preferably, the proximal hub/junction 639 and distal hub/junction 625 are hollow tubes formed from the same tube of memory metal, as described below. In some embodiments, the basket 611 includes a first row of two, three, or four crowns (i.e., the proximal crowns 638 of the proximal cells 638) and then subsequent repeating rows of twice as many crowns as compared to the number of proximal crowns 638 (i.e., four, six, or eight crowns) along the basket length 667.

The system further includes a guide catheter 630 and a microcatheter 632, which is wider and shorter than the guide catheter 630, so that the microcatheter 632 can fit inside the guide catheter 630. The microcatheter 632 has a hollow interior 615, a proximal end 616 leading to said interior 615 and a distal end 614 leading to said interior 615. The microcatheter 632 is comprised of a biocompatible material. As used herein, the terms "guide catheter", "microcatheter" and "catheter" generally refers to any suitable tube through which the system 610 can be deployed. Preferably, the catheters are sterile and comprised of a biocompatible material (i.e., a material that does not irritate the human body during the course of a 45 minute operation that involves using the system 610 to remove a clot 617 from an intracranial blood vessel 688). The catheter can be any suitable shape, including but not limited to generally cylindrical. For purposes of the present invention, when it is said that the catheter envelopes the system 610, it will be understood that the catheter envelopes at least one component of the system 610 (preferably, the distal basket 611, the lead wire 631, which is a wire that extends distally from the pull wire 643, and the pull wire 643). In some embodiments, the microcatheter 632 is about 2.5 French in diameter. Optionally, the catheter is delivered to the region of the lumen that has the obstruction 617 as follows: a guide wire is delivered to the obstruction region past the obstruction 617; the catheter is delivered over the guide wire; the guide wire is removed; and the system 610 is delivered with its pull wire 643 and lead wire 631 through the catheter. Optionally, the pull wire 643 is used to push the system 610 through the catheter as well as to retrieve the distal basket 611 after capturing the obstruction 617 as described below. The system 610 may utilize a plurality of catheters as described above, such as, for example, a wider catheter that travels to the brain and a very flexible, smaller diameter microcatheter that is delivered from the first catheter and travels through the small arteries of the brain.

Preferably, a coaxial tube 618, which has a hollow interior 620 and is slideable along at least a portion of the pull wire 643 is attached to the proximal hub/junction 639.

Figure 46A:
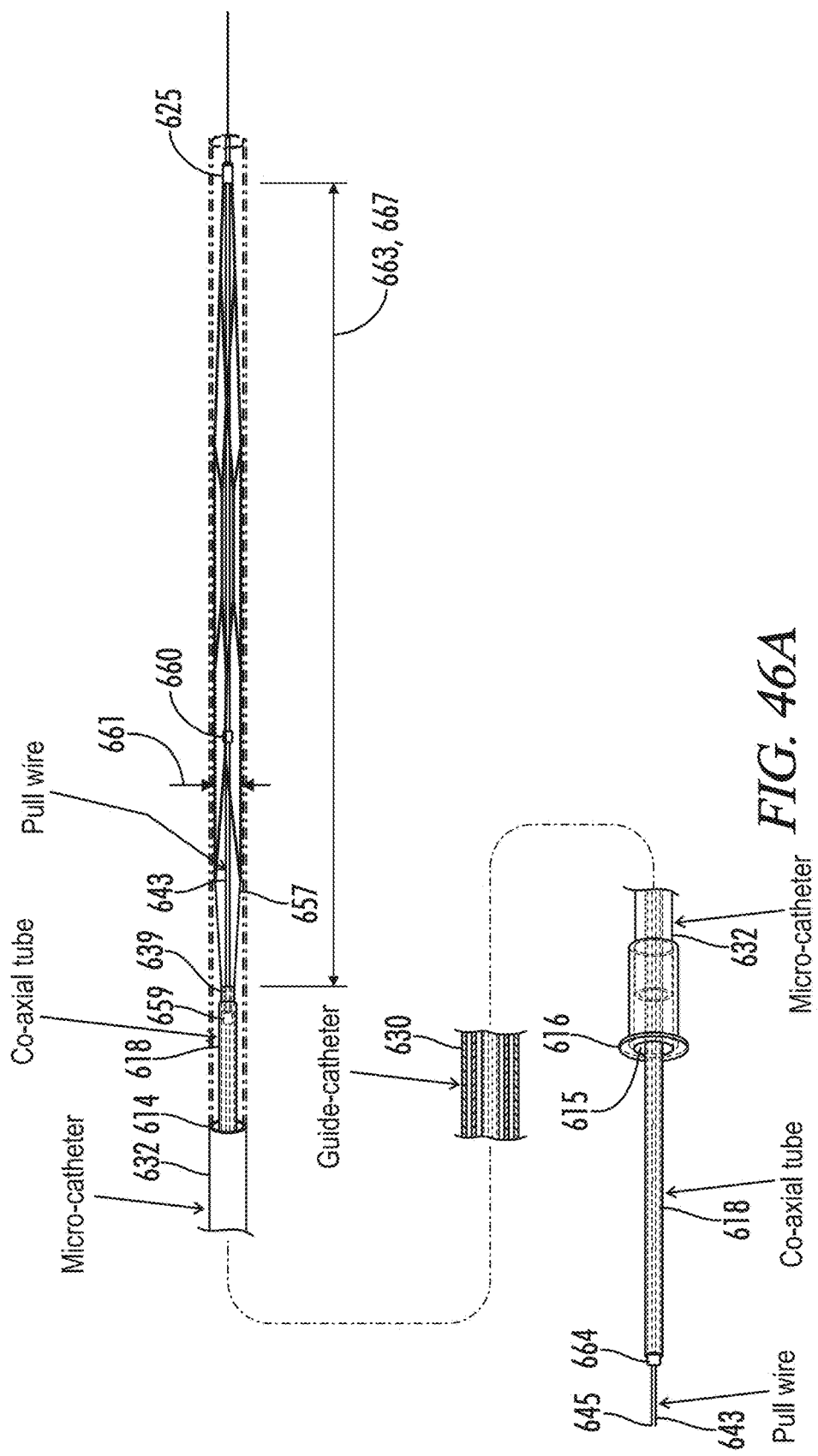
FIGS. 46A-46E illustrate a side, perspective view of stepwise deployment and use of a basket system with relatively thin and short proximal tether memory metal strips.

FIG. 46A shows the distal basket 611 collapsed inside a microcatheter 632. The distal basket 611 is in what's referred to as the proximal collapsed state. In this state, the system 610 is able to be located inside the microcatheter 632 and the basket height 661 is collapsed. For purposes of the present invention, the basket height 661 generally refers to the height at a particular location (e.g., at the proximal-most crown 638 of the distal basket 611 or the distal-most crown 623 of the proximal basket 633), it being understood that the height of the distal basket 611 and proximal basket 633 may vary along the distal basket length 667 and the length of the proximal basket 633.

In FIG. 46A, the proximal hub/junction 639 is located a maximum distance from the distal hub/junction 625. The distance from the proximal hub/junction 639 to the distal hub/junction 625 changes by exerting force on the proximal hub/junction 639, as described herein, and the distance is shown in the drawings using the numeral 663. This distance is also generally equal to the length of the basket 667, as shown.

Figure 46B:
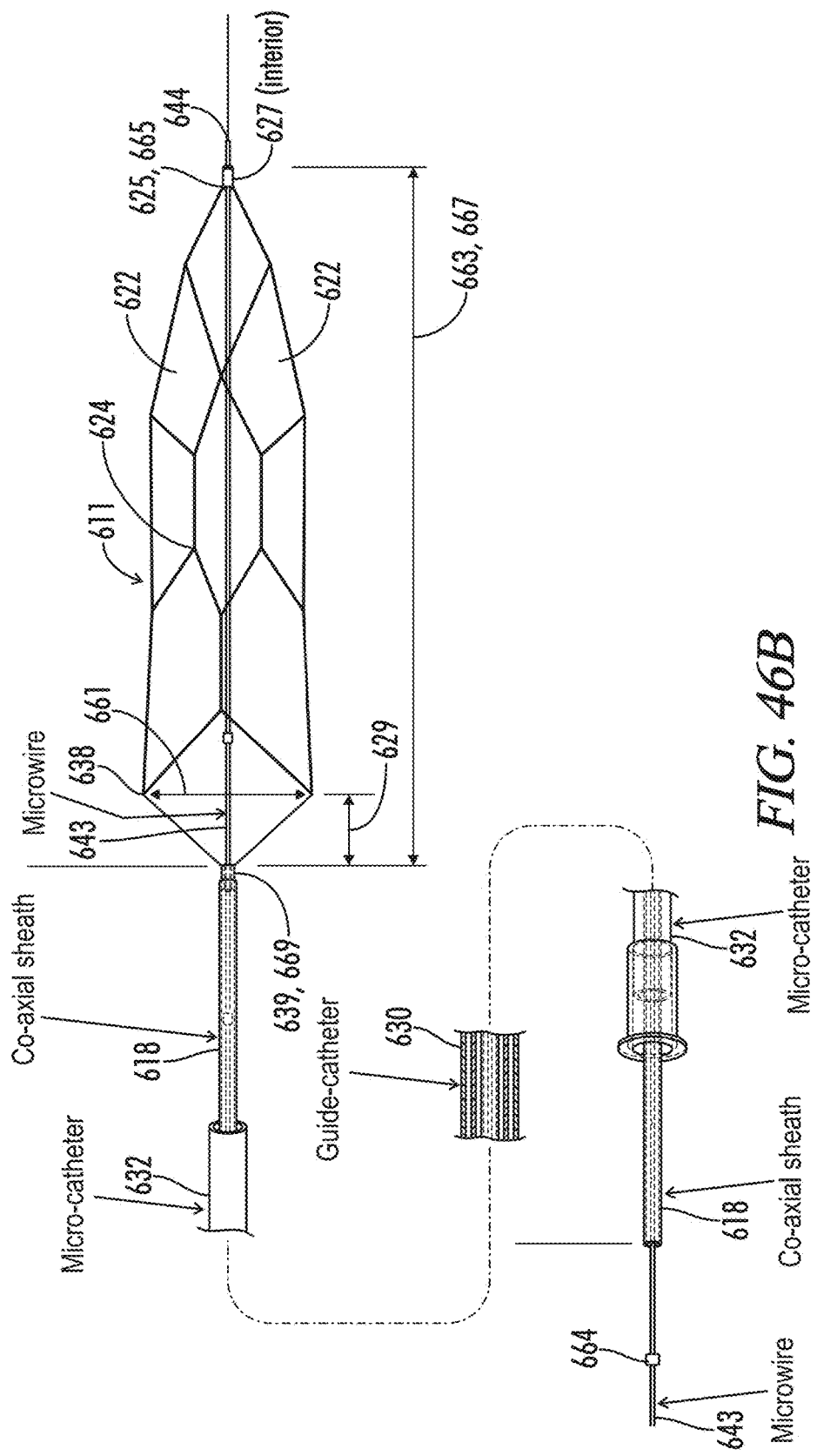

FIG. 46B shows the same basket system as FIG. 46A, except that the basket 611 has been deployed from the distal end 614 of the microcatheter 632 by pulling the microcatheter 632 proximally. As shown in FIG. 46B, the basket 611 is now in a relaxed state and the basket height 661 has increased. In the relaxed state exemplified, the proximal tube 639 is located a short distance 629 proximal to the proximal-most crown 638. In addition, the basket length 667 and the distance 663 between the proximal and distal hubs/junctions 639 and 625 has decreased as the basket 611 has relaxed. In addition, the user has moved the coaxial tube 618 proximally relative to the pull wire 643 as shown by the line in the lower part of FIG. 46B, which indicates that the distance between the proximal stop 664 and the coaxial tube proximal end 621 has increased from FIG. 46A to FIG. 46B. The present invention may utilize a variety of stops, such as a proximal stop 664, which is any barrier that prevents the coaxial tube 618 from moving proximally beyond the proximal stop 664. In some forms, the proximal stop 664 is merely an enlargement or x-ray marker 658 in the pull wire 643 that is taller and/or wider than the open coxial tube interior 620 (i.e., the inner diameter of the coaxial tube 618). Instead of stops or in addition to stops, the pull wire 643 may be etched to provide guidance to the surgeon on the distance to push and pull the coaxial tube 618.

Figure 46C:
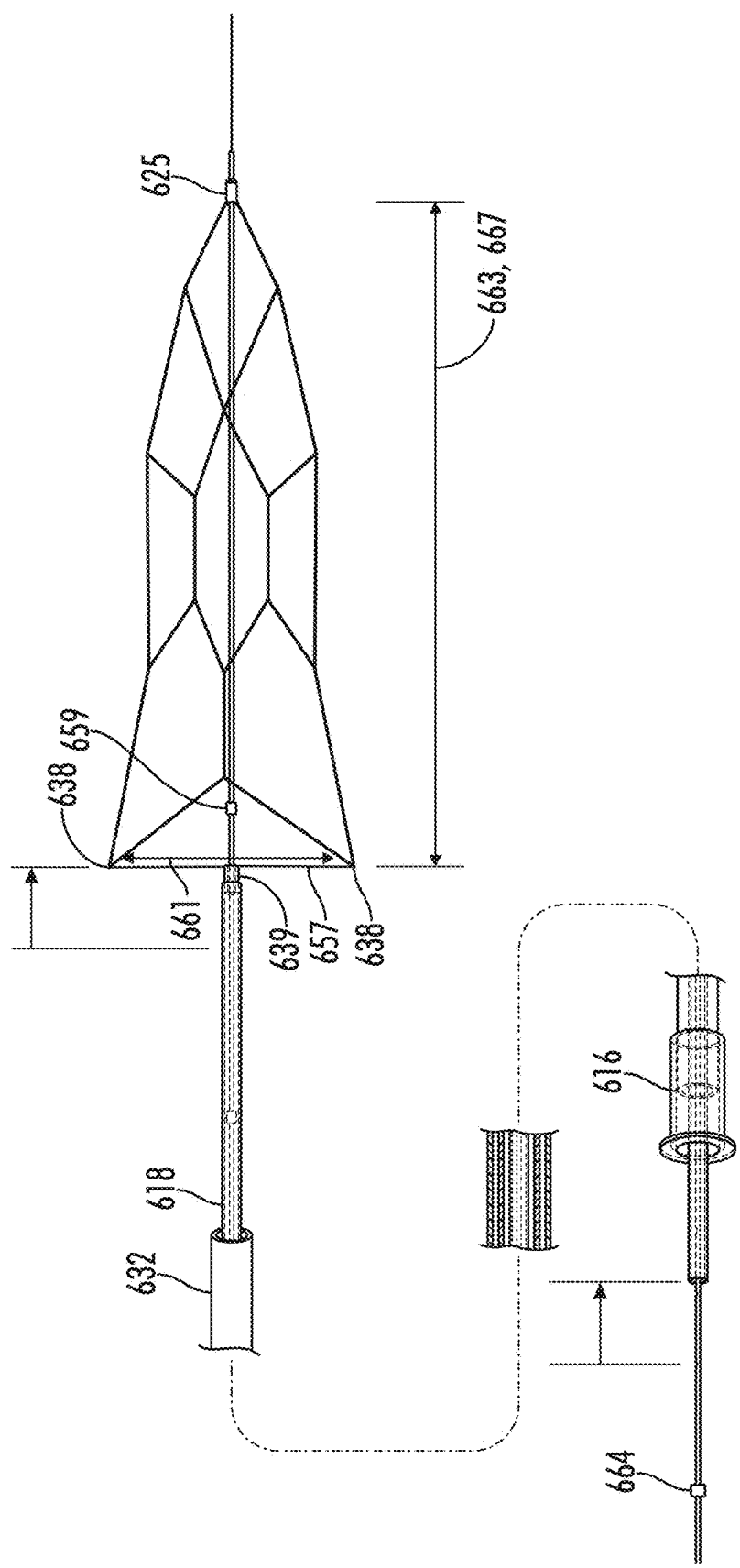

FIG. 46C exemplifies what is referred to as the gaping state of the basket 611. To move the basket 611 from the relaxed state to the gaping state, a user merely pushes the proximal hub/junction 639 distally towards the stationary distal hub/junction 625. This causes the proximal tether memory metal strips 657 to increase the height 661 of the distal basket 611 at the proximal-most crown 638. The proximal tether memory metal strips 657 of the embodiment shown in FIGS. 46, 47 and 50 are relatively short. The proximal tether memory metal strips 657 are relatively thin compared to the memory metal strips 666 that make up the proximal cells 636, which makes the proximal tether memory metal strips 657 easy to bend. Preferably, in the gaping state of short, relatively thin proximal tether memory metal strips 657, the proximal memory metal strips 657 are substantially perpendicular (e.g., about 75 to about 105 degrees) relative to the longitudinal axis of the pull wire 646.

Figure 46D:
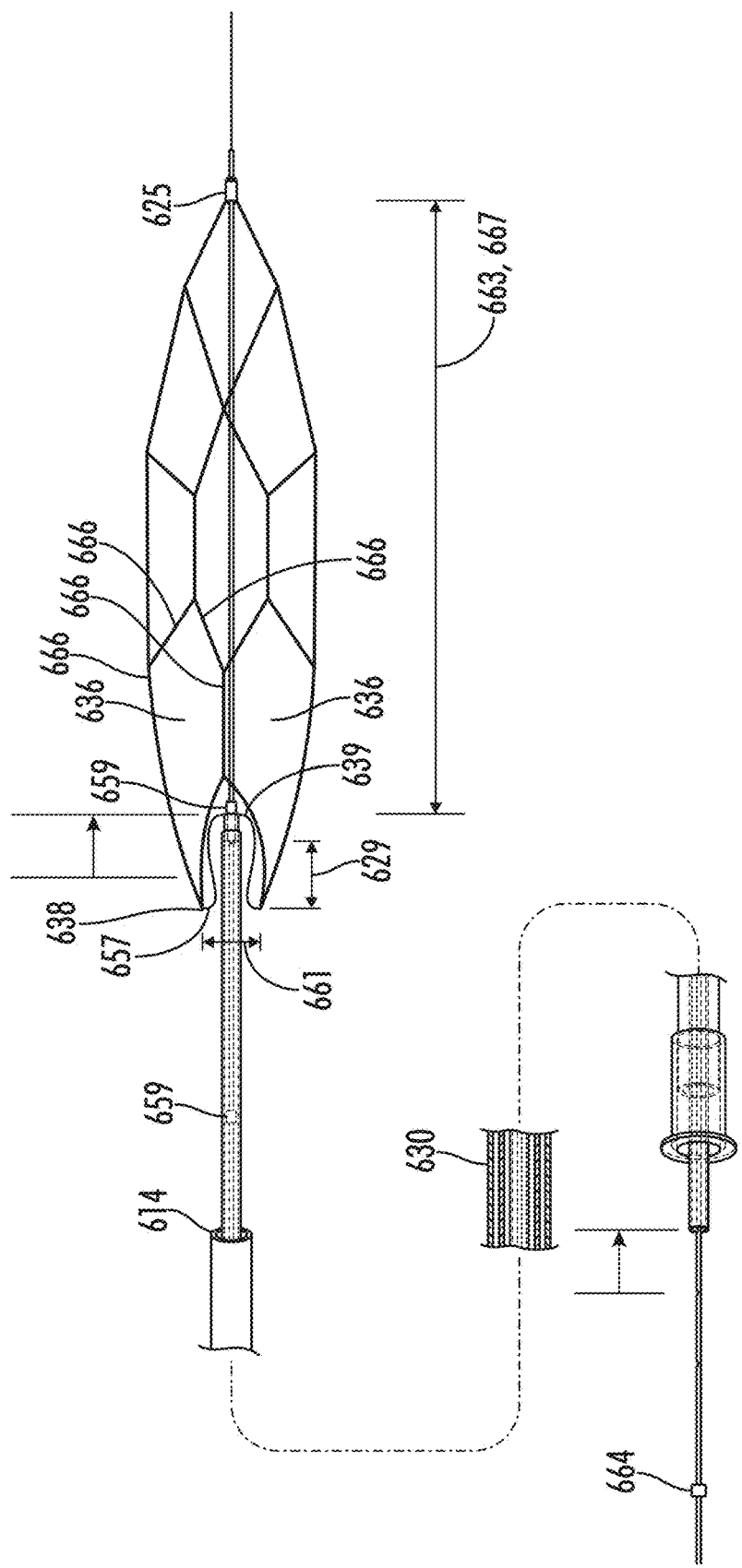

FIG. 46D exemplifies what is referred to as the distal collapsed state. To move the basket 611 from the gaping state to the distal collapsed state, a user merely pushes the proximal hub/junction 639 distally towards the stationary distal hub/junction 625. This causes the proximal tether memory metal strips 657 to reduce the height 661 of the distal basket at the proximal-most crown 638, which in certain embodiments, allows the user to recapture the system 610 in the microcatheter 632. This is particularly helpful if the system 610 was deployed at the wrong location. Preferably, the pull wire 643 includes a distal stop 660, which prevents the proximal hub/junction 39 from moving too far distally and breaking.

Figure 46E:
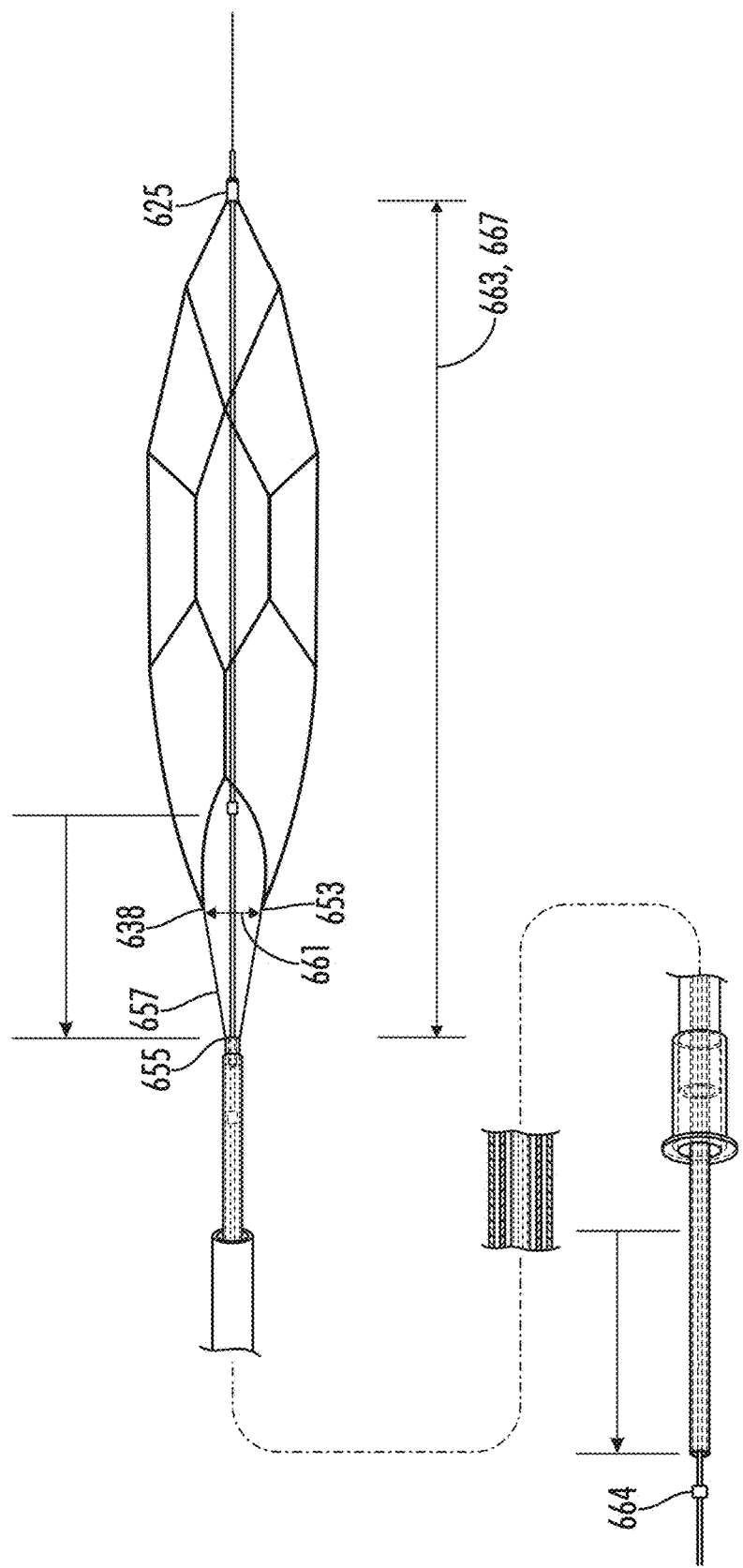
Figure 47C:
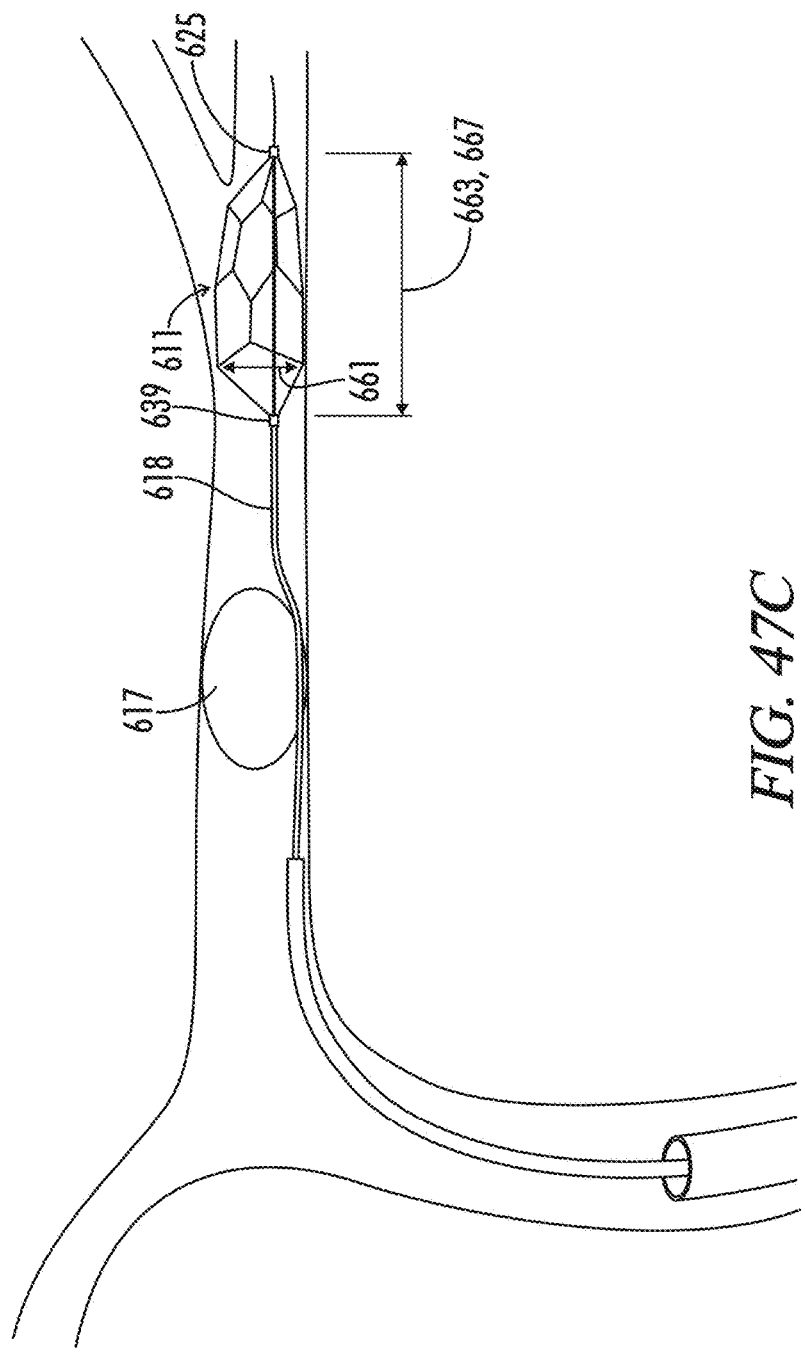
Figure 47D:
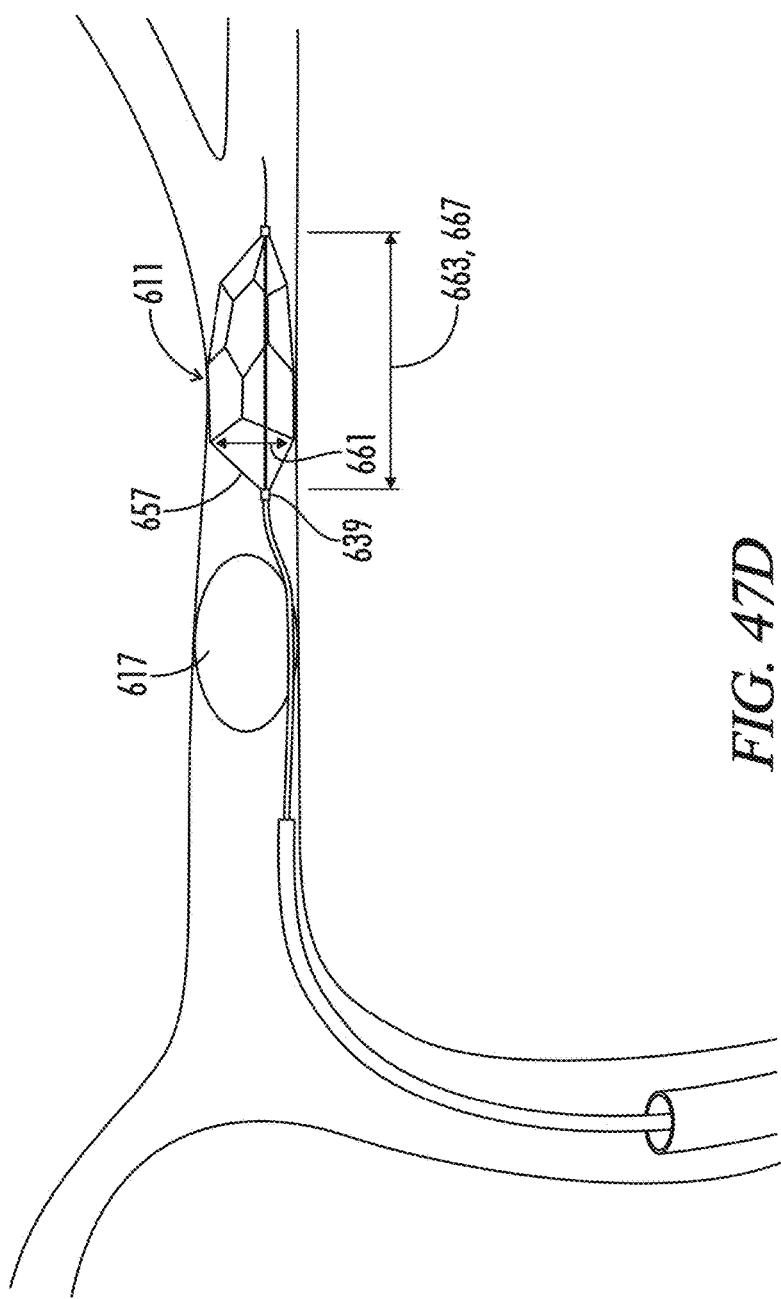
Figure 47E:
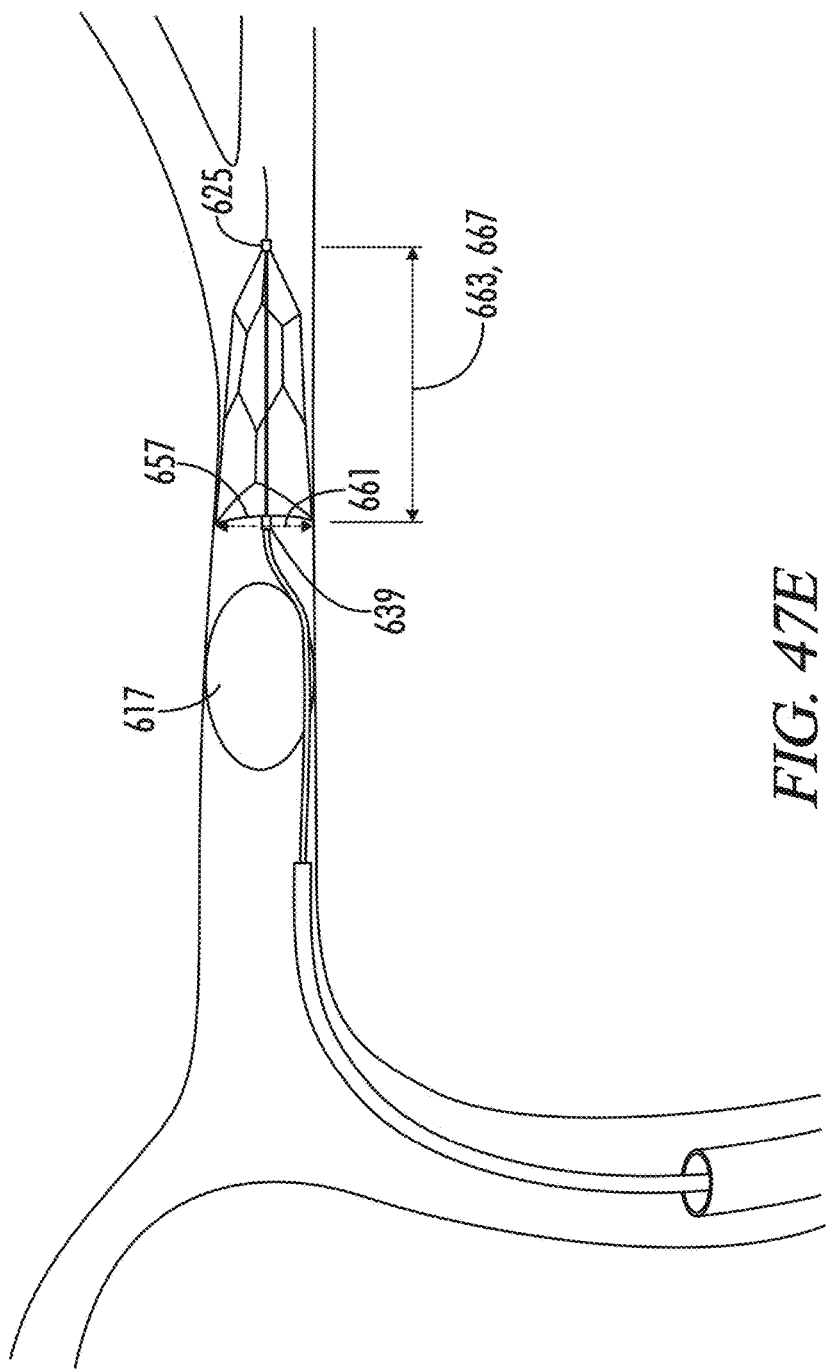
Figure 47H:
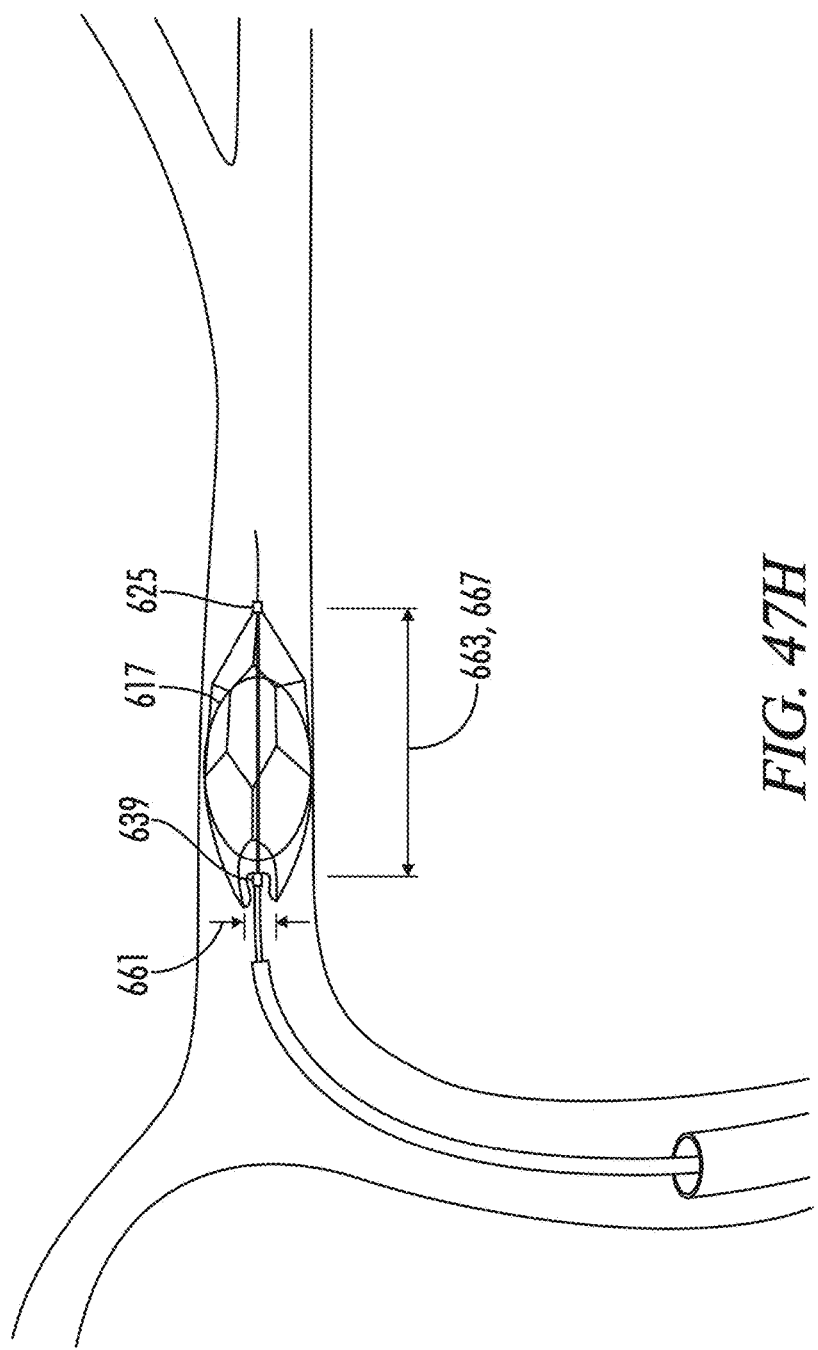

FIG. 46E also exemplifies the proximal collapsed state. To move the basket 611 from the relaxed state to the proximal collapsed state, a user merely pulls the proximal hub/junction 639 away from the stationary distal hub/junction

625. This causes the proximal tether memory metal strips 657 to reduce the height 661 of the distal basket at the proximal-most crown 638, which in certain embodiments, allows the user to recapture the system 610 in the microcatheter 632. This is particularly helpful if the system 610 was deployed at the wrong location. Preferably, the pull wire 643 includes a middle stop 655, which prevents the proximal hub/junction 639 from moving too far proximally.

FIG. 47 illustrates use of the basket system shown in FIG. 46 in an intracranial artery 688. As shown in FIG. 47A, first the guide catheter 630 is deployed proximal to the clot 617. The microcatheter 632 is then advanced distally beyond the clot 617. The basket 611 is collapsed inside the microcatheter 632. Next, as shown in FIG. 47B, the microcatheter 632 is moved proximally to deploy the basket 611 distal to the clot 617. The basket 611 is now in the relaxed state. Next, as shown in FIG. 47C, the user continues to move the microcatheter 632 proximally. Then, as shown in FIG. 47D, the basket 611 is moved closer to the clot 617 by a user pulling the pull wire 643 and coaxial tube 618 proximally at the same time. Then, as shown in FIG. 47E, the user uses the coaxial tube 618 to move the proximal hub/junction 639 toward the distal hub/junction 625 so that the basket 611 is in the gaping state. The gaping state is particularly important, as it believed to allow the basket 611 to capture the clot 617 without having the clot 617 collapse the basket 611. Then, as shown in FIG. 47F, the basket 611 is moved proximally over the clot 617. Then, as shown in FIG. 47G, the coaxial tube 618 is moved further proximally to close the proximal end 669 around the clot 617. The system 611 is moved proximally by moving the pull wire 643 and the coaxial tube 618 proximally simultaneously.

FIG. 50A shows a close-up view of the proximal end of the basket 611, including the proximal tube interior 641, the attachment of the proximal tether memory metal strips 657 at the distal end 655 of the proximal hub/junction 639, and the proximal crowns 638 of the proximal cells 636. In FIG. 50A, all proximal crowns 638 of the proximal cells 636 are attached to a proximal tether memory metal strip 657. FIG. 50B illustrates an alternative embodiment in which two proximal crowns 638a of a proximal cell 636 (the top and bottom crowns 638a) are attached to a proximal tether memory metal strip 657 and one proximal crown 638b of a proximal cell 636 is not attached to a proximal tether memory metal strip 657. FIGS. 50C-50E illustrate that the basket system may include, for example, between 2 and 4 proximal tether memory metal strips 657.

Figure 56:
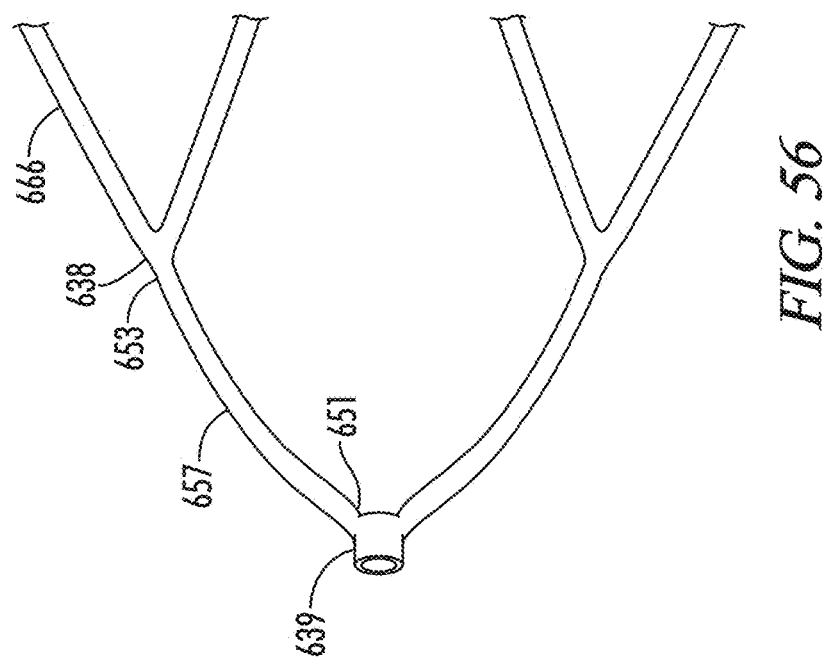
FIG. 56 illustrates a side, perspective view of a basket system with relatively thick and short proximal tether memory metal strips.

FIG. 56 illustrates a side, perspective view of a basket system 610 with relatively thick and short proximal tether memory metal strips 657 (i.e., the proximal tether memory metal strips 657 are slightly thicker than the memory metal strips 666 making up the proximal cells 636.

In, FIG. 57 the proximal tether memory metal strips 657 are thicker than the memory metal strips 666 forming the proximal cells 636 of the distal basket 611. In these embodiments with thicker proximal tether memory metal strips 657, the proximal tether memory metal strips 657 resist deforming when the proximal hub/junction 635 is translated distally toward the stationary distal hub/junction 629 and instead the proximal tether memory metal strips 657 are bowed out laterally, dissecting through or around the clot 617 and centering, buttressing and strengthening the opening of the basket 611. In particular, as illustrated in FIG. 57A, the basket 611 is deployed distal to the clot 617. The basket 611 is move distally so that the clot 617 partially collapses the proximal tether memory metal strips 657. See FIG. 57B. The proximal hub/junction 614C is moved distally to slice the proximal tether memory metal strips 657 through the clot 617. See FIG. 57C. The basket 611 is moved proximally to ensnare the clot 617. See FIG. 57. The tether proximal memory metal strips 657 are partially withdrawn into the microcatheter 632 and the system is removed from the body. See FIG. 57E.

FIG. 51 illustrates a similar to basket system 610 to FIGS. 46, 47 and 50. In FIG. 51, the proximal tether memory metal strips 657 are relatively thin and short and the proximal memory metal strips making up the remainder of the basket are thickest at the proximal-most crown 38 and decrease gradually along the distal basket length 667.

FIG. 52 illustrates a similar to basket system 610 to FIGS. 46, 47, 50, and 51. Again, the proximal tether memory metal strips 657 are relatively thin and short. In this embodiment, the length 654A of the first proximal memory metal strip 657A and the length 654B of the second proximal memory metal strip 657B are equal to the height 661 of the basket 611 in the relaxed state, as measured at the proximal-most crown 638, plus or minus two mm. Thus, if for example, the height of the vessel 688 is 4 mm and the length of the proximal tether memory metal strips is 3 mm, the height 661 of the basket 611 as measured at the proximal-most crown 638 could be 4 mm. This is believed to allow the basket 611 in the gaping state to fill the vessel 688.

Figure 48A:
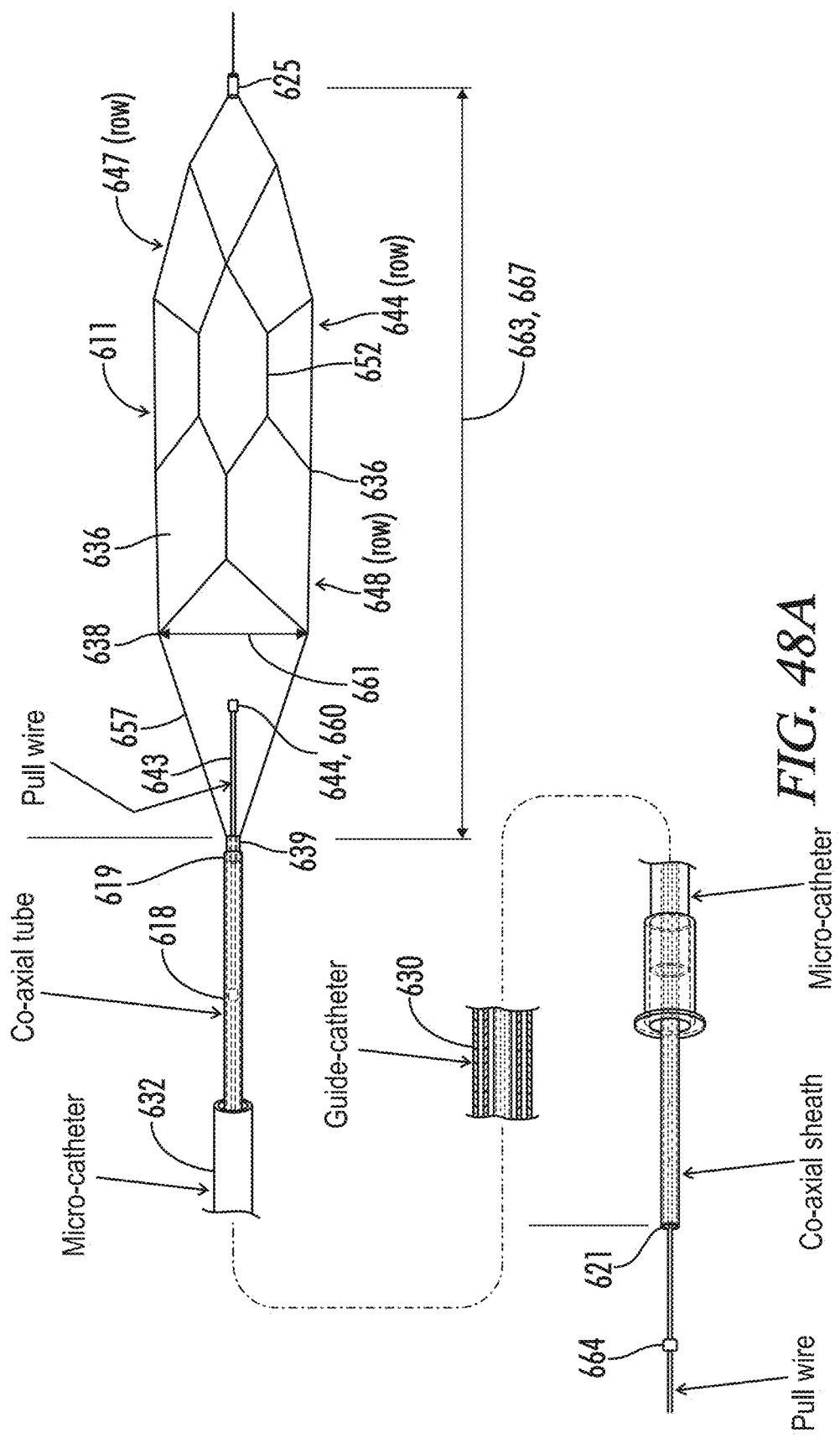

FIG. 48 illustrates another embodiment of the basket system 610. In this embodiment, the pull wire 643 does not extend through the entire basket 611 but rather ends at distal stop 660. As compared to the embodiment of FIGS. 46, 47 and 50, the proximal tether memory metal strips 657 of the embodiment of FIG. 48 are about the same thickness as the thickness 656 of the proximal cell memory metal strips 666, which makes the basket 611 relatively rigid and the proximal tether memory metal strips 657 relatively inflexible, which may be desired for certain applications. As shown, moving the basket 611 from the relaxed state (see FIG. 48A) to the gaping state by moving the coaxial tube 618 proximally does not greatly enhance the basket height 661 in this embodiment due to the rigidity.

FIGS. 49A-49C illustrate stepwise deployment and use of a basket system 610 with three relatively thin and short proximal tether memory metal strips 657; the system 610 is deployed in a blood vessel 688 to retrieve a clot 617.

FIG. 53 illustrates another embodiment of the basket system 610. In this embodiment, the proximal tether memory metal strips 657 are relatively thin (like the embodiment of FIGS. 46, 47 and 50) but longer than the FIGS. 46, 47, and 50 prior embodiment. This length allows the basket 611 to open asymmetrically around the clot 617 (see FIG. 53C), which is helpful if the microcatheter 632 and pull wire 643 are pushed against the vessel 688 wall by the clot 617. As shown in FIG. 53B, the length 654A of the first proximal tether memory metal strip 657A also may be two times the height 661 of the basket 611, as measured at the proximal-most crown 638 plus or minus 2 mm and the length 654B of the second proximal tether memory metal strip 657B may be two times the height 661 of the basket 611 plus or minus 2 mm. Thus, for example, if the vessel 688 has a height of 4 mm and the length 654A and 654B of the proximal tether memory metal strips 657A and 657B are 7 mm each, the height 661 of the distal basket 611 as measured at the proximal-most crown may be set to for example 4 mm in the relaxed state.

It will be noted that the proximal end of the system 610 is shown at the bottom end of FIGS. 45-62 and the distal end of the system 610 is shown at the top end of FIGS. 45-62 because a principal use of the system 610 is to remove a blood clot 617 from a human intracranial artery 688, in which case the system 610 generally will enter the artery 688 at its proximal end by the surgeon entering the patient's body near the groin and pushing the catheter 632 towards the brain. The diameter of human arteries 688 generally decrease from their proximal end to their distal end. However, when used in other types of lumens, the distal basket 611 may be located proximally relative to the catheter 632 as the term proximally and distally are used in that lumen.

FIG. 54 illustrates another embodiment of a basket system 611. In this embodiment, the system 611 includes a proximal hub/junction 639 that is slideable towards a distal hub/junction 625 (similar to the prior embodiments). The difference is that the tether memory metal strips 657 actually join the proximal basket 633 and the distal basket 611. More particularly, the proximal basket 633 is comprised of a plurality of proximal cells 636 attached to the proximal hub/junction 639 and a plurality of distal cells 622 and the distal basket is comprised of a plurality of proximal cells 636 attached to the proximal hub/junction 639 and a plurality of distal cells 622 and the tether memory metal strips 657 join a distal crown 623 of a distal cell 622 of the distal basket 611 with a proximal crown 638 of a proximal cell 636 of the proximal basket 633. As shown, in FIG. 54B, movement of the proximal hub/junction 639 toward the distal hub/junction 625 increases the height 634 of the proximal basket 633 as measured at the distal-most crown 623 of the distal basket 611.

FIGS. 55A and 55B illustrate an embodiment of the proximal tether memory metal strips 657 rotating about said pull wire longitudinal axis 646 such that the distal end 653 of a proximal tether memory metal strip 657 is located between about 90 and about 270 degrees relative to said proximal end 655 of the same proximal tether memory metal strip 657. In addition, the proximal tether memory metal strips 657 may rotate around their longitudinal axis 654 such that a distal end 653 of a proximal tether memory metal strip 657 rotates about 90 and about 270 degrees around this tether longitudinal axis 654 from the distal end 653 to the proximal end 655 of the same proximal memory metal strip 657. FIG. 55C illustrates an exemplary embodiment, where the proximal end 655A of the first proximal tether memory metal strip 657A is located attached to the proximal tube 639 at the 12 o'clock position and the distal end 653A of the same proximal tether memory metal strip 657A is attached to a proximal-most crown 639 at the 9 o'clock position. In addition, the second proximal tether memory metal strip 657B is located attached to the proximal tube 639 at the 6 o'clock position and the distal end 653B of the same proximal tether memory metal strip 657*b* is attached to the other proximal-most crown 639 at the 3 o'clock position. FIGS. 55D and 55E illustrate a similar embodiment with the proximal tether memory metal strips 657A and 657B rotating 180 degrees. FIG. 55D illustrates an exemplary embodiment, where the proximal end 655A of the first proximal tether memory metal strip 657A is located attached to the proximal tube 639 at the 12 o'clock position and the distal end 653A of the same proximal tether memory metal strip 657A is attached to a proximal-most crown 639 at the 6 o'clock position. In addition, the second proximal tether memory metal strip 657B is located attached to the proximal tube 639 at the 6 o'clock position and the distal end 653B of the same proximal tether memory metal strip 657*b* is attached to the other proximal-most crown 639 at the 12 o'clock position.

Figure 45A:
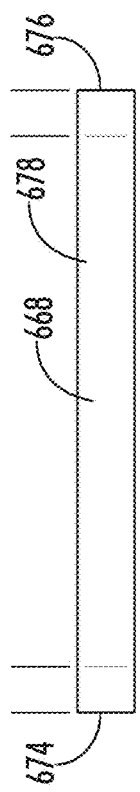
FIGS. 45A-45D illustrate a side, perspective view of a stepwise sequence of making an embodiment of the basket system of the present invention.
Figure 45B:
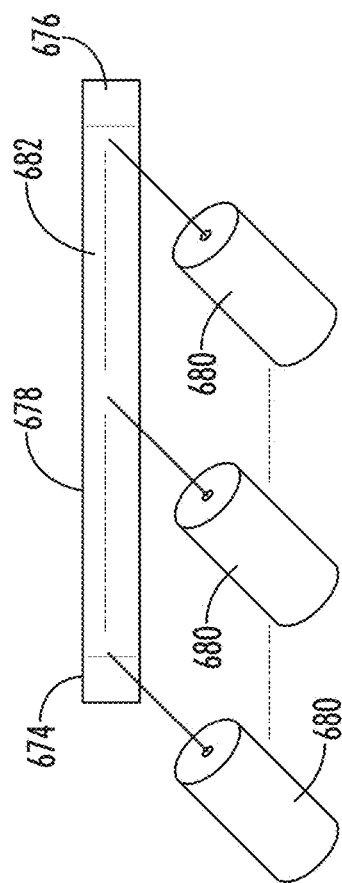
Figure 45C:
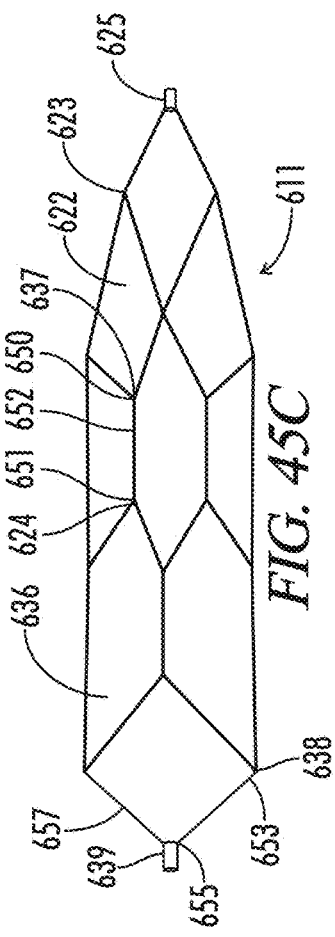
Figure 45D:
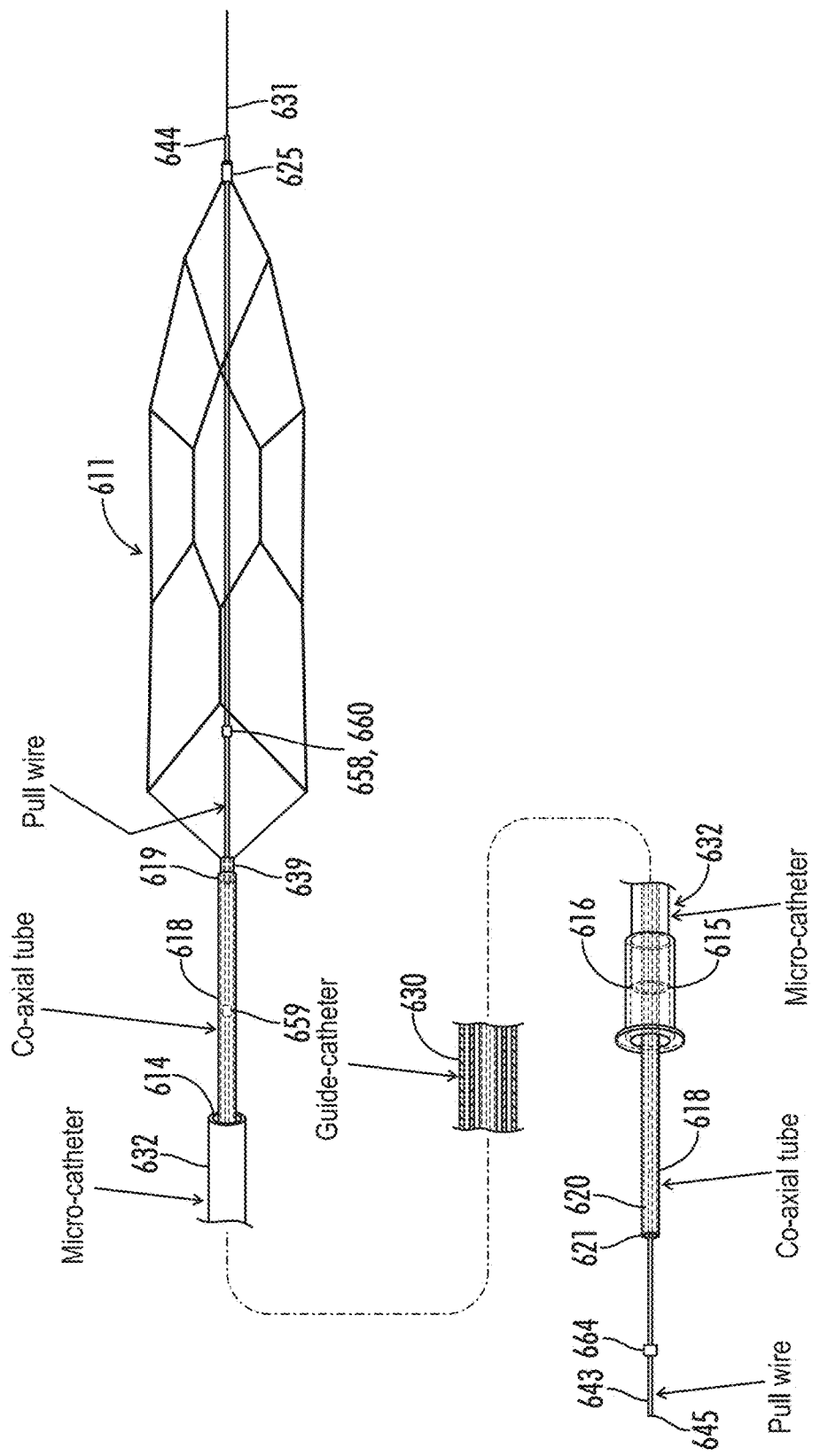

In some embodiments, the basket system 610 is prepared by a process that includes one or more of the following steps, as illustrated in FIG. 45:

a) providing a single tube 668 comprised of a memory metal such as nitinol, the single tube 668 having an exterior, a substantially hollow interior, a wall 682 separating the exterior from the substantially hollow interior, an open proximal end 674, an open distal end 676, a middle portion 678 between the open proximal end 674 and the open distal end 676 (see FIG. 45A);

b) cutting the wall of the middle portion 678 with a laser 680 (see FIG. 45B);

c) removing the pieces of the middle portion cut by the laser 680 to form a basket system 610 comprising a proximal tube 639 comprising a hollow interior 641 extending through said proximal tube 639, said proximal tube having a proximal end 642 and a distal end 640, a distal tube 625 comprising a hollow interior 641 extending through said distal tube 625, and a middle portion 678 located between said proximal tube 639 and said distal tube 625 and comprising a plurality of proximal tether memory metal strips 657, each proximal tether memory metal strip 657 having a proximal end 655 attached to the distal end 640 of the proximal tube 639 and a distal end 653;

d) altering the shape of the middle portion 678 using a mandrel and allowing the middle portion 678 to expand relative to the distal tube 676 and proximal tube 674 to form a basket that includes cells 623 and 636;

e) quenching the middle portion 678 at room temperature;

f) removing the mandrel from the middle portion 678:

g) mechanically or chemically electropolishing the middle portion 678 to remove oxides (see FIG. 45C);

h) inserting a pull wire 643 through said proximal tube interior 641 so that said proximal tube 639 is slideable along at least a portion of said pull wire 643, said pull wire 643 having a proximal end 645 and a distal end 644; and i) attaching said pull wire 643 to said distal tube 625 so that the distal tube 625 is not slideable along the pull wire 643 but instead the distal tube 625 moves with the pull wire 643 (see FIG. 45D).

In other embodiments, steps h) and i) above replaced with the steps of inserting a pull wire comprising a proximal end, a distal end, a stop located adjacent to said distal end, through said proximal tube interior, said stop having a width and/or height that is greater than said proximal tube interior, said stop located distal relative to said proximal tube interior, so that said proximal tube is slideable distally until the proximal hub/junction reaches said stop, said pull wire not contacting said distal tube; and attaching a leader wire to said distal tube.

In some embodiments, the middle portion 678 is expanded by heating the mandrel and the middle portion 678 by, for example, placing the mandrel and the middle portion 678 in a fluidized sand bath at about 500° C. for about 3 to about 7 minutes. As the middle portion 678 is heated, the heating causes the crystalline structure of the memory metal tube 668 to realign. Preferably, the mandrel is tapered (e.g., substantially conical or bullet in shape) so that the portion of the distal basket 611 formed from the middle portion 678 tapers from the proximal-most crown 638 to the distal end 666. Preferably, the proximal and distal ends of the tube 674 and 676 are not shape set by the mandrel and are not cut by the laser 680 so that the proximal and distal ends 674 and 676 do not change in shape and only slightly expand in size under heating and return to the size of the native tube 668 after the heat is removed. Preferably, the laser cuts are programmed via a computer. To ensure that the laser cuts only one surface of the tube wall at the time (and not the surface directly opposite the desired cutting surface), the laser 680 is preferably focused between the inner and outer diameter of the desired cutting surface and a coolant is passed through the memory metal tube 668 so that the laser 680 cools before reaching the surface directly opposite the desired cutting surface.

The portions of the wall not cut by the laser 680 create the proximal and distal tubes 674 and 676 as well as the other components of the distal basket 611, and memory metal strips 657 and 666, as described.

Preferably, the memory metal selected for the native tube 668 has a heat of transformation below average human body temperature (37° C.) so that the distal basket 611 has sufficient spring and flexibility after deployment from the catheter 632 in the human blood vessel 688.

In some embodiments, the native tube 668 (and hence the distal and proximal tubes 674 and 676) have an outer diameter of less than about 4 French, e.g., a diameter of about 1 to about 4 French. In some embodiments, the diameter of the pull wire 643 is between about 0.008 inches and about 0.051, as noted above, and in such embodiments, the diameter of the pull wire 43 may be approximately equal to the inner diameter 672 of the native nitinol tube 668.

Without being bound by any particular theory, it is believed that manufacturing the distal basket 611 from a single memory metal tube 668 provides ease of manufacturing and safety from mechanical failure and provides tensile strength necessary for the system 610 to remove hard thrombus 617 and other obstructions.

In some embodiments, the method further includes providing a coaxial tube 618, said coaxial tube 618 comprising a hollow interior 620 receiving said pull wire 643, a proximal end 621, and a distal end 619, and attaching said distal end 619 of said coaxial tube 643 to said proximal tube 625. In some embodiments, the method of attaching said distal end 619 of said coaxial tube 618 to said proximal tube 625 comprises welding or soldering said distal end 619 of said coaxial tube 618 to said proximal tube 625. In other embodiments, the method of attaching said distal end 619 of said coaxial tube 618 to said proximal tube 625 comprises shrink wrapping said distal end 619 of said coaxial tube 618 to said proximal tube 625. In other embodiments, the method of attaching said distal end 619 of said coaxial tube 618 to said proximal tube 625 comprises gluing said distal end 619 of said coaxial tube 618 to said proximal tube 625.

Optionally, after step e, the basket 611 further comprises a row 648 of proximal cells 636, each proximal cell 636 defined by a plurality of memory metal strips 666 and comprising a proximal crown 638 located at a proximal end of the cell 636 and pointing in the proximal direction and a distal crown 624 located at a distal end of the cell and pointing in the distal direction and further wherein each of said proximal crowns 638 of said proximal cells 636 is attached to a distal end 653 of a proximal tether memory metal strip 657. Optionally, after step e, the basket 610 further comprises a row 647 of distal cells 622 located distal to said proximal cells 636 and connected to said distal crowns 624 of said proximal cells 636, each distal cell 622 defined by a plurality of memory metal strips 666 and comprising a proximal crown 637 located at a proximal end of the cell 622 and pointing in the proximal direction and a distal crown 623 located at a distal end of the cell 622 and pointing in the distal direction, and further wherein the number of distal cells 622 is twice the number of proximal cells 636. Optionally, after step e, the basket system 610 further comprises a row 649 of strut memory metal strips 652, each strut memory metal strip 652 having a proximal end 651 attached to a distal crown 624 of a proximal cell 636 and a distal end 650 attached to a proximal crown 637 of a distal cell 622. Optionally, the basket 611 comprises no welded or soldered components and said proximal tether memory metal strips 657 are integral with said proximal cell crowns 638.

Optionally, after step e, the basket system 611 comprises between two and four proximal tether memory metal strips 657. Optionally, prior to cutting the memory metal tube 668, the memory metal tub 668 has an outer diameter 686 that is from about 0.011 inches to about 0.054 inches and an inner diameter 684 that is from about 0.008 inches to about 0.051 inches. Optionally, after step e), the proximal tube 639 and distal tube 625 have an outer diameter that is from about 0.02 inches to about 0.03 inches and an inner diameter that is from about 0.01 inches to about 0.02 inches. Optionally, the method further includes placing said basket 611 inside a catheter 632 comprised of a biocompatible material. Optionally, the method further includes the steps of placing the basket 611 inside a lumen 688 of an animal and using the basket to retrieve an object 617 located inside said lumen 688.

In other embodiments, as shown in FIGS. 58-60, the basket system 610 does not include a proximal hub/junction 639 and the system 610 includes a plurality of cords 703 (e.g., 2-4 cords 703) instead of or in addition to said proximal tether memory metal strips 657. For example, FIG. 15-17 shows a first set of embodiments, where soft cords made of rubber, nylon, suture material, braided catheter material, platinum coils, and ultrathin nitinol for example, are used. The cords 703 have a proximal end 704 attached to the distal end 619 of the coaxial tube 618 and a distal end 705 attached to a proximal crown 638 of a proximal cell 636. FIG. 58 illustrates one embodiment in which the cords 703 are relatively long. FIG. 59 illustrates another embodiment in which the cords 703 are relatively short.

Figure 60A:
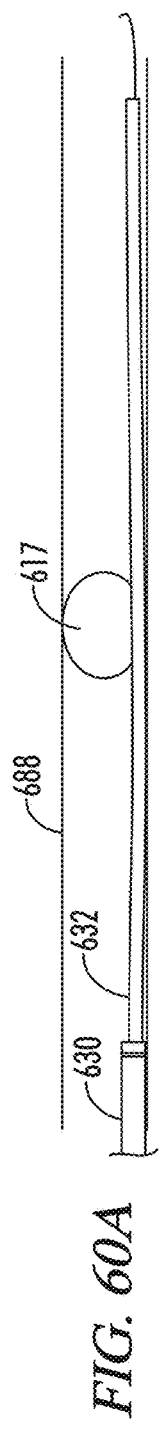
FIGS. 60A-F illustrate a perspective view of deployment of the basket system of FIGS. 59A-59B.
Figure 60B:
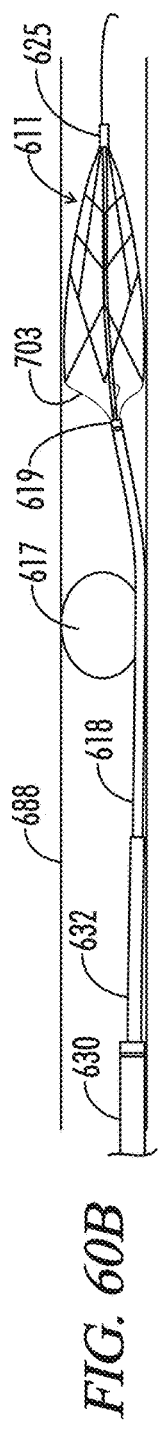
Figure 60C:
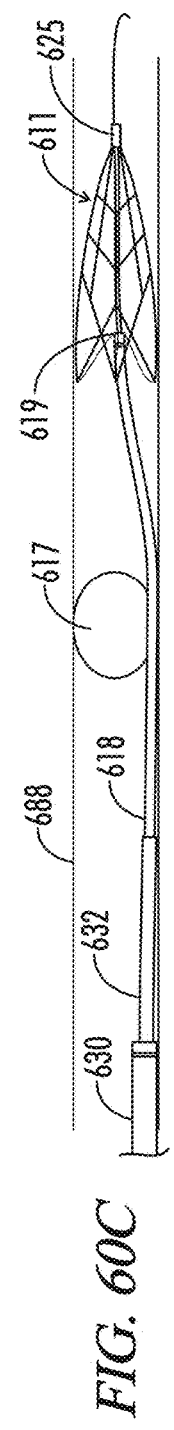
Figure 60D:
Figure 60E:
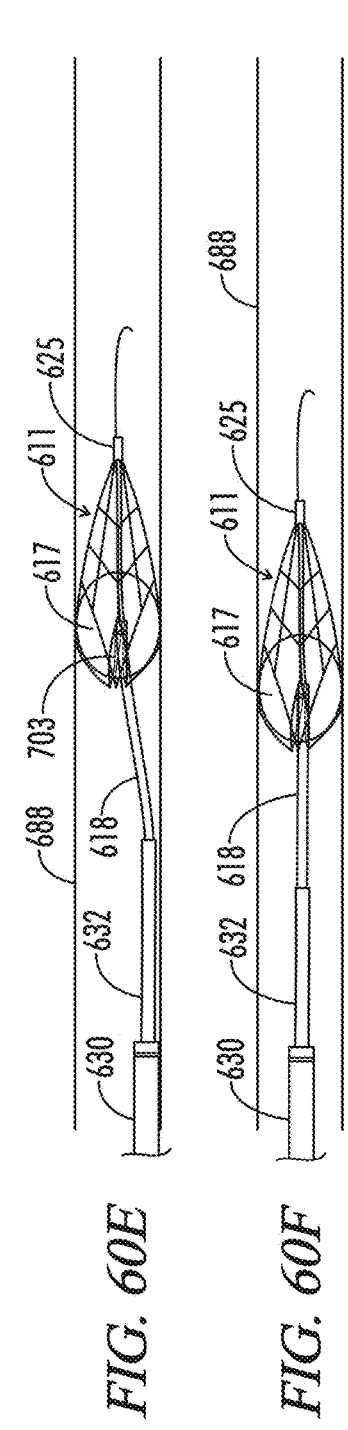
Figure 60F:

In some embodiments, the system 610 is used in a method that includes a) providing the system 610;

b) positioning the system 610 in said lumen 688, said basket 611 located in said catheter 632 in a collapsed state (see FIG. 60A);

c) deploying said distal basket 611 from said distal end 614 of said catheter 632 so that said proximal crowns 638 of said proximal cells 636 are distal to said obstruction 617;

d) allowing said distal basket 611 to move to said relaxed state (see FIG. 60B);

e) moving said coaxial tube 618 distally relative to said distal hub/junction 625 so that said coaxial tube 618 moves distally to the proximal-most crown 638 (see FIG. 60C);

f) moving said distal basket 611, said pull wire 643 and said coaxial tube 618 proximally simultaneously so that said distal basket 611 moves over said obstruction 617 (see FIG. 60D);

g) moving said coaxial sheath 618 distally relative to said distal hub/junction 625 so that said distal basket height 661, as measured at the proximal-most crown 638, decreases and said coaxial tube 618 is closer to said distal hub/junction 625 as compared to the proximal-most crown 638 (see FIG. 60E); and h) removing said distal basket 611 and said obstruction 617 from said lumen 688 (see FIG. 60F).

In other embodiments, steps g-h above are replaced with the steps below:

g) moving said coaxial sheath 618 proximally relative to said distal hub/junction 625 so that said distal basket height 661, as measured at the proximal-most crown 661, decreases:

h) moving said catheter 632 distally relative to said distal hub/junction 625 so that said catheter 632 re-sheaths said coaxial sheath 618 and partially re-sheaths said cords, thereby decreasing said distal basket height 661, as measured at the proximal-most crown 638;

i) removing said distal basket 611 and said obstruction 617 from said lumen 688.

As shown, an advantage of this embodiment is that the cords 703 move distally to the proximal-most crowns 638 so they do not obstruct entry way of the clot 617 into the distal basket 611.

In other embodiments, as shown in FIGS. 61 and 62, the system 610 includes cords 703 and proximal tether memory metal strips 657. In such embodiments, the proximal tether memory metal strips 657 have a proximal end 655 attached to the distal end 619 of the coaxial tube 618. The cords have a proximal end attached to the distal end 653 of the proximal memory metal strips 657 and a distal end attached to a proximal crown 638 of a proximal cell 636.

In some embodiments, the system 610 is used in a method of removing an object from an interior lumen 688 of an animal, said lumen 688 having an interior wall forming said lumen 688 that includes:

a) providing the system 610;

b) positioning the system 610 in said lumen 688, said basket 611 located in said catheter 632 in a collapsed state;

c) deploying said distal basket 611 from said distal end 614 of said catheter 632 so that said proximal crowns 638 of said proximal cells 636 are distal to said obstruction 617, said coaxial sheath 618 is proximal to said obstruction 617, said proximal tether memory metal strips 657 are proximal to said obstruction 617, and said cords are adjacent to said obstruction 617;

d) allowing said distal basket 611 to move to said relaxed state (see FIG. 62A);

e) moving said coaxial tube 618 distally relative to said distal hub/junction 625 and moving said basket 611 proximally so that said proximal tether memory metal strips 657 move distally relative to the proximal-most crown 638 and said obstruction 617 is sandwiched between said proximal tether memory metal strips 657 and said proximal crowns 638 of said proximal cells 636 (see FIG. 62B); and f) removing said distal basket 611 and said obstruction 617 from said lumen 688.

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention, as defined and limited solely by the following claims. In particular, although the system has been exemplified for use in retrieving blood clots, the system may be used to retrieve other objects from animal lumens. In addition, the steps of any method described herein may be performed in any suitable order and steps may be performed simultaneously if needed.

Terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A system for removing objects within an interior lumen of an animal, the system comprising:

a pull wire having a proximal end, a distal end and a pull wire longitudinal axis extending from the proximal end to the distal end;

a coaxial sheath having a hollow interior, an open proximal end leading to the interior, and an open distal end leading to the interior, a length extending from the open proximal end to the open distal end, the coaxial sheath length of at least about 50 centimeters, the coaxial sheath enveloping the pull wire, the coaxial sheath slideable along at least a segment of the pull wire;

a distal basket comprising an interior, a proximal end, a distal end, a distal basket length extending from the distal basket proximal end to the distal basket distal end, a distal basket height perpendicular to the distal basket length, a plurality of proximal cells defined by a plurality of proximal cell memory metal strips, each proximal cell comprising a proximal crown located at the proximal end of the proximal cell and pointing generally in the proximal direction and a distal crown located at the distal end of the proximal cell and pointing generally in the distal direction, and a plurality of distal cells distal to the proximal cells;

a plurality of proximal strips, each proximal strip having a proximal end extending from the coaxial sheath, a distal end attached to a proximal crown of a proximal cell and a length extending from the proximal end to the distal end; and a catheter having a hollow interior, a proximal end leading to the interior and a distal end leading to the interior, the catheter comprised of a biocompatible material, the distal basket comprised of a memory metal and having a relaxed state in which the distal end of the coaxial sheath is located at a first position along the pull wire, the first position located a first distance proximal to the proximal crowns, and in which the distal basket, as measured at the proximal-most crown, has a first height, a proximal collapsed state in which the distal end of the coaxial sheath is located at a second position along the pull wire, the second position located a second distance proximal to the proximal crowns, and in which the distal basket, as measured at the proximal-most crown, has a second height, the second distance greater than the first distance, the second height less than the first height, and a distal collapsed state in which the distal end of the coaxial sheath is located at a third position along the pull wire, the third position distal to the proximal crowns and located in the basket interior, and in which the distal basket, as measured at the proximal-most crown, has a third height, the third height less than the first height wherein the catheter is configured to envelope the distal basket when the distal basket is in the proximal collapsed state;

wherein the distal basket is configured to move from the relaxed state to the proximal collapsed state by moving the distal end of the coaxial sheath proximally to the second position while keeping the distal basket at a fixed location along the pull wire; and wherein the distal basket is configured to move from the relaxed state to the distal collapsed state by moving the distal end of the coaxial sheath distally to the third position while keeping the distal basket at a fixed location along the pull wire, and further wherein the distal end of the distal basked is fixed relative to the pull wire.

2. The system of claim 1, wherein each proximal crown comprises a proximal tip and further wherein each proximal strip is configured to cover a proximal tip when the distal basket is in the distal collapsed state.

3. The system of claim 1, wherein each proximal crown comprises an eyelet and further wherein each proximal strip passes through an eyelet.

4. The system of claim 3, wherein the distal end of each proximal strip comprises a loop attaching the proximal strip to an eyelet.

5. The system of claim 1, wherein each proximal crown has an interior surface facing the distal basket interior and an exterior surface opposite the interior surface and further wherein each proximal strip contacts an exterior surface of a proximal crown in the proximal collapsed state and in the distal collapsed state.

6. The system of claim 1, wherein the pull wire extends through the distal basket interior and further wherein the proximal crowns are configured to move towards each other and towards the pull wire when the distal basket moves from the relaxed state to the distal collapsed state and when the distal basket moves from the relaxed state to the proximal collapsed state.

7. The system of claim 1, wherein the proximal crowns are configured to remain a fixed distance from the distal end of the distal basket when the distal basket moves from the relaxed state to the distal collapsed state.

8. The system of claim 1, wherein the coaxial sheath is a braided catheter comprised of a plurality of braids, and further wherein the proximal segments of the braids are wound together to form the braided catheter and further wherein an unwound distal segment of each braid forms a proximal strip.

9. The system of claim 1 wherein at least one proximal crown further comprises an x-ray marker.

10. The system of claim 1, wherein the proximal ends of the proximal strips are integral with the coaxial sheath.

11. The system of claim 1, wherein the proximal ends of the proximal strips are attached to the coaxial sheath.

12. The system of claim 1, wherein the system comprises between two and four proximal strips and the proximal strips are spaced substantially evenly apart.

13. The system of claim 1, wherein the proximal strips have a length of from about 5 millimeters to about 40 millimeters in the relaxed state.

14. The system of claim 1, wherein the pull wire extends through the basket interior from the distal basket proximal end to the distal basket distal end.

15. The system of claim 1, wherein the coaxial sheath interior has a size and shape, and further wherein the size and shape of the coaxial sheath interior are configured to prevent a segment of the pull wire located in the basket interior and distal relative to the distal end of the coaxial sheath from moving through the coaxial sheath interior.

16. The system of claim 1, wherein the distal end of the distal basket comprises a distal tube having an open proximal end and an open distal end, the distal tube comprised of a memory metal.

17. The system of claim 16, wherein the distal basket and the distal tube were prepared from the same memory metal tube.

18. The system of claim 16, wherein the distal tube is attached to the pull wire such that the distal tube is not slideable along the pull wire.

19. The system of claim 1, wherein all proximal crowns of the proximal cells are attached to a proximal strip.

20. The system of claim 1, wherein the second and third positions along the pull wire each comprise an x-ray marker.

21. A method of removing a clot from a blood vessel of an animal, the blood vessel having an interior wall forming the blood vessel, the method comprising the steps of:
  a) providing the system of claim 1, wherein the coaxial sheath is located in the catheter interior and the distal basket is located in the catheter interior in a collapsed state;
  b) positioning the catheter in the blood vessel;
  c) deploying the distal basket from the distal end of the catheter so that the proximal crowns of the proximal cells are distal to the clot;
  d) allowing the distal basket to move to the relaxed state;
  e) holding the coaxial sheath in a user's hand and moving the coaxial sheath to a fourth position along the pull wire, the fourth position located distal to the proximal crowns but proximal to the third position;
  f) capturing the clot in the distal basket interior;
  g) holding the coaxial sheath in a user's hand and moving the coaxial sheath further distally into the basket interior so that the distal basket height, as measured at the proximal-most crown, decreases and the proximal crowns move toward each other and the pull wire; and
  h) moving the system proximally out of the blood vessel.

* * * * *